(12) United States Patent
Wang

(10) Patent No.: US 6,906,179 B2
(45) Date of Patent: Jun. 14, 2005

(54) ANTIBODY TO SNIP1

(75) Inventor: Tongwen Wang, Seattle, WA (US)

(73) Assignee: The General Hospital Corporation, MA (US)

(*) Notice: Subject to any disclaimer, the term of this patent is extended or adjusted under 35 U.S.C. 154(b) by 168 days.

(21) Appl. No.: 09/927,738

(22) Filed: Aug. 10, 2001

(65) Prior Publication Data
US 2002/0076799 A1 Jun. 20, 2002

Related U.S. Application Data

(63) Continuation-in-part of application No. PCT/US00/03561, filed on Feb. 11, 2000.
(60) Provisional application No. 60/119,786, filed on Feb. 11, 1999.

(51) Int. Cl.$^7$ .............................................. C07K 16/18
(52) U.S. Cl. ................. 530/387.1; 530/350; 530/387.9; 435/183
(58) Field of Search ............................. 530/350, 387.1, 530/387.9, 388.1, 389.1; 435/183

(56) References Cited

U.S. PATENT DOCUMENTS 6,063,906 A  *  5/2000  Brenner et al.
6,139,837 A     10/2000 Bandman et al.

FOREIGN PATENT DOCUMENTS

| WO | WO98/53066 | 11/1998 |
|---|---|---|
| WO | WO 99/57132 | 11/1999 |
| WO | WO 200047102 A2 * | 8/2000 |

OTHER PUBLICATIONS

Liang et al., Antibody binding to a peptide but not the whole protein by recognition of the C–terminal carboxy group, Arch. Biochem. Biophys., 329(2): 208–214 (May 15, 1996).*

Lin et al., A novel link beween the proteasome pathway and the signal transduction pathway of the Bone Morphogenetic Proteins (BMPs), BMC Cell Biology 3:15 (Jun. 21, 2002).*

Kawakami, T. et al.,; "NEDO human cDNA Sequencing Project"; Database Genbank; (2000) Accession: AK000340.

Nagase, et al.; "Prediction of the Coding Sequences of Unidentified Human Genes. XIII. The Complete Sequences of 100 New cDNA Clones from Brain Which Code for Large Proteins in vitro"; (1999); DNA Research; 6: 63–70.

Nagase, et al.; "Prediction of the Coding Sequences of Unidentified Human Genes. XVIII. The Complete Sequences of 100 New cDNA Clones from Brain Which Code for Large Proteins in vitro"; (2000); DNA Research; 7: 273–281.

Osman, et al.; "Identification and Characterization of a Smad2 Homologue from Schistosoma mansomi, a Transforming Growth Factor–β Signal Transducer"; (2001); The Journal of Biological Chemistry; vol. 276, 13: 10072–10082.

Gruendler, et al.; "Proteasomal Degradation of Smad1 Induced by Bone Morphogenetic Proteins"; (2001); The Journal of Biological Chemistry; vol. 276, 49: 46533–46543.

Liu, et al.; "A novel ability of Smad3 to regulate proteasomal degradation of a Cas family member HEF1"; (2000), The EMBO Journal; vol. 19, 24: 6759–6769.

Hillier, et al.; "Generation and Analysis of 280,000 Human Expressed Sequence Tags"; (1996); Genome Research; 6: 807–828.

PCT International Search Report for International Application No.: PCT/US00/03561 dated Jan. 28, 2002.

Abdollah, et al., "TBRI Phosphorylation of Smad2 on Ser$^{465}$ and Ser$^{467}$ Is Required for Smad2–Smad4 Complex Formation and Signaling", Journal of Biological Chemistry, 272, (1997): 27678–27685.

Baker, J. & Harland, R.M., "A Novel Mesoderm Inducer, Madr2, Functions in the Activin Signal Transduction Pathway", Genes and Development, 10, (1996): 1880–1889.

Chen, Y., et al., "Regulation of Transforming Growth Factor Beta– and Activin–Induced Transcription by Mammalian Mad Proteins", PNAS—Processings of the National Academy of Sciences, 93, (1996): 12992–12997.

Chen, X., et al., "Smad4 and FAST–1 in the Assembly of Activin–Responsive Factor", Nature, 389, (1997): 85–89.

de Caestecker, M.P., et al., "Characterization of Functional Domains within Smad4 / DPC4", Journal of Biological Chemistry, 272, (1997), 13690–13696.

Dennler, S., et al., "Direct Binding of Smad3 and Smad4 to Critical TGF–Inducible Elements in the Promoter of Human Plasminogen Activator Inhibitor–Type 1 Gene", Embo Journal, 17, (1998): 3091–3100.

(Continued)

Primary Examiner—Lorraine Spector
Assistant Examiner—Claire M. Kaufman
(74) Attorney, Agent, or Firm—Kathleen M. Williams; Palmer & Dodge LLP

(57) ABSTRACT

The invention provides novel compositions comprising a Smad protein and an isolated protein component of the proteasome-mediated degradation pathway. The invention also provides novel compositions comprising a Smad1 protein and a substrate for proteasome-mediated degradation. The invention also provides methods of screening for compounds that modulate the interaction between the proteins comprising these compositions. The invention also provides methods of screening for compounds that modulate the activity of the proteins comprising these compositions. The invention also provides methods of detecting proteasome-mediated degradation of novel Smad interacting proteins. A further aspect of the invention is a kit for detecting proteasome-mediated degradation of novel Smad interacting proteins. The invention also provides methods of treating diseases which are associated with aberrant levels of activity of a TGF-β superfamily member.

1 Claim, 45 Drawing Sheets

OTHER PUBLICATIONS

Hata, A., et al., "Mutations Increasing Autoinhibition Inactivate Tumour Supressors Smad2 and Smad4", *Nature*, 388, (1997): 82–87.

Kim, J., et al., "Drosophila Mad Binds to DNA and Directly Mediates Activation of Vestigial by Decapentaplegic", *Nature*, 388, (1997): 304–308.

Kretzschmar, M., et al., "The TGF–Beta Family Mediator Smad1 is Phosphorylated Directly and Activated Functionally by the BMP Receptor Kinase", *Genes and Development*, 11, (1997): 984–995.

Lagna, G., et al., "Partnership Between DPC4 and SMAD Proteins in TGF–Beta Signalling Pathways", *Nature*, 383, (1996): 832–836.

Liu, F., et al., "A Human Mad Protein Acting as a BMP–regulated Transcriptional Activator", *Nature*, 381, (1996) 620–623.

Macias–Silva, M., et al., "MADR2 is a Substrate of the TGFbeta Receptor and Its Phosphorylation is Required for Nuclear Accumulation and Signaling", *Cell*, 87, (1996): 1215–1224.

Schutte, M., et al., "DPC4 Gene in Various Tumor Types", *Cancer Research*, 56, (1996): 2527–2530.

Souchelnytskyi, S., et al., "Phosphorylation of $Ser^{465}$ and $Ser^{467}$ in the C Terminus of Smad2 Mediates Interaction with Smad4 and is Required for Transforming Growth Factor–Beta Signaling", *Journal of Biological Chemistry*, 272, (1997): 28107–28115.

Yingling, J. M., et al., "Tumor Suppressor Smad4 is a Transforming Growth Factor Beta–Inducible DNA Binding Protein", *Molecular and Cellular Biology*, 17, (1997): 7019–7028.

Wu, R. Y., et al., "Heteromeric and Homomeric Interactions Correlate with Signaling Activity and Functional Cooperativity of Smad3 and Smad4/DPC4", *Molecular and Cellular Biology*, 17, (1997): 2521–2528.

Zawel, L., et al., "Human Smad3 and Smad4 are Sequence–Specific Transcription Activators", *Molecules and Cells*, 1, (1998): 611–617.

Zwickl, P., et al., "Critical Elements in Proteasome Assembly", *Nature Structural Biology*, 1, (1994): 765–770.

* cited by examiner

Figure 1

Clone S1+27 protein sequence (SEQ ID No. 1)

```
  1 KSSPLLIRMEESLNIVKYTAFLYNDQLIWSGLEQDDMRILYKYLTTSLFP  50
 51 RHIEPELAGRDSPIRAEMPGNLQHYGRFLTGPLNLNDPDAKCRFPKIFVN 100
101 TDDTYEELHLIVYKAMSAAVCFMIDASVHPTLDFCRRLDSIVGPQLTVLA 150
151 SDICEQFNINKRMSGSEKEPQFKFIYFNHMNLAEKSTVHMRKTPSVSLTS 200
201 VHPDLMKILGDINSDFTRVDEDEEIIVKAMSDYWVVGKKSDRRELYVILN 250
251 QKNANLIEVNEVKKLCATQFNNIFFLD 277
```

Figure 2

Clone S1+28 protein sequence (SEQ ID No. 2)

```
  1 FAVDAKALPQNKPRPLTQEEIAQRRERARQRHAEKLAAAQGQAPLEPTQD  50
 51 GSAIETCPKGDEPRGDEQQVESMTPKPVLQEENNQESFIAFARVFSGVAR 100
101 RGKKIFVLGPKYSPLEFLRRVPLCFSAPPDGLPQVPHMAYCALENLYLLM 150
151 GRELEYLEEVPPGNVLGIGGLQDFVLKSATLCSLPSCPPFIPLNFEATPI 200
201 VRVAVEPKHPSEMPQLVKGMKLLNQADPCVQILIQETGEHVLVTAGEVHL 250
251 QRCLDDLKERFAKIHISVSEPIIPFRETITKPPKVDMVNEEIGKQQKVAV 300
301 IHQMKEDQSKIPEGIQVDSDGLITITTPNKLATLSVRAMPLPEEVTQILE 350
351 ENSDLIRSMEQLTSSLNEGENTHMIHQKTQEKIWEFKGKLEQHLTGRRWR 400
401 NIVDQIWSFGPRKCGPNILVNKSEDFQNSVWTGPADKASKEASRYRDLGN 450
451 SIVSGFQLATLSGPMCEEPLMGVCFVLEKWDLSKFEEQGASDLAKEDRRK 500
501 MKPVLVEMKTKSYKMAALRPLRRGHHRKENLHSLTAMDLSQDS 543
```

Figure 3

Clone S1+19 protein sequence (SEQ ID No. 3)

```
  1 MKAVKSERERGSRRRHRDGDVVLPAGVVVKQERLSPEVAPPAHRRPDHSG  50
 51 GSPSPPTSEPARSGHRGNRARGVSRSPPKKKNKASGRRSKSPRSKRNRSP 100
101 HHSTVKVKQEREDHPRRGREDRQHREPSEQEHRRARNSDRDRHRGHSHQR 150
151 RTSNERPGSGQGQGRDRDTQNLQAQEEEREFYNARRREHRQRNDVGGGGS 200
201 ESQELVPRPGGNNKEKEVPAKEKPSFELSGALLEDTNTFRGVVIKYSEPP 250
251 EARIPKKRWRLYPFKNDEVLPVMYIHRQSAYLLGRHRRIADIPIDHPSCS 300
301 KQHAVFQYRLVEYTRADGTVGRRVKPYIIDLGSGNGTFLNNKRIEPQRYY 350
351 ELKEKDVLKFGFSSREYVLLHESSDTSEIDRKDDEDEEEEEVSDS 396
```

Figure 4

Protein sequence of NIPP-1 domain (SEQ ID No. 4) homologous to SNIP 1.

```
 1 YLFGRNPDLCDFTIDHQSCSRVHAALVYHKHLKRVFLIDLNSTHGTFLGH 50
51 IRLEPHKPQQIPIDSTVSFGASTRAYTLREKP 82
```

Figure 5

Clone S1+19 Smad binding domain protein sequence (SEQ ID No. 5)

```
  1 RHRGHSHQRRTSNERPGSGQGQGRDRDTQNLQAQEEEREFYNARRREHRQ  50
 51 RNDVGGGGSESQELVPRPGGNNKEKEVPAKEKPSFELSGALLEDTNTFRG 100
101 VVIKYSEPPEARIPKKRWRLYPFKNDEVLPVMYIHRQSAYLLGRHRRIAD 150
151 IPIDHPSCSKQHAVFQYRLVEYTRADGTVGRRVKPYIIDLGSGNGTFLNN 200
201 KRIEPQRYYELKEKDVLKFGFSSREYVLLHESSDTSEIDRKDDEDEEEEE 250
251 EVSDS 255
```

Figure 6

Clone S1+19 C. elegans homology protein sequence (SEQ ID No. 6)

```
  1 GALTEDTNTFRGVVIKYNEPPEAKKPNARWRLYPFKGEESLQVLYIHRQS  50
 51 AYLIGRDHKIADIPVDHPSCSKQHAVLQFRSMPFTRDDGTKARRIMPYII 100
101 DLGSGNGTFLNEKKIEPQRYIELQEKDMLKFGFSTREYVVMKEREITEEE 150
151 LAEGEDVKKEESD 163
```

Figure 7

Clone S1+12 protein sequence (SEQ ID No. 7)

```
  1 EFGTRRMMEGLDDGPDFLSEEDRGLKAINVDLQSDAALQVDISDALSERD  50
 51 KVKFTVHTKSSLPNFKQNEFSVVRQHEEFIWLHDSFVENEDYAGYIIPPA 100
101 PPRPDFDASREKLQKLGEGEGSMTKEEFTKMKQELEAEYLAIFKKTVAMH 150
151 EVFLCRVAAHPILRRDLNFHVFLEYNQDLSVRGKKKKKNSRSFGLLRQ   198
```

Figure 8

Clone S1+12-2 protein sequence (SEQ ID No.8)

```
  1 HASGLGAAMMEGLDDGPDFLSEEDRGLKAINVDLQSDAALQVDISDALSE  50
 51 RDKVKFTVHTKSSLPNFKQNEFSVVRQHEEFIWLHDSFVENEDYAGYIIP 100
101 PAPPRPDFDASREKLQKLGEGEGSMTKEEFTKMKQELEAEYLAIFKKTVA 150
151 MHEVFLCRVAAHPILRRDLNFHVFLEYNQDLSVRGKNKKEKLEDFFKNMV 200
201 KSADGVIVSGVKDVDDFFEHERTFLLEYHNRVKDASAKSDRMTRSHKSAA 250
251 DDYNRIGSSLYALGTQDSTDICKFFLKVSELFDKTRKIEARVSADEDLKL 300
301 SDLLKYYLRESQAAKDLLYRRSRSLVDYENANKALDKARAKNKDVLQAET 350
351 SQQLCCQKFEKISESAKQELIDFKTRRVAAFRKNLVELAELELKHAKGNL 400
401 QLLQNCLAVLNGDT 414
```

Figure 9

Clone S1+12-5 protein sequence (SEQ ID No.9)

```
  1 MTTLTEIKLLPSLVLLVCCEYLAIFKKTVAMHEVFLCRVAAHPILRRDLN  50
 51 FHVFLEYNQDLSVRGKNKKEKLEDFFKNMVKSADGVIVSGVKDVDDFFEH 100
101 ERTFLLEYHNRVKDASAKSDRMTRSHKSAADDYNRIGSSLYALGTQDSTD 150
151 ICKFFLKVSELFDKTRKIEARVSADEDLKLSDLLKYYLRESQAAKDLLYR 200
201 RSRSLVDYENANKALDKARAKNKDVLQAETSQQLCCQKFEKISESAKQEL 250
251 IDFKTRRVAAFRKNLVELAELELKHAKGNLQLLQNCLAVLNGDT       294
```

Figure 10

Clone S3+1 DNA sequence (SEQ ID No. 10)

```
  1 ATGTCAAGTGGAATTTGGCAGAGAGGCAAAGAAGAAGAAGGAGTTTATGG  50
 51 TTTTCTAATAGAAGATATCAGGAAGGAAGTGAATAGAGCTTCTAAACTGA 100
101 AATGCTGTGTTTGCAAGAAAAATGGTGCTTCAATTGGATGTGTTGCACCC 150
151 CGATGTAAACGAAGTTATCATTTCCATGTGGACTTCAGAGAGAATGTAT  200
201 TTCCAGTTTACTGGCAATTTTGCGTCATTTGTTGGGACCATCGACCTG   250
251 TTCAAATAATTACATCTAATAATTATAGAGAGTCCTTACCATGCACCATT 300
301 TGCTTGGAATTTATTGAGCCTATTCCAAGTTATAACATATTACGAAGTCC 350
351 TTGTTGTAAGAACGCTTGGTTTCATAGAGACTGTTTACAGGTTCAAGCAA 400
401 TAAATGCGGGAGTGTTTTTCTTTAGGTGTACAATATGCAATAATAGTGAC 450
451 ATCTTTCAGAAGAGATGTTGAGAATGGGAATTCATATTCCTGAAAAAGA  500
501 TGCTTCCTGGGAATTAGAGGAAAACGCTTATCAAGAGCTTCTGCAGCACT 550
551 ATGAGCGTTGTGATGTTCGAAGATGTCGTTGCAAAGAAGGGCGAGACTAT 600
601 AATGCACCTGATAGCAAATGGGAATAAAGCGCTGTCAGTGTTGTGGTTC  650
651 CAGTGGCACACATTTAGCCTGCTCCTCATTACGGTCATGGGAGCAAAATT 700
701 GGGAGTGTTTGGAATGTAGGGGTATTATCTACAATTCAGGAGAGTTCCAA 750
751 ACAGCCAAAAACATGTATTACCCAATTCTAATAATGTGGGGATTACAGA  800
801 TTGTTTGTTGGAAGAGTCATCACCTAAATTACCCAGACAGTCACCTGGAT 850
851 CCCAGAGTAAAGATCTACTGAGGCAAGGCAGCAAATTTAGAAGAAATGTA 900
901 TCAACACTATTAATAGAGTTAGGATTCCAAATTAAAAAAAAAAAAAAAA  950
951 ACTCGAGAAGNTTGGANTNTTCGCCAGAGGTTTGGTCAA 989
```

Figure 11
Clone S3+1 protein sequence (SEQ ID No. 11)

```
  1 MSSGIWQRGKEEEGVYGFLIEDIRKEVNRASKLKCCVCKKNGASIGCVAP  50
 51 RCKRSYHFPCGLQRECIFQFTGNFASFCWDHRPVQIITSNNYRESLPCTI 100
101 CLEFIEPIPSYNILRSPCCKNAWFHRDCLQVQAINAGVFFFRCTICNNSD 150
151 IFQKEMLRMGIHIPEKDASWELEENAYQELLQHYERCDVRRCRCKEGRDY 200
201 NAPDSKWEIKRCQCCGSSGTHLACSSLRSWEQNWECLECRGIIYNSGEFQ 250
251 TAKKHVLPNSNNVGITDCLLEESSPKLPRQSPGSQSKDLLRQGSKFRRNV 300
301 STLLIELGFQIKKKKKKLEKXGXFARGLV 329
```

Figure 12

Clone S3+12 DNA sequence (SEQ ID No. 12)

```
   1 AGGAAAGCTACAGAAATTAGCACTGCAGTGGTTCAGAGGTCAGCTACCAT   50
  51 TGGCAGTTCTCCAGTTCTCTATAGCCAGTCAGCTATAGCTACAGGTCACC  100
 101 AGGCAGCAGGGATTGGAAACCAGGCAACAGGAATTGGACATCAGACAATA  150
 151 CCAGTTAGCCTTCCAGCAGCAGGAATGGGTCATCAGGCCAGAGGAATGAG  200
 201 CCTGCAGTCAAATTACCTTGGACTAGCGGCAGCACCTGCAATTATGAGTT  250
 251 ATGCAGAATGTTCTGTCCCAATTGGAGTGACTGCTCCCTCATTGCAGCCA  300
 301 GTTCAGGCCCGAGGTGCTGTGCCTACCGCTACCATTATAGAACCACCACC  350
 351 ACCACCTCCTCCTCCTCCTCCACCACCACCAGCTCCCAAAATGCCAC     400
 401 CACCTGAAAGACAAAAAAGGAAGGAAAGACAAGGCAAAGAAGAGTAAG    450
 451 ACCAAAATGCCATCTTTGGTAAAAAAGTGGCAGAGTATCCAGCGTGAGTT  500
 501 AGATGAAGAGGACAATTCTAGTTCCAGTGAAGAGGATCGGGAATCAACTG  550
 551 CACAGAAGCGAATTGAAGAGTGGAAACAGCAGCAGCTGGTTAGTGGCATG  600
 601 GCAGAGAGAAATGCTAATTTTGAAGCCCTTCCTGAGGATTGGAGAGCAAG  650
 651 GCTGAAGAGAAGGAAAATGGCTCCAAACACATAGTTTTAAGTTTTTAAA   700
 701 ACTTTTTTGTATTATTGTTTGTTTTGTGTTCAGTTCAAAGTCTTAACCAG  750
 751 TTTATTGTCAAATAAACTATAAATGTTATGGGGAGATCTTATAAATTT    800
 801 CCTGGGCAAGAGTGTATGCATACAAAGTTTTCACTTTTGTGAAATGTAAT  850
 851 TTTTCTGTTTTTGCAAAGGGATGAGGTGATTGGAATTGCTTTGACCATGC  900
 901 TGCCTTTATTCTCAAACTGGCAAACTTAGCATGTTAGGTGTATTAACCTC  950
 951 ATCAGTCTTGAAGAACATGTGGCTCATGAGTATAACACTTCTGTAGAGGA 1000
1001 CTCCCTGACAAAGTGAAGAATTAACTTCTCCTCCAGAACAAGTGCAATT  1050
1051 CAGAAGGCAGCTCTGCATTCTACCTTGCTTGACTGGAATTGTCTGAAGCT 1100
1101 TTTTCTGGCCTCTTTTCTCTAGTCGGCCACCCCTGAAGTGCTGAGGTCTA 1150
1151 AGTGGTTTACCTCGTGCTGATAGATGGCCACACTCTTTAGAGTAGTTCTC 1200
1201 ATAAGTTCTAGAACTGGTAGCTCGGTCGTTTCGCACACTAGGTGGCATAC 1250
1251 AGGCAGCAGCAGGTGTTCATATCCTTGATTTTGAGAATTTCCCCTCAAGT 1300
1301 ATGTGGCAGTAAATACAACAAGACACTCTATGTATTAATGTCTCCATTGT 1350
1351 CTTAACCCTGTTCCAAAACAAAATTCACCTCCTTTCTTTATGTGAATGTA 1400
1401 TTCTCCATAAAATTCCAGTATTTAAAAGCAGTTTACTGTTCTGTACTTT  1450
1451 CTGTTGTATCACAATCAGGTAAAAGTCACTTTAAACTGAGGAAACGGCAA 1500
1501 ATTGTGTTTAAAGCTCTTTGTATTTCTCCAGTTTCTGACCTTGTAAATT  1550
1551 TGTATATATGCACTAATAAAGCTTTTTTATAATCCTGAAAAAAAAAAAA  1600
1601 AAAAAAAAAAAAACTCGAGAAGCTTTGGACTTCTTCGCCAGAGGTTTGG  1650
1651 TCAAGTCTCCAATCAAGGTTGTC 1673
```

Figure 13

Clone S3+12 protein sequence (SEQ ID No. 13)

```
  1 EFGTRRRKATEISTAVVQRSATIGSSPVLYSQSAIATGHQAAGIGNQATG  50
 51 IGHQTIPVSLPAAGMGHQARGMSLQSNYLGLAAAPAIMSYAECSVPIGVT 100
101 APSLQPVQARGAVPTATIIEPPPPPPPPPPPPPAPKMPPPEKTKKGRKD  150
151 KAKKSKTKMPSLVKKWQSIQRELDEEDNSSSSEEDRESTAQKRIEEWKQQ 200
201 QLVSGMAERNANFEALPEDWRARLKRRKMAPNT                 233
```

Figure 14

Clone S3+103 DNA sequence (SEQ ID No. 14)

```
  1 GAATTCGGCACGAGGCGGACGTCATTGAGCTGCGACCCTTGTTCAACGCC  50
 51 GTTGGGCAAGCCAGCTGCTGGAGGTGCCGAGAATCTGAGTTTCGGCAAGC 100
101 AGCCAGGTCTGGAAACTAATATTTTAAAAATGACTACACCAAACAAGACA 150
151 CCTCCTGGTGCTGACCCCAAGCAGTTGGAAAGGACTGGAACAGTACGGGA 200
201 AATTGGGTCACAAGCTGTTTGGTCACTCTCATCTTGCAAACCAGGATTTG 250
251 GAGTGGATCAGTTACGAGATGACAATCTAGAAACTTATTGGCAATCAGAT 300
301 GGTTCCCAGCCTCATTTAGTGAACATCCAATTCAGAAGAAAAACAACAGT 350
351 GAAGACATTATGTATTTATGCAGACTACAAATCTGATGAAAGCTATACTC 400
401 CAAGCAAGATCTCAGTCAGAGTAGGAAATAATTTTCACAACCTTCAAGAA 450
451 ATTCGGCAACTTGAGTTGGTGGAACCAAGTGGCTGGATTCATGTTCCCTT 500
501 AACTGACAATCATAAGAAGCCAACTCGTACATTCATGATACAGATTGCTG 550
551 TTCTAGCCAATCACCAGAATGGAAGAGACACCCATATGAGACAAATTAAA 600
601 ATATACACACCAGTAGAAGAGAGCTCCATTGGTAAATTTCCTAGATGTAC 650
651 AACTATAGATTTCATGATGTATCGTTCAATAAGGTGACTTTAAAATGAGA 700
701 CGAAAATCATTAAACGTATCTTTGTTCTTATCCTGTATTTAAATAATATA 750
751 TCATGTACCTTTATTGAACAAGGCATCCGTTATATCTAATTTTGTATATG 800
801 TTTAAAAATATTTTATTGTAACTTTGACAAATAAATTTGGGGTCATATTA 850
851 TCTTTATTTTCTTTAACATGTAATAAGCTCACATATTTTACATTAAAAA  900
901 AAAAAAAAAAAAAAAACTCGAGAAG 926
```

Figure 15

Clone S3+103 protein sequence (SEQ ID No. 15)

```
  1 EFGTRRTSLSCDPCSTPLGKPAAGGAENLSFGKQPGLETNILKMTTPNKT  50
 51 PPGADPKQLERTGTVREIGSQAVWSLSSCKPGFGVDQLRDDNLETYWQSD 100
101 GSQPHLVNIQFRRKTTVKTLCIYADYKSDESYTPSKISVRVGNNFHNLQE 150
151 IRQLELVEPSGWIHVPLTDNHKKPTRTFMIQIAVLANHQNGRDTHMRQIK 200
201 IYTPVEESSIGKFPRCTTIDFMMYRSIR*L*NETKIIKRIFVLILYLNNI 250
251 SCTFIEQGIRYI*FCICLKIFYCNFDK*IWGHIIFIFFNM**SSHILH*K 300
301 KKKKKNSR 308
```

Figure 16

Clone S3+125 DNA sequence (SEQ ID No. 16)

```
  1 CAGGAATCTGTCCGAAGATAATTGAGGCAGAAGAGTCCAGAATGGGCCTC  50
 51 ATCATCGTCAATGCCTGGTACGGGAACTTTGTCAATGACAAGAGCAGGAA 100
101 GAGCGAGAAGGTGAAGGTGATTGACGTGACTGTGCCTGCAGTGCCTGGG 150
151 TAAGGACTCGAAGCTCATCCTCACGAGGCCTCCAAGCTGGGCTGCCTGGC 200
201 TTTTATGACCCGTGTGTGGGGGAAGAGAAGAACCTGAAAGTGCTCTATCA 250
251 GTTCCGGGGCGTCCTGCATCAGGTGATGGTGCTGGACAGTGAGGCCCTCC 300
301 GGATACCAAAGCAGTCCCACAGGATCGATACAGATGGATAAACTGCCAAG 350
351 AACCAGATTTTTAAAAGGCCGCAAAAAATCTTTTCCTGGGAGTCTACAAA 400
401 TTTGGAAATGAAAAAACCCAGACATCAGATGTTTTATTTTATATTATTA 450
451 TTATAGAAGGTGGTACCATTATCAATTATGTGAAGGGACATGCAGACACC 500
501 CCAGCACTGGTATCTGAGTAACGGCTAAGAACCTCCTTCCTCTGGTTTTG 550
551 AAAAGCAGTTCGGGTTGTCCAATTCTGTAACATTCATCTCCATTTTTTAA 600
601 AAAGGTTTCTCTGACGGCCCCACGGCCCGAGCCGCGGTGAGCGTCGTGTT 650
651 GCATGAGCCTGGGCCCCGGGCTTCCCGTGCGCCTCTGCCGCAGGTGCTTC 700
701 TGGGCACCCATCCTCTGCGTTTCATTTGCAGTCGACTGTACAGAAGGCAC 750
751 TCACCACAATAAACCTTTCCTGAAAGCAAAAAAAAAAAAAAAAAACTCG 800
801 AGAAGGTTTGGACTTGTTCGCCAGAGGTTTGGTCAAGTNTCCAA 844
```

Figure 17

Clone S3+125 protein sequence (SEQ ID No. 17)

```
  1 IRHEAAGICPKIIEAEESRMGLIIVNAWYGNFVNDKSRKSEKVKVIDVTV  50
 51 PCSAWVRTRSSSSRGLQAGLPGFYDPCVGEEKNLKVLYQFRGVLHQVMVL 100
101 DSEALRIPKQSHRIDTDG 118
```

Figure 18

Clone S1+30 DNA sequence (SEQ ID No. 18)

```
  1 GAATTCGGCACGAGGCGGACAAAGGGAATCAAAGTTGTGGGAAAATGGAA  50
 51 GGAAGTGAAGATTGACCCAAATATGTTTGCAGATGGACAGATGGATGACT 100
101 TGGTGTGCTTTGAGGAATTGACAGATTACCAGTTGGTCTCCCCTGCCAAG 150
151 AATTCCCTCCAGCTCTCTTCTCAAAGGAAGCACCCAAGAGAAAGGCACAA 200
201 GCTGTTTCAGAAGAAG 216
```

Figure 19

Clone S1+30 protein sequence (SEQ ID No. 19)

```
 1 EFGTRRTKGIKVVGKWKEVKIDPNMFADGQMDDLVCFEELTDYQLVSPAK 50
51 NSLQLSSQRKHPRERHKLFQKK 72
```

Figure 20

Clone S3+14 5' DNA sequence (SEQ ID No. 20)

```
  1 CGATTTCTAGCGTATATGGAGGATCGCAGAAAACAGAAGTGGCAAAGATG  50

51 TAAAAAAATAATAAGGCAGAATTGAACTGTTTGGGAATGGAACCAGTAC  100

101 AGACAGCTAACTCTAGAAATGGGAAAAGGGTCATCACACTGAAACGGTG  150

151 TTCAACCGGGTTTTGCCAGGGCCTATTGCACCAGAGAGCAGCAAGAAGCG  200

201 GCCCGTAGATGCGACCAGACCTTTCTAAGATGATGGCCCTCATGCAGGTG  250

251 GAAGCATCGGT  261
```

Figure 21

Clone S3+14 3' DNA sequence (SEQ ID No. 21)

```
  1 AGAGGCCCTCATGCAGGGTGGAAGCACTGGGTCTCTATCTCTGCATAACA  50
 51 CGTTCCAACACAGCAGTAGTGGCCTACAGTCTGTGTCATCTTTGGGTCAC 100
101 AGCAGTGCCACTTCTGCATCTTTGCCTTTTATGCCATTTGTGATGGGTGG 150
151 TGCACCATCATCCCCTCATGTAGACTCCAGCACCATGCTTCATCACCACC 200
201 ACCACCACCCCACCCCACCATCACCACCATCACCATCCAGGCTTGAGA 250
251 GCCCCTGGCTACCCTCTTCACCAGTGACTACCGCCTCTGGTACTACCTT 300
301 GCGGTTGCCACCACTGCAACCTGAGGAGGATGACGATGAGGATGAAGAAG 350
351 ATGATGATGACTTATCTCAGGGCTATGATAGCTCAGAAAGGGACTTCTCA 400
401 CTCATTGATGATCCTATGATGCCAGCTAACTCAGACTCCAGTGAAGATGC 450
451 TGATGACTGAAGCCCCAGCATGGGCCCCATTGCTTGGGCGGCTGCTGTAT 500
501 TTTCATTTACTCTGGCCCTTGGACTATGGAAACGTGGGAGGGGCAGG    547
```

Figure 22

Clone S3+14 protein sequence (SEQ ID No. 22)

```
  1 EALMQGGSTGSLSLHNTFQHSSSGLQSVSSLGHSSATSASLPFMPFVMGG  50
 51 APSSPHVDSSTMLHHHHHHPHPHHHHHHHPGLRAPGYPSSPVTTASGTTL 100
101 RLPPLQPEEDDDEDEEDDDDLSQGYDSSERDFSLIDDPMMPANSDSSEDA 150
151 DD 152
```

FIGURE 27
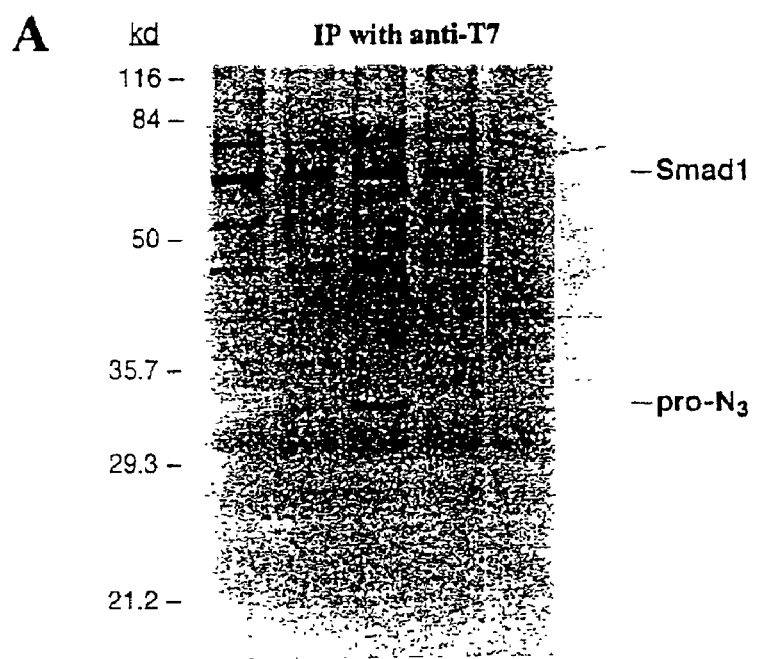
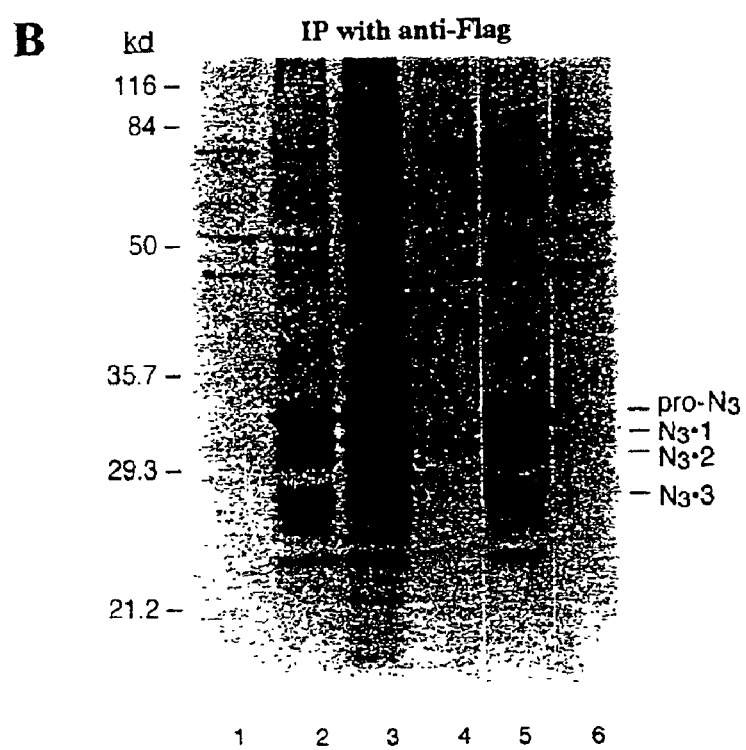

FIGURE 30
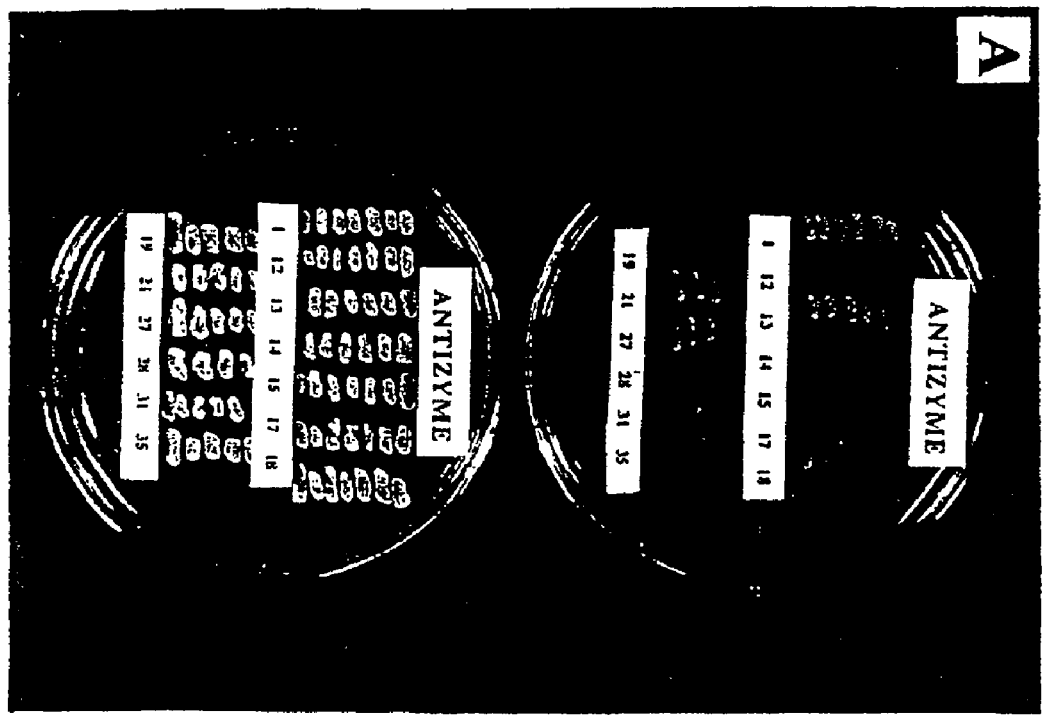
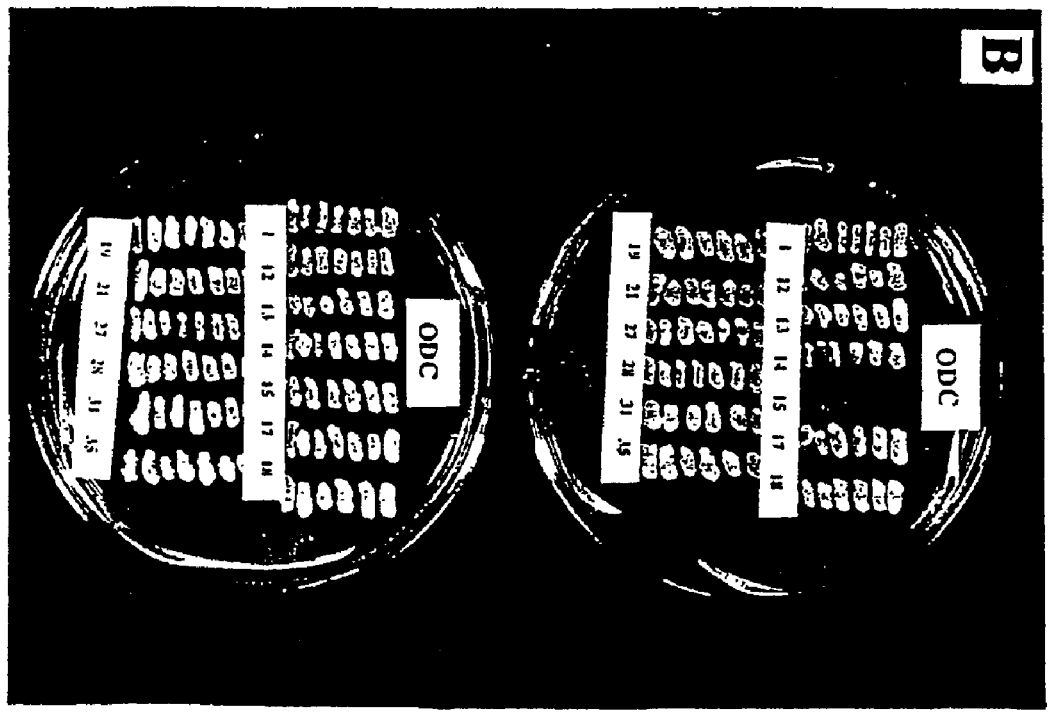

FIGURE 32
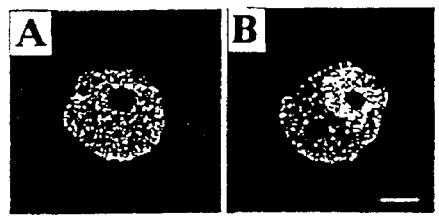
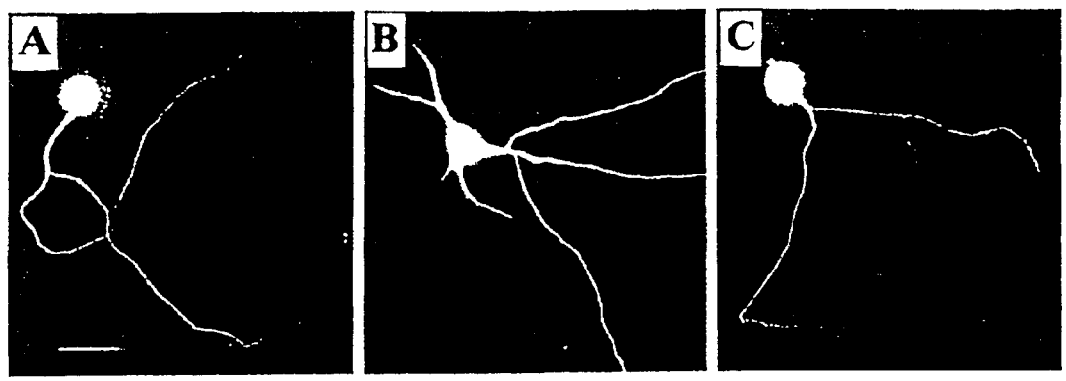
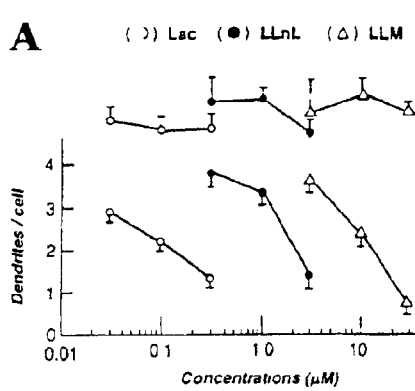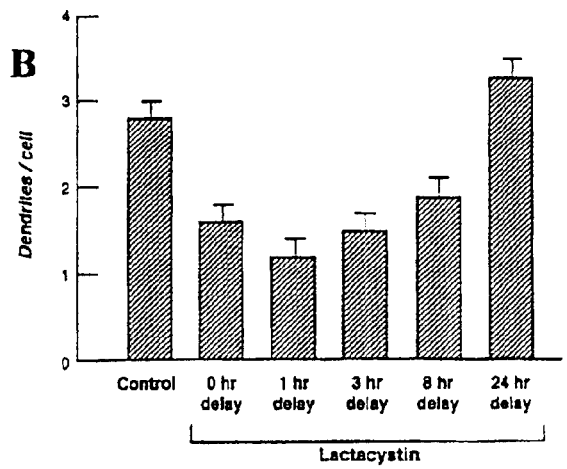

Figure 33

Clone S1+19 cDNA sequence (SEQ ID No. 23)

```
  1 GAGGAGCTCAACTGATCTGTTTTCTTTCGCCCAGCCAAAATCACAGAATG   50
 51 AAGGCGGTGAAGAGCGAACGGGAGCGAGGGAGCCGGCGAAGACACCGGGA  100
101 CGGGGACGTGGTGCTGCCGGCGGGGGTGGTGGTGAAGCAGGAGCGTCTCA  150
151 GCCCAGAAGTCGCACCTCCCGCCCACCGCCGTCCGGACCACTCCGGTGGT  200
201 AGCCCGTCTCCGCCGACCAGCGAGCCGGCCCGCTCGGGCCACCGCGGGAA  250
251 CCGAGCCCGAGGAGTTAGCCGGTCCCCACCCAAAAAGAAAAACAAGGCCT  300
301 CAGGGAGAAGAAGCAAGTCTCCTCGCAGTAAGAGAAACCGAAGTCCTCAC  350
351 CACTCAACAGTCAAAGTGAAGCAGGAGCGTGAGGATCATCCCCGGAGAGG  400
401 ACGGGAGGATCGGCAGCACAGGGAACCATCAGAACAGGAACACAGGAGAG  450
451 CTAGGAACAGTGACCGGGACAGACACCGGGGCCATTCCCACCAAAGGAGA  500
501 ACGTCTAACGAGAGGCCTGGGAGTGGGCAGGGTCAGGGACGGGATCGAGA  550
551 CACTCAGAACCTGCAGGCTCAGGAAGAAGAGCGGGAGTTTTATAATGCCA  600
601 GGCGACGGGAGCATCGCCAGAGGAATGACGTTGGTGGTGGCGGCAGTGAG  650
651 TCTCAGGAGTTGGTTCCTCGGCCTGGTGGCAACAACAAAGAAAAGAGGT   700
701 GCCCGCTAAAGAAAACCAAGCTTTGAACTTTCTGGGGCACTTCTTGAGG   750
751 ACACCAACACTTTCCGGGGTGTAGTCATTAAATATAGTGAGCCCCAGAA   800
801 GCACGTATCCCCAAAAACGGTGGCGTCTCTACCCATTTAAAAATGATGA   850
851 GGTGCTTCCAGTCATGTACATACATCGACAGAGTGCGTACCTACTGGGTC   900
901 GACACCGCCGCATTGCAGACATTCCAATTGATCACCCGTCTTGTTCAAAG   950
951 CAGCATGCGGTCTTTCAATATCGGCTTGTGGAATATACCCGTGCTGATGG  1000
```

```
1001 CACAGTTGGCCGAAGAGTGAAGCCCTACATCATTGACCTTGGCTCAGGCA 1050
1051 ATGGAACCTTCTTAAACAACAAACGTATTGAGCCACAGAGATACTATGAA 1100
1101 CTAAAAGAAAAGGATGTACTCAAATTTGGATTCAGTAGCAGAGAATACGT 1150
1151 CTTGCTCCATGAGTCGTCGGACACTTCTGAAATAGACAGGAAAGATGACG 1200
1201 AGGATGAGGAGGAGGAGGAAGAAGTGTCTGACAGCTAGCAAACTAAGAAC 1250
1251 CCAAACTATTGATACACGGTTTCCTTCTTGGAAGTCTTTGATTGACTCAG 1300
1301 AGAGCACTATGGTGGTGGGTCCAGCACTATGGTGCTCTCTGTAATGCCTC 1350
1351 TTACTGCCTTAAGTCTTTCCTCTGTTGCTGACCAGATTGTGTTACCATTT 1400
1401 GAATACACTGACTAATGTTTGTTAAACTTTTTCTGTGGCACCTTGGCCAC 1450
1451 ATGCCTGCAGGCATTTGTTTTCAGAACAGTCTCACCAATTACAACACACC 1500
1501 GTGTTTTAGTAGAAGTGTTGTGGTTTTAGTTGGTGCTTTCAGAACTGCTG 1550
1551 CCTAGGAAACTATAAACCCTTGGTTAAGGGGAAATCATGGCTTGTTCTCT 1600
1601 TTGTACAGTTACTTTATTTATATAGGTGTTAAGCTTTGTGGACCAGGTGT 1650
1651 TTTTCTTTTGGGGCGAACCCCTGAGCAGAGAATCTTACTAGGCTTTGGTT 1700
1701 ATCACCAAAACAACCTCCAGTATATACCAAAGCTTTGACTTGTTTGAGCT 1750
1751 CTTGAGCTTAGAAGTTGATTTGCACTTATTTTTTGGGGGTGGGAATG 1800
1801 TACTGCAGTCAGTAAACATTATTGACTGTTTAACTTAAACAGATGCTTTA 1850
1851 TGGCACCTGCTCAAGCCCGTGACTGTACAGAAGGATCCTGGTTGCTACCA 1900
1901 GTGGGTGCTGATTCAGCATCACAAGTGACTGAAATTGGCTGTGGATCTGT 1950
1951 TCTTTGTGAAAGAATTCCTGATTTCTCCATGGAGCATGTACAACAATT 2000
2001 TTGATCATATTAACTGTACTTCAGTTTTGCATTTTTATTCAAATGTTATC 2050
2051 TCTTTTTTTCTTTGAGAAATAAACTGTCACTGATGTGACAGCGTTCTTTC 2100
```

```
2101 TTTATTCTAATAACATGTATAGATCTAAAGCAGGTTGTGTTGTTTACATG 2150

2151 TTTCTACACATTTCATCCTTTAAAAAGTTGTTGAGAGAGGTTGTATTTAC 2200

2201 CTTCCCAAGGTTGGAAAGCAGGGGAATTTCCCAGTGTCCTAGTTTTCCAC 2250

2251 CAGAGGAATATGTGTAAGTAGCAAAGTATTTGCTGCTTACATATAGTGTG 2300

2301 TATGTATGTATATATGTAAATTGTGTGTTAAAGAGCTGATACTGATTTTC 2350

2351 ATATGACAATGTTAGGCAAAGGCCTCCCTGCATTTGAAGAGCAGGTTTTC 2400

2401 ATTTATATGTATTTTTGGGATAAAAAATAAATTTGTAAATATAGCCCC 2450

2451 CAAAAAAAAAAAAAAAAAAAAAAAAAAAAAAAAAAAAAAAAAAAA 2496
```

Figure 34

Clone S1+12-2 cDNA sequence (SEQ ID No. 24)

```
  1 CCCACGCGTCCGGCCTCGGAGCAGCCATGATGGAAGGCCTGGACGACGGC  50
 51 CCGGACTTCCTCTCAGAAGAGGACCGCGGACTTAAAGCAATAAATGTAGA 100
101 TCTTCAAAGTGATGCTGCTCTGCAGGTGGACATTTCTGATGCTCTTAGTG 150
151 AGCGGGATAAAGTAAAATTCACTGTTCACACAAGAGTTCATTGCCAAAT 200
201 TTAAACAAAACGAGTTTTCAGTTGTTCGGCAACATGAGGAATTTATCTG 250
251 GCTTCATGATTCCTTTGTTGAAAATGAAGACTATGCAGGTTATATCATTC 300
301 CACCAGCACCACCAAGACCTGATTTTGATGCTTCAAGGGAAAAACTACAG 350
351 AAGCTTGGTGAAGGAGAAGGGTCAATGACGAAGGAAGAATTCACAAAGAT 400
401 GAAACAGGAACTGGAAGCTGAATATTTGGCAATATTCAAGAAGACAGTTG 450
451 CGATGCATGAAGTGTTCCTGTGTCGTGTGGCAGCACATCCTATTTTGAGA 500
501 AGAGATTTAAATTTCCATGTCTTCTTGGAATATAATCAAGATTTGAGTGT 550
551 GCGAGGAAAAAATAAAAAGAGAAACTTGAAGACTTCTTTAAAAACATGG 600
601 TTAAATCAGCAGATGGAGTAATCGTTTCAGGAGTAAAGGATGTAGATGAT 650
651 TTCTTTGAGCACGAACGAACATTTCTTTTGGAGTATCATAACCGAGTTAA 700
701 GGATGCATCTGCTAAATCTGATAGAATGACAAGATCCCACAAAAGTGCTG 750
751 CAGATGATTACAATAGAATTGGTTCTTCATTATATGCTTTAGGAACTCAG 800
801 GATTCTACAGATATATGCAAGTTTTTTCTCAAAGTTTCAGAACTGTTCGA 850
851 TAAAACAAGAAAAATAGAAGCACGAGTGTCTGCTGATGAAGACCTCAAAC 900
901 TTTCTGATCTTTTAAAATATTACTTAAGAGAATCTCAAGCTGCTAAGGAT 950
951 CTCCTGTATCGAAGGTCTAGGTCACTAGTGGATTATGAAAATGCTAATAA 1000
```

```
1001 AGCACTGGATAAAGCAAGAGCAAAAAATAAAGATGTTCTACAGGCCGAAA 1050

1051 CTTCCCAACAATTATGTTGTCAGAAATTTGAAAAAATATCTGAGTCTGCA 1100

1101 AAACAAGAACTTATAGATTTTAAGACAAGAAGAGTTGCTGCATTCAGAAA 1150

1151 AAATTTAGTGGAACTGGCAGAGTTAGAACTGAAGCATGCAAAGGGTAATC 1200

1201 TACAGTTGCTGCAGAACTGCCTGGCAGTGTTAAATGGAGACACATAAGCC 1250

1251 ACACTCCGCCTTCCTGTTAAAAGGGCTGCCTTCCTTCAAATTTTATTTT 1300

1301 TGTTTTCTTAATGATGTTAAGCATTTATGCTCACTGGAAACAAACAAAAA 1350

1351 GCAGCTGAAAAAGTGCATCAACTCCTCTTTTTCTGAGAAACATGGAGCAG 1400

1401 CGCACGCCCAGGCGATGCCAGTCTGTGTGCCGTGATGCCGCACTGTGTTC 1450

1451 CCCATGACAGTGGTCCATCATCGTGCACTCGTCATACTCAGAAGTCCAAA 1500

1501 GTTCATTCTTCTTTAAAGTAGCCTCTATAACTCTGTTTATTTTATAAATA 1550

1551 GTATTCCTTATGGCTGCCACTCTTATTTACCTTTAAATAATTTCTGAAAT 1600

1601 TTAACCTTTTCAGAATGCATTGTTGAAACAAGATAAAGATTGCCTTTTTT 1650

1651 GAATTTTTAAATTTTGTTTTTAAAAGCATATACCACCTTAGTTCATTCA 1700

1701 TGTATCCTGGTAAAGCATCTTAATCAGACTTATTTTAATTACTGAATAT 1750

1751 TTCTTAGACGTTTTGGGACAGATTTTATGTAATCTTTATAAGTATGATTT 1800

1801 CTGAAGAAAGCAAATGCATTAGTATGTTTGCCTTAAACTTGTAGACTAA 1850

1851 ACCAAGTATTGTAAAATAAACAGCGATAACAGTGATAGTTTTTAACTCTA 1900

1901 TGGTCATTGTATCACTCTGGAAATGTGGAGTAGCTGTAATAAATCTACT 1950

1951 CCTGTATTATGCTTT 1965
```

Figure 35

Clone S1+12-5 cDNA sequence (SEQ ID No. 25)

```
  1 GCGGCGCCGAGTCCCGGGAGCGCGGTGGGGGCAGCGGGCGCGGGGCGGGC  50
 51 GCGGGGACCGCGCCAGCCTGTCACTAATGTCTCCCTTTGTGTCTCCCCCA 100
101 TCTCATCCTTTTCCCCGGCGCGCCGTGCCCGCCGACCCCACAGGAAGGCC 150
151 TGGACGACGGCCCGGACTTCCTCTCAGAAGAGGACCGCGGACTTAAAGCA 200
201 ATAAATGTAGATCTTCAAAGTGATGCTGCTCTGCAGGTGGACATTTCTGA 250
251 TGCTCTTAGTGAGCGGGATAAAGTAAAATTCACTGTTCACACAAAGAGTT 300
301 CATTGCCAAATTTTAAACAAAACGAGTTTTCAGTTGTTCGGCAACATGAG 350
351 GAATTTATCTGGCTTCATGATTCCTTTGTTGAAAATGAAGACTATGCAGG 400
401 TTATATCATTCCACCAGCACCACCAAGACCTGATTTTGATGCTTCAAGGG 450
451 AAAAACTACAGAAGCTTGGTGAAGGAGAAGGGTCAATGACGAAGGAAGAA 500
501 TTCACAAAGATGAAACAGGAACTGGAAGCGGGTTGGATAACAGAGAACCT 550
551 TGGGTTTATTCTACTGCTACCTCCATCCTCTGCATCCTTCTTTTTTGTCT 600
601 TCACTGAATGACTACCCTCACAGAGATCAAACTTCTCCATCATTGGTCC 650
651 TGCTGGTTTGCTGTGAATATTTGGCAATATTCAAGAAGACAGTTGCGATG 700
701 CATGAAGTGTTCCTGTGTCGTGTGGCAGCACATCCTATTTTGAGAAGAGA 750
751 TTTAAATTTCCATGTCTTCTTGGAATATAATCAAGATTTGAGTGTGCGAG 800
801 GAAAAAATAAAAAGAGAAACTTGAAGACTTCTTTAAAAACATGGTTAAA 850
851 TCAGCAGATGGAGTAATCGTTTCAGGAGTAAAGGATGTAGATGATTTCTT 900
901 TGAGCACGAACGAACATTTCTTTTGGAGTATCATAACCGAGTTAAGGATG 950
951 CATCTGCTAAATCTGATAGAATGACAAGATCCCACAAAAGTGCTGCAGAT 1000
```

```
1001 GATTACAATAGAATTGGTTCTTCATTATATGCTTTAGGAACTCAGGATTC 1050

1051 TACAGATATATGCAAGTTTTTCTCAAAGTTTCAGAACTGTTCGATAAAA 1100

1151 CAAGAAAATAGAAGCACGAGTGTCTGCTGATGAAGACCTCAAACTTTCT 1150

1201 GATCTTTTAAAATATTACTTAAGAGAATCTCAAGCTGCTAAGGATCTCCT 1200

1251 GTATCGAAGGTCTAGGTCACTAGTGGATTATGAAAATGCTAATAAAGCAC 1250

1301 TGGATAAAGCAAGAGCAAAAATAAGATGTTCTACAGGCCGAAACTTCC 1300

1351 CAACAATTATGTTGTCAGAAATTTGAAAAATATCTGAGTCTGCAAAACA 1350

1401 AGAACTTATAGATTTTAAGACAAGAAGAGTTGCTGCATTCAGAAAAATT 1400

1451 TAGTGGAACTGGCAGAGTTAGAACTGAAGCATGCAAAGGGTAATCTACAG 1450

1501 TTGCTGCAGAACTGCCTGGCAGTGTTAAATGGAGACACATAAGCCACACT 1500

1551 CCGCCTTCCTGTTAAAAGGGCTGCCTTCCTTCAAATTTTATTTTTGTTT 1550

1601 TCTTAATGATGTTAAGCATTTATGCTCACTGGAAACAAACAAAAAGCAGC 1600

1651 TGAAAAAGTGCATCAACTCCTCTTTTCTGAGAAACATGGAGCAGCGCAC 1650

1701 GCCCAGGCGATGCCAGTCTGTGTGCCGTGATGCCGCACTGTGTTCCCCAT 1700

1751 GACAGTGGTCCATCATCGTGCACTCGTCATACTCAGAAGTCCAAAGTTCA 1750

1801 TTCTTCTTTAAAGTAGCCTCTATAACTCTGTTTATTTTATAAATAGTATT 1800

1851 CCTTATGGCTGCCACTCTTATTTACCTTTAAATAATTTCTGAAATTTAAC 1850

1901 CTTTTCAGAATGCATTGTTGAAACAAGATAAAGATTGCCTTTTTTGAATT 1900

1951 TTTTAAATTTTGTTTTTAAAAGCATATACCACCTTAGTTCATTCATGTAT 2000

2001 CCTGGTAAAGCATCTTAATCAGACTTATTTTAATTACTGAATATTTCTT 2050

2151 AGACGTTTTGGGACAGATTTTATGTAATCTTTATAAGTATGATTTCTGAA 2100

3001 GAAAAGCAAATGCATTAGTATGTTTGCCTTAAACTTGTAGACTAAACCAA 2150
```

```
3151 GTATTGTAAAATAAACAGCGATAACAGTGATAGTTTTTAACTCTATGGTC 2200

3201 ATTGTATCACTCTGGAAAATGTGGAGTAGCTGTAATAAATCTAATCCTGT 2250

3251 ATTATGCTTTAAAAAAAAAAAAAAAAAAAAAAAAAAAAAAAAAAAAAAAA 2300

3301 AAAAAAAAAAAAAAAAAA 3319
```

Figure 36 clone S1+27 cDNA sequence (SEQ ID No. 26)

```
  1 GTCGACCCACGCGTCCGGCGGGCCGTGGGAGGGTCCCGAGGTGGGGGTCG   50
 51 GGGCGGGATGGCTGCAGCGGCGGCCGGGGCCGGGAGCGGGCCCTGGGCGG  100
101 CCCAGGAGAAGCAGTTCCCGCCGGCGCTGCTGAGTTTCTTCATCTACAAC  150
151 CCGCGCTTCGGGCCGCGCGAAGGACAGGAGGAAAATAAGATTTTATTTTA  200
201 TCATCCAAATGAGGTAGAAAAGAATGAGAAGATTAGAAATGTCGGATTGT  250
251 GTGAAGCTATTGTACAGTTTACAAGGACATTTAGCCCATCAAAACCTGCA  300
301 AAATCTTTACATACACAGAAGAACAGACAGTTCTTCAATGAACCAGAAGA  350
351 AAATTCTGGATGGTCATGGTTGTTCGGAATCCTATAATTGAAAAACAGA   400
401 GTAAAGATGGAAAACCAGTTATTGAATATCAAGAGGAGGAGTTGTTGGAC  450
451 AAGGTTTATAGCTCGGTGCTGCGGCAGTGCTACAGCATGTACAAGCTTTT  500
501 TAATGGTACATTTCTGAAAGCCATGGAAGACGGAGGCGTCAAGCTTCTGA  550
551 AAGAAAAATTAGAGAAATTCTTCCATCGGTATTTGCAAACGCTACATTTG  600
601 CAGTCATGTGACCTACTTGACATTTTTGGTGGAATCAGCTTCTTCCCGTT  650
651 GGATAAAATGACTTATTTGAAAATCCAGTCCTTTATTAATAAGAATGGAG  700
701 GAAAGCCTGAATATAGTCAAATACACTGCTTTTCTCTATAACGATCAGCT  750
751 CATCTGGAGTGGATTAGAACAAGATGACATGAGAATTTTATACAAATACC  800
801 TTACCACCTCCCTTTTCCCAAGGCACATCGAACCTGAGTTAGCAGGAAGG  850
851 GATTCTCCAATAAGAGCAGAAATGCCAGGAAATCTTCAACACTATGGAAG  900
901 ATTTCTTACCGGACCCTTGAACCTCAATGATCCAGATGCAAAATGCAGAT  950
951 TCCCCAAAATTTTTGTAAATACAGATGACACTTATGAAGAGCTCCATTTA 1000
```

```
1001 ATCGTTTATAAGGCCATGAGTGCGGCTGTGTGCTTTATGATCGACGCCTC 1050
1051 TGTCCACCCAACGTTGGATTTTGCCGAAGACTGGACAGCATCGTTGGGC 1100
1101 CCCAGCTCACAGTGCTGGCCTCTGACATCTGTGAACAGTTTAACATCAAC 1150
1151 AAGAGGATGTCCGGGTCTGAGAAGAACCCCAGTTTAAGTTTATCTACTT 1200
1201 CAACCACATGAATCTCGCCGAGAAGAGCACAGTTCACATGAGGAAAACGC 1250
1251 CCAGCGTGTCGCTCACTTCCGTGCACCCGGATTTAATGAAGATTCTCGGT 1300
1301 GACATCAACAGTGACTTTACCAGAGTGGATGAAGATGAGGAGATCATTGT 1350
1351 GAAGGCCATGAGTGATTACTGGGTTGTTGGAAGAAGTCTGATCGGCGGG 1400
1401 AGCTCTATGTTATTTTGAATCAAAAAAATGCAAACCTGATTGAAGTAAAT 1450
1451 GAGGTCAAGAAACTTTGTGCAACGCAGTTCAACAACATCTTCTTCTTGGA 1500
1501 TTGACGGATGACGGCTCACTGAGAGCATATCTAAAAAACACTCTGCAAAC 1550
1551 ATTTGGTCACATGCAAGTTAGTGGTCATATGACGGACTGCATTCAGGACA 1600
1601 AGGGTAAAGCAATACTTGCTTTGAAGAATCACATTTCGACTCGGTCTGCT 1650
1651 GATCTGAGGTTTTTAGATTTTAAATATTTATGTGGAATTAATTAAAGGTA 1700
1701 GTTGGCTATATCGCTATCATTTCATTCTTTTGACATTATGTGAATATTTT 1750
1751 ACTGGAAAATAAGACTAATAAATTGTTAAAAGTTTTTAAAAAAAAAAAA 1800
1801 AAAAAAAAAAAAAAAAAAAAAAAAAAGGGCGGCC 1834
```

Figure 37 clone S1+28 cDNA sequence (SEQ ID No. 27)

```
  1 GTTTGCAGTTGATGCTAAGGCCTTGCCTCAGAATAAGCCAAGGCCTCTCA  50
 51 CTCAAGAAGAAATTGCTCAGAGACGTGAGCGTGCAAGACAAAGGCATGCA 100
101 GAGAAGCTTGCAGCAGCACAGGGACAGGCACCCTTGGAGCCCACCCAAGA 150
151 TGGGAGTGCCATTGAAACATGTCCAAAGGAGACGAGCCAAGAGGTGACG 200
201 AGCAACAGGTGGAAAGTATGACCCCTAAACCTGTGCTCCAGGAAGAAAAC 250
251 AACCAAGAGTCTTTTATTGCATTTGCTCGGGTGTTCAGTGGTGTGGCTCG 300
301 AAGAGGAAAGAAAATTTTTGTCTTGGGGCCCAAATACAGTCCTCTTGAGT 350
351 TTTTACGAAGGGTACCATTATGCTTCTCAGCTCCACCAGATGGCCTCCCC 400
401 CAAGTCCCCCACATGGCATACTGTGCTCTGGAAAACCTGTATCTTCTGAT 450
451 GGGAAGGGAACTGGAATATCTAGAGGAGGTACCTCCAGGAAATGTGCTAG 500
501 GAATAGGAGGCCTTCAAGATTTTGTGCTGAAATCTGCAACACTGTGTAGC 550
551 CTGCCATCCTGCCCACCATTTATACCACTCAACTTCGAAGCCACTCCTAT 600
601 TGTGAGAGTTGCTGTTGAACCAAAACATCCAAGTGAAATGCCTCAGCTCG 650
651 TAAAAGGAATGAAACTGTTAAACCAGGCTGATCCCTGTGTCCAGATTTTA 700
701 ATTCAGGAAACGGGAGAGCACGTTTTAGTCACAGCAGGAGAAGTCCACCT 750
751 TCAGCGATGCCTGGATGACTTAAAAGAAAGGTTTGCAAAGATTCATATCA 800
801 GTGTATCTGAACCTATTATTCCATTCAGAGAAACAATCACAAAACCCCCA 850
851 AAAGTTGACATGGTCAATGAAGAAATAGGCAAACAGCAAAAGTTGCAGT 900
901 CATACACCAAATGAAAGAAGATCAAAGCAAAATCCCTGAAGGAATCCAAG 950
951 TTGACTCTGACGGGCTAATCACCATAACAACTCCCAATAAACTTGCCACG 1000
```

```
1001 CTCAGTGTTCGAGCCATGCCCCTTCCAGAAGAAGTCACCCAGATTCTGGA 1050

1051 AGAAAATAGTGATTTGATTCGTTCTATGGAGCAGTTGACATCCTCTTTGA 1100

1101 ATGAGGGTGAAAATACTCACATGATTCATCAGAAGACCCAAGAGAAAATT 1150

1151 TGGGAATTCAAAGGAAAACTGGAGCAACACCTAACAGGGAGAAGATGGAG 1200

1201 GAACATTGTTGACCAAATCTGGTCATTTGGCCCAAGAAAATGTGGGCCCA 1250

1251 ACATACTAGTCAATAAAGTGAAGATTTTCAGAACTCAGTATGGACAGGT 1300

1301 CCAGCTGACAAAGCTTCAAAAGAAGCCAGTAGATACCGAGATTTGGGCAA 1350

1351 TAGCATTGTGAGTGGCTTCCAACTAGCAACCCTCTCTGGCCCCATGTGTG 1400

1401 AGGAGCCTCTCATGGGTGTCTGTTTTGTTCTGGAAAAATGGGACCTAAGT 1450

1451 AAATTTGAGGAACAAGGAGCAAGTGATCTGGCAAAAGAGGACAGGAGGAA 1500

1501 AATGAAACCTGTTCTGGTGGAAATGAAAACCAAGAGCTACAAGATGGCTG 1550

1551 CTCTGAGGCCTTTGAGAAGAGGACATCACAGAAAGGAGAATCTCCACTCA 1600

1601 CTGACTGCTATGGACCTTTCTCAGGACAGCTAATTGCCACCATGAAAGAA 1650

1651 GCATGTCGCTATGCACTGCAAGTGAAACCTCAGCGCCTGATGGCAGCTAT 1700

1701 GTACACATGTGACATCATGGCCACTGGTGATGTTCTCGGTCGAGTCTATG 1750

1751 CTGTCTTGTCAAAGAGAAGGTCGGGTACTTCAAGAAGAAATGAAAGAA 1800

1801 GGGACAGACATGTTCATCATCAAGGCTGTGCTGCCTGTTGCTGAAAGCTT 1850

1851 TGGTTTTGCTGATGAAATCAGGAAGAGGACAAGTGGCCTGGCCAGCCCAC 1900

1901 AACTAGTATTCAGCCATTGGGAGATCATTCCCAGTGACCCTTCTGGGTGC 1950

1951 CAACTACTGAGGAGGAATACTTGCACTTTGGGGAGAAGGCTGACTCTGAG 2000

2001 AACCAAGCCCGGAAGTACATGAACGCAGTACGAAAGCGGAAGGGGCTTTA 2050

2051 TGTGGAAGAAAGATTGTGGAGCATGCAGAAAAGCAGAGGACACTCAGCA 2100
```

```
2101 AAAATAAGTAGCTACCTACTACTGGTGGATTCTTTTCCTTATAGTGAATT 2150

2201 TAAAAGTATCATCAAGGGTTTAATATTGGGAAAATTTCTTTTTGCCACAT 2250

2251 TATCTCTGTTTATTCACTTTCAATAAAGTTGATCCATATAAATATTTTAA 2300

2301 AGAGGATGTTAAAAAAAAAAAAAAAA 2327
```

ANTIBODY TO SNIP1

This invention is a Continuation-in-Part of PCT/US00/03561, filed on Feb. 11, 2000 and claims priority to U.S. Provisional Ser. No. 60/119,786, filed Feb. 11, 1999.

FIELD OF THE INVENTION

The invention relates in general to the screening of candidate pharmacological compositions and to disease treatment.

BACKGROUND OF THE INVENTION

TGFβ Family

TGFβ1 is the prototypical member of a family of cytokines important in the regulation of phenomena including cell growth, differentiation, apoptosis and morphogenesis in species from insects to mammals. Members of the TGFβ family, include the TGFβs, Activin, Bone Morphogenetic Proteins (BMP's) and Mullerian Inhibitory Substance. These cytokines share structural characteristics, usually occur as disulfide-linked homodimers, and signal via structurally similar plasma membrane receptors (reviewed in Massagué et al., 1997, *Trends Cell Biol.*, 7: 187–192). TGFβ family receptors are distinct from most known plasma membrane receptor kinases in that they are serine/threonine kinases. Based on sequence similarities, the TGFβ family receptors fall into two categories, termed type I and type II, are functionally different. Type I receptors are distinguished from type II receptors by inclusion of a conserved region termed a GS domain, located in the juxtamembrane intracellular region, which is rich in glycine and serine residues. Both type I and type II receptors are necessary for signaling (reviewed in Heldin, 1997, *Nature*,390: 465–471). Each receptor type exists in the plasma membrane in an oligomeric form (Henis et al., 1994, *J. Cell Biol.*, 126: 139–154; Chen & Derynck, 1994, *J. Biol. Chem.* 269: 22868–22874).

Ligand binding to the type II receptor activates the receptor kinase activity (Wrana et al., 1994, *Nature*, 370: 341–347). The activated receptor-ligand complex then recruits the type I receptor, activating it by phosphorylation of the GS domain (Wrana et al., 1994, supra; Weiser et al., 1995, *EMBO J.* 14: 2199–2208). The ligand-bound, active receptor complex is thought to be a heterotetramer, containing taco type II and two type I receptor molecules (Yamashita et al., 1994, *J. Biol. Chem.*, 269: 20172–20178). Overexpression and mutagenesis studies have indicated that the type I receptor acts downstream of the type II receptor. Thus, the identity of the type I receptor determines the specificity of the signals generated (Carcamo et al., 1994, *Mol. Cell. Biol.*, 14: 3810–3821).

Smads

Until recently, little was known of the signaling mechanisms and intracellular effector proteins mediating the complex responses following TGFβ family receptor activation. This changed with the discovery of Mad, a *Drosphila* protein which suppressed a mutation in the BMP2/BMP4 homolog Decapentaplegic (Sekelsky et al., 1995, *Genetics*, 139: 1347–1358). Mad was found to act downstream of the *Drosophila* type I receptor, Thick veins (Wiersdorff et al., 1996,*Development*, 122: 2153–2162). Similarly, C. Elegans proteins termed Sma2, Sma3 and Sma4 were found to act downstream of, and to be required for, signaling through the BMP2/BMP4 homolog Daf4. Sma2, Sma3 and Sma4 are structurally related to each other and to Mad (Savage et al., 1996, *Proc. Natl. Acad. Sci. USA*, 93: 790–794). A family of at least nine factors, termed Smads, have been identified from Xenopus to man and shown to be components of the signaling pathway downstream of TGFβ receptors.

Smads are of a relative molecular weight of 42 to 60 kD, and bear two regions of homology, termed MH1 and MH2, located at the amino and carboxy-terminal ends of the molecule, respectively. A proline-rich linker separates MH1 and MH2 (Heldin et al., 1997, supra). Different members of the Smad family have different roles in signaling. Smad1, Smad2, Smad3, Smad5 and possibly Smad8 are activated by specific type I receptors. They are thus referred to as ligand-responsive, or pathway restricted Smads. For example, Smad1, Smad5 and possibly Smad9 function downstream of BMP type I receptors, while Smad2 and Smad3 are activated by TGFβ and Activin type I receptors (Hoodless et al., 1996, *Cell*, 85: 489–500; Graf et al, 1996, *Cell*, 85: 479–487; Thomsen et al, 1996, *Development*, 122: 2359–2366; Yamamoto et al., 1997, *Biochem. Biophys. Res. Commun.*, 238: 574–580; Baker & Harland, 1996, *Genes Dev.*, 10: 1880–1889; Eppert et al., 1996, *Cell*, 86: 543–552; Lechleider et al., 1996, *J. Biol. Chem.*, 271: 17617–17620; Yingling et al., 1996, *Proc. Natl. Acad. Sci. USA*, 93: 8490–8944; Zhang et al., 1996, *Nature*, 383: 168–172; Nakao et al., 1997, *EMBO J.*, 16: 5353–5362). In contrast to the pathway restricted Smads, Smad4, also known as DPC4, functions as a common signaling partner, interacting with all ligand-responsive Smads. Following activation by type I receptors, pathway restricted Smads, cytoplasmically located in their non-activated state, rapidly translocate to the nucleus. This nuclear localization is mediated by association of pathway restricted Smads with the common mediator Smad4 (Zhang et al., 1996, supra; Kretzschmar et al., 1997, *Genes Dev.*, 11: 984–995; Lagna, et al., 1996, *Nature*, 383: 832–836; Wu et al., 1997, *Mol. Cell. Biol.*, 17: 2521–2528).

The actual mechanism of activation of pathway restricted Smads is thought to involve direct phosphorylation of the three most C-terminal serine residues in a Ser-Ser-X-Ser motif, located near the C terminus of the MH2 region, by activated type I receptors (Kretzschmar et al., 1997, supra; Marcias-Silva et al., 1996, *Cell*, 87: 1215–1224; Souchelnytskyi et al., 1997, *J. Biol Chem.*, 272: 28107–28115; Abdollah et al., 1997, *J. Biol. Chem.*, 272: 27678–27685). Following phosphorylation of MH2, the pathway restricted Smads form heteromeric complexes with Smad4.

There is evidence that MH1 and MH2 interact when Smads are in the inactive state. It is thought that MH2 phosphorylation by type I receptors may destabilize the intramolecular interaction of MH1 and MH2, thereby allowing Smad 4 to interact with the MH2 domains of ligand responsive Smads (Souchelnytskyi et al., 1997, supra; Hata et al., 1997, *Nature*, 388: 82–87). This implies that MH1 is an inhibitory domain, an implication supported by the identification of MH1 mutations in Smad2 and Smad4 in certain tumors which result in strengthened affinity of the MH1 domain for the corresponding MH2 domain (Eppert et al., 1996, supra; Schutte, 1996, *Cancer Res.*, 56: 2527–2530; Hata et al., 1997, supra).

In addition to its likely role in regulating Smad4 interaction, the MH2 region of pathway restricted Smads may serve as an effector domain in signal transduction. This is suggested by the ability of MH2 to transactivate a transcriptional response when fused to the yeast Gal4 DNA binding domain (Liu, 1996, *Nature*, 381: 620–623), and by the finding that an isolated MH2 domain derived from Smad2 supports a full range of Activin responses (Baker & Harland, 1996, supra). In Smad4, however, a portion of the linker between MH1 and MH2, not conserved to other Smads, is required for signaling in addition to MH2

(deCaestecker et al., 1997, *J. Biol. Chem.*, 272: 13690–13696).

The nuclear translocation of the pathway-restricted Smad:Smad4 complexes, and the ability of some Smads to associate with DNA-binding factors or to directly bind to specific DNA sequences suggest Smads may have transcriptional regulatory functions (Chen et al., 1996, *Proc. Natl. Acad. Sci. USA*, 93: 12992–12997; Chen et al., 1997, *Nature*, 389: 85–89; Liu et al., 1996, supra; Kim et al., 1997, *Nature*, 388: 304–308; Yingling et al., 1997, *Mol. Cell. Biol.*, 17: 7019–7028; Dennler et al., 1998, *EMBO J.*, 17: 3091–3100; Zawel et al., 1998, *Mol. Cell*, 1: 611–617). However, it is not clear how Smads regulate transcription or whether Smads also have other nuclear functions.

Proteasome-mediated Protein Degradation Pathway

It has been demonstrated that key events within the cell are regulated by controlled degradation of proteins. In particular, it has been demonstrated that the ubiquitin (Ub)-proteasome pathway plays a critical role in the regulation of processes including the cell cycle, cell metabolism, apoptosis, signal transduction, the immune response, and protein quality control (Reviewed in Coux et al., 1996, *Ann. Rev. Biochem.*, 65: 810–847). In the (Ub)-proteasome pathway, proteins modified by the enzymatic addition of polyubiquitin chains are rapidly and selectively degraded by large proteolytic complexes, termed proteasomes, present in both the nucleus and cytoplasm of all eukaryotic cells.

The primary component of the proteasome protein degradation pathway is the multi-subunit 20S proteasome complex, which has a molecular weight of 700–750 kD and comprises the functional proteolytic activities. Two additional multi-subunit complexes, termed the 19S (or 22S or PA700) and 11S complexes, serve regulatory functions. The overall structure of the 20S core complex is conserved from eubacteria through mammals and consists of a cylinder made up of four stacked rings (Kleinschmidt et al., 1983, *Eur. J. Cell Biol.*, 32: 143–156; Baumeister et al., 1988, *FEBS Lett.*, 241: 239–245). The rings are made up of protein subunits of two classes, termed α and β, each of which has seven sub-classes. The top and bottom rings of the stack are composed of α subunits, and the middle two rings are composed of β subunits. Each ring of the α or β class is itself made up of seven non-identical protein subunits, one from each respective sub-class. A number of subunits representing all sub-classes have been isolated and cloned (Coux et al., 1996, supra). All α subunits are distinguished by a conserved N-terminal motif which is necessary for ring assembly and absent from members of the β class. The α subunits assemble into rings independently, and allow the subsequent assembly of β subunit rings (Zwickl et al., 1994, *Nat. Struct. Biol.*, 1: 765–770). Functionally, the α subunits, being located at the ends of the open cylinder, form a physical barrier preventing access of cytosolic proteins to the proteolytic core of the cylinder. In addition, the α subunits are the sites of binding by the 19S and 11S regulatory complexes. The β subunit rings make up the active proteolytic core of the 20S complex and are characterized by an N-terminal prosequence which is cleaved during assembly to reveal a threonine residue required for catalysis by the active site. The assembled 20S complex has multiple peptidase activities, but requires unfolding of protein substrates and lacks specificity for ubiquitin-modified proteins (Wilk & Orlowski, 1983, *J. Neurochem.*, 40: 842–849; Orlowski, 1990, *Biochemistry*, 29: 10289–10297). Importantly, the identity of the various members of the α and β subunit rings of the 20S core may vary within a given species, among different tissues, and at different stages of development. These differences may have significant physiological impacts (Brown, 1993, *J. Immunol.*, 151: 1193–1204; Akayama, 1994, *FEBS Lett.*, 343: 85–88; Haass, 1989, *Exp. Cell Res.*, 180: 243–252; Ahn, 1991, *J. Biol. Chem.*, 266: 15746–15749; Hong, 1994, *Biochem. Mol. Biol. Int.*, 32: 723–729; Van Kaer, 1994, *Immunity*, 1: 533–541).

Selectivity of the 20S proteasome for ubiquitinated proteins is conferred by the ATP-dependent association of the 20S proteasome with the 19S regulatory complex to form the 26S proteasome, which has a molecular weight of approximately 2000 kD (Yoshimura et al., 1993, *J. Struct. Biol.*, 111: 200–211; Hoffman et al., 1992, *J. Biol. Chem.*, 267: 22362–22368). The 19S complex contains at least 18 subunit proteins, ranging in size from 24 to 105 kD. Together, they confer a means of recognizing ubiquitinated proteins, removing the polyubiquitin chains, increasing the activity of the 20S core, and unfolding and introducing the substrate proteins to the 20S core for degradation. A number of 19S subunits have been isolated and cloned, including at least six that have ATPase activity. The reasons for the existence of so many different ATPase subunits or the specific functions of these and the other, non-ATPase subunits are not well understood (Coux et al., 1996, supra; Tanaka, 1998, *Biochem. Biophys. Res. Commun.*, 247: 537–541).

While most substrates for the proteasome degradation pathway are modified or "tagged" by the addition of ubiquitin chains, this is not necessarily so in all cases. An alternative means of targeting proteins to the 26S proteasome pathway involves the protein antizyme, originally characterized as a naturally-occurring 26.5 kD inhibitor of ornithine decarboxylase (ODC) enzyme activity (Heller et al., 1976, *Proc. Natl. Acad. Sci. USA*, 73: 1858–1862). Antizyme was subsequently shown not only to inhibit ODC activity, but also to target the protein to the 26S proteasome for degradation, independently of ubiquitin (Murakami & Hayashi, 1985, *Biochem. J.*, 226: 893–896; Hayashi & Murakami, 1995, *Biochem. J.*, 306: 1–10). Analogous to the ubiquitin-mediated pathway, antizyme itself is removed and recycled to mediate further targeted degradation (Murakami et al., 1992, *Biochem. J.*, 283: 661–664). Much less is known about the antizyme-dependent versus the ubiquitin-dependent degradation pathway. In particular, it is not known how many proteins other than ODC are degraded in an antizyme-dependent manner. There is a need in the art for fully understanding the signaling mechanism of Smad proteins.

There is also a need in the art for identifying proteins that are binding partners for Smad proteins.

There is also a need in the art for identifying proteasome substrates and understanding how these substrates are targeted to the proteasome.

There is also a need in the art for identifying antizyme substrates.

There is also a need in the art for identifying proteins that are binding partners for proteasome components, including ubiquitin and antizyme.

There is also a need in the art for understanding how ubiquitin and antizyme target proteins for proteasome-mediated degradation.

SUMMARY OF THE INVENTION

The invention encompasses novel polynucleotides and the novel polypeptides encoded by them which are functional binding partners Smads, proteins involved in signaling by TGF-β family member ligands. The invention further encompasses expression vectors comprising the novel polynucleotides and host cells transformed with such expression vectors.

The invention further encompasses antibodies which bind to the novel polypeptides of the invention.

The invention further encompasses compositions comprising Smad1 and an interaction partner protein including, but not limited to HsN3, antizyme, PAG, GST, tumor associated gene, AIP4, U1SnRNP, TRIP4, Ran GTP Binding Protein 5, P0 Acidic Ribosomal Phosphoprotein, β-tubulin, KIAA 00104, and the novel proteins of SEQ ID Nos. 1–3, 7, 11, 13, 15 and 19.

The invention further encompasses the DNA sequences encoding novel Smad1 interactor proteins, represented by SEQ ID Nos. 23–27.

The invention further encompasses compositions comprising Smad2 and an interaction partner including, but not limited to GST, AIP4, TRIP4, KIAA 00104 and the novel proteins of SEQ ID No. 3.

The invention further encompasses compositions comprising Smad3 and an interaction partner protein including, but not limited to HsN3, KIAA 00104, HEF1, FKBP25, AIP4, SnRNP C, RBP2, TRIP4, hnRNP A1, GST and the novel proteins of SEQ ID Nos. 4, 11, 13, 15, 17 and 22.

The invention also encompasses a composition comprising a ternary complex comprising Smad1, HsN3 and antizyme, and a composition comprising a quaternary complex comprising Smad1, Smad4, HsN3 and antizyme. These complexes are also recognized herein as targets for the development of drugs to modify TGF-β superfamily signalling pathway activities.

The invention also encompasses compositions comprising antizyme and HsN3, ubiquitin and HsN3, HEF1 and HsN3, or HEF1 and antizyme. The complexes of these compositions are also recognized herein as targets for the development of drugs to modify TGF-β superfamily signalling pathway activities.

The invention also encompasses a composition comprising the novel Smad-interacting protein SNIP1 and the transcription co-activator CBP/p300; the complex of SNIP1 and CBP/p300 is also a drug target for the modification of TGF-β superfamily signalling pathway activities.

The invention further encompasses the DNA sequences encoding novel Smad3 interactor proteins, represented by SEQ ID Nos. 10, 12, 14, 16, 18, 20 and 21.

The invention further encompasses a method of modulating the biological activity of TGF-β family member ligands comprising administering to a mammal a modulator of proteasome activity.

The invention further encompasses a method of modulating the biological activity of TGF-β family member ligands comprising administering to a mammal a modulator of cellular redox activity.

The invention further encompasses a method of modulating the biological activity of TGF-β family member ligands comprising administering to a mammal a modulator of NF-κB activity.

The invention further encompasses a method to identify a compound which modulates the interaction of a protein with a known interaction partner protein in vitro, such method comprising the steps of contacting a protein comprising a first protein with a protein comprising a known interaction partner of said first protein in the presence and absence of candidate modulator compounds, and detecting the amount of said interaction partner bound to said first protein. In this method, an increase in bound interaction partner indicates the candidate compound is an agonist of the interaction, and a decrease in the bound interaction partner indicates the candidate compound is an antagonist of the interaction.

The invention further encompasses a method to identify a compound which modulates the interaction of a first protein and a known interaction partner of said first protein in yeast cells, such method comprising the steps of: 1) transforming yeast cells with expression constructs comprising: i) a reporter gene functionally linked to a DNA sequence bound by a DNA binding domain of a protein; ii) a gene comprising said first protein fused to the protein DNA binding domain which recognizes the DNA binding sequence of said reporter gene; and iii) a gene comprising said known interaction partner of said first protein fused to a transactivation domain; 2) culturing the transformed yeast cells of 1) in the presence and absence of a candidate modulator compound; and 3) detecting the expression of the reporter gene. In this method, an increase in the expression of the reporter gene indicates the candidate modulator compound is an agonist of the )interaction, whereas a decrease in reporter gene expression indicates the candidate modulator compound is an antagonist of the interaction.

The invention further encompasses a method to identify a compound which modulates the interaction of a first protein and a known interaction partner of said first protein in mammalian cells, such method comprising the steps of: 1) transfecting mammalian cells with expression constructs comprising: i) a reporter gene functionally linked to a DNA sequence bound by a second protein; ii) a gene comprising said first protein fused to a DNA binding domain of said second protein; and iii) a gene comprising said known interaction partner of said first protein fused to a transactivation domain; 2) culturing the transfected mammalian cells of 1) in the presence and absence of a candidate modulator compound; and 3) detecting the expression of the reporter gene. In this method, an increase in the expression of the reporter gene indicates the candidate modulator compound is an agonist of the interaction, whereas a decrease in reporter gene expression indicates the candidate modulator compound is an antagonist of the interaction.

The invention further encompasses a method of modulating the biological activity of TGF-β family member ligands comprising administering to a mammal a modulator of protein:protein interactions, occurring between proteins involved in cell signaling by TGF-β family members, identified using the methods described herein.

The invention further encompasses methods to identify compounds which modulate the interaction of a Smad protein and known interaction partners of Smad proteins. The invention further encompasses a method to identify compounds which modulate the interaction of HsN3 with known functional interaction partners of HsN3. The invention further encompasses a method to identify compounds which modulate the interaction of antizyme with known functional interaction partners of antizyme.

The invention further encompasses methods to identify a compound which modulates the activity of an enzyme involved in cell signaling by TGF-β family member ligands, such methods comprising the steps of expressing the enzyme from a recombinant expression construct and measuring the activity of the recombinant enzyme in the presence and absence of a candidate modulator compound. In such methods, an increase in the activity of the enzyme in the presence of the candidate compound indicates the compound is an agonist of the enzyme, whereas a decrease in the activity indicates the compound is an antagonist of the enzyme. According to the invention, the enzyme may be expressed in a cell free system, or in cultured cells. Also according to the invention, the enzyme may be, but is not limited to GST or a phosphatase.

The invention further encompasses a method for monitoring the proteasome-mediated proteolysis of a protein of interest, such method comprising the steps of contacting an isolated polypeptide comprising a protein of interest with isolated proteasomes and a mammalian cell extract in the presence and absence of a specific inhibitor of the proteasome and detecting the level of the protein of interest. In this method, a decrease in the amount of the protein of interest in the absence, but not in the presence of the specific inhibitor of the proteasome, indicates the protein degradation is proteasome dependent.

The invention further encompasses a method to identify a compound which modulates the proteolysis of a protein of interest comprising the steps of: 1) transforming yeast cells with expression constructs comprising: i) a hybrid protein comprising, from the amino terminus to the carboxyl terminus, a DNA binding domain, a protein of interest and a transactivation domain; and ii) a reporter gene comprising a DNA sequence bound and transactivated, respectively, by the DNA binding domain and transactivation domain of i); 2) culturing the transformed cells in the presence and absence of a candidate modulator compound; and 3) detecting the amount of reporter gene expression. According to this method, a decrease in reporter gene expression indicates the candidate compound is an agonist of proteolysis, and an increase in reporter gene expression indicates the compound is an antagonist of proteolysis.

The invention further encompasses a method to identify a compound which modulates the proteolysis of a protein of interest, such method comprising the steps of: 1) transforming yeast cells with expression constructs comprising: i) a hybrid protein comprising, from the amino terminus to the carboxyl terminus, a DNA binding domain, a protein of interest and a transactivation domain; and ii) a reporter gene comprising a DNA sequence bound and transactivated, respectively, by the DNA binding domain and transactivation domain of i); and iii) a constitutively active mutant of a TGF-β family ligand receptor; 2) culturing the yeast cells in the presence and absence of a candidate modulator compound; and 3) detecting the amount of reporter gene expression. According to this method, an increase in reporter gene expression indicates the compound is an antagonist of proteolysis, and a decrease in reporter gene expression indicates the compound is an agonist of proteolysis.

The invention further encompasses a method of monitoring proteolysis of a protein of interest in mammalian cells, such method comprising the steps of: 1) transfecting mammalian cells with expression constructs comprising: i) a hybrid protein comprising, from the amino terminus to the carboxyl terminus, a DNA binding domain, a protein of interest and a transactivation domain; and ii) a reporter gene comprising a DNA sequence bound and transactivated, respectively, by the DNA binding domain and transactivation domain of i); and 2) detecting the expression of the reporter gene. According to this method, expression of the reporter gene indicates the protein of interest is intact.

The invention further encompasses a method to identify a compound which modulates the proteolysis of a protein of interest in mammalian cells, such method comprising the steps of: 1) transfecting mammalian cells with expression constructs comprising: i) a hybrid protein comprising, from the amino terminus to the carboxyl terminus, a DNA binding domain, a protein of interest and a transactivation domain; and ii) a reporter gene comprising a DNA sequence bound and transactivated, respectively, by the DNA binding domain and transactivation domain of i); 2) culturing the transfected cells in the presence and absence of a candidate modulator compound; and 3) detecting the expression of the reporter gene. According to this method, an increase in the expression of the reporter gene in the presence of the candidate modulator compound indicates the candidate modulator compound is an antagonist of proteolysis, whereas a decrease in the expression of the reporter gene in the presence of the candidate modulator compound indicates the compound is an agonist of proteolysis.

The invention further encompasses a method to identify novel, tissue specific Smad interactors, such method comprising the steps of: 1) transforming yeast cells with expression constructs comprising: i) a hybrid gene comprising the coding sequences for a full length Smad and a DNA binding domain; ii) a cDNA library, derived from a single tissue or cell type, cloned into a vector which fuses the library sequences to a transactivation domain; and iii) a reporter gene, comprising a DNA sequence bound and transactivated, respectively, by the DNA binding domain and transactivation domain of i) and ii), respectively; 2) selecting yeast cell clones which express the reporter gene; 3) probing DNA isolated from such clones with probes specific for all known Smad interactor proteins to identify clones which are novel; and 4) using the sequences of clones identified in step 3 as probes of multi-tissue Northern (RNA) blots to confirm tissue-specific expression of the clones identified in step 3.

The invention further encompasses a method of identifying novel Smad proteins, such method comprising the steps of: 1) transforming yeast cells with expression constructs comprising: i) a hybrid gene comprising the coding sequences for a full length Smad and a DNA binding domain; ii) a cDNA library, cloned into a vector which fuses the library sequences to a transactivation domain; and iii) a reporter gene, comprising a DNA sequence bound and transactivated, respectively by the DNA binding and transactivating domains of i) and ii), respectively; 2) selecting yeast cell clones which express the reporter gene; 3) probing DNA isolated from such clones with nucleic acid probes derived from known Smads under conditions which permit the identification of yeast colonies which contain sequences which hybridize with known Smad sequences; 4) isolating and sequencing the plasmid DNA sequences identified in step 3; and 5) comparing the resulting sequences with known Smad sequences, such that clones with sequences which are not identical to the sequence of any known Smad are identified as novel.

The invention further encompasses the use of proteasome inhibitors, antioxidants and inhibitors of NF-κB activities to treat diseases associated with hyperactivities of TGF-β family ligands or signaling pathways.

The invention further encompasses the use of proteasome activators, inducers of oxidative stress and activators of NF-κB activities to enhance TGF-β responses for therapeutic benefit.

Further features and advantages of the invention will become more fully apparent in the following description of the embodiments and drawings thereof, and from the claims.

BRIEF DESCRIPTION OF DRAWINGS

FIG. 1 shows the protein sequence of clone S1+27 (SEQ ID No. 1).

FIG. 2 shows the protein sequence of clone S1+28 (SEQ ID No. 2).

FIG. 3 shows the protein sequence of clone S1+19 (SEQ ID No. 3).

FIG. 4 shows the protein sequence of the domain of NIPP-1 (SEQ ID No. 4) which is homologous to SNIP-1 (SEQ ID No. 3).

FIG. 5 shows the peptide sequence of the Smad binding domain (SBD, SEQ ID No. 5) of clone S1+19 (SEQ ID No. 3).

FIG. 6 shows the protein sequence of a *C. elegans* clone (SEQ ID No. 6) with homology to S1+9 (SEQ ID No. 3).

FIG. 7 shows the protein sequence of clone S1+12 (SEQ ID No. 7).

FIG. 8 shows the protein sequence of clone S1+12-2 (SEQ ID No.8).

FIG. 9 shows the protein sequence of clone S1+12-5 (SEQ ID No. 9).

FIG. 10 shows the DNA sequence of clone S3+1 (SEQ ID No. 10).

FIG. 11 shows the protein sequence of clone S3+1 (SEQ ID No. 1).

FIG. 12 shows the DNA sequence of clone S3+12 (SEQ ID No. 12).

FIG. 13 shows the protein sequence of clone S3+12 (SEQ ID No. 13).

FIG. 14 shows the DNA sequence of clone S3+103 (SEQ ID No. 14).

FIG. 15 shows the protein sequence of clone S3+103 (SEQ ID No. 15); asterisks indicate stop codons.

FIG. 16 shows the DNA sequence of clone S3+125 (SEQ ID No. 16).

FIG. 17 shows the protein sequence of clone S3+125 (SEQ ID No. 17).

FIG. 18 shows the DNA sequence of clone S1+30 (SEQ ID No. 18).

FIG. 19 shows the protein sequence of clone S1+30 (SEQ ID No. 19).

FIG. 20 shows the 5'DNA sequence of clone S3+14 (SEQ ID No. 20).

FIG. 21 shows the 3'DNA sequence of clone S3+14 (SEQ ID No. 21).

FIG. 22 shows the protein sequence of clone S3+14 (SEQ ID No. 22).

FIG. 27 shows experiments examining the effect of BMP type I receptor activation on Smad1 interaction with HsN3. Panel A shows results of an immunoprecipitation experiment performed using anti-T7 antibodies on COS cell extracts. Panel B shows results of a similar experiment, performed using anti-Flag antibodies.

FIG. 28 shows experiments examining the localization of HsN3 and Smad1. Shown are confocal micrographs of untransfected (Panel A). Smad1 Overexpressing (Panel B), and Smad1 and ALK30233D overexpressing (Panel C) cells. COS cells were transfected with the wild-type BMP type I receptor, ALK3. the BMP type II receptor, and Smad1. Cells were treated with BMP7 (20 ng/ml) for either 30 mins (FIG. 28E). or 60 mins (FIG. 27F). and compared with untreated cells (FIG. 28D). Sub-Panels D1, E1 and F1 show HsN3 localization. Sub-panels D2, E2 and F2 show Smad1 localization, and D3, E3, and F3 show colocalization of HsN3 and Smad1.

FIG. 30 shows experiments examining the interaction of Smad1 interactors with antizyme. Interaction of the thirteen isolated clones with Antizyme (Panel A), and ODC (Panel B) are shown in a yeast two-hybrid assay.

FIG. 32 shows experiments examining the effect of proteasome inhibitors on TFG-β family ligand activity. Top Panels A and B show the translocation of Smad1 from the cytoplasm to the nucleus upon OP-1 treatment of sympathetic neurons. The middle Panels A–C and the lower Panel A show the concentration-dependent inhibition of dendrite formation upon exposure to lactacystin. Lower Panel B shows the the time course of sensitivity to lactacystin with respect to the signaling pathway of OP-1.

FIG. 33 (*a–c*) shows the cDNA sequence of clone S1+19 (SEQ ID No. 23).

FIG. 34 (*a,b*) shows the cDNA sequence of clone S1+12-2 (SEQ ID No. 24).

FIG. 35 (*a–c*) shows the cDNA sequence of clone S1+12-5 (SEQ ID No. 25).

FIG. 36 (*a,b*) shows the cDNA sequence of clone S1+27 (SEQ ID No. 26).

FIG. 37 (*a–c*) shows the cDNA sequence of clone S1+28 (SEQ ID No. 27).

DESCRIPTION OF THE INVENTION

Figure 23:
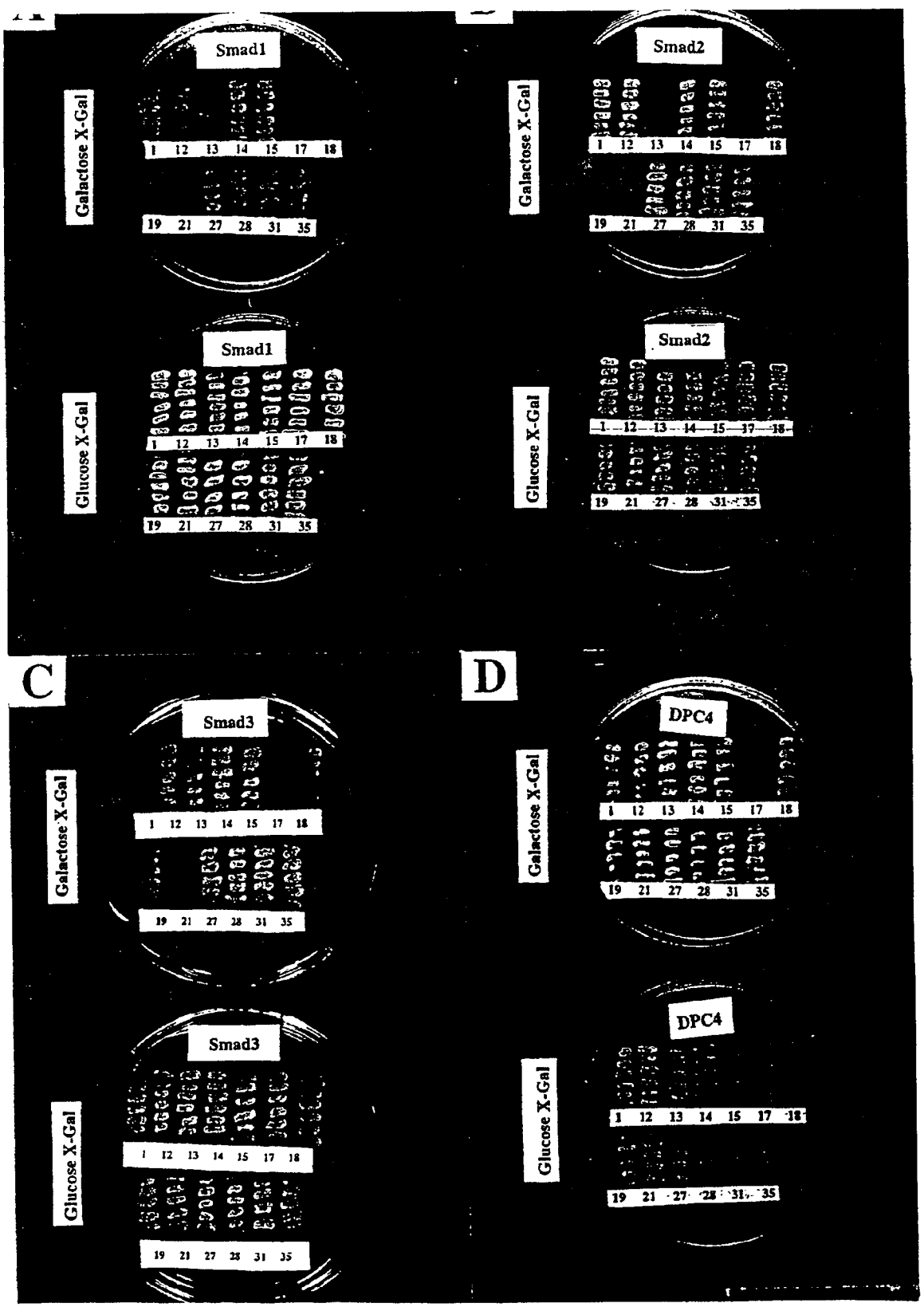
FIG. 23 shows yeast two-hybrid assays to identify Smad interactors. Thirteen cDNAs identified in the screen were tested for interaction with Smad1 (Panel A): Smad2 (Panel B); Smad3 (Panel C); and DPC4 (Panel D).

The invention is based upon the discovery that Smads, proteins involved in the signal transduction pathways controlled by TGF-β family ligands functionally interact with part of the proteasome-dependent protein degradation pathway, and further, that signaling by TGF-β family ligands requires proteasome activity.

The invention is based upon the discovery of binding partners of Smad1, Smad2, Smad3 and Smad4, among which are found proteins involved in the proteasome-mediated degradation system as well as new proteasome substrates.

The invention is also based upon the discovery of binding partners of an integral proteasome component (HsN3).

The invention is also based upon the discovery of many binding partners of a key player of the ubiquitin-independent proteasome pathway (antizyme).

The invention is also based upon the discovery that an isolated Smad protein binds AIP4, a ubiquitin ligase involved in targeting proteins for proteasome mediated degradation.

The invention is also based upon the discovery of binding partners of a novel forkhead protein that is a binding partner of HsN3, antizyme and Smad1 (SNIP-1).

The invention is also based upon the identification of interaction domains on Smad1 that are involved in physical association with its binding partners.

The invention is also based upon the identification of proteasome substrates whose degradation is regulated by TGF-β, BMPs and activin.

The invention is also based upon the identification of domains on Smad1 and Smad3 binding partners that are sufficient for Smad1 or Smad3 binding.

The invention is also based upon the discovery that proteasome inhibitors such as lactacystin, ZLLF and LLnL are able to inhibit the biological activities of BMPs and TGF-beta.

The invention provides targets for the modification (increase or decrease) of the biological activities of all members of the TGF-β superfamily, as well as methods for the identification of compounds which modulate those activities.

Using the discoveries of the invention and methods described herein, one may identify means to modulate TGF-β family activities by focusing on targets including but not limited to the following: 1) the protein-protein interactions discovered; 2) the Smad interacting partners with enzymatic activities (e.g., GST, enolase); 3) the catalytic activities of the integral proteasome component HsN3; 4) the known catalytic activities of the known catalytic subunits of the 20S proteasome; 5) antizyme-mediated proteolysis; 6) the proteolysis of the novel forkhead protein SNIP1 (S1+clone 19); 7) the proteolysis of NIPP-1; 8) the phosphatase activity of PP1; 9) the proteolysis of the novel Smad1 binding partner SIP2 (S1+clone 27); 10) the proteolysis of the Smad3 binding partners RBP2, HEF1, FAST1, FAST2, c-Jun and c-Fos; 11) the proteolysis of the HsN3 binding partners FNTA, FNTB, GGTB, Myc, Mxi1, and Myx; and 12) the proteolysis of Smad1, 2, 3 and 4.

The invention is based on the discovery that the interaction of Smad1 protein and its binding partners with proteins of the proteasome-mediated degradation pathway, including HsN3, antizyme and ubiquitin, has functional relevance in signaling through TGF-β family receptors. The activation of BMP type I receptors stimulates the assembly of a ternary complex comprising Smad1, the proteasome component HsN3, and antizyme. In response to the activation of BMP type I receptors, Smad1, HsN3 and antizyme associate prior to the assembly of HsN3 into the proteasome. The recruitment of Smad1 into the complex mediates the degradation of Smad1 by the proteasome, which degradation can be blocked by inhibiting the assembly of HsN3 into the proteasome (e.g., by overexpression of a dominant-negative assembly-defective pro-sequence-less HsN3 mutant).

The invention is further based upon functional evidence, obtained through comparison of Smad1 degradation in the presence and absence of antizyme that antizyme is involved in positive regulation of Smad1 degradation. Taken together, the evidence upon which the invention is based shows that the BMP type I receptor activation-induced Smad1 degradation involves HsN3 assembly into the proteasome and requires the presence of antizyme.

The invention is further based on the discovery that Smad4 associates with Smad1 in response to BMP type I receptor activation and is also targeted for degradation by the proteasome in a process that further involves HsN3 and antizyme. Smad4 appears to play a positive role in the targeting of Smad1 to the proteasome, through the formation of a complex comprising Smad4, Smad1, HsN3 and antizyme, which complex is formed prior to assembly of HsN3 into the proteasome. The programmed assembly of HsN3 into the proteasome allows HsN3 to bring antizyme and antizyme-bound Smad1, Smad4 and other Smad interactors to the proteasome in a BMP type I receptor-regulated manner in both the nucleus and the cytoplasm.

The invention is further based upon the discovery that the nuclear complex comprising Smad1, Smad4, antizyme, HsN3 also recruits the novel nuclear protein SNIP1 (SEQ ID NO: 3; method of isolation and characteristics described herein below) to bind antizyme, and that such binding targets the SNIP1 protein for proteasomal degradation. The binding of SNIP1 to Smad4 is induced by activation of TGF-β type I receptors, and the degradation of SNIP1 by the proteasome in response to BMP type I receptor activation requires Smad4.

The invention is further based upon the discovery that SNIP1 constitutively interacts with the transcriptional co-activator CBP/p300, which has been previously recognized as a co-factor in Smad-mediated gene activation. Indeed, SNIP1 is a potent repressor of CBP/p300 transcriptional activation activity and inhibits all tested Smad-mediated gene activation. Therefore, the invention is based on the recognition that the complex comprising Smad1, Smad4, HsN3 and antizyme can recruit a nuclear repressor of CBP/p300, SNIP1 to the proteasome for degradation. The invention is therefore based on the recognition that the proteasome-recruitment activity of the Smads may be instrumental in the regulation of gene activity by TGF-β superfamily factors, and, as such, that the interactions involved in the recruitment activity are targets for drug regulation of pathways regulated by TGF-β superfamily factors. It is believed that there exists a novel signaling mechanism wherein Smad1 interacts with both proteasome components and nuclear regulators that are proteasome substrates, and targets these nuclear regulators to the proteasome for antizyme dependent degradation or processing.

Further, it is believed that the functional interaction of Smads with antizyme and HsN3 in the degradation of nuclear or even cytoplasmic interactors is not necessarily unique to Smad1 and Smad4. For example, Smad3 is shown herein to bind antizyme and HsN3 in response to activation of TGF-β signaling pathways. The functional relevance of this is shown herein by the demonstration that the multi-domain adaptor protein HEF1, which is reported to be involved in integrin, T cell receptor, B cell receptor and calcitonin signaling pathways, is recruited to a complex comprising Smad3, the recruitment resulting in TGF-β and activin type I receptor activation-dependent degradation of HEF1. Therefore, the interaction of Smad3 and HEF1 is a potential target for drug modulation of multiple signaling pathways influenced by TGF-β superfamily members.

Definitions

As used herein, "proteasome-mediated degradation pathway" refers to a method of protein proteolysis that requires the presence of proteasomes. Both ubiquitinated and non-ubiquitinated proteins (e.g. ornithine decarboxylase) can be proteolyzed by the proteasome-mediated degradation pathway. As used herein, "proteasome" refers to a eukaryotic ATP-dependent protease, present in two distinct forms with apparent sedimentation coefficients of 20S and 26S in cells. The 26S proteasome is an eukaryotic ATP-dependent, dumbbell shaped protease complex with a molecular mass of approximately 2000 kDa, consisting of a central 20S proteasome, functioning as a catalytic machine, and two large V-shaped terminal modules, having possible regulatory roles, composed of multiple subunits of 25–110 kDa attached to the central portion in opposite orientations. As used herein, "proteasome" additionally refers to the 20S proteasome complexed with various regulatory complexes (such as the 19S or the 11S complexes), to subproteasome complexes with proteolytic activities, or to any other proteasome complex containing HsN3.

As used herein, "anti-oxidant" refers to a compound with anti-oxidant activity including, but not limited to GST, PAG, antizyme, enolase, DPI, PDTC, DFO, vitamin E and glutathione.

As used herein, "cellular redox modulator" refers to a compound which alters the intracellular equilibrium between oxidizing and reducing activities.

As used herein, "modulator of NF-κB activity" refers to a compound which increases or decreases the transactivation activity of one or more NF-κB family member proteins.

As used herein, "proteasome modulator" refers to a compound which alters the activity of the proteasome in a positive or negative manner.

As used herein, "proteasome inhibitor" refers to a compound that decreases the activity of the proteasome, including but not limited to LLnL, LLM, lactacystin, ZLLF and MG132.

As used herein, "MH1 domain" refers to the conserved aminoterminal domain (or N domain) present in all Smad family member proteins.

As used herein, "MH2 domain" refers to the conserved carboxy terminal domain (or C domain) present in all Smad family member proteins.

As used herein, "interaction partner protein" refers to a protein which functionally interacts with a given protein.

As used herein, "functionally interacts" refers to an interaction which is required for the proper function of a given biological pathway.

As used herein, "degradation" refers to the process of breaking down or reducing the complexity of. For example, protein degradation refers to breaking down a protein into peptides.

As used herein, "proteasome-mediated proteolysis" refers to the hydrolysis of proteins or peptides with formation of simpler products that requires the presence of the proteasome, defined above.

As used herein, "increases the proteasome-mediated proteolysis" refers to the effect of a compound to increase proteasome-mediated proteolysis, as defined above, by at least 10% relative to its basal level of activity in the absence of the compound. The increase in proteasome-mediated proteolysis may be greater than 10%, for example 20–50%, or 75–100%. As used herein, "basal level of activity" refers to the level of proteasome-mediated proteolysis in the absence of a compound.

As used herein, "decreases the proteasome-mediated proteolysis" refers to the effect of a compound to decrease proteasome-mediated proteolysis, as defined above, by at least 10% relative to its basal level of activity in the presence of the compound.

As used herein, "increases the activity" refers to the effect of a compound to increase a particular activity (for example an enzymatic activity), by at least 10% relative to the basal level of activity in the absence of the compound. The increase in activity may be greater than 10%, for example 20–50% or 75–100% or more.

As used herein, "decreases the activity" refers to the effect of a compound to decrease a particular activity (for example an enzymatic activity), by at least 10% relative to the basal level of activity. The decrease in activity may be greater than 10%, for example 25–500% or 75–100%.

As used herein, "tissue specific" and "cell type specific" refer to a characteristic which is limited to a particular tissue or cell type, respectively. A protein is said to be tissue or cell type specific if it is expressed only in a particular tissue or cell type.

As used herein, "treating a disease" refers to arresting or otherwise ameliorating the symptoms of a disease at least 10%, preferably 20–50% and more preferably 75–100%.

As defined herein, "Smads" refers to a family of signal transduction proteins (including the pathway restricted Smads 1, 2, 3, 5, 9 and the common mediator Smad, DPC4) which are downstream components of serine/threonine kinase receptors specific for TGF-β family ligands, and are activated upon phosphorylation by type I receptors specific for TGF-β family ligands. Following ligand stimulation and phosphorylation, the pathway restricted Smads form a complex with Smad4, translocate into the nucleus, and activate transcriptional responses (Heldin et al., 1997, supra).

As defined herein, "TGF-β family ligand" refers to protein factors which bind and activate TGF-β family receptors. TGF-β family ligands include but are not limited to TGFβs, Activin, Bone Morphogenetic Proteins (BMP's) and Mullerian Inhibitory Substance.

As used herein, "biological activity of TGF-β family ligands" refers to the activity of any biological pathway regulated by one or more TGF-β family receptors.

As defined herein, "HsN3" refers to a Beta subunit of the 20S proteasome, of mw 29.2 kDa.

As defined herein, "Uba 52" and "Uba 80" refer to ubiquitin fusion proteins.

As defined herein, "antizyme" refers to a 26.5 kDa protein that binds reversibly to ornithine decarboxylase (ODC) and targets ODC for proteasome mediated degradation. Specifically, antizyme accelerates the ATP-dependent degradation of ODC, a process catalyzed by the 26S proteasome (Hayashi et al., 1996, *TIBS*, 21:27–30).

As defined herein, "AIP4" refers to an Atropin-1 interacting protein and E3 ubiquitin ligase. AIP4 is involved in Dentatorubral pallidoluysian atrophy, a rare neurodegenerative disorder (Wood et al., 1998, *Mol. Cell. Neurosci.*, 11:149–160).

As defined herein, "PAG" refers to "Proliferation Associated Gene," an antioxidant protein.

As defined herein, "GST" refers to glutathione transferase, an antioxidant protein.

As defined herein, "enolase" refers to an enzyme involved in glucose metabolism, and also known to regulate c-myc oncogene transcription.

As defined herein, "U1SnRNP" refers to a ribonuclear protein.

As defined herein, "FKBP25" refers to a prolyl-isomerase.

As defined herein, "TRIP-4" refers to a protein that interacts with the thyroid hormone receptor.

As defined herein, "RBP2" refers to a protein that interacts with the tumor suppressor protein retinoblastoma (RB).

As defined herein, "NIPP-1" refers to nuclear inhibitor of protein phosphatase 1, a protein involved in the inhibiting the activity of nuclear protein phosphatase 1. NIPP-1, as defined herein, refers to a protein that is known to be rapidly processed into smaller heat-stable intermediates, a process that may be mediated by the proteasome (VanEynde et al., 1995, *J. Biol. Chem.*, 270:28068–28074).

As defined herein, "SNIP-1" or Smad1 Nuclear Interactor Protein 1 refers to a nuclear protein that interacts with Smad1, is a proteasome substrate, and has a carboxy terminal domain that is highly homologous to the amino terminus of the nuclear inhibitor of protein phosphatase 1.

As defined herein, "HEF1" refers to human enhancer of filamentation, a docking protein that plays a critical role in integrin pathways, and is essential for both ODC and ras-induced cell transformation.

As defined herein, "constitutively active" refers to permanently active such that no additional manipulations are required to induce activity.

As defined herein, "modification" refers to phosphorylation, stabilization, processing or assembly.

As defined herein, "FAST1" refers to forkhead activin signal transducer-1 (Chen et al., 1996, *Nature*, 383: 691–695).

As defined herein, "FAST2" refers to forkhead activin signal transducer-2 (Labbe et al., 1998, *Mol. Cell*, 2: 109–120).

As defined herein, "docking activity" refers to an activity which recognizes or binds proteasome substrates and assists in recruiting or bringing the substrate to the proteasome for degradation.

As used herein, "N" in a DNA sequence can be any one of the nucleotide bases G, A, T or C.

The relationship between TGF-β superfamily members and Smads is well established, as described above. Furthermore, protein components of the 20S/26S proteasome-mediated degradation system have been identified and characterized. The present invention represents the first, unexpected discovery of a physical and functional interaction between Smads (Smad1, 2, 3 and 4) and the proteasome system. The invention also represents the first discovery of physical interactions between an integral proteasome component, HsN3, and a number of known or potential proteasome substrates, the degradation of which is or may be regulated by TGF-β family ligands. The invention also represents the first discovery of physical interactions between antizyme and a number of known or potential proteasome substrates, the degradation of which is or may be regulated by TGF-β family ligands. The invention also represents the first discovery of a number of proteasome substrates whose degradation is regulated by TGF-β family ligands. The invention also represents the first discovery of the requirement of proteasome activities in the Smad-involving signalings of TGF-β family ligands.

The invention also represents the first discovery of the requirement of oxidative stress in the Smad-involved signalings of TGF-β family ligands.

The invention also represents the first discovery of the requirement of the NF-κB activities in a BMP-induced signaling pathway.

The invention therefore provides targets useful for screening compounds which may modulate the activity of a TGF-β superfamily member. The invention also provides targets useful for screening compounds which may modulate the activity of the proteasome system. The invention also provides methods for treating diseases that are characterized by increased or decreased levels of activity of a TGF-β superfamily ligand or diseases characterized by defects of signaling pathways either upstream of, or at the level of Smad activation.

The invention also provides methods for screening for compounds which mimic specific biological activities of TGF-β superfamily ligands.

The invention encompasses protein compositions comprising an isolated Smad protein and an additional isolated protein. Among the interactions encompassed by the invention are protein compositions comprising Smad1 and its binding partners, Smad2 and its binding partners, Smad3 and its binding partners Smad4 and its binding partners, HsN3 and its binding partners, antizyme and its binding partners, SNIP-1 and its binding partners, as well as isolated interaction domains of Smads 1–4 complexed with their respective binding partners.

The invention also encompasses methods of screening for compounds that modulate the interaction between the proteins comprising these compositions, the activity of the proteins comprising these compositions and/or the proteolysis of these compositions.

Also disclosed herein are methods for identifying peptides which modulate the interactions listed above.

Also disclosed herein are methods for identifying new Smads, as well as methods for identifying additional Smad functional partners in different tissues.

Vectors Useful According to the Invention

Nucleic acid vectors are useful according to the invention for the expression of screening assay components in cells.

A nucleic acid vector of use according to the methods of the invention may be either double- or single stranded and either naked or associated with protein, carbohydrate, proteoglycan and/or lipid or other molecules. Such vectors may contain modified and/or unmodified nucleotides or ribonucleotides. In the event that the gene to be transfected may be without its native transcriptional regulatory sequences, the vector must provide such sequences to the gene, so that it can be expressed once inside the target cell. It is also possible to design a vector that will express the gene of choice in the target cells at a specific time, by using an inducible promoter, which will not direct transcription unless a specific stimulus, such as heat shock, is applied.

A gene encoding a component of the assay system of the invention or a candidate modulator may be transfected into a cell or organism using a viral or non-viral DNA or RNA vector, where non-viral vectors include, but are not limited to, plasmids, linear nucleic acid molecules, artificial chromosomes and episomal vectors.

Vectors useful according to the invention include a vector that possesses the following characteristics:

i) High copy number bacterial origin of replication.

Vectors having relatively high copy number, i.e., in the range of 20–40 copies/cell up to 1000–2000 copies/cell, are especially useful according to the invention. For example, a vector that includes the pUC origin of replication is preferred according to the method of the invention. The pUC origin of replication permits more efficient replication of plasmid DNA and results in a tenfold increase in plasmid copy number/cell over, e.g., a pBR322 origin. The resulting high copy number greatly increases the ratio of plasmid DNA to chromosomal DNA, RNA, cellular proteins and co-factors, improves plasmid yield, and facilitates easier downstream purification.

ii) Small and stable vector backbone.

It is preferred according to the invention that the backbone of a vector used according to the methods described herein be small, i.e., less than 5 kb, and preferably 1–3 kb. The term "vector backbone" refers to the bacterial DNA necessary to maintain and propagate the vector in a bacterial host. Vectors of the invention which include both backbone and insert will be on the order of 15–50 kb in size, or even larger. Thus, a vector backbone useful in the invention will be capable of carrying inserts of approximately 10–50 kb or larger. The insert may include DNA from any organism, but will preferably be of mammalian origin, and may include, in addition to a gene encoding a protein component of a composition of the claimed invention, regulatory sequences such as promoters, polyadenylation sequences, enhancers, locus control regions, etc. The gene encoding a protein component of a composition of the claimed invention may be of genomic origin, and therefore contain exons and introns as reflected in its genomic organization, or it may be derived from complementary DNA.

The vector should also be stably inherited; that is, the vector backbone preferably contains no intrinsically unstable elements prone to rearrangement, deletion, etc, such as transposons, and is stably inherited in the presence of the selective agent.

Useful vectors according to the invention include pEAβGlu, pUC18/19tetΔAmp, pUC19tet, pGL2RSV, pGL2RSVluc, pAI6tet, pCD2tatRZfull and pFLAG-CMV4.

iii) Polylinker suitable for the insertion of therapeutic genes and regulatory sequences.

Vectors useful according to the invention include a polylinker comprising a variety of restriction sites that are useful in cleaving the vector and incorporating a gene of interest.

iv) Selective marker gene.

Vectors useful according to the invention may include a gene encoding a selectable marker, e.g., an antibiotic resistance gene such as the bacterial tetracycline resistance gene. Incorporation of the tetracycline resistance gene permits the use of tetracycline as a selective agent in the plasmid preparation procedure according to the invention. One advantage to the use of a tetracycline resistance gene is that tetracycline is not degraded in E. coli and therefore more tetracycline does not have to be added during fermentation. In addition, the tetracycline resistance gene is preferred over a gene encoding ampicillin resistance because tetracycline is prescribed less often as an antibiotic in a clinical setting, and adverse responses to tet are less frequent than for amp and other β-lactam antibiotics.

In addition to vectors of the broad classes described above, microbial plasmids, such as those of bacteria and yeast, are of use in the invention. Yeast plasmids, which are useful in the screening assays described herein as expression vectors in multiple-hybrid assays of protein interaction, are particularly preferred. Specific yeast plasmids and mammalian expression constructs useful according to the invention are described in Examples 1 and 3, respectively. Any plasmid which allows expression of the desired protein in the bacterial, yeast, or mammalian cell types used may be used within the invention.

Bacterial Plasmids

Of the frequently used origins of replication, pBR322 is useful according to the invention, and pUC is preferred. Although not preferred, other plasmids which are useful according to the invention are those which require the presence of plasmid encoded proteins for replication, for example, the pT181, FII, and FI origins of replication.

Examples of origins of replication which are useful in assays of the invention in E. coli and S. typhimurium include but are not limited to, pHETK (Garapin et al., 1981, Proc. Natl. Acad. Sci. U.S.A., 78: 815–819), p279 (Talmadge et al., 1980, Proc. Natl. Acad, Sci. U.S.A, 77: 3369–3373), p5-3 and p21A-2 (both from Pawalek et al., 1997, Cancer Res., 57: 4537–4544), pMB1 (Bolivar et al., 1977, Gene, 2: 95–113), Co1E1 (Kahn et al., 1979, Methods Enzymol., 68: 268–280), p15A (Chang et al., 1978, J. Bacteriol., 134: 1141–1156); pSC101 (Stoker et al., 1982, Gene, 18: 335–341); R6K (Kahn et al., 1979, supra); R1 (temperature dependent origin of replication, Uhlin et al., 1983, Gene, 22: 255–265); lambda dv (Jackson et al., 1972, Proc. Nat. Acad. Sci. U.S.A., 69: 2904–2909); pYA (Nakayama et al., 1988, infra). An example of an origin of replication that is useful in Staphylococcus is pT181 (Scott, 1984, Microbial Reviews 48: 1–23). Of the above-described origins of replication, pMB1, p15A and Co1E1 are preferred because these origins do not require plasmid-encoded proteins for replication.

Yeast Plasmids

Three systems are used for recombinant plasmid expression and replication in yeasts:

1. Integrating. An example of such a plasmid is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells. Regardless of the type of plasmid used, yeast cells are typically transformed by chemical methods (e.g. as described by Rose et al., 1990, Methods in Yeast Genetics, Cold Spring Harbor Laboratory Press, Cold Spring Harbor, N.Y.). The cells are treated with lithium acetate to achieve transformation efficiencies of approximately $10^4$ colony-forming units (transformed cells)/μg of DNA. Yeast perform homologous recombination such that the cut, selectable marker recombines with the mutated (usually a point mutation or a small deletion) host gene to restore function. Transformed cells are then isolated on selective media.

2. Low copy-number ARS-CEN, of which YCp is an example. Such a plasmid contains the autonomous replicating sequence (ARS1), a sequence of approximately 700 bp which, when carried on a plasmid, permits its replication in yeast, and a centromeric sequence (CEN4), the latter of which allows mitotic stability. These are usually present at 1–2 copies per cell. Removal of the CEN sequence yields a YRp plasmid, which is typically present in 100–200 copies per cell; however, this plasmid is both mitotically and meiotically unstable.

3. High-copy-number 2μ circles. These plasmids contain a sequence approximately 1 kb in length, the 2μ sequence, which acts as a yeast replicon giving rise to higher plasmid copy number; however, these plasmids are unstable and require selection for maintenance. Copy number is increased by having on the plasmid a selection gene operatively linked to a crippled promoter. This is usually the LEU2 gene with a truncated promoter (LEU2-d), such that low levels of the Leu2p protein are produced; therefore, selection on a leucine-depleted medium forces an increase in copy number in order to make an amount of Leu2p sufficient for cell growth.

As suggested above, examples of yeast plasmids useful in the invention include the YRp plasmids (based on autonomously-replicating sequences, or ARS) and the YEp plasmids (based on the 2μ circle), of which examples are YEp24 and the YEplac series of plasmids (Gietz and Sugino, 1988, *Gene*, 74: 527–534). (See Sikorski, "Extrachromosomal cloning vectors of *Saccharomyces cerevisiae*", in *Plasmids, A Practical Approach*, Ed. K. G. Hardy, IRL Press, 1993; and *Yeast Cloning Vectors and Genes, Current Protocols in Molecular Biology*, Section II, Unit 13.4, Eds., Ausubel et al., 1994). Additional yeast vectors useful for the invention include pJG4-5 and pEG202 (Brent et al., U.S. Pat. No. 5,580,736).

In addition to a yeast origin of replication, yeast plasmid sequences typically comprise an antibiotic resistance gene, a bacterial origin of replication (for propagation in bacterial cells) and a yeast nutritional gene for maintenance in yeast cells. The nutritional gene (or "auxotrophic marker") is most often one of the following (with the gene product listed in parentheses):

TRP1 (Phosphoribosylanthranilate isomerase, which is a component of the tryptophan biosynthetic pathway);

URA3 (Orotidine-5'-phosphate decarboxylase, which takes part in the uracil biosynthetic pathway);

LEU2 (3-Isopropylmalate dehydrogenase, which is involved with the leucine biosynthetic pathway);

HIS3 (Imidazoleglycerolphosphate dehydratase, or IGP dehydratase); or

LYS2 (α-aminoadipate-semialdehyde dehydrogenase, part of the lysine biosynthetic pathway).

Cells Useful According to the Invention

A variety of cell types are useful in screening assays of the invention.

The methods of the invention are broadly applicable to in vitro assays systems wherein a host cell is susceptible to transfection or transformation, such as bacteria (both gram-positive and gram-negative), cultured- or explanted vertebrate cells (e.g., mammalian stem cells) and yeast.

Organisms are currently being developed for the expression of therapeutic or prophylatic agents including DNA, RNA, proteins, non-proteinaceous compounds, and viruses. Such vector microorganisms include bacteria such as *Clostridium* (Parker et al., 1947, *Proc. Soc. Exp. Biol. Med.*, 66: 461–465; Fox et al., 1996, *Gene Therapy*, 3: 173–178; Minton et al., 1995, *FEMS Microbiol. Rev.*, 17: 357–364), *Salmonella* (Pawelek et al., 1997, *Cancer Res.* 57: 4537–4544; Saltzman et al., 1996, *Cancer Biother. Radiopharm.*, 11: 145–153; Carrier et al., 1992, *J. Immunol.*, 148: 1176–1181; Su et al., 1992, *Microbiol. Pathol.*, 13: 465–476; Chabalgoity et al., 1996, *Infect. Immunol.*, 65: 2402–2412), listeria (Schafer et al., 1992, *J. Immunol.*, 149: 53–59; Pan et al., 1995, *Nature Med.*, 1: 471–477) and Shigella (Sizemore et al., 1995, *Science*, 270: 299–302), as well as yeast, mycobacteria, slime molds (members of the taxa Dictyostelilda—such as of the genera *Polysphondylium* and *Dictystelium*, e.g. *Dictyosteliuim discoideum*—and Myxomycetes—e.g. of the genera *Physarum* and *Didymium*) and members of the Domain Archaea (including, but not limited to, archaebacteria), which have begun to be used in recombinant nucleic acid work, members of the phylum Protista, or other cell of the algae, fungi, or any cell of the animal or plant kingdoms.

Mammalian cells are also of use in the invention. Any cell type allowing high transfection efficiency is acceptable. Such cells include, but are not limited to fibroblasts, muscle cells, neuronal cells, cells of the immune system (such as T-cells, B-cells and macrophages), hematopoietic cells and dendritic cells. To study signaling by TGF-β family ligands one may either use cells which are responsive to TGF-β family ligands, including, but not limited to Mv1Lu, HepG2, HeCAT, p19, prostate cancer and PC12 cell lines, as well as rat sympathetic neuron primary cultures, osteoblasts, and osteoclasts, and transfect them with reporter gene constructs. Because TGF-β family ligands primarily affect epithelial cell types, however, any epithelial cell line can be appropriate for this type of study according to the invention. Reporter gene constructs include, but are not limited to 3TP-Lux (for TGF-β, BMPs and activin; Wrana et al., 1992, *Cell*, 71: 1003–1014), p21-Lux (for TGF-β; Datto et al., 1995, *Proc. Nat. Acad. Sci., U.S.A.*, 92: 5545–5549; Datto et al., 1995, *J. Biol. Chem.*, 270: 28623–28628), PAI-Lux (for TGF-β, activin and BMPs; Dennler et al., 1998, *EMBO J.*, 17: 3091–3100), ARE-Lux (for activin; Chen et al., 1996, supra), or gsc-Lux (for TGF-β or possibly BMPs; Labbe et al., 1998, supra).

As an alternative to the cell lines mentioned above, other cells which do not normally respond to TGF-β family ligands, including, but not limited to COS or 293 cell lines, may be transfected with the respective type I and type II receptors for any ligand in the TGF-β superfamily.

Screening Assays Useful According to the Invention

The invention provides methods for assaying agents which are potentially useful as modulators of an interaction between an isolated Smad protein and an isolated binding protein according to the invention. The invention also provides methods for assaying agents which are potentially useful as modulators of an interaction between an isolated SNIP-1 protein and an isolated binding protein according to the invention. The invention also provides methods for assaying agents which are potentially useful as modulators of an interaction between an isolated protein of the proteasome mediated degradation pathway and an isolated binding protein according to the invention. It should be understood that modulator compounds identified using the methods described herein may inhibit or enhance an interaction or process regulated by TGF-β family ligands. In addition, modulator compounds may, by altering the activity of components of the signal transduction pathway, or by, for example, interfering with the inhibitory intramolecular association of Smad MH1 and MH2 domains, mimic the activity of TGF-β family ligands.

Assays according to the invention may be performed in vitro in a cell free gene expression system, in a gene expression system including a cell extract, in a whole cell expression system, or in vivo. Minimally, an in vitro assay performed according to the invention will contain each of the proteins of the claimed composition.

Cell-free Assay Systems of the Invention

A cell-free assay system according to the invention is required to permit a particular protein:protein interaction to occur. Such a system may comprise a low-ionic-strength buffer (e.g. physiological salt, such as simple saline or phosphate- and/or Tris-buffered saline, a cell culture medium, of which many are know in the art), or a whole or fractionated cell lysate. The molecules comprising the claimed composition, as well as a candidate modulator, may be added into a buffer, medium or lysate or may have been expressed in cells from which a lysate is derived. Alternatively, a cell-free transcription- and/or translation system may be used to deliver one or more of these components, if it is so desired, to the assay system.

An assay of the invention is performed in a standard in vitro transcription/translation system. The TNT® T7 Quick Coupled Transcription/Translation System (Cat. # L1170; Promega) contains all reagents necessary for in vitro transcription/translation except the DNA of interest and the detection label. The TNT® Coupled Reticulocyte Lysate Systems (comprising a rabbit reticulocyte lysate) include: TNT® T3 Coupled Reticulocyte Lysate System (Cat. # L4950; Promega); TNT® T7 Coupled Reticulocyte Lysate System (Cat. # L4610; Promega); TNT® SP6 Coupled Reticulocyte Lysate System (Cat. # L4600; Promega); TNT® T7/SP6 Coupled Reticulocyte Lysate System (Cat. # L5020; Promega); TNT® T7/T3 Coupled Reticulocyte Lysate System (Cat. # L5010; Promega).

An assay involving a cell lysate or a whole cell may be performed in a cell lysate or whole cell preferably eukaryotic in nature (e.g., yeast, fungi, insect (e.g., *Drosophila*), mouse, or human). An assay in which a cell lysate is used is performed in a standard in vitro system. A rabbit reticulocyte lysate alone is also available from Promega, either nuclease-treated (Cat. # L4960) or untreated (Cat. # L4151).

One method of screening for compounds which potentially modulate protein:protein interactions involves the following steps: 1) a first protein, termed protein 1 is synthesized as an epitope-tagged protein either in *E. coli* or by cell free translation; 2) a second protein, termed protein 2, is synthesized either in *E. coli* or by cell free translation, and includes either an epitope tag distinct from that borne by protein 1 or a radiolabel or other such detectable labeling moiety; 3) protein 1 is immobilized on beads coated with an activity which recognizes the epitope tag; 4) protein 2 is contacted with the immobilized protein 1 and allowed to form complexes in either the presence or absence of a candidate modulator compound; 5) unbound protein 2 is removed; and 6) changes in the amount of protein 2 binding to protein 1 are detected relative to the presence or absence of a candidate modulator. As detailed below (*Determining the Activity of a Modulator*), an increase in binding indicates the candidate modulator is an agonist of the interaction, while a decrease indicates the compound is an antagonist.

The proteins for the assay described above may be synthesized with epitope tags including, but not limited to GST or polyhistidine, following insertion of their coding sequences in frame in an appropriate epitope-tagging vector (e.g., the pET (Invitrogen), pGEX (Pharmacia), and pQE (Qiagen) vectors or the like). Cell free synthesis of the proteins for the assay may be performed using any of the cell free transcription and translation systems described above, and may be performed in the presence of amino acids labeled with an isotope or other labeling moiety. Alternatively, the proteins may be isolated from *E. coli* transformed with the vectors according to standard methods using beads coated with the appropriate moiety for recognition of the tag (e.g., glutathione, $Ni^{++}$, or other appropriate binding moiety).

The detection of bound protein 2 in the assay described above will be performed by ELISA using antibodies specific to protein 2, or by measuring the amount of radiolabel or other detectable labeling moiety bound after removing unbound material if protein 2 is labeled. Alternatively, bound protein 2 may be detected by Western blotting according to standard methods.

Appropriate control reactions will include incubation of beads alone (without protein 1) with protein 2. It should be understood that the assay described above and any others described herein for the identification of modulatory compounds may be scaled up so that large numbers (tens to hundreds to thousands) of candidate modulators may be screened simultaneously.

In vitro Cellular Assay Systems of the Invention

When performed in vitro in an assay system using cells, the methods of the invention are broadly applicable to a host cell susceptible to transfection or transformation, such as bacteria (both gram-positive and gram-negative), cultured- or explanted vertebrate cells (e.g., mammalian stem cells) and yeast. In vitro cellular assay systems wherein the host cell is a yeast cell or a mammalian cell are described in detail below.

1. Yeast Assay System

A modified yeast two-hybrid system developed by Brent and colleagues is used to isolate Smad1 interactors, as described previously (Wang et al., 1994, Science, 265:674–676, Wang et al., 1996b, Science, 271:1120–1122). Briefly, yeast strain EGY48, which has an integrated Leu2 reporter, is first transformed with a LacZ reporter. The selected transformants are transformed again with the bait construct Smad1pEG202 (described in Example 1) or with another appropriate bait coding sequence fused in frame with the DNA binding domain of LexA (AA 1-202) in the vector pEG202 or its equivalent. The selected bait transformants are transformed with a human fetal brain cDNA library (a gift from Roger Brent) or other library in the pJG4-5 plasmid vector, which fuses the cDNA sequences with the activation domain of B42. It is expected that approximately one million original transformants will be obtained. From the pooled stock of the transformants, ten million cells are screened on $U^-H^-W^-L^-$ galactose plates containing X-gal. Only those that form blue colonies are picked as candidate positives. The cDNAs from the candidate positives are purified, retested for Smad1 interaction in yeast and then sequenced according to methods of sequencing well known in the art (see Ausubel et al., supra and Sambrook et al., 1989, *Molecular Cloning. A Laboratory Manual.*, 2nd Edition, Cold Spring Harbor Laboratory Press, Cold Spring Harbor, N.Y.). Methods of sequencing employ such enzymes as the Klenow fragment of DNA polymerase I, Sequenase® (US Biochemical Corp, Cleveland, Ohio), Taq polymerase (Perkin Elmer, Norwalk, Conn.), thermostable T7 polymerase (Amersham, Chicago, Ill.), or combinations of recombinant polymerases and proofreading exonucleases such as the ELONGASE Amplification System (Gibco BRL, Gaithersburg, Md.). Preferably, the process is automated with machines such as the Hamilton Micro Lab 2200 (Hamilton, Reno Nev.), Peltier Thermal Cycler (PTC200; MJ Research, Watertown, Mass.) and the ABI 377 DNA sequencers (Perkin Elmer). For testing the interaction between a particular clone according to the invention (e.g. clone 18) and Smad1, or Smad1 deletions, the same yeast strain is first transformed with e.g., clone 18, selected on $U^-W^-$ plates, then retransformed with pEG202 constructs and selected on $U^-H^-W^-$ plates. The transformants are first streaked onto a master plate, then replicated onto two testing plates: $U^-H^-W^-$ glucose plates with X-gal; $U^-H^-W^-$ HW galactose/raffinose plates with X-gal.

Once an interaction between two proteins is defined as described above, candidate modulators can be screened to identify those which increase or decrease the level of interaction detected. Candidate modulators are added to the medium of yeast cells exhibiting the protein:protein interaction to be modulated. Changes in the interaction of the two proteins are monitored by measuring the β-galactosidase activities of the yeast, using methods well known in the art, in minimal U−H−W− galactose/raffinose medium for yeast treated or untreated with the candidate modulator. Control reactions will include measurement of β-galactosidase activities of the same yeast in minimal U−H−W− glucose medium, since the fusion protein expressed from the pJG4-5 vector is not expressed in yeast grown in glucose medium. Values obtained from such control cultures will be subtracted from values obtained in minimal U−H−W− galactose/raffinose medium to obtain the specific activity.

2. Mammalian Assay System

A COS cell system is used to determine if protein:protein interactions according to the invention occur in mammalian cells. Any readily transfectable mammalian cell line is acceptable for assays of this kind, however.

There are at least two types of assay which may be performed using mammalian cells. In the first, plasmids encoding the interactor proteins are transfected into the cells, lysates are prepared and complex formation is monitored by co-immunoprecipitation. In the second type of assay, a system analogous to the yeast two hybrid assay is established wherein the proteins whose interaction is to be monitored are fused in frame with domains which reconstitute a transactivation system when the proteins of interest interact, driving expression of a reporter gene.

For the assay system involving co-immunoprecipitation from lysates, equal amounts of total plasmid are used to transiently transfect, for example, COS-1 cells using the DEAE dextran method (Hoodless et al., 1996, supra). For metabolic labeling, cells are incubated with 250 $\mu$Ci $^{35}$S-methionine per plate for four hours, two days after transfection. Lysates are prepared by washing transfected cells with cold HBSS, scraping them, and lysing them on ice in 300 $\mu$l lysis buffer (20 mM Tris, pH 7.4, 150 mM NaCl, 0.5% Triton-X-100, 1 mM EDTA) containing protease inhibitors. The level of protein expression is determined by Western blot analysis (according to the method of Towbin et al., 1979, *Proc. Natl. Acad. Sci., USA.*, 76:4350–4354) of 20 $\mu$l aliquots of cell lysates prior to immunoprecipitation assays. For immunoprecipitation, 150 $\mu$l aliquots of cell lysate are precleared with protein A sepharose beads (Pharmacia), and incubated on ice overnight with 3 $\mu$l of anti-T7 antibody (1 mg/ml) or anti-FLAG antibody (3 mg/ml) (M2 monoclonal, IBI, Eastman Kodak). Protein A sepharose beads are used to absorb the antibodies, immunoprecipitated complexes are washed as described (Wang et al., 1996), treated with protein sample buffer to elute the immunoprecipitated protein, and analyzed on a 12% SDS-polyacrylamide gel. Coprecipitated proteins are detected by autoradiography if the proteins are metabolically labeled, or by Western blot using an ECL kit (Amersham). Assays of this type performed on lysates of transfected cells treated either with or without candidate modulators will indicate the effect of such candidate modulators. As for other assays of this sort, modulators which increase the detected complex formation will be indicated as agonists, while modulators which decrease the detected complex formation will be indicated as antagonists.

For the second type of assay using cultured mammalian cells, interactions between two proteins are monitored by fusing one protein in frame with a DNA binding domain, such as LexA (AA 1-202) or the Gal4 DNA binding domain, and fusing the second protein in frame with a transactivation domain, such as B42 or the Gal4 transactivation domain. These fusion proteins are transfected into a cell containing a reporter gene containing a recognition element(s) for the DNA binding domain fused to one of the protein partners. Appropriate reporters include, but are not limited to Luciferase, CAT or GFP (green fluorescent protein). Vectors and assays for the expression of Luciferase, CAT or GFP are well known to those skilled in the art and can be modified to contain the appropriate DNA binding protein recognition elements using standard methods known to those of skill in the art. In this assay system, the association of the two proteins of interest in a cell containing the reporter gene construct results in the activation of the reporter gene, which may then be measured using assays appropriate to the chosen reporter activity. The assay will be performed in the presence and absence of the candidate modulator compound, with differences in measured reporter activity reflecting the modulatory activity of the tested compound. Relevant controls will include assays of candidate modulators performed in the absence of transfected fusion proteins to control for modulators which affect reporter expression independent of their effects upon the protein interactions being tested. In addition, candidate modulators identified in this manner will be further tested, for example by Western blot analysis of treated versus untreated cells transfected with all components of the system, to control for effects of such candidate modulators on the plasmid directed expression of the test proteins themselves.

In vivo Assay Systems of the Invention

Alternatively, the screening system may operate in vivo, i.e., in an intact, living multicellular organism, such as an insect or a mammal. For example, mice which are transgenic for gene expression constructs encoding one or more of a protein component of a claimed composition (e.g., one of Smads 1 through 5 and/or a protein component of the proteasome mediated degradation pathway, such as HsN3 or antizyme) are useful according to the invention. Methods of generating transgenic *Drosophila*, mice and other organisms are well known in the art (described below). A candidate modulator according to the invention is administered (e.g. by feeding or injection) to a test organism (including, but not limited to, a fly or mouse) and protein:protein complex formation is assayed. After sufficient time has passed to allow for gene expression and inhibition or activation of protein:protein binding by the candidate modulator, a detection procedure may be performed by a method including, but not limited to, molecular, biochemical (including enzymatic assay) and histological (including immunohistochemical and enzymatic staining) methods.

Production of Transgenic Animals

Transgenic mice provide a useful tool for genetic and developmental biology studies and for the determination of a function of a novel sequence. According to the method of conventional transgenesis, additional copies of normal or modified genes are injected into the male pronucleus of the zygote and become integrated into the genomic DNA of the recipient mouse. The transgene is transmitted in a Mendelian manner in established transgenic strains.

Constructs useful for creating transgenic animals comprise genes under the control of either their normal promoters or an inducible promoter, reporter genes under the control of promoters to be analyzed with respect to their patterns of tissue expression and regulation, and constructs containing dominant mutations, mutant promoters, and artificial fusion genes to be studied with regard to their specific developmental outcome. Transgenic mice are useful according to the invention for analysis of the interaction of protein components comprising compositions of the claimed invention, in the presence or absence of a candidate modulator compound. Typically, DNA fragments on the order of 10 kilobases or less are used to construct a transgenic animal (Reeves, 1998, New Anat., 253:19). Transgenic animals can be created with a construct comprising a candidate gene encoding a protein component of a composition according to the claimed invention according to methods well known in the art (reviewed in Reeves et al., supra).

Measurement of Enzymatic Activity of Smad1 Interacting Proteins

Certain Smad1 interacting proteins have enzymatic activities. The claimed invention provides methods of screening for compounds that modulate the activity of these proteins. These proteins include, but are not limited to GST, alpha enolase and SNIP-1. SNIP-1 is homologous to a nuclear inhibitor of protein phosphatase 1. Therefore, assays for measuring protein phosphatase 1 (PP-1) activity are also useful according to the invention.

1) GST activity is measured as described in Brogden and Barber, 1990, Comp. Biochem. Physiol. 96B:339–342. Briefly, GST activities are measured using 1-chloro-2,4-dinitrobenzene (CDNB) and 3,4-dichloronitrobenzene (DCNB) as substrates with reduced glutathione (GSH). Equine GST, GSH and CDNB can be obtained from Sigma Chemical Company, St. Louis, Mo. DCNB can be obtained from Aldrich Chemical Company, Milwaukee, Wis. Reagents are prepared daily prior to use. Activity with CDNB is measured at pH 6.8 and 7.4 at 25 and 37° C. in 0.05M potassium phosphate buffer using microplate and quartz cuvette assays formats. Activity with DCNB as substrate is measured at pH 7.4 and 9.0 at the same temperatures with the same instruments, using phosphate buffer and 0.1M-Tris-HCl buffer, respectively. Microplate assays are read at absorbances of 340 and 410 nm in a plate reader, for example Titertek Multiskan MCC/340 (Flow Laboratories, McLean, Va.). Total reaction volumes are 300 μl, consisting of 100 μl each of triturate, GSH and CDNB or DCNB. Cuvettes are read at absorbances of 344 and 414 nm in a Beckman (Irvine, Calif.) DU-50 spectrophotometer equipped with a temperature controller and kinetics module. Total reaction volume is 1.5 ml, consisting of 0.5 ml each of triturate, GSH and CDNB or DCNB. Rate measurements are corrected for the non-enzyme-catalyzed reaction and u.v. transparency of plastic microtiter plates. Molar absorptivities for conversion of absorbance values to conversion rates are established for the microplate format and compared to published values (9.6 mM$^{-1}$ cm$^{-1}$ for CDNB and 8.56 mM$^{-1}$ cm$^{-1}$ for DCNB). Protein concentration is measured using the Bradford method (Bradford, 1976, Analyt. Biochem., 72:248) modified for use in microtiter plates.

2) Enolase activity is measured as described in Herraez-Dominguez et al., 1976, Enzyme, 21:211–224. Briefly, enolase is assayed by coupling the reaction with pyruvate kinase (PK) and lactate dehydrogenase (LDH) to give oxidation of NADH. This is carried out at 37° C. in a final volume of 1 ml containing 40 mmol/triethanolamine buffer, pH 7.4; 70 mmol/L KCl; 3.3 mmol/L EDTA; 8 mmol/L MgSO$_4$; 1 mmol/L ADP; 0.2 mmol/L NADH; 4 U/ml LDH, and 1.5 U/ml PK. The reaction is started by addition of 50 μl of 30 mmol/L 2-phosphoglycerate. The enzyme activity is expected to be proportional to concentration to an absorbance change of 0.075/min.

3) PP-1

PP-1 activity is measured as described in Connor et al., 1998, J. Biol. Chem., 16:27716–21124.

The enzymatic activities of Smad interacting proteins may be used in assays to identify compounds which modulate those activities, and thereby the signals transduced by TGF-β family ligands. Such assays may be performed in several ways.

In cell free systems, candidate modulator compounds may be added directly to in vitro reactions which measure the activity of the enzyme, with changes in activity indicating modulation by the test compound.

An alternative to cell free screening systems involves the expression of the enzyme of interest in cultured cells. Such cells may be treated with candidate modulator compounds and changes in the activity of the enzyme monitored in total cell extracts, or in preparations of the enzyme isolated from the treated cells (e.g., Histidine epitope tagged ("His-tagged") GST can be isolated from mammalian cells using a Ni$^{++}$ column). A necessary control in such assays will be to monitor the levels of the enzyme itself to control for potential effects of candidate modulators on the expression of the enzyme.

Measuring Proteasome Mediated Proteolysis of Smad Proteins

The proteasome mediated proteolysis of Smad proteins can be measured by Western blot analysis using anti-Smad antibodies or anti-epitope antibodies that are capable of binding to the aminoterminal domain of the Smad of interest. The proteolysis process is induced by the activation of the type I receptor that is specific for the Smad protein of interest. Constitutively active mutants of the type I receptors have been particularly useful in these studies. These mutants generally exploit the discovery by Weiser et al. (1995, supra) that introduction of a charged residue in place of a specific conserved residue in the GS domain of different type I receptors renders the receptor constitutively active. The mutant termed R2TD is a constitutively active form of the type I activin receptor known as R2, ALK4 or ActR1B (Attisano et al., 1996, Mol. Cell. Biol., 16: 1066–1073). Similarly, R4TD is a constitutively active form of the type I TGF-β receptor known as R4, ALK5 or TbR1. R1QD is a constitutively active form of the type I receptor for BMPs known as R1, ALK2, ActR1, or Tsk7L. ALK3QD and ALK6QD are constitutively active forms of the BMP type I receptors known as ALK3 and ALK6, respectively (Kretzschmar et al., 1997, supra; Hoodless, 1996, supra). Smad1, for example, is degraded upon the coexpression of ALK3QD (provided by Joan Massagué), while Smad2, 3 and 4 are degraded upon the coexpression of the constitutively active type I receptors of activin and TGF-β, R2TD and R4TD, respectively.

Proteasome substrates whose degradation is regulated by TGF-β family ligands and are of interest as targets for modulating signal transduction include, but are not limited to antizyme, HsN3, HC5, Smad1, PAG, S1+clone 27 (SIP2; SEQ ID No. 1), SNIP1 (SEQ ID No. 3), Myc, Mxi1, Myx, Smad2, Smad3, Smad4, FAST1, HEF1, RBP2, FNTA, FNTB, GGTB, TGF-β type 1 and type 2 receptors, activin type 1 and BMPs type 1 and type 2 receptors.

To determine whether a protein of interest is a proteasome substrate, one may co-express the protein of interest with all necessary partner proteins, and then monitor protein degradation. A decrease in protein levels in cells co-expressing a constitutively active receptor protein indicates the receptor may affect proteolysis of the given protein. Specific inhibitors of the proteasome pathway can be used to demonstrate that the degradation pathway involves the proteasome. Protein levels may be monitored, for example, by labeling the cells with $^{35}$S-methionine, followed by immunoprecipitation and quantitation of radioactivity in the immunoprecipitated material. Protein half-life may be determined by pulse chase analysis, wherein cells are labeled for a given period of time and then switched to medium without label, after which samples are evaluated at various times to examine the rate at which the level of labeled protein of interest is degraded. Alternatively, Western blotting may be performed to monitor the level of the protein, and thereby its half-life.

This assay can be performed in mammalian cells according to the following method. COS cells are transfected with Flag-tagged Smad1, and ALK3QD. Control cells are transfected with Flag-tagged Smad1 and the wild type ALK3 (which is not active, and normally requires BMPs in the presence of the BMP type II receptor to be activated). Forty hours after transfection, cells are lysed with standard lysis buffer (20 mM Tris, pH 7.4, 150 mM NaCl, 0.5% Triton-X-100, 1 mM EDTA) containing protease inhibitors. The cell lysates are analyzed by SDS-PAGE and Western blot using an anti-Flag monoclonal antibody. Typically, the F-Smad1 signal detected by Western blot is reduced in cells transfected with ALK3QD, as compared to the control cells. The proteasome-mediated proteolysis of F-Smad1 can be demonstrated by blocking the reduction of an F-Smad1 signal on a Western blot by adding 10 nM lactacystin (a specific proteasome inhibitor) for ten hours before cell lysis to cells transfected with F-Smad1 and ALK3QD. A similar approach can be used to demonstrate the proteasome-mediated proteolysis of Smad2, 3 and 4.

The proteasome mediated degradation of proteins involved in signal transduction can be exploited in an assay to identify compounds which modulate the degradation, and thereby modulate signal transduction. One means of doing this in mammalian cell culture is to make a fusion protein with a DNA binding domain (e.g., LexA or Gal4 DNA binding domain) and a transcription activation domain (e.g., B42 or Gal4 transactivation domain) flanking the protein of interest. For such a protein one may first demonstrate that the fusion protein is still degraded by the proteasome pathway in mammalian cell culture as described above using specific proteasome inhibitors. Candidate modulator compounds may then be tested by adding them to cells expressing the fusion protein and a reporter gene (for example, luciferase or CAT) which is regulated through a DNA element recognized by the DNA binding domain of the fusion protein. Binding of the fusion protein to the regulatory elements of the reporter construct brings the transactivation domain into proximity of the promoter and allows transactivation of the reporter gene. The effect of candidate modulators on the protein of interest will be reflected by changes in the activity of the reporter, such that increased reporter activity indicates an inhibitory effect on proteolysis and decreased reporter activity indicates a stimulatory effect on proteolysis.

The proteasome mediated proteolysis of Smad proteins can also be measured in yeast cells. A hybrid protein comprising from the amino terminus to the carboxyl terminus a DNA binding domain (LexA), a Smad or Smad interactor, and then an activation domain (B42) can be constructed and used in the yeast two-hybrid system. Such a protein can bind to a reporter gene (Leu2, for example) that is under the control of a LexA-binding sequence, thus allowing the expression of the reporter (in this example reporter expression allows the cells to grow on plates lacking leucine). If such a yeast is transformed by the constitutively active ALK3 (ALY3QD), contained on a separate vector, these yeast will no longer be able to grow on plates lacking leucine, since the activated ALK3 will induce the proteasome-mediated proteolysis of the Smad or Smad interactor, thus disconnecting LexA from B42, and inactivating transactivation by the fusion protein. The role of the proteasome in the proteolysis of Smad1 can be demonstrated in this assay by either adding proteasome inhibitors, or mutating one or more of the regulatory components of the 20S proteasome, which will only prevent proteolysis if such proteolysis is indeed proteasome mediated. When Leu2 is used as a reporter, the read out for inhibition of Smad proteolysis is the ability of yeast cells containing ALK3QD to resume growth on plates lacking leucine. A reporter expressing β-galactosidase may also be used as a readout through inclusion of X-gal in the medium. Colonies rendered unable to metabolize X-gal by proteolysis of the Smad or Smad interactor protein will be white, while those which can metabolize X-gal will be blue.

This assay can be used to screen for compounds that block proteolysis induced by activation of TGF-β signal transduction pathways. Small compounds may be screened by adding them to the established degradation system and monitoring changes in reporter gene activities. Alternatively, a peptide library may be screened by transforming the yeast containing the degradation system with the library and selecting those colonies which exhibit altered reporter activity.

Compounds identified in such a screen would be candidate drugs for blocking the hyperactivities of TGF-β family ligands associated with different diseases (described below), in particular kidney fibrosis caused by hyperactivity of TGF-β and progressive osseous heteroplasia. Progressive osseous heteroplasia is a rare developmental disorder of mesenchymal differentiation characterized by cutaneous osteomas in infancy and by progressive heterotopic intramembranous ossification of skin and deep connective tissue (Rosenfeld and Kaplan, 1995, Clin. Orthopaedics & Rel. Res., 317:243–245). This assay is also useful for identifying novel proteasome inhibitors.

The assay can be modified such that it is useful for identifying compounds that can potentiate the proteolysis of Smads, or function as general activators of proteasome activities. The modification to this assay is to replace the Leu2 reporter, with an apoptotic factor such as Bax, or a toxin. Overexpression of such a protein (e.g. Bax or a toxin) will prevent the growth of the transformed yeast cells. According to the method of this modified assay, the expression of the fusion protein will be under the control of a GAL4 promoter. Yeast are initially transformed with ALK3, the fusion protein, and the reporter. The transformants are selected on glucose plates, thus suppressing the expression of the fusion protein. In order to screen for compounds that can potentiate Smad (e.g. Smad1) proteolysis, cell are plated on galactose plates, allowing the expression of the fusion protein. The cells can only grow in the presence of a compound that activates proteasome mediated proteolysis of Smad1. If compounds are found to induce Smad1 proteolysis in the presence of ALK3, these compounds may either activate ALK3, or directly activate proteasome. The above assay can allow us to distinguish between these two possibilities by testing whether the compound can still allow the cells to grow if the yeast is not transfected with ALK3.

In addition to assays of proteasome activity performed in yeast or mammalian cells, cell free in vitro assays may be performed. Such an assay uses purified proteasomes (isolated according to the method of Hough et al., 1987, supra), and a tagged (e.g., Histidine or GST) substrate of interest isolated from E. coli. The proteasomes and test substrate are mixed, together with cell extracts or components from cells transfected with Smads or with the wild-type or constitutively active TGF-β family receptors. Such mixtures are monitored for degradation of the test substrate by Western blot or by methods which take advantage of the tag, as described above. Compounds which modulate the proteolytic activity may be screened by performing proteolysis reactions in the presence and absence of candidate compounds. Additional information may be gained from this assay by fractionation of the cell extracts to identify that fraction which allows the proteolysis of the protein of interest upon its addition to the mixture of proteasomes and test substrate. Methods for preparation of cell extracts and fractionated cell extracts (i.e., nuclear, cytoplasmic, or microsomal fractions) are discussed by Hoffman et al., 1992, J. Biol. Chem., 267: 22362–22368, Palmer et al., 1996, Biochem. J., 316: 401–407, and references therein. The nuclear fraction may be further fractionated, for example, into nuclear matrix and non-matrix fractions. The microsomal fraction may be further divided into plasma membrane, smooth and rough endoplasmic reticulum and Golgi complex and mitochondrial fractions. The cytosolic fraction could be separated according to protein charge and weights using appropriate ion exchange and size exclusion columns (Hoffman et al., 1992, supra; Palmer et al., 1996, supra, and references therein). Once identified, the mixture of proteasomes, test substrate and activating cell fraction will constitute a kit for screening compounds that modulate the proteolysis of a protein of interest.

Almost all advanced cancers are associated with TGF-β resistance. If the resistance is caused by defects of Smad proteolysis, compounds identified in the screening assays described above, may be useful as potential anti-cancer therapeutics. A non-limiting list of cancers for which activators of TGF-β sensitivity may prove therapeutic include colorectal, pancreatic, head and neck, prostate and breast cancers.

BMPs are important bone modeling agents. New drugs useful for treating osteoporosis are expected to be derived from agents that can mimic the activities of BMPs. Thus, compounds identified in the above screens may be candidate drugs for novel osteoporosis therapeutics.

Method for Mapping the Interaction Domains of Proteasome Interactors

The invention provides methods of mapping the domains of proteasome interactors which are required for the identified interaction to occur. One such method uses the yeast two hybrid approach. Briefly, yeast (strain EGY48) containing a LexA-driven LacZ reporter and a Leu2 reporter are first transformed with a construct encoding a fusion of the B42 activation domain with the proteasome subunit HsN3 under the control of the Gal4 promoter. Transformants which grow on selective minimal medium plates (U$^-$W$^-$ glucose) are then transformed again with constructs encoding LexA fusions with full length and deletion constructs of the protein of interest. The transformants are first streaked onto selective minimal medium plates (U$^-$H$^-$W$^-$ glucose) and then replica plated onto test plates containing X-gal with either glucose or galactose. Because it is under the control of the Gal4 promoter, the B42-HsN3 fusion is not expressed on glucose plates but is strongly expressed on galactose plates. Interaction of the HsN3 fusion with the LexA test protein fusion activates β-galactosidase activity, resulting in blue colonies. Comparison of LexA fusions bearing different deletions of the protein of interest (e.g., a Smad or other protein found to interact with the HsN3 proteasome subunit) using this assay will allow determination of the region(s) of the protein required for the interaction. Knowledge of the domain mediating the interaction will be useful in identifying or designing modulators of the interaction.

In addition to the yeast two hybrid method, an in vitro binding assay may be used to identify the domain(s) necessary for protein interaction with a proteasome component. To perform such an assay, the HsN3 protein is subcloned into a His-tag vector (such as PET28a (Invitrogen), which tags the amino terminus with a hexahistidine motif), then expressed in and isolated from E. coli by incubation with Ni$^{++}$-coated beads. COS, or other readily transfected mammalian cell line cells are transfected with Flag-tagged full length and deletion mutant test proteins. The expression of the Flag-tagged proteins is checked by Western blotting with anti-Flag antibodies. Lysates from cells transfected with the Flag-tagged test interactors are mixed with Ni$^{++}$ coated beads bearing the HsN3 protein, and the beads are washed, boiled in protein sample buffer and the eluted proteins analyzed by Western blotting with anti-Flag antibodies. Differences in recovery of Flag-tagged test interactors will allow determination of the domain(s) necessary for the observed interaction. In addition to this method, the mammalian two-hybrid method described herein may be used to map interaction domains.

Measuring Modifications of the Proteasome β-Subunit by TGF-β Family Signaling

The invention provides methods of measuring modifications of the proteasome β-Subunit including, but not limited to phosphorylation, stability, processing, and assembly of proteasome beta subunits. In particular, the invention provides methods of measuring modifications of the N3 subunit of the proteasome.

Phosphorylation can be measured in vivo according to the following method. TGF-β and BMP responsive cells are treated with TGF-β or BMPs in the presence of $^{32}$P-orthophosphate. A replicate sample of control cells are not treated with TGF-β or BMPs. Cell lysates are immunoprecipitated with antibodies capable of binding to specific beta subunits. Phosphorylation of beta subunits is detected by SDS-PAGE and autoradiography.

The stability of various proteasome β-subunit proteins is determined by measuring the amount of a particular proteasome β-subunit protein in a cell lysate by Western blot analysis using anti-beta subunit antibodies. Western blot analysis is performed as described above.

The processing of proteasome β subunits can be measured by pulse chase assays according to the following method. TGF-β and BMP responsive cells are metabolically labeled with $^{35}$S methionine for 2 hours. Cells are then "chased" for various amounts of time, by incubation in media lacking $^{35}$S methionine. Proteins are immunoprecipitated with specific antibodies capable of binding to specific proteasome β-subunit proteins, and analyzed on two-dimensional gels. The pulse chase assay can also be used to analyze the assembly of proteasome β-subunits.

To measure the effects TGF-β family ligands have on the assembly or processing of the β subunits, the methods reported by Thompson et al., 1996, Biochem. J., 315: 733–738, Chen et al., 1996, Cell, 86: 961–972, Frentzel et al., 1994, J. Mol. Biol., 236: 975–981, and Nadndi et al., 1997, EMBO J., 16: 5363–5375 may be used. In these assays, TGF-β family ligands are introduced to TGF-β-responsive cells, followed by assays for assembly or processing as described. β subunits may be immunoprecipitated directly from cell lysates with anti-β antibody, or the cell lysates may be fractionated by sucrose or glycerol gradient prior to immunoprecipitation from the different fractions.

Measuring Proteasome-Mediated Degradation of a Substrate in Response to Type I Receptor Activation In Vivo BMPs are found to induce the degradation of a set of Smad1 interacting proteins including a number of known proteasome substrates such as Smad1, 2, 3,4, SNIP-1 (clone 19 of Smad1 interacting protein; SEQ ID No. 3), clone 51 and 21 (SEQ ID No. 1), antizyme, FAST1 (Smad2 interacting), FAST2 (Smad2 interacting), HEF1 and RBP2 (Smad3 interacting protein, clone 63). The invention provides a method of measuring BMP-induced proteolysis of various Smad1 interacting proteins by the proteasome.

According to this method, COS cells are transfected with Smad1, and a Smad1 interacting protein of interest, in conjunction with either ALK3QD, or, as a control, ALK3. Western blot analysis of each Smad1 interactor is then carried out to measure the amount of proteasome substrate present in a sample, as described. Lactacystin is added to demonstrate that the degradation is occurring via a proteasome specific mechanism.

Pulse chase assays (described above) can also be performed to detect proteolysis of Smad1 interacting proteins.

Proteasome mediated degradation of SNIP-1 upon ALK3QD expression requires the simultaneous expression of antizyme, Smad1 and Smad4. Therefore, assays designed to measure the proteolysis of SNIP-1 are performed in COS cells transfected with SNIP-1, Smad1, Smad4 and ALK3QD. Since the proteasome mediated degradation of other Smad1 interacting proteins may be enhanced in the presence of Smad4, it may be useful to measure the proteolysis of Smad1 interacting proteins in COS cells transfected with the Smad1 interacting protein of interest, along with Smad1, Smad4 and ALK3QD. The proteolysis of other factors in the TGF-β family signal transduction pathway may be assessed in a similar fashion.

Evidence indicating that proteasome-mediated proteolysis of proteins is induced upon the activation of the TGF-β family type I receptors (TGF-beta type I receptor R4, also called ALK5, BMP type I receptor ALK3 and ALK2, activin type I receptor R2, also called ALK4) has been obtained. Such proteins (HsN3, HC5, antizyme, PAG, SNIP1, SIP2, HEF1, RBP2, FAST1, Smad1, Smad2, Smad3, Smad4) and the conditions for their proteolysis by the proteasome have been identified. Therefore, the proteolysis of these proteins will be an important target for screening of small compounds or peptides that can modulate such proteolysis, thereby modulating the biological activities of the TGF-β family ligands.

Combinations of factors to co-express with wild-type or constitutively active type 1 and type 2 receptors to examine the proteolysis of specific factors are suggested below.

To examine the proteolysis of antizyme, one should cotransfect constructs expressing: Smad2, Smad3, Smad4, antizyme and R2 or R2TD; and Smad1, Smad4, antizyme, SNIP-1 and ALK3 or ALK3QD.

To examine the proteolysis of Smad1, 2, 3 and 4, one should co-transfect constructs expressing: Smad1, Smad 4 and ALK3 or ALK3QD; Smad1, Smad4, antizyme and ALK3 or ALK3QD; Smad2, Smad3, Smad4 and R4 or R4TD; and Smad2, Smad3, Smad4 and R2 or R2TD.

To examine the proteolysis of HsN3, one should co-transfect constructs expressing: Smad1, HsN3 and ALK3 or ALK3QD; Smad2, HsN3 and R2 or R2TD; Smad1, HsN3 and ALK3 or ALK3QD; Smad2, HsN3 and R4 or R4TD; Smad3, HsN3 and R2 or R2TD; and Smad3, HsN3 and R4 or R4TD.

To examine the proteolysis of HC5, one should co-transfect constructs expressing: Smad1, HC5 and ALK3 or ALK3QD; Smad2, HC5 and R2 or R2TD; Smad2, HC5 and R4 or R4TD; Smad3, HC5 and R2 or R2TD; and Smad3 and R4 or R4TD.

To examine the proteolysis of SNIP-1, one should co-transfect constructs expressing: Smad1, Smad4, antizyme, SNIP1 and ALK3 or ALK3QD; and Smad1, Smad4, antizyme, SNIP1 and R1 or R1QD.

To examine the proteolysis of SIP2, one should co-transfect constructs expressing: Smad1, Smad4, Antizyme, SIP2 and ALK3 or ALK3QD; and Smad1, Smad4, Antizyme, SIP2 and R1 or R1QD.

To examine the proteolysis of RBP2, one should co-transfect constructs expressing: Smad1, Smad4, Antizyme, PAG and ALK3 or ALK3QD; and Smad1, Smad4, Antizyme, PAG, R1 or R1QD.

To examine the proteolysis of FAST1, one should co-transfect constructs expressing: FAST1 and Smad2 or Smad2C; and FAST1, Smad2 and R2 or R2TD.

To examine the proteolysis of HEF1, one should co-transfect constructs expressing: HEF1 and Smad1; HEF1 and Smad3; HEF1, Smad3 and R4 or R4TD; and HEF1, Smad3 and R2 or R2TD.

To examine the proteolysis of PAG, one should co-transfect constructs expressing: RBP2, Smad3 and R2 or R2TD; and RBP2, Smad3 and R4 or R4TD.

To examine the proteolysis of PAG, one should co-transfect constructs expressing: AIP4 and Smad3; AIP4, Smad3 and R2 or R2TD; and AIP4, Smad3 and R4 or R4TD.

Method of Measuring the Change in Proteasome β-Subunit Processing in Response to Type I Receptor Activation In Vivo Changes in proteasome β-Subunit processing in response to Type I Receptor activation can be measured in vivo by pulse chase assays according to the following method. TGF-β and BMP responsive cells are transfected with type I receptors (ALK1–7) and metabolically labeled with $^{35}S$ methionine for 2 hours. Cells are then "chased" for various amounts of time, by incubation in media lacking $^{35}S$ methionine. Proteins are immunoprecipitated with antibodies specific for proteasome β-subunits, and the processing of proteasome β-subunits is analyzed on two-dimensional gels. Alternatively, proteins may be fractionated by sucrose or glycerol gradient prior to immunoprecipitation with anti-β antibodies according to the methods of Thompson et al., 1996, supra, Chen et al., 1996, supra, Frentzel et al., 1994, supra, and Nadni et al., 1997, supra.

Method of Measuring the Change in Assembly of Proteasome β-subunits in Response to Type I Receptor Activation In Vivo Changes in proteasome β-Subunit assembly in response to Type I Receptor activation can be measured in vivo by pulse chase assays according to the following method. TGF-β and BMP responsive cells are transfected with type I receptors (ALK1–7) and metabolically labeled with $^{35}S$ methionine for 2 hours. Cells are then "chased" for various amounts of time, by incubation in media lacking $^{35}S$ methionine. Proteins are immunoprecipitated with antibodies specific for proteasome β-subunits, and the assembly of proteasome β-subunits is analyzed on two-dimensional gels.

Method of Measuring Changes in Proteasome Catalytic Activity and Substrate Specificity in Response to Type I Receptor Activation In Vivo TGF-β and BMP responsive cells are metabolically labeled with $^{35}S$ methionine for 2 hours. Replicate samples of cells are incubated in the presence or absence of a TGF-β family member ligand and then immunoprecipitated with proteasome specific antibodies. Proteasome activity is measured in vitro according to the method described by Hoffman et al. using different peptide substrates (Hoffman et al., 1992, supra).

Briefly, a standard assay mixture contains in a final volume of 100 μl buffer E (50 mM Tris-HCl, pH 7.8, 25 mM KCl, 10 mM NaCl, 1.1 mM MgCl$_2$, 1 mM DTT, 0.1 mM EDTA and 10% glycerol), $^{125}$I-lysozyme-ubiquitin conjugate, or 0.1 mM fluorogenic peptides plus the enzyme. Final concentrations of glycerol and Me$_2$SO were 10% and 1% respectively. In assay mixtures containing nucleotides, the final concentration was 2 mM. Proteolytic assays were quenched by the addition of 800 µl of ice-cold 1% BSA and 100 µl 100% trichloracetic acid. After 30 minutes on ice, the samples were centrifuged for 15 minutes in an Eppendorf microfuge. Radioactivity in the supernatants and the precipitated pellets was counted by gamma spectrophotometry. The peptide assays were quenched by the addition of 200 µl ice-cold absolute ethanol and fluorescence was measured (380 nm excitation, 440 nm emission) in a Spex spectrofluorometer. The fluorogenic data were calibrated to standard curves of free 4-methylcoumaryl-7-amide (MCA) (0–0.2 mM) and pronase digestions of the fluorogenic peptides. Data are expressed as the percentage of the total protein which was acid-soluble per unit time, or as the percentage of the total released from the peptides as free MCA. Assays for proteolytic activity were performed at 37° C. from 0 to 60 minutes. One unit of activity is defined as one nanomole of substrate hydrolyzed per minute at 37° C. Protein determination was done by the Bradford method using BSA and lysozyme as standards (Hough et al., 1987, *J. Biol. Chem.*, 262:8303–8313).

Method of Measuring Substrate Docking Activity of Antizyme During the Degradation of Smad1 Interacting Proteins The invention provides a method for measuring the substrate docking activity of antizyme that mediates degradation of Smad1 interacting proteins. Briefly, COS cells are cotransfected with antizyme (different concentrations of a plasmid expressing the antizyme protein) and a Smad1, Smad2 or Smad4 interacting protein of interest (e.g. SNIP-1). The degradation of the Smad interacting protein is measured by Western blot analysis (as described). According to this method, if antizyme functions as a docking protein during the degradation of a Smad interacting protein, the degradation of this protein will be dependent upon the presence of antizyme (e.g. degradation will not occur or will be decreased in the absence of antizyme protein).

Identifying Compounds that Modulate the Interaction Between a Smad Protein and A Smad Interacting Protein A modified yeast two-hybrid approach can be used to identify modulators that interfere with the interaction between a Smad protein and a Smad interacting protein, according to the invention. Similarly, a modified yeast two-hybrid approach can be used to identify modulators that alter the enzyme activity of Smad interacting proteins.

The yeast two-hybrid approach will utilize yeast (e.g. EGY48) containing a LacZ reporter plasmid, bait comprising a LexA-Smad1 fusion protein, and prey comprising fusion proteins comprising B42-Smad1 interacting protein chimeras. Alternatively, bait comprising LexA-Smad2 or 3 fusion proteins and prey comprising fusion proteins comprising B42-Smad2 or 3 interacting protein chimeras can be used.

To identify small peptide modulators that increase or decrease the interaction between a Smad protein and a Smad interacting protein, a yeast (containing a LacZ reporter plasmid, bait comprising a LexA-Smad fusion protein, and prey comprising fusions between B42 and a Smad interacting protein) is transformed with a peptide library. Yeast cells that demonstrate increased or decreased reporter gene activity (e.g. lacZ encoded β-galactosidase activity) are identified. To identify small molecules that increase or decrease the interaction between a Smad protein and a Smad interacting protein, a yeast (containing a LacZ reporter plasmid, bait comprising a LexA-Smad fusion protein, and prey comprising fusions between B42 and a Smad interacting protein) is grown on a plate to which a small molecule of interest has been directly applied. Yeast cells that demonstrate increased or decreased reporter gene activity (e.g. lacZ encoded β-galactosidase activity) are identified.

Identifying Compounds that Alter HsN3 Processing and/or Assembly

HsN3 processing and assembly represent targets for modulation of TGF-β family ligand activities (Thomson & Rivett, 1996, *Biochem. J.*, 315: 733–738; Nandi et al., 1997, *EMBO J.*, 16: 5363–5375). A modified yeast two-hybrid approach can be used to identify modulators that interfere with HsN3 processing and/or assembly.

The yeast two-hybrid approach will utilize yeast (e.g. EGY48) containing a LacZ reporter plasmid, bait comprising a LexA-HsN3 fusion protein, and prey comprising fusions between B42 and the proteins comprising the neighboring subunits of HsN3.

This assay can be used to identify small peptides and small compounds that modulate the interaction between HsN3 and its neighboring subunits, and in turn modulate proteasome activities. To identify small peptide modulators that modulate the interaction between HsN3 and its neighboring subunits, a yeast is transformed with a peptide library. Yeast cells (containing a LacZ reporter plasmid, bait comprising a LexA-HsN3 fusion protein, and prey comprising fusions between B42 and the proteins comprising the neighboring subunits of HsN3) that demonstrate increased or decreased reporter gene activity (e.g. lacZ encoded β-galactosidase activity) are identified. To identify small molecules that modulate the interaction between HsN3 and its neighboring subunits, a yeast (containing a LacZ reporter plasmid, bait comprising a LexA-HsN3 fusion protein, and prey comprising fusions between B42 and the proteins comprising the neighboring subunits of HsN3) is grown on a plate to which a small molecule of interest has been directly applied. Yeast cells that demonstrate increased or decreased reporter gene activity (e.g. lacZ encoded β-galactosidase activity) are identified.

Yeast Two-Hybrid Method for the Identification of Novel Smads

It has been demonstrated that Smads are capable of forming homo-oligomers and complexes with other Smads in yeast. Thus, a known Smad may be used to identify other novel Smads using a yeast two-hybrid system. This may be accomplished using the following steps: 1) make a hybrid protein fusing a full length Smad and a DNA binding domain; 2) introduce the hybrid protein into a yeast strain which contains the other necessary components of a yeast two-hybrid system as described elsewhere in this document (i.e., selectable marker/reporter genes); 3) introduce a cDNA library, prepared in a vector which fuses the library sequences to a transactivation domain (e.g., Gal4) into the yeast strain expressing the Smad:DNA binding domain fusion; 4) select clones which express the reporter gene function, an indicator that a productive or functional interaction (i.e, one which brings the DNA binding domain of the Smad fusion into association with the transactivation domain of the library fusion and allows expression of the reporter gene) has occurred in that clone; 5) probe the nucleic acid of such interaction-positive clones with $^{32}$P-labeled nucleic acid probes derived from different Smads to identify yeast colonies which contain cDNAs of Smad-like proteins; 6) isolate the plasmid DNA sequences from colonies identified in step 5 and sequence the cDNA; and 7) compare the sequence thus obtained with the sequences of known Smads, such that clones with sequences which are not identical to any known Smad are identified as novel Smads.

As used herein, the term "nucleic acid probe" refers to a nucleic acid molecule or polynucleotide of at least 8 nucleotides (nt), 10 nt, 15 nt, 20 nt, 30 nt, 40 nt, 50 nt, 75 nt, 100 nt, 200 nt, 500 nt, 1000 nt, up to the full length of the nucleic acid sequence sought to be detected. To be used in the identification of novel Smad proteins, such a probe will comprise one or more sequences of nucleotide bases which are complementary to a known Smad protein coding sequence.

As used herein, the term "sequence" as applied to DNA, a polynucleotide or oligonucleotide refers to a number of contiguous nucleotides having a length greater than or equal to two nucleotides, including 8, 10, 12, 20, 30, 50 or even up to 100 to 1000 or more nucleotides and a sequential order of nucleotide bases characteristic of a particular DNA, polynucleotide or oligonucleotide molecule.

As used herein, the term "oligonucleotide" refers to a sequence of nucleotides generally about 5 to 100 nucleotides in length.

The choice of Smad sequences to employ as a probe within the above-described assay for the identification of novel Smads will depend upon several factors. First, sequences drawn from the conserved regions of the Smad protein, including the MH1 and MH2 domains, are useful in that their conservation among known Smads indicates they may be present in the coding regions of novel Smad "target" genes. Second, sequences drawn from the less well-conserved regions of the coding sequence are useful in that they may hybridize with novel Smad gene family members which are more closely related to a particular Smad than to all other Smads in general. Of course, a probe or probes comprising the full length of a known Smad gene or an oligonucleotide probe or probes derived from any part of it may be used as a probe according to the invention.

In addition to the region of the known Smad gene chosen as a source of probe sequence, the length and nucleotide composition of the nucleic acid probe sequence are important factors in defining hybridization conditions. Generally, the greater the number of probe bases complementary to those of the target gene, the more stable and specific the hybridization between them will be, and the more stringent the hybridization conditions used may be. This applies to oligonucleotide probes as well as longer probes (i.e., those greater than 100 nt in length).

Additionally, the greater the proportion of G and C nucleotides relative to A and T (or U) nucleotides in the probe sequence, the more stably the probe will hybridize to the target sequence, and accordingly, the more stringent the hybridization conditions used may be.

The term "stable hybridization," as used herein, is meant to refer to hybridization which is detectable under a given set of hybridization conditions. The term "specific hybridization" is meant to refer to hybridization to a single nucleic acid target sequence. By definition, the hybridization of a probe sequence chosen or "derived" from a known Smad sequence to a sequence within a novel Smad sequence is not strictly specific. However, hybridization conditions under which specific hybridization occurs (referred to herein as "high stringency conditions") may be used by one of skill in the art, without undue experimentation, to design conditions of "reduced" stringency such that hybridization occurs with sequences which, although not 100% complementary to the probe sequence, are closely related to the probe sequence. For example, the two factors which most influence hybridization stringency are temperature and salt concentration. The presence, concentration or absence of formamide in the hybridization solution also plays a role.

In order to adjust the stringency of hybridization such sequences which are closely related, but not identical to the probe sequence are detected, one must first establish high stringency conditions for the probe sequence to be used. This may be done using control replica membranes (see Sambrook et al., *Molecular Cloning: A Laboratory Manual*, Second Edition, 1989, (Cold Spring Harbor Press, Cold Spring Harbor, N.Y. for the method of preparing replica membranes with immobilized yeast or bacterial DNA) containing DNA from yeast colonies expressing the same Smad as that being used as a hybridization probe (positive control) and yeast DNA (either on the same membranes or on separate membranes) from colonies not containing that DNA sequence (negative control). The probe, labeled according to methods known in the art (see Sambrook et al., 1988, supra, or Ausubel et al., 1988, *Current Protocols in Molecular Biology*, (John Wiley & Sons, Inc., NY, N.Y.)) is hybridized to the membrane(s) and washed as described below. The signal detected by autoradiography indicates specific hybridization if there is only signal on the colonies bearing the Smad gene positive control sequence. If, using the conditions below, there is signal on the negative control colonies, one of skill in the art may use the replica membranes for hybridizations in which one parameter at a time (salt concentration or temperature of hybridization and washes or formamide concentration in the hybridization) is varied to establish conditions which are specific for the probe being used.

The methods of nucleic acid hybridization are well known to those skilled in the art (Sambrook et al, 1988, supra; Ausubel et al., 1989, supra). The specific conditions given below are for hybridization using oligonucleotide probes less than or equal to 70 nucleotides long and DNA immobilized on nylon membrane. One of skill in the art may readily adapt these conditions for use with probes longer than 70 nt, for the use of double stranded probes, or for the use of membranes other than nylon according to the teachings of Sambrook et al., 1888, supra, or Ausubel et al., 1989, supra. Common adjustments include addition of formamide to the hybridization and pre-hybridization, inclusion of non-specific blocking agents such as denatured, sheared salmon sperm DNA in the pre-hybridization and hybridization, and inclusion of volume excluders such as dextran sulfate.

Methods for preparing membranes with immobilized yeast or bacterial colony DNA are described by Sambrook et al., 1988, supra, and methods of labeling oligonucleotide probes with $^{32}P$ are also described in both of these standard references.

For oligonucleotide probe hybridization of yeast colony DNA immobilized on membranes, the membranes are pre-hybridized in a hybridization solution containing 6×SSC (0.9 M NaCl, 90 mM trisodium citrate, pH 7.0), 5×Denhardt's reagent (0.1% (w/v) Ficoll 400 , 0.1% (w/v) polyvinylpyrrolidone, 1 mg/ml bovine serum albumin (Pentax Fraction V)), and 0. I % SDS. Membranes are pre-hybridized at 42° C. for 1 to 2 hours, with constant agitation.

Following pre-hybridization, the labeled probe is added to hybridization solution and incubated with the pre-hybridized membranes at 42° C. for 12 to 18 hours, with constant agitation.

For washing to remove unbound probe, it is critical that the $T_m$ of the probe sequence be calculated, as the temperature used during washing largely determines the stringency of the washes. $T_m$ is calculated using one of the following formulae: for oligonucleotides shorter than 18 bases, use the formula $T_m = 2°\text{ C.}(A+T) + 4°\text{ C.}(G+C)$; for oligonucleotides 14 bases and longer (up to 60–70 nucleotides), use the formula $T_m = 81.5 + 16.6(\log_{10}[Na^+]) + 0.41(\%G+C) - (600/n)$, where "n" is the chain length. Due to the effects of base stacking, near neighbor effect and buffering capacity, which will vary with the exact oligonucleotide sequence, this formula gives a close approximation of $T_m$. Using this temperature as a starting point, one may determine the optimal hybridization and wash temperatures according to the replica hybridization method described above.

After hybridization, the membranes are washed two times for 10 minutes each at room temperature in a large volume (as used herein, "large volume" means ≧300 ml per wash) of a wash solution containing 2×SSC buffer and 0.1% (w/v) SDS to remove the hybridization solution and any unbound probe. The membranes are then washed once for 30 minutes at a temperature 10° C. below the calculated $T_m$ in a large volume of a prewarmed wash solution containing 6× SSC buffer and 0.1% (w/v) SDS. Next, membranes are washed once for 30 minutes at a temperature 5° C. below the calculated $T_m$ in a large volume of a prewarmed wash solution containing 6×SSC buffer and 0.1% (w/v) SDS.

Washed membranes are immediately wrapped in plastic wrap, mounted in an x-ray cassette, marked for later orientation of the membranes with the film (radioactive ink or fluorescent markers may be used), and exposed to X-ray film at −80° C. with intensifying screens for 6 to 48 hours. Alternatively, a phosphorimager or high-sensitivity film may be used to shorten exposure times. After developing, the autoradiograph film is aligned on the mounted membrane, and the positions of the positive colonies identified.

The sequences of positive clones may be compared with those of known Smads with any of a number of widely available computer algorithms. One simple method is to search the GenBank nucleic acid and protein databases for sequences showing homology to the putative novel Smad. The GenBank nucleic acid sequence database may be searched for a sequence matching a particular test sequence using the BLAST suite of programs (Altschul et al., 1997, Nucl. Acids Res. 25: 3389) available online through the National Center for Biotechnology Information at http://www.ncbi.nlm.nih.gov/BLAST. The BLAST 2.0 program may be set in the following manner to identify database sequences with 100% identity to a test sequence: 1) select the program "blastn" and database "nr"; 2) select the "perform ungapped alignment" check box; 3) enter the sequence in FASTA format (details available in online link from this WWW page); 4) set parameters as follows: Filter, none (this forces the program to use the full length of the test sequence in its alignment; Descriptions, 50; Alignments, 500; Matrix, BLOSUM 62 (default settings); and "Other advanced options," -e-161; and 5) submit the query. Sequences will be reported in the order of their rank by similarity, and the number of identities at particular nucleotide sites will be indicated for each sequence reported, along with the percent identity. 100% identity over the full length of the sequence indicates that the test sequence is identical to the indicated sequence from the database. The failure of the program to identify sequences with 100% identity indicates the sequence is novel in the GenBank database. The default parameters of the program may also be used to identify a list of known protein coding sequences with varying degrees of similarity to the sequence used as a query.

For a sequence to be considered "closely related" to a given probe sequence, it can be from 100% to 20% complementary to the probe sequence. This broad range is acceptable according to the invention because this complementarity may be localized in stretches of contiguous nucleotide bases, distributed over various regions of the probe and disrupted by intervening non-complementary bases, or a combination of these. This is particularly true for non-oligonucleotide probes. For example, nucleotide sequences coding for a characteristic protein motif in a novel protein may be identical or only lack complementarity at the third base of each codon due to the redundancy of the genetic code. This motif, however, may only comprise 20% of the non-oligonucleotide probe sequence used. In such a case, the isolated gene would still be considered to be closely related to the gene from which the probe was derived. It is important to note in this description of the relatedness of sequences that sequences being analyzed by hybridization according to this aspect of the invention will, by virtue of their selection in the two-hybrid screen for interaction with a known Smad, necessarily encode motifs or domains allowing this interaction. In the example cited above, the identity or complementarity with the probe sequence may be restricted to only the sequence coding for the shared motif, but the sequences would still be considered "closely related." Additionally, nucleotide sequences coding for a similar, but non-identical motif may contain stretches of complementarity, corresponding to identical amino acids, separated by stretches of non-complementarity where the amino acid sequences differ.

A novel clone identified using the preceding methods may be considered a Smad if it has both sequence homology and functional roles in the signaling pathways of TGF-beta family ligands. There are three identified classes of Smads: R-Smads, which transduce active signaling and include Smads 1, 2, 3, 5 and 8; co-Smads, which function as a partner for the R-Smads and include Smad4; and anti-Smads, which are inhibitors of R-Smads and include Smads 6 and 7. The common homology between these proteins is within the carboxyl terminal MH2 domains. At the sequence level, greater than or equal to 20% identity and 30% similarity is required for a novel clone to be identified as a new Smad. However, the key determinant for inclusion of a novel protein in the Smad family is that it also plays one of the three functional roles identified above.

Yeast Two-Hybrid Method to Identify Novel Tissue Specific Smad Interactors

Smads are key signaling components of various TGF-β family ligands. Since each TGF-β family ligand exhibits tissue and cell type specific biological activities, Smads must interact with tissue and cell type specific functional partners. A method to identify such tissue and cell-type specific functional partners consists of the following steps: 1) make a hybrid protein fusing a full length Smad and a DNA binding domain; 2) introduce the hybrid protein into a yeast strain which contains the other necessary components of a yeast two-hybrid system as described elsewhere in this document (i.e., reporter genes); 3) introduce a cell type specific or tissue specific cDNA library, prepared in a vector which fuses the library sequences to a transactivation domain (e.g., Gal4) into the yeast strain expressing the Smad:DNA binding domain fusion; 4) select clones which express the reporter gene function, an indicator that a productive or functional interaction (i.e, one which brings the DNA binding domain of the Smad fusion into association with the transactivation domain of the library fusion and allows expression of the reporter gene) has occurred in that clone; 5) probe DNA isolated from interaction positive yeast colonies with probes specific for all known Smad interacting proteins disclosed herein (i.e., all of the Smad1 and Smad3 interactors identified) to identify clones which do not hybridize with known Smad interactors; 6) isolate and sequence the new Smad interactor clones; and 7) use the sequences of the clones isolated in steps 1–6 as probes of multi-tissue Northern (RNA) blots to confirm tissue specific expression of the genes encoding new Smad interacting proteins.

The methods of preparing Southern and Northern blot filters containing immobilized DNA and RNA, respectively, are well known in the art and are described in detail by both Sambrook et al., 1988, supra, and Ausubel et al., 1989, supra. The method for preparation of dot blot filters containing immobilized DNA is similarly well known in the art, and is described by Kafatos et al., 1979, *Nucl. Acids Res.*, 7:1541. Hybridization methods and conditions suitable for Southern, Northern and dot blot analyses are described in detail by both Sambrook et al., 1988, supra, and Ausubel et al., 1989, supra.

Tissue specific Smad interactors may be used as targets in screening assays as described herein to identify tissue specific modulators of TGF-β family ligands.

Use of Smad Expression as a Prognostic Indicator for Cancer Progression

Smad2, 3 and 4 have been found to be tumor suppressors (Massague, 1998, *Ann. Rev. Biochem.*, 67: 753–791; Takagi et al, 1998, *Brit. J. Cancer. Res.* 78: 1152–1155; Powell et al., 1997, *Cancer Res.*, 57: 4221–4224; Le Dai et al., 1998, *Cancer Res.*, 58: 4592–4597; Takei et al., 1998, *Cancer Res.*, 58: 3700–3705; Grau et al., 1997, *Cancer Res.*, 57: 3929–3934; Takenoshita et al., 1998, *Carcinogenesis*, 19: 803–807; Zhu et al., 1998, *Cell*, 94: 703–714; Nakao et al., 1997, *J. Biol. Chem.*, 272: 2896–2900; Zavadil et al., 1997, *Leukemia*, 11: 1187–1192; Wu et al., 1997, *Mol. Cell Biol.*, 17: 2521–2528; Weinstein et al., 1998, *Proc. Natl. Acad. Sci. U.S.A*, 95: 9378–9383; Zhou et al., 1998, *Proc. Natl. Acad. Sci. U.S.A.*, 95: 2412–2416; Howe et al., 1998, *Science*, 280: 1086–1088; Lemoine, 1997, *Digestion*, 58: 550–556; Sirivatanauksorn et al., 1998, *Langenbeck's Arch. Surg.*, 383: 105–115; Hata et al., 1998, *Mol. Med. Today*, 4: 257–262; Villaneuva et al., 1998, *Oncogene*, 17: 1969–1978; Reiss, 1997, *Oncol. Res.*, 9: 447–457). Defects in these Smads are found in many types of cancer and may underlie the resistance of various cancers (e.g., breast cancers, prostate cancers) to growth inhibition by TGF-β family members. Therefore, the expression of Smads and Smad-interacting proteins at both the mRNA and protein levels may be used as a measure of the progression of cancer or as an indicator of the prognosis for treatment. In addition, the identification of a specific protein defect in a tumor makes gene therapy approaches to treatment possible.

In order to monitor Smad expression as an indicator of disease progression according to the invention, samples taken from tumor tissue are examined for the levels of expression of Smads and/or Smad interacting proteins or their mRNAs. These levels are then compared with those in non-tumor tissue, preferably of the same tissue origin, and preferably, but not necessarily from the same individual. For factors whose expression is necessary for TGF-β family member-regulated growth inhibition, a lower level in the tumor tissue relative to the non-tumor tissue indicates that that factor is deficient in the tumor tissue and may be involved in the tumor cell phenotype. Conversely, overexpression of factors involved in down-regulating the growth inhibitory effects of TGF-β family members in tumor versus non-tumor tissue indicates that that factor may be involved in the tumor phenotype.

The expression levels of Smads and Smad interactors may be monitored in a number of ways according to this aspect of the invention. mRNA may be measured either directly, by methods such as Northern blot hybridization or in situ hybridization, or indirectly, by such methods as reverse-transcription PCR (RT-PCR).

Northern blot hybridization methods are well know n in the art and were discussed above. RT-PCR is similarly well known in the art (see Mullis & Faloona, 1987, *Methods Enzymol.*, 155:335), as are methods of quantitative and semiquantitative RT-PCR (Dassi et al., 1998, *Clin. Chem.*, 44:2416; Köhler et al., 1995, *Quantitation of mRNA by polymerase chain reaction*, Springer).

In situ hybridization involves the hybridization of labeled oligo- or polynucleotide probes to nucleic acids present in prepared tissue sections. The exact methodology for tissue preparation (i.e., fixation, embedding, sectioning) will vary from tissue to tissue. However, one of skill in the art may adapt the methodology to a given tissue without undue experimentation. Tissue preparation methods applicable to various tissues are described in detail by Humason et al., 1979, *Animal Tissue Techniques, 4th ed.* (W. H. Freeman & Co., San Francisco).

In addition to variations in the fixation and sample preparation conditions, the actual procedures and conditions for the hybridization of the probe to the sample will vary according to how the tissue/cell sample was prepared. As a non-limiting example, methods used for hybridization to paraffin-embedded sections are discussed below.

Sections of paraffin-embedded tissue immobilized on glass slides are treated as follows:

Slides are dewaxed in staining dishes by three changes in xylenes, for 2 minutes each (dewaxing is not necessary for non-embedded single cells). Dewaxed samples are then rehydrated using the following procedure: 100% ethanol, two times, for two minutes, then subsequent 2 minute incubations in 95%, 70%, and 50% ethanol. Samples are denatured by incubation for 20 minutes at room temperature in 0.2 N HCl, followed by heat denaturation for 15 minutes at 70° C. in 2×SSC. Samples are then rinsed in 1×PBS for 2 minutes. In some situations, usually empirically determined, a pronase digestion step may be included here which later allows improved access of the probes to the nucleic acids contained within the tissue sections. In such cases, samples are digested for 15 minutes at 37° C. with predigested, lyophilized pronase at an empirically determined concentration which allows hybridization yet preserves the cellular morphology (0.1 to 10 μg/ml). Digested samples are incubated for 30 seconds in 2 mg/ml glycine in 1×PBS to stop the digestion. Samples are then post-fixed using freshly prepared 4% paraformaldehyde in 1×PBS, for 5 minutes at room temperature. Fixation is then stopped by a 5 minute incubation in 3×PBS, followed by two 30 second rinses in 1×PBS. Samples are then soaked in 10 mM DTT, 1×PBS, for 10 minutes at 45° C. Samples are then soaked 2 minutes in freshly made 0.1 M triethanolamine, pH 8.0 (triethanolamine buffer). Next, samples are placed in fresh triethanolamine buffer to which acetic anhydride is added to 0.25% final concentration, followed by mixing and 5 minutes' incubation with gentle agitation. After the 5 minutes, more acetic anhydride is added to a final concentration of 0.5%, followed by 5 minutes' further incubation. Samples are blocked 5 minutes in 2×SSC, followed by dehydration through successive soaking in 50%, 70%, 95% (once each), and 100% ethanol (two times) for 2 minutes each at room temperature. Samples are air dried or dried with desiccant before proceeding to the hybridization step.

RNA probe, made and labeled with, for example, $^{35}S$, according to methods known in the art (see Ausubel et al., 1992, *Short Protocols in Molecular Biology*, 3rd ed. (John Wiley & Sons, Inc., New York), p. 14–16 to 14–17) is dissolved in 5 μl of 50 mM dithiothreitol (DTT), and added to 2.5 μl (i.e., an amount approximately equal to one half the mass of labeled probe added) of non-specific riboprobe competitor (RNA made in the same manner as the labeled specific probe, except from a transcription template with non-specific sequences (for example, vector with no insert) and no labeled ribonucleoside in the reaction). This probe/non-specific competitor mixture is heated at 100° C. for 3 minutes, followed by addition of hybridization buffer (50% (v/v) deionized formamide, 0.3 M NaCl, 10 mM Tris (pH 8.0), 1 mM EDTA, 1× Denhardt's solution, 500 μg/ml yeast tRNA, 500 μg/ml poly(A), 50 mM DTT, 10% polyethylene glycol 6000) to 0.3 μg/ml final probe concentration (estimate of amount of probe synthesized is based on calculation of the percent of the label incorporated and the proportion of the labeling base in the probe molecule as a whole). The probe/hybridization mix is incubated at 45° C. until applied to sample slides as a thin layer of liquid. Hybridization reactions are then incubated in a moist chamber (closed container containing towels moistened with 50% deionized formamide, 0.3 M NaCl, 10 mM Tris (pH 8.0), 1 mM EDTA) at 45° C. If background proves to be a problem, a 1 to 2 hour pre-hybridization step using only non-specific, unlabeled riboprobe competitor in hybridization buffer can be added prior to the step in which labeled probe is applied.

Hybridization is carried out for 30 minutes to 4 hours, followed by washing to remove the unbound probe. Samples are washed in an excess (100 ml each wash) of the following buffers: 50% formamide, 2×SSC, 20 mM β-mercaptoethanol, two times, for 15 minutes at 55° C.; 50% formamide, 2×SSC, 20 mM β-mercaptoethanol, 0.5% Triton X-100, two times, for 15 minutes at 55° C.; and 2×SSC, 20 mM β-mercaptoethanol, two times, for 2 minutes at 50° C. The samples are then subjected to an RNAse digestion for 15 minutes at room temperature using a solution containing 40 μg/ml RNase A, 2 μg/ml RNase T1, 10 mM Tris (pH 7.5), 5 mM EDTA and 0.3 M NaCl. After RNase digestion, slides are soaked two times for 30 minutes each in 2×SSC, 20 mM β-mercaptoethanol at 50° C., followed by two washes in 50% formamide, 2×SSC, 20 mM β-mercaptoethanol at 50° C. and two washes of 5 minutes each in 2×SSC at room temperature. Hybridized, washed slides are dehydrated through successive two minute incubations in the following: 50% ethanol, 0.3 M ammonium acetate; 70% ethanol, 0.3 M ammonium acetate; 95% ethanol, 0.3 M ammonium acetate; 100% ethanol. Slides are air dried overnight, followed by coating with emulsion for autoradiography according to standard methods.

Sections prepared, for example, from frozen tissues, may be hybridized by a similar method except that the dewaxing and paraformaldehyde fixation steps are omitted. For details, see Ausubel et al., 1992, supra, pp. 14–15 to 14–16.

It is assumed that the adaptation of these procedures to the specific needs of varying sample types is within the ability of one of ordinary skill in the art. It is also assumed that one skilled in the art may select and employ appropriate methods of detection (Ausubel et al., 1992, supra, pp. 14–18 to 14–19, describes autoradiographic detection) and counterstaining of the tissue sections (e.g., with hematoxylin/eosin, among others, described in Ausubel et al., 1992, supra, pp. 14–19 to 14–22) to make hybridization signal and cell and tissue morphology readily apparent by microscopy methods.

Protein levels in tumor versus non-tumor tissues may be measured by such standard methods as Western blotting or immunohistochemistry, or by other standard immunologically-based assay systems, such as ELISAs. Methods of detecting specific proteins are described in detail by Harlow and Lane, 1989, *Antibodies,* Cold Spring Harbor Laboratory Press, Cold Spring Harbor, N.Y. Additional methods are described by Ausubel et al., 1992, supra. In addition to methods of directly measuring the amount of a protein in a tissue sample, it may be possible in some cases to measure the enzymatic activity of the target protein, as described herein above ("*Measurement of Enzymatic Activity of Smad1 Interacting Proteins*").

Detection Methods Useful According to the Invention

Protein Detection

Detection of a protein may be performed either directly, such as through purification (for example, affinity purification of the protein using a receptor or ligand which will bind the protein, a dimeric pairing partner of the protein, or an antibody directed against the protein), immunological detection (e.g., on a Western blot or immunohistochemically, by in situ binding of an antibody to proteins of a fixed or frozen cell or tissue preparation) or by measurement of energy absorption (for example, spectrophotometrically) of the protein before and after sufficient time for protein production to have occurred.

Methods of Detecting Protein:Protein Complexes

1. Immunoprecipitation

Protein:protein complexes comprising the protein binding components of interest of a claimed composition can be precipitated from solution (whether from a protein binding buffer or from a cell or tissue lysate, as described above) by antibodies specific for any one of the protein components of a claimed composition. As described below, an antibody may be produced by methods well known in the art, if one of the desired specificity is not publicly available (e.g. from a public repository such as the American Type Culture Collection or from a commercial supplier). In order to confirm that both binding partners are present in the precipitate, serial immunoprecipitation may be performed in which proteins are first precipitated through their association with an antibody specific for one binding partner, and then resuspended and precipitated again using an antibody specific for another binding protein. The end-product should be limited to protein:protein complexes having epitopes present on both target proteins. An increase or decrease of at least 20% in the recovery of complexes comprising the proteins of a claimed composition in immunoprecipitations of samples in the presence of a candidate modulator, relative to control samples, is indicative of efficacy of the modulator according to the invention.

2. Immunoprecipitation Followed by Western Blot Analysis

Alternatively, protein:protein complexes can be detected by immunoprecipitation with an antibody to one protein component of a claimed composition followed by Western blot analysis with an antibody capable of binding to a second protein component of a claimed composition. The method of Western blot analysis is well known in the art and is described in Towbin et al., supra. An increase or decrease of at least 20% in the recovery of complexes comprising the proteins of a claimed composition in immunoprecipitations, as detected by Western blot analysis, of samples in the presence of a candidate modulator, relative to control samples, is indicative of efficacy of the modulator according to the invention.

Methods for the preparation of antibodies are well known in the art, and are briefly summarized as follows:

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g. by fusion with an immortalizing fusion partner) to produce monoclonal antibodies.

Polyclonal Antibodies

The antigen protein may be conjugated to a conventional carrier in order to increase its immunogenicity, and an antiserum to the peptide-carrier conjugate is raised. Coupling of a peptide to a carrier protein and immunizations may be performed as described (Dymecki et al., 1992, *J. Biol. Chem.*, 267: 4815–4823). The serum is titered against protein antigen by ELISA (below) or alternatively by dot or spot blotting (Boersma and Van Leeuwen, 1994, *J. Neurosci. Methods*, 51: 317). At the same time, the antiserum may be used in tissue sections prepared as described below. The serum is shown to react strongly with the appropriate peptides by ELISA, for example, following the procedures of Green et al., 1982, *Cell*, 28: 477–487.

Monoclonal Antibodies

Techniques for preparing monoclonal antibodies are well known, and monoclonal antibodies may be prepared using a candidate antigen whose level is to be measured or which is to be either inactivated or affinity-purified, preferably bound to a carrier, as described by Arnheiter et al., *Nature*, 294, 278–280 (1981).

Monoclonal antibodies are typically obtained from hybridoma tissue cultures or from ascites fluid obtained from animals into which the hybridoma tissue is introduced. Nevertheless, monoclonal antibodies may be described as being "raised to" or "induced by" a protein.

Monoclonal antibody-producing hybridomas (or polyclonal sera) can be screened for antibody binding to the target protein. As used herein, "antibody" refers to a specific class of protein molecules characterized by being from the immunoglobulin fraction of blood or secreted by cultured cells derived from the immune system and having a specific reaction with a corresponding ligand referred to as an antigen. The term antibody according to the invention also refers to constructions using the binding (variable) region of such an antibody, and other antibody modifications, a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

3. Affinity Purification

As an alternative to precipitation from solution, either an antibody or another protein having affinity for a protein component of a composition according to the invention, may be bound to a solid or semi-solid support (e.g. a membrane, filter or chromatography column resin), which is then incubated with a buffer or lysate derived from cells or tissue, which buffer or lysate comprises the components of a composition according to the invention either with or without the candidate modulator, under conditions which permit formation of the complex in the absence of the candidate modulator. A candidate modulator is judged to be efficacious if it results in a reduction of at least 20%, or an increase of at least 20% in the yield of affinity-purified complexes comprising the protein components of a claimed composition relative to that observed with control purifications in which the protein components are absent.

If a protein complex according to the invention is to be isolated, an antibody specific for either member of the protein complex may be used.

4. Additional Use of Crosslinking Agents

In the isolation procedures described above, conditions (e.g., temperature or buffer composition) which favor the dissociation of protein:protein complexes are often required in order to improve yield sufficiently to permit recovery of a rare species or to free hydrophobic proteins from membranous structures. Methods for covalently crosslinking proteins to proteins or other biomolecules with which they may associate intracellularly or in a cell-free assay system are well know in the art. Table 1 provides a non-exhaustive list of chemical crosslinking substances which are widely available, along with their catalog numbers from one commercial supplier (Sigma; St. Louis, Mo.).

| Product Number | Name; synonyms | Type<br>= Homobifunctional<br>< Heterobifunctional<br>Cleavable x | Specificity<br>Primary Reaction | Secondary Reaction | Linker arm (atoms) | Comments |
| --- | --- | --- | --- | --- | --- | --- |
| A 1251 | S-Acetylmercaptosuccinic anhydride; SAMSA | < | amine | maleimide | 3 | Charged; incorporates protected-SH; readily S-deacelylated |
| A 9043 | S-Acetylthioglycolic acid NHS ester; SATA | < | amine | maleimide | 3 | Incorporates protected-SH; readily S-deacelylated |
| A 5261 | S-Acetylthiopropionic acid NHS ester; SAPTA | < | amine | maleimide | 4 | Incorporates protected-SH readily S-deacelylated |
| A 0638 | Adipic acid dihydrazide | = | carbohydrate | | 10 | Reacts with aldehyde of periodate-oxidized carbohydrate |
| A 9048 | 4-Azidobenzoic acid NHS ester; HSAB | < | amine | photoactive | 6 | Aryl azide photoaffinity reagent |
| A 3282 | N-(5-Azido-2-nitrobenzoyloxy)succinimide | < | amine | photoactive | 5 | Aryl azide photoaffinity reagent |

-continued

| Product Number | Name; synonyms | Type = Homobifunctional < Heterobifunctional Cleavable x | Specificity Primary Reaction | Specificity Secondary Reaction | Linker arm (atoms) | Comments |
|---|---|---|---|---|---|---|
| A 3407 | 6-(4-Azido-2-nitrophenylamino)-hexanoic acid NHS ester | < | amine | photoactive | 11 | Aryl azide photoaffinity reagent |
| A 6057 | p-Azidophenacyl bromide; APB | < | sulfhydryl | photoactive | 7 | Aryl azide photoaffinity reagent |
| A 3532 | N-(4-Azidophenylthio)phthalimide; APTP | < | sulfhydryl | photoactive | 6 | Aryl azide photoaffinity reagent |
| A 9173 | 4-Azidosalicylic acid NHS ester | < | amine | photoactive | 6 | Aryl azide photoaffinity reagent; may be radioiodinated |
| B 4412 | 4-Benzoylbenzoic acid NHS ester | < | amine | photoactive | 6 | Benzophenone photoaffinity reagent |
| B 8271 | Bromoacetic acid NHS ester | < | amine | sulfhydryl | 2 | Haloacetyl group reacts preferentially with -SH nucleophile |
| C 1526 | Carbonyl-bis(L-methionine p-nitro-phenyl ester) | = x | amine | | 7 | Cleavable by cyanogen bromide |
| D 7147 | 2-Diazo-3,3,3-trifluoropropionic acid p-nitrophenyl ester | < | amine | photoactive | 2 | Diazo photoaffinity reagent; trifluoromethyl group improves stability and efficiency |
| D 5378 | 1,5-Difluoro-2,4-dinitrobenzene; DFNB | = | amine | | 3 | Aryl halide reaction with nucleophile other than amine is readily reversible |
| D 3514 | 4,4'-Diisothiocyanatostilbene-2,2'-disulfonic acid | = | amine | | 14 | Negatively charged; specific inhibitor of cellular anion permeability |
| D 0172 | Diethyl malonimidate | = | amine | | 3 | Water soluble; amidine product is charged; base-labile |
| D 8138 | Dimethyl adipimidate; DMA | = | amine | | 6 | Water soluble; amidine product is charged; base-labile |
| D 2388 | Dimethyl 3,3'-dithiobispropion-imidate; DTPB | = x | amine | | 8 | Water soluble; amidine product is charged; base labile; cleavable by mercaptan |
| D 8388 | Dimethyl pimelimidate; DMP | = | amine | | 7 | Water soluble; amidine product is charged; base labile |
| D 7636 | Dimethyl suberimidate; DMS | = | amine | | 8 | Water soluble; amidine product is charged; base labile |
| D 7272 | 4,4'-Dithiobis(phenyl azide); DABP | = x | photoactive | | 12 | Aryl azide photoaffinity reagent; cleavable by mercaptan |
| D 3669 | 3,3'-Dithiobis(propionic acid NHS ester); DTSP; Lomant's Reagent | = x | amine | | 8 | Cleavable by mercaptan |
| E 3257 | Ethylene glycol bis(succinic acid NHS ester); EGS-NHS | = x | amine | | 12 | Cleavable by hydroxylamine |
| F 9382 | 4-Fluro-3-nitrophenyl azide; FNA | < | amine | photoactive | 5 | Aryl azide photoaffinity reagent |
| F 3626 | bis(4-Fluoro-3-nitrophenyl) sulfone | = x | amine | | 9 | Aryl halide; cleavable with base |
| F 7640 | p-Formylbenzoic acid NHS ester | < | amine | amine | 6 | Second reaction requires reductive amination |
| MANY | Glutaraldehyde | = | amine | | varies | Used for protein conjugation |
| I 6256 | 2-Iminothiolane | < | amine | maleimide | 5 | Thiolating reagent; amidine product is charged |
| I 1007 | 6-(Iodoacetamido)caproic acid NHS ester | < | amine | sulfhydryl | 9 | Haloacetyl group reacts preferentially with sulfhydryl nucleophile |
| I 9760 | Iodoacetic acid NHS ester | < | amine | sulfhydryl | 2 | Haloacetyl group reacts preferentially with sulfhydryl nucleophile |
| M 3884 | Maleimidoacetic acid NHS ester; AMAS | < | amine | sulfhydryl | 5 | Used for protein conjugation |
| M 2786 | m-Maleimidobenzoic acid NHS ester; MBS | < | amine | sulfhydryl | 7 | Used for protein conjugation; aryl maleimide is less stable than alkyl |
| M 9775 | 4-(N-Maleimido) benzophenone | < | sulfhydryl | photoactive | 8 | Benzophenone photoaffinity reagent |
| M 7642 | γ-Maleimidobutyric acid NHS ester | < | amine | sulfhydryl | 7 | Used for protein conjugation |
| M 9794 | ε-Maleimidocaproic acid NHS ester | < | amine | sulfhydryl | 9 | Used for protein conjugation |
| M 5525 | 4-(N-Maleimidomethyl)cyclohexane-carboxylic acid NHS ester; SMCC | < | amine | sulfhydryl | 9 | Used for protein conjugation |
| M 6035 | 4-(N-Maleimidomethyl)cyclohexane-carboxylic acid 3-sulfo-NHS ester; Sulfo-SMCC | < | amine | sulfhydryl | 9 | Used for protein conjugation; water soluble derivative |
| M 0155 | β-Maleimidopropionic acid NHS ester; BMPS | < | amine | sulfhydryl | 6 | Used for protein conjugation |
| M 5148 | N,N'-bis(3-Maleimidopropionyl)-2-hydroxy-1,3-propanediamine | = | sulfhydryl | | 17 | Water soluble |
| P 0158 | 1,4-Phenylene diisothiocyanate | = | sulfhydryl | | 8 | |
| P 7518 | N,N'-o-Phenylenedimaleimide | = | sulfhydryl | | 8 | |
| P 3396 | N,N'-p-Phenylenedimaleimide | = | sulfhydryl | | 10 | |

-continued

| Product Number | Name; synonyms | Type<br>= Homobifunctional<br>< Heterobifunctional<br>Cleavable x | Specificity<br>Primary Reaction | Secondary Reaction | Linker arm (atoms) | Comments |
|---|---|---|---|---|---|---|
| P 2672 | Polyoxyethylene bis(glycidyl ether); PEG bis(glycidyl ether) | = | amine or sulfhydryl | | >200 | Hydrophilic; oxirane requires basic pH to react |
| P 2050 | bis[Polyoxyethylene bis(glycidyl ether)] | = | amine or sulfhydryl | | >1000 | Hydrophilic; oxirane requires basic pH to react; contains 4 reactive groups |
| P 5532 | Polyoxyethylene bis(imidazolyl-carbonyl); PEG bis(CDI) | = | amine | | >200 | Hydrophilic |
| P 9532 | bis[Polyoxyethylene bis()imidozolyl-carbonyl)] | = | amine | | >1000 | Hydrophilic; contains 4 reactive groups |
| P 9299 | Polyoxyethylene bis(p-nitrophenyl carbonate); PEG bis(p-nitrophenyl carbonate) | = | amine | | >200 | Hydrophilic |
| P 3415 | 3-(2-Pyridyldithio)propionic acid NHS ester; SPDP | < | amine | sulfhydryl | 4 | May undergo thiol/disulfide interchange or be reduced to incorporate free sulfhydryl; used for protein conjugation |
| S 1885 | Suberic acid bis(NH ester) | = | amine | | 8 | |

5. Double-labeled Antibody in situ

Procedures by which labeled antibodies specific for target proteins are used in protein detection are well known in the art. According to the present invention, double-labeling strategies, in which antibodies directed at each member of a protein complex according to the invention are differentially labeled (e.g. with distinct fluorescent dyes, of which four, including 6-carboxy-fluorescein (FAM), tetrachloro-6-carboxy-fluorescein (TET), 2,7-dimethoxy-4,5-dichloro-6-carboxyfluorescein (JOE) and hexachloro-6-carboxy-fluorescein (HEX), are currently available), and permit the extra- or intracellular co-localization of the two target proteins to be measured by confocal microscopy. Confocal microscopy is carried out on a Leica TCS 4D Confocal Laser Scanning Microscope. Alternatively, immunological tests may rely on the use of either monoclonal or polyclonal antibodies and include enzyme-linked immunoassays (ELISA), immunoblotting and immunoprecipitation (see Voller, 1978, *Diagnostic Horizons*, 2: 1–7, Microbiological Associates Quarterly Publication, Walkersville, Md.; Voller et al., 1978, *J. Clin. Pathol.*, 31: 507–520; U.S. Reissue Pat. No. 31,006; UK Patent 2,019,408; Butler, 1981, *Methods Enzymol.*, 73: 482–523; Maggio, E. (ed.), 1980, *Enzyme Immunoassay*, CRC Press, Boca Raton, Fla.) or radioimmunoassays (RIA) (Weintraub, B., *Principles of radioimmunoassays*, Seventh Training Course on Radioligand Assay Techniques, The Endocrine Society, March 1986, pp. 1–5, 46–49 and 68–78). For analyzing tissues for the presence or absence of a protein in the present invention, immunohistochemistry techniques may be used. Tissue samples to be assayed by these methods are prepared as described below. It will be apparent to one skilled in the art that the antibody molecule will have to be labeled to facilitate easy detection of a target protein. Techniques for labeling antibody molecules are well known to those skilled in the art (see Harlow and Lane, 1989, *Antibodies*, Cold Spring Harbor Laboratory, pp. 1–726). A method of performing immunocytochemistry according to the invention is described in detail in Example 5.

Alternatively, other techniques can be used to detect the target proteins, including chromatographic methods such as SDS PAGE, isoelectric focusing, Western blotting, HPLC and capillary electrophoresis. SDS-PAGE may be performed on cell lysates according to Weber and Osborn (1975, in: H. Neurath and R. Hill, eds., *The Proteins*, Ed. 3, Vol I, Academic Press, New York, pp. 179–223, herein incorporated by reference) or immunoblots are performed according to Towbin et al., supra. Primary antibodies to many antigens may be obtained from commercial or other public sources (e.g. ATCC), or may be prepared by methods well known in the art (described above). Secondary antibodies prepared against immunoglobulins of numerous species (including, but not limited to, rat, mouse, rabbit and goat) and suitable for use in a number of chromogenic, chemiluminescent and fluorescent detection protocols are commercially available (for example, from Promega, Madison, Wis.; Vector Laboratories, Burlingame, Calif.). Antibody dilution, incubations and detections are performed according to manufacturer's suggested conditions.

Preparation of Histological Samples

Tissue samples intended for use in in situ detection of either RNA or protein are fixed using conventional reagents; such samples may comprise whole or squashed cells, or may instead comprise sectioned tissue. Fixatives adequate for such procedures include, but are not limited to, formalin, 4% paraformaldehyde in an isotonic buffer, formaldehyde (each of which confers a measure of RNAase resistance to the nucleic acid molecules of the sample) or a multi-component fixative, such as FAAG (85% ethanol, 4% formaldehyde, 5% acetic acid, 1% EM grade glutaraldehyde). Note that for RNA detection, water used in the preparation of an aqueous component of a solution to which the tissue is exposed until it is embedded is RNase-free, i.e. treated with 0.1% diethylprocarbonate (DEPC) at room temperature overnight and subsequently autoclaved for 1.5 to 2 hours. Tissue is fixed at 4° C., either on a sample roller or a rocking platform, for 12 to 48 hours in order to allow fixative to reach the center of the sample.

Prior to embedding, samples are purged of fixative and dehydrated; this is accomplished through a series of two- to ten-minute washes in increasingly high concentrations of ethanol, beginning at 60%- and ending with two washes in 95%- and another two in 100% ethanol, followed by two ten-minute washes in xylene. Samples are embedded in one of a variety of sectioning supports, e.g. paraffin, plastic polymers or a mixed paraffin/polymer medium (e.g.

Paraplast®Plus Tissue Embedding Medium, supplied by Oxford Labware). For example, fixed, dehydrated tissue is transferred from the second xylene wash to paraffin or a paraffin/polymer resin in the liquid-phase at about 58° C., which is then replaced three to six times over a period of approximately three hours to dilute out residual xylene, followed by overnight incubation at 58° C. under a vacuum, in order to optimize infiltration of the embedding medium into the tissue. The next day, following several more changes of medium at 20 minute to one hour intervals, also at 58° C., the tissue sample is positioned in a sectioning mold, the mold is surrounded by ice water and the medium is allowed to harden. Sections of 6 µm thickness are taken and affixed to 'subbed' slides, which are those coated with a proteinaceous substrate material, usually bovine serum albumin (BSA), to promote adhesion. Other methods of fixation and embedding are also applicable for use according to the methods of the invention; examples of these are found in Humason, G. L., 1979, *Animal Tissue Techniques*, 4th ed. (W.H. Freeman & Co., San Francisco), as is frozen sectioning (Serrano et al., 1989, supra).

6. Yeast Two-Hybrid Analysis

A technique termed the "two-hybrid" system, for monitoring protein:protein interactions in vivo has been developed in the yeast system for the isolation of protein binding partners. Typically, chimeric proteins are produced in which a protein for which partners are to be found (the "bait") is fused to the DNA-binding domain of a monomeric half of a heterodimeric transcription factor, while a library of potential binding partners are fused to the DNA-binding domain of the second half of that same heterodimer. If plasmids encoding the bait and a protein which will bind to it are present in the same cell, a functional transcription complex is formed and a marker gene under control of a regulatory element specific for that complex is expressed. Either plasmid carries a different selectable marker (e.g., an auxotrophic marker), as described above.

According to the invention, the assay is performed in the presence of a candidate modulator; control reactions are performed without the modulator. A modulator may be delivered to the cells on a third yeast plasmid, which is maintained using a third selective marker, or may be present in the culture medium from which it is taken up by the cells.

A decrease of at least 20% in marker gene in the presence of the candidate modulator relative to that observed in controls in which it is absent indicates effective inhibition.

A detailed description of a modified yeast two-hybrid system is included in Example 1.

Candidate Modulators

Candidate Modulators

A "candidate modulator" as used herein, is any compound with a potential to either modulate the interaction of two proteins comprising a claimed composition according to the invention or modulate the activity of either of the proteins comprising a claimed composition according to the invention. As used herein, "modulate" refers to increase or decrease the binding affinity with which proteins of a claimed composition interact, or increase or decrease the activity (as defined above) of either of the proteins of the claimed composition.

A candidate inhibitor is tested in a concentration range that depends upon the molecular weight of the molecule and the type of assay. For example, for inhibition of protein/protein complex formation, small molecules (as defined below) may be tested in a concentration range of 1 pg–100 µg/ml, preferably at about 100 pg–10 ng/ml; large molecules, e.g., peptides, may be tested in the range of 10 ng–100 µg/ml, preferably 100 ng–10 µg/ml.

Candidate modulators will include peptide and polypeptide inhibitors having an amino acid sequence based upon the components of the novel heterodimers described herein. For example, a mutant Smad1 or a mutant version of a protein component of the proteasome mediated degradation pathway, or a fragment of a mutant or wild-type Smad1 protein or a fragment of a mutant or wild-type version of a protein component of the proteasome mediated degradation pathway, may act as a competitive inhibitor with respect to heterodimerization or activity. Candidate modulators useful according to the invention include proteasome inhibitors including but not limited to LlnL, LLM, lactacystin, ZLLf and MG132. Candidate modulators also useful according to the invention include anti-oxidants including but not limited to GST, PAG, antizyme, enolase, DPI, PDTC, DFO, vitamin E and glutathione.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (N.C.), or are readily produceable by methods well known in the art. Additionally, natural and synthetically produced libraries and compounds are readily modified through conventional chemical, physical, and biochemical means.

Useful compounds may be found within numerous chemical classes, though typically they are organic compounds, and preferably small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Determination of Activity of a Modulator

A candidate modulator of protein:protein interactions, assayed according to the invention as described above, is determined to be effective if its use results in an increase or decrease of about 20% or greater of protein:protein interaction or protein activity.

The level of modulation by a candidate modulator of a protein:protein interaction or a protein activity, may be quantified using any acceptable limits, for example, via the following formula, which describes detections performed with a radioactively labeled probe (e.g., a radiolabeled antibody in an immunobinding experiment or a radiolabeled nucleic acid probe in a Northern hybridization).

$$\text{Percent Modulation} = \frac{(CPM_{Control} - CPM_{Sample})}{(CPM_{Control})} \times 100$$

where $CPM_{Control}$ is the average of the cpm in antibody/ligand complexes or on Northern blots resulting from assays that lack the candidate modulator (in other words, untreated controls), and $CPM_{Sample}$ is the cpm in antibody/ligand complexes or on Northern blots resulting from assays containing the candidate modulator. A similar calculation is performed where the assay comprises use of a labeling system or system of measuring enzymatic activity in which there is a linear relationship between the amount of label detected and the amount of protein or nucleic acid being represented per unit of label or the amount of protein or nucleic acid represented by a unit of enzymatic activity.

Diseases

1. Kidney Disease Caused by Excessive Fibrosis

The invention provides methods of treating kidney diseases caused by excessive fibrosis.

TGF-β is a key regulatory molecule in the control of the activity of fibroblasts that has been implicated in several disease states characterized by excessive fibrosis. In the kidney, TGF-β promotes tubuloepithelial cell hypertrophy and regulates glomerular production of almost every known molecule of the extracellular matrix, including collagens, fibronectin, tenascin, and proteoglycans, as well as the integrins that are receptors for these molecules. Furthermore, TGF-β blocks the destruction of newly synthesized extracellular matrix by upregulating the synthesis of protease inhibitors and downregulating the synthesis of matrix-degrading proteases such as stromelysin and collagenase. Increased extracellular matrix production is an underlying feature of kidney diseases that are caused by excessive fibrosis. There is a strong body of evidence that TGF-β in involved in a variety of kidney diseases including glomerulonephritis, as well as chronic renal disorders characterized by hypertrophy and sclerosis, such as diabetic nephropathy (Sharma and Ziyadeh, 1994, *Am. J. Physiol.*, 266: F829–F842).

Glomerulonephritis

Glomerulonephritis is an inflammation of the kidney characterized by the accumulation of extracellular matrix within the damaged glomeruli, impaired filtration and proteinuria. In its progressive form, the disease destroys kidney function leading to uraemia and death, unless dialysis therapy or kidney transplantation is available. The pathogenesis of glomerulonephritis is incompletely understood, but the eliciting factor is thought to be an immunological injury to mesangial and/or other resident cells in the glomeruli.

An animal model of acute glomerulonephritis has been developed wherein glomerulonephritis is induced in rats with a single injection of antithymocyte serum. Briefly, anti-thymocyte serum (ATS) is produced by immunizing New Zealand white rabbits with $1 \times 10^6$ rat thymocytes in complete Freund's adjuvant, followed by boosting with $1 \times 10^6$ thymocytes given intravenously 2 and 4 wk later. Preimmunization serum is collected from the same animal and used in control experiments as normal rabbit serum. Before use, ATS and normal serum are absorbed three times each with packed rat erythrocytes and rat liver powder. The serum is then heat inactivated at 56° C. for 30 min. Glomerulonephritis is induced in Sprague-Dawley rats (4–6 wk old) by intravenous administration of 1 ml ATS per 100 g of body weight followed immediately by 1 ml of normal rabbit serum as a source of complement. Control animals receive 2 ml of normal rabbit serum instead of ATS (Okuda et al., 1990, *J. Clin. Invest.*, 86:453–462).

This animal model of acute glomerulonephritis has been used to demonstrate that this disease is associated with increased production and activity of TGF-β1, an inducer of extracellular matrix. It has been further demonstrated that administration of antibodies capable of binding to TGF-β1 at the time of induction of the glomerular disease suppresses the increased production of extracellular matrix and causes a dramatic attenuation of the histological manifestations of the disease (Border et al., 1990, *Nature*, 346: 371–374).

Chronic glomerulonephritis, also known as chronic nephritic syndrome, is a disorder that is characterized by damaged glomeruli and degeneration of kidney function over a period of years, and is associated with several diseases.

The syndrome of chronic glomerulonephritis causes no symptoms for years and therefore goes undetected in most individuals. This disorder may be discovered by the presence of protein, and possibly cells in the urine, or by kidney failure. Symptoms can include fluid retention and high blood pressure.

Methods of treatment of glomerulonephritis include drugs that reduce high blood pressure and restriction of salt intake and protein intake. Kidney failure is treated by dialysis or kidney transplantation. (Berkow et al., editors, 1997, *The Merck Manual of Medical Information*, Merck & Co., Inc., New Jersey).

Diabetic Nephritis

Diabetic Nephritis (also known as diabetic nephropathy) is characterized by hypertrophy of both glomerular and tubular elements, thickening of the glomerular and tubular basement membranes, progressive accumulation of extracellular matrix components in the glomerular mesangium, and tubulointerstitial fibrosis. Investigations in glomerular mesangial cells and proximal tubule cells have demonstrated that an elevated glucose concentration in the culture medium stimulates the biosynthesis of collagen and other extracellular matrix components and modulates the growth of the cells, including the development of tubular epithelial hypertrophy. In general, these effects of high glucose concentration may arise as a consequence of increased de novo synthesis of diacylglycerol and activation of protein kinase C, early or advanced nonenzymatic glycation, increased activity of the polyol pathway and disordered myo-inositol metabolism or enhanced synthesis and/or response to hormones, cytokines or growth factors (Sharma and Ziyadeh, 1995, *Diabetes*, 44:1139–1146).

TGF-β has been implicated as an important mediator of the high glucose-induced effects on renal tubular and mesangial cell growth and collagen biosynthesis associated with diabetic nephritis (Sharma and Ziyadeh, supra). An increase in TGF-β1 production has been demonstrated in the kidneys of diabetic patients, as compared to non-diabetic control individuals (Sharma et al., 1997, *Diabetes*, 46:854–859). Thus, it has been suggested that elevated TGF-β production plays an important role in stimulating excessive extracellular matrix production in fibrotic states in target tissues, such as in diabetic nephropathy.

Diabetic nephritis affects patients with both type I and type II diabetes. This disease can be divided into five phases. Phase I, referred to as hyperfiltration, is associated with an increased glomerular filtration rate, an increased albumin excretion rate, hypertrophy and an increase in intraglomerular pressure. During phase II, patients may develop glomerulosclerosis, with thickening of the glomerular capillary basement membrane and expansion of the collagen matrix within the mesangial region. Patients with higher blood glucose levels are more likely to begin the progression to end-stage renal failure at this stage. These patients enter phase III, also termed incipient diabetic nephropathy. During this phase of the disease, microalbuminuria (defined as an albumin excretion rate of 20–200 µg/min) is present. As the microalbuminuria increases, the glomerular filtration rate decreases. At this stage, the decline into renal failure can be slowed by regulating blood glucose levels and hypertension, and by the administration of angiotensin-converting enzyme (ACE) inhibitors. Phase IV of the disease is characterized by dipstick positive proteinuria correlating with an albumin excretion rate >200 µg/min, a progressive decrease in the glomerular filtration rate and hypertension. Methods of treatment during phase IV of the disease include control of hypertension, the administration of ACE inhibitors, and a low-protein diet. Most patients who develop clinical proteinuria due to diabetic nephropathy enter Phase V, also termed end stage renal disease. This phase of the disease is typically treated by dialysis (Andreoli et al., 1997, *Cecil Essentials of Medicine*, 4Edition, W. B. Saunders, Philadelphia).

An animal model for diabetic nephropathy has been developed wherein the kidneys of rats are made diabetic by the administration of streptozotocin, a drug that causes insulin deficiency. Briefly, diabetes is induced in male Sprague-Dawley rats weighing 150 g by a single i.v. injection of streptozotocin (Sigma) at 6.5 mg/100 g of body weight in citrate buffer (Yamamoto et al., 1993, *Proc. Natl. Acad. Sci. USA*, 90:1814–1818). This model is useful for studying diabetic nephropathy because the time course and morphological changes in the kidney that occur in this animal model, closely resemble the human disease.

Chronic Rejection of Kidney Allograft

Chronic renal rejection is the most common cause of graft loss in renal transplantation. The most characteristic histopathological features of chronic rejection in renal allografts are intimal fibrosis mainly in the cortical arteries, glomerular ischemic simplification, interstitial fibrosis and tubular atrophy. T cell mediated immunity plays a critical role in allograft rejection. A variety of interactions have been implicated in the rejection process, including cytokines such as IL-1, IL-2, and TGF-β1, 2 and 3. The initial targets of rejection appear to be the graft endothelial structures. Interstitial mononuclear cells (lymphocytes, macrophages, plasma cells, eosinophil cells) infiltrate the rejected graft and serve as histological indicators of chronic cell-mediated rejection. Studies have indicated that the induction of growth factors may play a pathobiological role in experimental acute and chronic rejection. It has been demonstrated by Northern blot analysis that the levels of TGF-β1, 2 and 3 are decreased in chronically rejected renal cortex samples, compared to normal controls. In contrast, the glomeruli and the cortical vessels of the rejected kidney exhibit strong immunostaining for TGF-β1 and 3. The increase in TGF-β1 and 3 immunoreactivity in the glomeruli suggests that there is a redistribution in TGF-β expression in chronic renal allograft rejection (Horvath et al., 1996, *Kidney International*, 50:489–498). These data suggest that TGF-βs may play a role in the regulation of renal allograft rejection. In particular, TGF-βs may effect chronic renal allograft rejection via their regulation of the immune response, or via their immunosuppressive effects upon target cells within the immune system.

Obstructive Nephropathy

Renal interstitial fibrosis is a common consequence of chronic kidney obstruction. While several cytokines may initiate fibrogenesis, TGF-β is considered to be a major stimulating factor. It has been reported that TGF-β1 regulates extracellular matrix synthesis, that thromboxane stimulates extracellular matrix protein synthesis, and that angiotension II increases expression of TGF-β1 mRNA in rat aortic smooth muscle cells. A rat model of obstructive nephropathy wherein the rats have unilateral ureteral obstruction (UUO), has been used to further investigate the role of TGF-β in this disease. This model has demonstrated that TGF-β1 mRNA levels in contralateral kidneys of rats with UUO did not change during a 14 day obstruction period while, in contrast, in the obstructed kidney TGF-β1 mRNA levels were significantly increased as compared to control kidneys of unoperated rats. The increase in TGF-β1 mRNA expression in the obstructed kidney cortex was found in tubular cells rather than glomeruli (Kaneto et al., 1993, *Kidney Int.*, 44:313–321). These data suggest that in obstruction, TGF-β1 is increased at the transcriptional level and thus may play a role in initiating fibrogenesis in obstructive nephropathy.

Progressive Kidney Disease

Several lines of evidence suggest that local production of TGF-β contributes to renal disease, particularly to the accumulation of the extracellular matrix protein that characterizes glomerulosclerosis and interstitial fibrosis. Studies have demonstrated that transgenic mice with chronically elevated circulating levels of TGF-β1 exhibit progressive glomerulosclerosis and suggest a role for this cytokine in progressive kidney disease (Kopp et al., 1996, *Lab. Invest.*, 74:991–1003).

Polycystic Kidney Disease

Polycystic kidney disease is characterized by massive kidney enlargement due to the development of epithelial lined cysts derived from renal tubules and collecting ducts. The formation of cysts is thought to be due to abnormalities in cell growth, cell-matrix interactions and/or increased fluid secretion.

A murine model for the autosomal dominant form of polycystic kidney disease (DBA/2FG-pcy mice) has been developed. The renal findings of DBA/2FG-pcy mice have been previously described. Briefly, at 8 wk of age, DBA/2FG-pcy mice showed slightly larger kidneys than DBA/2-mice. The kidneys of DBA/2FG-pcy mice enlarged progressively with age. Although 16-wk-old animals exhibited significant renal cystic change, azotemia was not apparent until later. At 30 wk of age, cysts dominated the kidneys and an external, slightly cobblestone-like appearance developed. Cysts could be found in all segments of the renal tubules. Small epithelial micropolyps or mounds of cells were observed in some collecting duct cysts. Focal interstitial inflammatory infiltrates and increased interstitial connective tissue were found in cystic kidneys at 16 and 30 wk of age but were not detectable before that time. Inflammatory cells aggregated along the arcuate vessels at the corticomedullary junction. The inflammatory cells at this site appeared to be predominantly lymphocytes, plasma cells, and macrophages.

It has been demonstrated that the levels of TGF-β1 are increased with the progression of cystic lesions in the kidneys of DBA/2Fg-pcy mice (Nakamura et al., J. Am. Soc. Nephrol., 1993, 3:1378–1386), and may contribute to the progression of cystic lesions in these mice.

Increased extracellular matrix production is an underlying feature of kidney diseases that are caused by excessive fibrosis, including but not limited to glomerulonephritis, diabetic nephritis, chronic rejection of kidney allograft, obstructive nephropathy, progressive kidney disease and polycystic kidney disease. Thus, it is possible that the ability of TGF-β to induce extracellular matrix production may be associated with the development of kidney diseases associated with excessive fibrosis. Therapeutic agents that may be useful for treating kidney diseases caused by excessive fibrosis include proteasome inhibitors or anti-oxidants that repress TGF-β activity, and in particular the ability of TGF-β to stimulate extracellular matrix production. Furthermore, BMP-7 has been identified as a TGF-β antagonist in renal diseases. Specific activators of BMP-7 signaling may be useful for treating kidney diseases associated with aberrant levels of TGF-β activity.

2. Cardiovascular Diseases

The invention also provides methods of treating cardiovascular diseases.

Myocardial Infarction (Heart Attack)

The term myocardial infarction refers to a medical emergency wherein a portion of the heart's blood supply is suddenly severely restricted or cut off, thereby causing heart muscle (myocardium) to die from a lack of oxygen.

Myocardial infarction is usually caused by a blockage (e.g. from a blood clot) in a coronary artery. Symptoms of a heart attack include intermittent chest pain, shortness of breath and or fatigue, a few days prior to the heart attack. The most recognizable symptom is pain in the middle of the chest that may spread to the back, jaw or left arm. Other symptoms include faintness, and a heavy pounding of the heart.

Diagnosis of a heart attack is confirmed by an electrocardiogram (ECG). Additionally, the levels of certain enzymes (e.g. CK-MB) in the blood can be measured to diagnose a heart attack. CK-MB is normally located in heart muscle and is released into the blood when heart muscle is damaged. Further diagnostic information can be obtained from an echocardiogram or from radionuclide imaging.

Methods of treating a heart attack include the administration of either aspirin to reduce the clot, a beta blocker to slow the heart rate or oxygen. Thrombolytic therapy (involving drugs such as streptokinase, urokinase and plasminogen activator) can also be used to dissolve a blood clot. In some cases, treatment protocols include angioplasty or coronary artery bypass surgery instead of thrombolytic therapy. Both morphine and nitroglycerin can be administered to decrease the work of the heart and reduce pain (Berkow et al., supra).

An animal model of acute myocardial infarction has been used to investigate the role of TGF-β in this disease. According to this model, adult, male Sprague-Dawley rats were anesthetized with halothane, a left thoracotomy was performed, the pericardium was opened, and the heart was briefly exteriorized. The left coronary artery was ligated 1–2 mm from its origin with a 7-0 silk suture. Then the heart was returned to its normal position with the pericardium left open; and the thorax was closed. The same procedure was followed for sham-operated control animals, but the coronary ligature was left untied.

The electrocardiogram (ECG) was used on selective rats with extensive infarction of the left ventricle. Six standard and limb leads and three precordial leads were evaluated. Only animals with large Q waves in leads I, VL, and V5 were utilized. Extensive infarction was also confirmed by gross examination at the time of euthanasia.

Immediately before being euthanized, the rats were anesthetized with Innovar (1.3 ml/kg im), the right external carotid artery was cannulated with a 2-Fr microtip pressure transducer catheter (model PR 407, Millar Instruments, Houston, Tex.), and the right jugular vein was cannulated with saline-filled polyethylene-50-tubing connected to a pressure transducer (Spectromed, Gould, Cleveland, Ohio). After arterial blood pressures were obtained, the catheters were advanced into the left and right ventricles, respectively, and left ventricular pressures, pressure time derivative (dP/dt), and right ventricular pressures were measured. To be certain that the experimental cohort consisted of animals with large infarcts, only animals with left ventricular end-diastolic pressures ≧16 mm Hg were included from the infarct groups (Yue et al., 1998, *Am. J. Physiol.*, 275:H250–H258).

This animal model was used to demonstrate that TGF-β1 and TGF-β3 mRNA expression are elevated in nonmyocytes by 1 week postinfarction and return to baseline by 6 weeks postinfarction (Yue et al., supra). This model system also demonstrated that the mRNA expression of the main components of the extracellular matrix (type I and type III collagens) is increased 1 week after myocardial infarction in nonmyocytes. It has also been demonstrated that there is progressive loss of TGF-β1 staining of ventricular myocytes within 1 hour of coronary ligation. However, by 24–48 hours after ligation, intense staining of myocytes at the margin of infarcted areas is observed. Northern blot analysis of infarcted myocardium 48 hours after ligation shows a 3–4 fold increase in TGF-β1 mRNA (Thompson et al., 1998, *Growth Factors*, 1:91–99).

Fibrosis and other alterations in the extracellular matrix are important aspects of the postinfarction remodeling process affecting both the infarcted and noninfarcted myocardium and these changes are thought to play a role in the evolution of left ventricular dysfunction. Although myocardial infarction may result in substantial loss of functional myocardium and lead to acute cardiac decompensation, it is now well recognized that the subsequent changes in the noninfarcted myocardium play an important role in the longer term. This process, which involves changes in myocytes (hypertrophy, dysfunction) and in the extracellular matrix, has been termed remodeling.

It has been demonstrated that there is a correlation between increases in collagen gene expression after myocardial infarction and expression of TGF-β1 and TGF-β3. It has also been demonstrated that myocyte size increased during the postinfarction period, indicating the development of significant cellular hypertrophy. The time period during which an increase in myocyte size is observed follows an increase in nonmyocyte TGF-β1 and TGF-β3 expression. TGF-β1 is known to be a hypertrophic stimuli for myocytes. It has been suggested that the increased production of these, and other cytokines play an important role in postinfarct myocyte hypertrophy and contractile protein expression.

Hypertension

Hypertension or high blood pressure refers to an abnormally high pressure in the arteries that increases the risk of disorders including stroke, aneurysm, heart failure, heart attack and kidney damage. Normally, hypertension does not cause symptoms until a vital organ becomes damaged. High blood pressure is defined as a resting systolic pressure that averages 140 mm Hg or more, a resting diastolic pressure that averages 90 mm Hg or more, or both. When left untreated, high blood pressure can increase an individual's risk of developing heart disease, kidney failure or stroke.

Hemodynamic factors are important in the localization and initiation of atherosclerotic lesions and hypertension seems to accelerate atherogenesis in experimental animal models as well as in humans. Even in species resistant to dyslipidemia and lipid deposition in the arterial wall, such as the rat, hypertension causes a large number of functional and morphological alterations in the vessel wall, including hypertrophy and increased turnover of endothelial cells, polyploidy and intimal migration of medial smooth muscle cells, adhesion and subendothelial migration of blood mononuclear cells and extracellular matrix accumulation (Sarzani et al., 1989, *J. Clin. Invest.,* 83:1404–1408).

Arterial blood pressure can be increased as a result of an increase in the force with which the heart pumps, a stiffening of the large arteries, vasoconstriction (a constriction of the tiny arteries as a result of stimulation by nerves or hormones in the blood), or an increase in the amount of blood in the system (e.g. resulting from a kidney malfunction wherein insufficient quantities of salt and water are removed from the body). Many kidney diseases and kidney abnormalities (e.g. a narrowing of the artery supplying blood to one of the kidneys, kidney inflammation or kidney injury) can cause high blood pressure.

Hypertension can be treated by maintaining an ideal body weight, regulating diet and cholesterol levels, regulating sodium intake and by administering drugs that reduce blood pressure (including thiazide diuretic, adrenergic blockers, ACE inhibitors, angiotensin II blockers, calcium antagonists, direct vasodilators). In the case of hypertensive emergencies drugs such as diazoxide, nitroprusside, nitroglycerin and labetal can be administered to rapidly lower blood pressure (Berkow et al., supra).

The molecular mechanisms whereby increased intravascular pressure affects the vessel wall in vivo are unknown. However, studies using cultured cells have indicated that a number of different polypeptide growth factors can influence vascular cell function and proliferation. Several growth factors have been shown to be made in vitro by endothelial cell, smooth muscle cells and blood mononuclear cells. Multiple effects of different growth factors on these cell types led to suggestions that complex autocrine and paracrine control mechanisms exist in vivo in vascular tissue (Sarzani et al., supra).

TGF-β may play a role in the vascular remodeling process and myocardial hypertrophy induced by hypertension. A rat model of hypertension has been used to study the role of TGFβ in hypertension. According to this model, male Wistar rats are uninephrectomized at 10 wk of age and a pellet containing 100 mg deoxycorticosterone acetate (DOC; Innovative Research of America, Toledo, Ohio) is implanted subcutaneously 1 week after uninephrectomy. At the same time, animals are given 1% NaCl as drinking water. Control treatments include uninephrectomy alone and uninephrectomy plus DOC implant but with low sodium diet pellets (0.4% NaCl; Teklad Inc., Madison, Wis.) and tap drinking water. Systolic blood pressure is measured by tail cuff plethysmography and a photoelectric cell detector. Blood pressure measurements are made 1 day before killing the animals, and those with 150 mm Hg (and above) of systolic pressure are considered hypertensive. Aortas are cleaned of periadventitial tissues, rinsed in cold physiological saline solution and quickly frozen in liquid nitrogen. For some experiments aortas are opened longitudinally and the endothelium scraped with a scalpel blade, followed by rinsing in cold physiological saline solution. Microscopic evaluation of comparable aortas is expected to show complete loss of endothelium except in areas around the orifices of branch vessels.

TGF-β1 mRNA has been found to be increased several fold in the aorta of deoxycorticosterone-salt hypertensive rats compared with normotensive rats (Sarzani et al., supra), and vascular smooth muscle cells of spontaneously hypertensive rats show an altered responsiveness to TGF-β1 as well as autocrine TGF-β expression (Agrotis et al., 1994, *Hypertension,* 23:593–599). In vivo data indicate that infusion of TGF-β1 or transfection of TGF-β1 cDNA into injured arteries strongly accelerates lesion formation by increasing cellularity and extracellular matrix accumulation. It has been demonstrated that monocytes derived from hypertensive patients have an increased capacity to produce active TGF-β due to increased levels of TGF-β1 and 2 mRNA (Porreca et al., 1997, *Hypertension,* 30(Part 1):134–139). These data suggest that monocyte synthesis of TGF-β may play a role in the pathophysiology of vascular matrix remodeling associated with hypertensive disease.

TGF-β is a multifunctional modulator of cell metabolism and growth in vitro and affects both cultured endothelial cells and smooth muscle cells by either inhibiting or modulating growth patterns. In cultured smooth muscle cells, TGF-β may stimulate synthesis and secretion of proteoglycans and other components of the extracellular matrix. Several of the effects produced by TGF-β in various cultured cell systems also occur in aortic tissue during different forms of hypertension, including DOC/salt treatment. If increased TGF-β synthesis and secretion accompany the increased expression of this gene in the aortic tissue, this may be an important factor in the modulation of cell growth, phenotypic expression, and extracellular matrix accumulation in the aorta of DOC/salt hypertensive rats (Sarzani et al., supra).

Bronchopulmonary Dysplasia

Bronchopulmonary dysplasia is a lung injury that occurs in infants that remain on a ventilator for a prolonged period of time. Most likely, the lung injury results from inflammation and subsequent scarring of the lungs due to stretching of the air-spaces by the high pressure required for inflation of the lungs, and by the concentration of oxygen administered.

This condition can be treated by gradually weaning the infant from the ventilator, by restricting fluid intake, and by administering diuretics (Berkow et al., supra).

The cells involved in the reparative process of the premature lung are not well defined. The process by which the injured tissue is repaired is a highly standardized process in which the most important cells are activated/modulated fibroblasts or myofibroblasts. TGF-β plays an important role in regulating the repair process and appears to mediate a fibrosing process that causes scarring of the lungs (Toti et al., 1997, *Pediatr. Pulmonol.,* 24:22–28). It has been suggested that antagonists of TGF-β may function as antifibrinogenic agents and that antibodies capable of binding to TGF-β may be capable of inhibiting pulmonary fibrosis. These type of agents, as well as compounds such as proteasome inhibitors and anti-oxidants that modulate TGF-β activity, may impede the fibrosing process that is typical of the healing lung in bronchopulmonary dysplasia, and may therefore be useful for protecting neonates at high risk of developing bronchopulmonary dysplasia Atherosclerosis Arteriosclerosis refers to several diseases wherein the wall of an artery becomes thicker and less elastic. Atherosclerosis, the most common of these diseases, is characterized by accumulation of fatty material under the inner lining of the arterial wall. Atherosclerosis can affect the arteries of the brain (possibly leading to stroke), heart (possibly leading to heart attack), kidneys, other vital organs and the arms and legs.

Atherosclerosis begins with the migration of monocytes from the bloodstream into the wall of the artery, and the transformation of these cells into cells that accumulate fatty materials. As these cells accumulate, they cause a thickening (termed atherosclerotic plaque or atheroma) in the inner lining of the artery. These plaques are filled with fatty materials, primarily cholesterol, smooth muscle cells and connective tissue cells. Arteries that are affected with atherosclerosis become less elastic and more narrow. Eventually, atheromas collect calcium deposits, and may become brittle and rupture. Blood may enter a ruptured atheroma, further narrowing the artery and/or the fatty contents of a ruptured atheroma may spill and trigger the formation of a blood clot which may either further narrow the artery, or detach, float downstream and cause an occlusion or embolism.

Symptoms of atherosclerosis are not apparent until an artery is severely narrowed or obstructed. The symptoms will vary depending on the location of the atherosclerosis. The initial symptoms of a narrowing artery can be pain or cramps due to an inability of the blood flow to meet the body's demand for oxygen (Berkow et al., supra).

Recent in vitro evidence has suggested that another blood component, TGF-β may regulate atherogenesis. Atherosclerotic lesions of the coronary vessels are thought to originate from injury or dysfunction of the endothelium, although the mechanisms responsible for the initial injury are not well defined. In response to various agents acting at the site of injury, including platelet-derived growth factor, other mitogens and chemotactic agents, the underlying vascular smooth muscle cells (VSMCs) migrate into the lumen and proliferate to form an intima. TGF-β inhibits both the migration and proliferation of VSMCs in cell culture. Human VSMCs produce TGF-β in a latent, inactive form which is activated proteolytically from plasminogen by tissue plasminogen activator (tPA) on the cells and the risk factors Lp(a) and PAI-1 block the activation of latent TGF-β by competitively inhibiting tPA. PAI-1 and Lp(a) therefore promote human VSMC proliferation in culture by relieving the autocrine inhibition by active TGF-β (Grainger et al., 1995, *Nat. Med.*, 1:74–79).

The component of Lp(a) that acts as an inhibitor of plasminogen activation is apolipoprotein(a) (apo(a)) which has 80% amino-acid sequence homology with the corresponding domains in plasminogen. Evidence from a transgenic mouse model of atherosclerosis in which human apo(a) is expressed has provided in vivo support for a close correlation between accumulation of apo(a) on the vessel wall and inhibition of TGF-β activation. At the sites of apo(a) accumulation, the VSMCs are activated and vascular lesions subsequently develop. Thus, it has been suggested that active TGF-β is a key inhibitor of atherogenesis (Grainger et al., supra). This hypothesis is supported by data demonstrating that a population of patients with advanced atherosclerosis all have less active TGF-β in their sera than patients with normal coronary arteries (Grainger et al., supra). Thus, TGF-β may be a potential therapeutic target.

TGF-β family members may be involved in the development of certain cardiovascular disorders for the following reasons. TGF-β inhibits the growth of vascular smooth muscle cells (Halloran et al., *Am. J. Surg.*, 1995, 170:193–197). The ability of TGF-β to induce extracellular matrix production suggests that TGF-β may function in matrix remodeling during vasculature development. It has also been demonstrated that TGF-β is involved in the responses of blood vessels to inflammation and injury. Compounds including proteasome inhibitors and antioxidants, which modulate TGF-β activity, may be useful for treating certain cardiovascular disorders associated with increased or decreased levels of activity of TGF-β family members.

3. Osteoporosis

The invention also provides methods of treating osteoporosis.

Osteoporosis, the most common form of metabolic bone disease, is characterized by a reduction in bone mineral and bone matrix that produces bone that is of a normal composition but is decreased in density and is therefore more likely to fracture. Typically, osteoporosis results from the normal effects of menopause in women, and aging, in both men and women. However, other disorders including glucocorticoid excess, hypogonadism, hyperthyroidism, hyperparathyroidism, vitamin D deficiency, gastrointestinal diseases, bone marrow disorders, immobilization, connective tissue diseases and certain drugs can cause osteoporosis.

In the absence of the occurrence of a fracture, osteoporosis is asymptomatic. Following the occurrence of bone collapse or fracture, bone pain may occur and deformities may develop. The most common types of fractures in patients with osteoporosis are vertebral compression fractures or fractures of the wrist, hip, pelvis or humerus. Osteoporosis can be diagnosed prior to the occurrence of a fracture by a variety of methods that measure bone density. These measurements can also be used to predict the development of certain osteoporotic fractures.

Although presently, established osteoporosis cannot be reversed, methods of early intervention can prevent osteoporosis in most individuals, and later intervention can inhibit the progression of the disease. Methods of treatment of osteoporosis include increasing dietary calcium (calcium can slow but not prevent bone loss in women in the early stages of menopause), estrogen treatment (estrogen replacement therapy prevents bone loss in estrogen deficient women), calcitonin treatment (calcitonin appears to prevent loss of bone in the spine of women in either the early or late stages of menopause without affecting appendicular bone loss), biophosphonates (biophosphonates inhibit resorption of osteoclastic bone) and vitamin D and its metabolites (Andreoli et al., supra and Berkow et al., supra).

Several animal models have been useful for studies of osteoporosis, most notably the ovariectomized (OVX) rat. OVX rats display significantly decreased trabecular bone volume (41%) and decreased mechanical strength of the femoral neck (15.8%) (Peng et al., 1994, *Bone*, 15:523–532).

Recombinant proteins can be useful for attenuating osteoporosis. Bone morphogenetic protein (BMP) is a family of bioactive factors that stimulate new bone formation in ectopic sites by inducing the differentiation of primitive mesenchymal cells into bone producing cells (Strates et al., 1988, *Am. J. Med. Sci.*, 296:266–269). Therefore, recombinant human bone morphogenetic protein (rhBMP) may be useful for the treatment of osteoporosis (Urist et al., 1985, *Progress in Clinical and Biological Research*, 187:77–96).

TGF-β has powerful modulatory effects on the skeletal system, enhancing bone formation and decreasing matrix degradation, thus playing a part in the maintenance of bone mass (Boonen et al., supra). Bone matrix is a major repository for TGFβ, and TGFβ is thought to play an important role in bone development and remodeling. TGFβ is synthesized by bone cells, is secreted as a latent complex, is stored in the extracellular matrix, and can be released by bone resorption. Although TGFβ has biphasic effects on osteoblastic proliferation, depending on cell density and differentiation state, as well as on TGFβ concentration, its effects on bone formation or type I collagen synthesis are generally stimulatory both in vitro and in vivo. However, overexpression of TGFβ2 in osteoblasts in vivo causes bone loss. TGFβ inhibits bone resorption in rat long bone cultures. In contrast, in mouse calvariae, TGFβ can stimulate prostaglandin G (PG) dependent resorption. TGFβ has biphasic effects on the production of osteoclast-like cells in mouse bone marrow cultures; low TGFβ concentrations stimulate a PG-dependent increase in formation, whereas at high TGFβ concentrations one observes a PG-independent inhibition. In addition to stimulating PG production in neonatal mouse calvariae, TGFβ can stimulate $PGE_2$ production in the clonal osteoblast-like MC3T3-E1 cell line and enhance the stimulatory effects of other cytokines, such as interleukin 1 on PG production (Pilbeam et al., 1997, *Endocrinology*, 138:4672–4682).

Compounds including proteasome inhibitors and antioxidants that regulate the activity of TGF-β family members may be useful for treating osteoporosis.

4. Scleroderma (Systemic Sclerosis)

The invention also provides methods of treating scleroderma.

Scleroderma is a chronic, multisystem connective tissue disorder characterized by degenerative and sclerotic changes in the skin, joints, and internal organs, and by blood vessel abnormalities. Typically, the initial symptoms of scleroderma are thickening and swelling of the ends of the fingers, as well as Raynaud's phenomenon wherein the fingers become pale and tingle, or become numb in response to cold or emotional upset. Additionally, scleroderma patients may experience joint pain as an early manifestation of the disease.

Scleroderma can result in damage to either large areas of the skin or just the fingers. As the disease progresses, the skin becomes taut, shiny and unusually dark. The skin on the face tightens, spider veins appear on the fingers, chest, face, lips and tongue, and bumps composed of calcium can develop on the fingers, on other bony areas, or at the joints.

Often, a grating sound can be heard as the inflamed tissues move over each other, particularly at and below the knees. The fingers, wrists, and elbows can become fixed in contracted positions due to the scarring that has occurred in the skin. Sores can develop on the fingertips and knuckles.

As a result of scarring, damage to the lower end of the esophagus can occur. Consequently, the damaged esophagus is unable to transport food to the stomach efficiently, and swallowing difficulties and heartburn develop. Some scleroderma patients experience abnormal cell growth in the esophagus which can increase the risk of esophageal blockage or cancer. Intestinal damage can interfere with food absorption thereby resulting in weight loss. The drainage system from the liver may become blocked by scar tissue, resulting in liver damage and jaundice. Scleroderma can also result in scar tissue accumulating in the lungs, resulting in abnormal shortness of breath during exercise, life threatening heart abnormalities including heart failure and abnormal rhythm, and severe kidney disease.

Scleroderma can be diagnosed by the characteristic changes in the skin and internal organs.

Although drug treatment cannot stop the progression of scleroderma, drugs can be used to relieve some of the symptoms of the disease and reduce organ damage. Nonsteroidal anti-inflammatory drugs or, in some cases, corticosteroids, can relieve muscle and joint pain and weakness. Penicillamine can be administered to slow the rate of skin thickening and delay the involvement of additional internal organs. Heartburn can be relieved by eating small meals and taking antacids and histamine blocking drugs to inhibit stomach acid production. Constricted areas of the esophagus can be dilated. Tetracycline and/or other antibiotics can help prevent intestinal malabsorption caused by the overgrowth of bacteria in the damaged intestine. Nifedipine may be administered to relieve the symptoms of Raynaud's phenomenon. Antihypertensive drugs can be administered to treat kidney disease and high blood pressure (Berkow et al., supra).

Systemic sclerosis is also characterized by excessive accumulation of extracellular matrix, resulting in progressive fibrosis and dysfunction of a number of organs. The skin is most commonly involved and here there is a progression of fibrosis associated with microvascular changes. The fibrosis is of unknown aetiology, although a number of causes have been implicated. These include activation of atypical fibroblast clones, vascular phenomena, autoimmunity, and environmental toxins. At the molecular level, investigators have been pursuing the concept that, as in other 'fibrotic' disorders, TGFβ has a central role to play in pathogenesis (Cotton et al., 1998, *J. Pathol.*, 184:4–6).

Pulmonary fibrosis is responsible for many of the deaths of patients with systemic sclerosis. The pathogenesis of pulmonary fibrosis is poorly understood but recent evidence suggests that polypeptide mediators, including TGFβ1, play a key role. TGFβ1 has potent stimulatory effects on the synthesis of procollagens, fibronectins, and glycosaminoglycans by lung fibroblast cells lines and this is associated with an increase in steady-state levels of mRNA for these proteins, compatible with its playing a role in the pathogenesis of pulmonary fibrosis (Corrin et al., 1994, *Histopathology*, 24:145–150).

TGFβ has wide-ranging cellular actions. It is a potent chemoattractant for human dermal fibroblasts, from which it may induce synthesis of collagen, which suggests that it may have a central role to play in the pathogenesis of scleroderma sclerosis. This is supported to some extent by in vitro studies demonstrating that scleroderma sclerosis fibroblasts produce more collagens and fibronectin than normal fibroblasts. Although the precise role of TGFβ in scleroderma sclerosis has not been elucidated, data suggests that TGFβ is a mediator of fibrosis in this disorder.

TGF-β may play an important role in the pathogenesis of scleroderma. Thus, inhibitors of TGF-β activity may be useful for treatment of this disease.

5. Male Fertility

The invention also provides methods of treating abnormalities of male fertility.

A role for bone morphogenetic protein 8B (BMP8B) in the regulation of male fertility has been demonstrated in BMP8B knock out mice. The mice were produced as described in detail in Zhao et al., 1996, *Genes & Devel.*, 10:1657–1669.

It has been demonstrated that homozygous $Bmp_8B^{tm1blh}$ mutant males exhibit various degrees of germ-cell deficiency and infertility. First, during puberty (2 weeks old or younger) the germ cells of all homozygous mutants either fail to proliferate or show a marked reduction in proliferation and a delayed differentiation. Second, in adults, there is a significant increase in programmed cell death (apoptosis) of spermatocytes, leading to germ-cell depletion and sterility. Sertoli cells and Leydig cells appear relatively unaffected in mutants. This study provides evidence that a murine germ cell-produced factor, BMP8B, is required for the resumption of male germ-cell proliferation in early puberty, and for germ-cell survival and fertility in the adult.

These data suggest that compounds that can modulate the activity of TGFβ superfamily member ligands, in particular BMP8B, may be useful for treating abnormalities in spermatogenesis and male fertility.

6. Neurodegenerative Diseases

The invention also provides methods of treating neurological disorders, including neurodegenerative diseases (e.g. Parkinson's disease, Huntington's disease or Alzheimer's disease).

Parkinson's Disease

Parkinson's disease is a slowly progressing, degenerative nervous system disorder characterized by tremors when at rest, sluggish initiation of movements and muscle rigidity. In Parkinson's disease, nerve cells in the basal ganglia degenerate, resulting in lower production of dopamine and fewer connections with other nerve cells and muscles.

Generally, Parkinson's disease begins with a tremor in the resting hand that decreases when the hand moves purposefully and disappears during sleep. Eventually, the tremor may progress to the other hand, the arms, the legs, and effect the jaw, tongue, forehead and eyelids. Individuals with Parkinson's disease often have difficulty initiating a movement, and experience muscle stiffness. As a result of these symptoms, any type of minor physical activity becomes extremely difficult.

A variety of drugs may be used to treat Parkinson's disease. These drugs include levodopa, bromocriptine, pergolide, selegiline, anticholinergics, antihistamines, antidepressants, propranolol and amantadine. Although these drugs do not stop the progression of, or cure Parkinson' disease, they may make physical activity easier.

The mobility of a Parkinson's patient can be maintained by continuing to perform daily activities, exercising, physical therapy and the use of mechanical aids such as wheeled walkers (Berkow et al., supra).

Parkinson's disease is characterized by the idiopathic and progressive loss of mesencephalic dopaminergic neurons of the substantia nigra leading to a loss of dopamine in the striatura, the main projection field of these neurons. This neuronal degeneration results in the major symptoms of Parkinson's disease, i.e., tremor, muscular rigidity, difficulty in movement initiation, and loss of postural reflex (Pratt and McPherson, 1997, Cytokine and Growth Factor Reviews, 8:267–292).

Several research groups have reported that the various TGF-β isoforms can provide enhancement of in vitro survival and function of some types of neurons cultured under "normal" or basal conditions. Given these observations on the neurotrophic effects of TGF-β on diverse types of neurons, several laboratories have investigated the effects of TGF-β on the survival of tyrosine hydroxylase positive (TH+) dopaminergic neurons, i.e. those affected in Parkinson's disease. It has been reported that all three isoforms of TGF-β promote a dose-dependent increase of in vitro survival of embryonic rat dopaminergic neurons (Pratt and McPherson, 1997, supra).

In situ hybridization studies have revealed that during embryonic development in the rat, transcripts for TGF-β2 and glial cell line-derived neurotrophic factor (GDNF), another neurotrophic factor for dopaminergic neurons and a member of the TGF-β superfamily, can be detected in close proximity to the TH+ neurons in the ventral midbrain during the period of dopaminergic axonal outgrowth and initial target innervation. Following birth, TGF-β2 and GDNF signals disappear from the ventral midbrain but are upregulated in the innervation targets of the midbrain dopaminergic system. These data suggest that TGF-β2 and GDNF normally support the survival of dopaminergic neurons while they project to their targets during embryonic outgrowth. When these dopaminergic fibers contact their innervation sites, expression of these two cytokines is shut off in the ventral midbrain but TGF-β2, 3 and GDNF are upregulated in the various innervation targets. Since expression of each of these neurotrophic factors is restricted to specific innervation sites, it is possible that they provide targeting signals for proper innervation during development (Pratt and McPherson, 1997, supra).

Given the effects of TGF-β and GDNF on dopaminergic cell survival in vitro, investigators have evaluated the neuroprotective effects of TGF-β3 and GDNF in a rodent model of Parkinson's disease. Intracerebral administration of GDNF for 4 weeks following unilateral 6-hydroxydopamine lesioning of the dopaminergic terminals in the striatum which produces a progressive degeneration of the ipsilateral nigral dopamine neurons, completely prevented nigral cell death and atrophy. A single 10 µg injection at 1 week post-lesion has a partial protective effect. Similar dosing strategies with TGF-β3 had no effect on nigral cell death or atrophy (Pratt and McPherson, 1997, supra).

The data on levels of TGF-β in Parkinson's disease patients are extremely limited. It has been reported that TGF-β1 and TGF-β2 levels are elevated in the striatum and in the ventricular cerebrospinal fluid (VCSF) of patients with Parkinson's disease. It appears that at least some of the TGF-β1 in the VCSF may be derived from plasma, although it is also possible that elevated TGF-β1, and probably most of the TGF-β2 may be a consequence of neuroprotective compensatory cell mediated events in the vicinity of dopaminergic neuronal degeneration (Pratt and McPherson, 1997, supra).

Alzheimer's Disease

Alzheimer's disease is the most common form of dementia. Although the exact cause of Alzheimer's disease is not known, genetic factors play a role in the occurrence and development of this disease. Furthermore, TGFβ has been implicated in the development of Alzheimer's disease. Patient's with Alzheimer's disease suffer from degeneration of parts of the brain, resulting in the destruction of cells and the reduction of the responsiveness of the remaining cells to the chemicals that transmit signals in the brain. Abnormal tissues, termed senile plaques, neurofibrillary tangles, and abnormal proteins appear in the brain. During an autopsy, Alzheimer's disease can be diagnosed by the presence of abnormal brain tissue, characterized by a loss of nerve cells, the presence of tangles within the remaining nerve cells, and plaques made of amyloid scattered throughout the brain tissue.

The progression of Alzheimer's disease can be slowed but not stopped with a number of drugs including tacrine, and donepezil.

Dementia resulting from Alzheimer's disease normal begins subtly and results in a gradual deterioration of memory. The first sign of dementia is usually forgetfulness (Berkow et al., supra).

Alzheimer's disease (AD) is a progressive neurodegenerative disease characterized by neuronal loss primarily in the temporal lobes and neocortex. This neuronal loss causes progressive loss of cognitive function and ultimately leads to severe dementia. Histological analysis of brains from AD patients has revealed that they contain numerous neuritic plaques consisting substantially of aggregates of β amyloid peptide (Aβ), a 39–43 amino acid peptide derived from a larger transmembrane protein referred to as the amyloid precursor protein (APP). Numerous investigators have shown that Aβ is neurotoxic in vitro and in vivo, which has led to the conclusion that Aβ accumulation is a key factor in the development of AD. The cause of increased accumulation of Aβ in the brains of AD patients is not known but is believed to be a consequence of increased production of APP and/or abnormal processing of the protein ultimately leading to elevated levels of Aβ.

Interest in the potential role of TGF-β in AD has been derived from numerous observations during the past few years. Initially, it was discovered that TGF-β2 produced by microglial cells in culture was associated with APP as demonstrated by immunoprecipitation and cross-linking experiments. Subsequently, it was reported that TGF-β1 could be immunohistochemically visualized in some senile plaques, particularly those in both the dentate gyrus of the hippocampus and the entorhinal cortex. This observation was intriguing in light of the work of other investigators who have shown that co-administration of TGF-β was required to stimulate plaque formation in a model of long-term infusion of Aβ into the rat brain.

While it is not clear whether TGF-β1 levels are generally elevated in AD patients, evidence has been presented which indicates that TGF-β2 levels are significantly elevated in the brains of AD patients. TGF-β2 was localized to glial cells and tangle bearing neurons of AD patients. Tangle bearing neurons are thought to be degenerating neurons and are characterized by the accumulation of intracytoplasmic filamentous materials described as neurofibrillary tangles. Quantitation of TGF-β2 by isoform-specific ELISA in the brains of AD patients and normal individuals has demonstrated an average 3.2-fold increase in levels of the growth factor in the brains of the former group, as compared with cognitive normal controls. Consistent with these data are additional observations indicating that TGF-β levels are statistically increased in the sera and cerebral spinal fluid of AD patients and that the level of TGF-β in the serum correlates with disease severity. Since the TGF-β levels in these studies were determined by bioassay, the TGF-β isoform distribution in these body fluids is not established.

It is possible that increased levels of TGF-β may also contribute to AD pathology. In addition to potentially mediating plaque formation, as mentioned above, TGF-β1 has also been reported to substantially increase the in vitro production of APP mRNA and protein by astrocytes and microglia.

Since it appears that Aβ plaque formation is a consequence of abnormal processing of APP, it is clear that increased production of APP or perturbation of normal ration of APP isoforms by an agent such as TGF-β could further disturb protein processing and accelerate plaque formation by increasing local concentrations of Aβ. In addition to inducing plaque formation it has been reported that Aβ can directly effect neuronal cell health by destabilizing calcium homeostatsis and rendering the cells more susceptible to glutamate cytotoxicity. At least one report indicates that Aβ plus TGF-β1, in the absence of excitatory amino acids, can significantly increase intracellular calcium levels in certain neuronal cells. These data suggest a direct mechanism for Aβ mediated neuronal cell toxicity, in which increases in intracellular $Ca^{2+}$ levels and subsequent cell death are a consequence of Aβ accumulation in the brains of AD patients in conjunction with elevated levels of TGF-β, as opposed to Aβ mediated enhancement of glutamate excitotoxicity. Thus, it appears that elevated TGF-β levels in the brains of AD patients could contribute to disease pathology through several different pathways.

Paradoxically, there are also several reports in the literature that indicate TGF-β can have a neuroprotective role in AD-related pathologies. TGF-β1 has been shown to provide a dose-dependent protection of human fetal neuronal cells against the cytotoxic actions of Aβ. Similar neuroprotective effects for all three TGF-β-isoforms have been reported for rat hippocampal neurons treated with Aβ or active fragments derived from the peptide.

Taken together, the data present a complex role for TGF-β in neurodegeneration related to AD. Clearly, increased levels of TGF-β in specific areas of the brain may contribute to AD pathogenesis via the various mechanisms described. Alternatively, those same levels of TGF-β may serve to provide neuroprotection by sustaining mitochondrial function and upregulating the expression of such proteins as clusterin which could influence plaque formation and may reduce complement mediated cell destruction. Thus, while the cause and effect relationships of all three TGF-β isoforms in AD remain to be clarified, it is almost certain that these growth factors play an important role in the progression of this neurodegenerative disease (Pratt and McPherson, supra).

Stroke

A stroke (also termed cerebrovascular accident) is the death of brain tissue (cerebral infarction) resulting from lack of blood flow and insufficient oxygen to the brain. A stroke can be either ischemic, wherein the blood supply to part of the brain is cut off because either atherosclerosis or a blood clot has blocked a blood vessel, or hemorrhagic, wherein a blood vessel bursts, preventing normal flow and allowing blood to leak into an area of the brain and destroy it.

The major risk factors for stroke are high blood pressure and atherosclerosis. How a stroke affects the body depends on the location in the brain where the blood supply is cut off or where bleeding occurs. Loss of function due to damage to brain cells associated with a stroke may only be temporary if brain cells are only injured. Occasionally a stroke can occur when blood flow is normal but the blood does not contain enough oxygen (e.g. in cases of severe anemia, during carbon monoxide poisoning, or with conditions such as leukemia or polycythemia that produce abnormal blood cells or abnormal blood clotting).

In the case of an ischemic stroke, blockage can occur at any location along the arterial pathways to the brain. Blockage associated with an ischemic stroke can be caused by fatty material (atheroma) or from blood clots from in the heart that break loose (embolus). A stroke can also occur if inflammation or an infection narrows blood vessels that lead to the brain. Drugs, including cocaine and amphetamines can narrow the blood vessels in the brain and cause stroke. A sudden, severe, prolonged drop in blood pressure can also result in stroke.

Most strokes begin suddenly, develop rapidly and cause brain damage within minutes. The symptoms of a stroke can vary depending on which part of the brain is affected. Although the symptoms of a stroke can be similar to those of a transient ischemic attack, the neurologic dysfunction that results from a stroke is more likely to be severe, widespread, associated with a coma or stupor and permanent. Strokes can also cause edema in the brain wherein the resulting pressure can damage brain tissue thereby making neurological problems worse.

Typically a stroke can be diagnosed from the history of events and from a physical examination. Often, a computed tomography (CT) or magnetic resonance imaging is performed to confirm the diagnosis.

It is important to determine the cause of a stroke so that the underlying problem can be corrected.

Administration of oxygen may be useful for treating the early stages of a stroke. Anticoagulants may also be used to treat a stroke before it has been completed. If the stroke has been caused by a clot, paralysis and other symptoms may be prevented or reversed by the action of drugs that break up clots, such as streptokinase or tissue plasminogen activator. Following a small stroke or a transient ischemic attack, removal of blockages may reduce the risk of future strokes. Swelling and increased pressure on the brain can be alleviated by administration of drugs such as mannitol, or less commonly, corticosteroids. It may be useful to put a patient who has suffered a severe stroke on a respirator because of pneumonia, or to maintain adequate breathing. Often, stroke victims must be treated for accompanying problems including heart failure, irregular heartbeats, high blood pressure, and lung infections (Berkow et al., supra).

Ischemia is a reduction in normal blood flow to a level insufficient to meet cellular metabolic demand. Prolonged oxygen depravation, as part of ischemia, leads to depletion of energy reserves within the neurons and glial cells which, in turn, reduces the function of energy-dependent ion transporters, resulting in a loss of resting membrane potential. As a consequence of this presynaptic depolarization, glutamate is released in an uncontrolled and persistent fashion onto the post-synaptic NMDA (N-methyl-n-aspartate) receptors. The overstimulation of NMDA receptors leads to a pathological increase in intracellular $Ca^{2+}$ and the resultant excitatory injury and cell death (Pratt and McPherson, supra).

The hippocampus, a structure in the inferior medial region of the temporal lobe of the cortex, is a particularly sensitive target of hypoxic and excitatory injury. The hippocampus plays a key role in learning and long-term memory. Loss of neural circuits within and connecting to the hippocampus are associated with anterograde amnesia, learning deficits, and Alzheimer's disease. The hippocampus contains five major anatomic subregions, four within the cornu anumonis (CA1–CA4) and the dentate gyrus. Within each of these regions are discrete zones of neurons and glial cells which show differential sensitivity of hypoxic and excitatory cellular injury (Pratt and McPherson, supra).

In animals, the two most common models for ischemic injury to the brain are transient or permanent unilateral middle cerebral artery occlusion (MCAO) and transient forebrain global ischemia (TFGI) created by the temporary occlusion of the carotid arteries which may be combined with transient systemic hypotension. In either model selective neuronal cell death is observed in pyramidal cells of the cornu ammonis and dentate gyrus of the hippocampus, as well as other discrete areas of the cortex (Pratt and McPherson, supra).

In the normal adult brain expression of TGF-β1 is restricted to meningial cells and is absent from neurons while TGF-β2 and TGF-β3 are present in many neuronal cell populations within the developing and adult brain (Pratt and McPherson, supra).

In the rat MCAO model, TGF-β1 mRNA was elevated in the pyramidal cell layers of CA1, CA2 and the dentate gyrus of the ipsilateral hippocampus following as little as 15 minutes of ischemia. The extent and intensity of elevated TGF-β1 mRNA expression was dependent on the duration of ischemia. Following 90 minutes of ischemia TGF-β1 mRNA expression extended to the CA3 pyramidal cell layer as well as several locations within the cortex. Likewise, the duration of TGF-β1 mRNA expression within the injured hippocampus was dependent on the severity of injury. Five days after 15 minutes of ischemia, TGF-β1 mRNA returned to normal levels within the hippocampus. In contrast, following permanent MCAO, TGF-β1 mRNA remained elevated at least 15 days after injury. In the rat TFGI model, TGF-β1 mRNA was also elevated in the hippocampus, the peak times and areas of expression coincided with areas of neuronal degeneration and glial cell activation (Pratt and McPherson, supra).

Another group has also evaluated the neural expression of mRNA and proteins of all three TGF-β isoforms in the TFGI model. In the first three days after TFGI, TGF-β mRNA expression in CA1–CA4 pyramidal cells did not always correlate with either cell survival or protein immunoreactivity. However, a very good spatial correlation was observed between protein immunoreactivity of all three isoforms and pyramidal cell survival, namely TGF-β protein immunoreactivity was diminished in the CA1 pyramidal cell layer and those neurons died while TGF-β immunoreactivity in the CA2–CA4 pyramidal cell layer remained at or above control levels and those neurons survived. These data are consistent with the possibility that the presence of TGF-β within CA2–CA4 pyramidal neurons is important for their survival following TFGI (Pratt and McPherson, supra).

The only human data on TGF-β1 expression in the brain following ischemic injury is the following. In post-mortem samples obtained from individuals who have previously suffered from ischemic stroke, elevated levels of TGF-β1 mRNA and protein were observed in neurons, glial cells, endothelia and macrophages of the infarcted and penumbral areas. While not providing definitive data on the temporal and spatial localization of TGF-β production following ischemic injury, these data are consistent with the hypothesis that TGF-β is involved in the pathogenic or protective processes following ischemic injury (Pratt and McPherson, supra).

Several groups have evaluated exogenously administered TGF-β1 as a neuroprotective agent against in vivo ischemic injury. In a permanent MCAO mouse model, the effect of prophylactic administration of TGF-β1 in infarct size has been examined. When given as a single intracerebroventricular (ICV) injection of 1 μg/kg at 2, 4 or 6 hour before TFGI, TGF-β1 provided a small (≈10%) but significant decrease in ischemic area of the neocortex when assessed 48 hours after ischemic injury. In a rat TFGI model, it was demonstrated that when given as a single 4 ng intrahippocampal injection, 1 h prior to TFGI, TGF-β1 provided a significant increase in pyramidal cell survival (50% vs 20% in control) when assessed 7 days after TFGI. When the same amount was administered by ICV, a smaller but still significant effect (48% vs 29%) on CA1 pyramidal cell survival was observed. When given in higher or lower doses (0.5 or 50 ng ICV), no neuroprotection was observed (Pratt and McPherson, supra).

The therapeutic effect of administration of TGF-β1 on neuronal survival, infarct area and microglial activation was demonstrated in a transient carotid artery ligation model in rats. When given as a single ICV dose of 10 ng 2 hours after ischemic injury, TGF-β1 provided significant neuroprotection in several areas of the cortex, thalamus, striatum and dentate gyrus when assessed 5 days after ischemic injury. However, CA1–CA4 hippocampal neurons were not protected. Doses of either 2 or 50 ng given on the same schedule did not provide significant neuroprotection in any of the evaluated areas of the brain. A bell-shaped dose-response effect of TGF-β1 on area of cortical infarction was also observed, i.e. a significant effect at either 2.5 or 50 ng. Consistent with the neuroprotective effect, when evaluated at 48 hours after ischemic injury 10 ng of TGF-β1 also significantly reduced the intensity of microglial activation, particularly within the thalamus and cortex. In additional studies, the effects of TGF-β1 on impaired learning behavior following ischemic injury were studied. It was observed that the 10 ng of ICV dose improved both deficits in water maze learning ability and also asymmetry in somatosensory functions during the first 10 days after injury. These therapeutic effects of TGF-β1 on ischemia and reperfusion injury within the central nervous system are reminiscent of similar therapeutic actions of TGF-β in myocardial and splanchnic ischemia reperfusion injury (Pratt and McPherson, supra).

Based on the limited in vivo data currently available, TGF-β1 appears to have biologically relevant prophylactic and therapeutic neuroprotective effects in models of ischemic brain injury (Pratt and McPherson, supra).

Multiple Sclerosis

Multiple sclerosis (MS) is a central nervous system disease characterized by plaques of demyelination in nerve fibers of the brain and spinal cord Hallmarks of multiple sclerosis include elevated circulating levels of B and T cells which are responsive to myelin basic protein (MBP) and proteolipid protein (PLP), perivascular inflammatory cell infiltration within the CNS, and the localized destruction of oligodendrocytes within the demyelinating lesions (Pratt and McPherson, supra). Demyelination causes multiple and varied neurologic symptoms and signs such as neurologic dysfunction including abnormal movement, abnormal sensations, tingling and numbness, loss of strength or dexterity, and visual abnormalities. The physical manifestations of multiple sclerosis result from the demyelination process slowing or blocking the conduction of nerve impulses. MS is typically characterized by periods of relapses and remissions, and eventually becomes progressive in most patients. Although the etiology of multiple sclerosis is not known, it is thought that this disease is caused by both immunologic and genetic factors. The most sensitive method for diagnosing multiple sclerosis is magnetic resonance imaging to detect a loss of myelin as white matter lesions located in the brain and/or spinal cord (Berkow et al., supra).

Currently methods exist for treating the symptoms of multiple sclerosis rather than the disease. The frequency of relapses associated with multiple sclerosis can be decreased with beta-interferon treatment. Beta-interferon also reduces the rate of appearance of cerebral demyelinating lesions. Corticosteroids have also been used to treat multiple sclerosis (Berkow et al., supra). Another protein that may be useful for the treatment of multiple sclerosis is the neuroprotectant molecule annexin-1, a calcium-dependent phospholipid binding protein. A useful animal model for MS is provided by female SJL/J mice with experimental autoimmune encephalomyelitis (EAE), a disease that exhibits symptoms that mimic MS (Ding et al., 1998, *J. Immunol.,* 160: 2560–2564).

At the present time, there is extremely limited information on the expression of TGF-β within the CNS of MS patients. In initial studies, TGF-β1 and TGF-β2 mRNA and TGF-β1 protein were found, post mortem in the brains of MS patients. More recently, it as been demonstrated that in active lesions (characterized by a cuff of activated microglia), TGF-β1 and TGF-β3 were present in leukocytes while only TGF-β2 was present in the peri-lesional microglia, and to a lesser extent in astrocytes. In chronic active lesions (characterized by the presence of intralesional astrocytes and a relative paucity of reactive microglia) within the white matter, intralesional astrocytes expressed all three TGF-β isoforms. In contrast, astrocytes within chronic active lesions in the cortex expressed only TGF-β2 (Pratt and McPherson, supra).

There are no data on the ability of exogenously administered TGF-β to affect the disease course of MS. There is however, a reasonable body of data demonstrating an inverse correlation between TGF-β levels and the severity of the ongoing disease process. Specifically, the percentage of blood mononuclear cells or T cells expressing TGF-β1 mRNA is inversely correlated with disease state, i.e. higher in patients in remission or with minimal disability, and lower in patients in relapse or with greater disability. Similarly, TGF-β1 mRNA and protein is elevated in blood mononuclear cells and T cells from MS patients in remission as compared with patients in relapse. Furthermore, serial measurements in relapsing-remitting MS patients have shown that clinical relapses are preceded by a drop in TGF-β1 mRNA and protein production in blood mononuclear cells, while recovery from a relapse is correlated with elevated levels of TGF-β1 mRNA and protein in the same cell population. Experimentally, it has been shown by in vitro culture of blood mononuclear cells from MS and optic neuritis patients that the addition of TGF-β1 will suppress antigen driven upregulation of cytokines, IFN-γ, TNF-α, TNF-β, IL-4, and IL-6, as well as decreasing proportion of cells expressing these cytokines (Pratt and McPherson, supra).

The mouse model of EAE has provided further insight into the role of TGF-β in ms. Numerous investigators have demonstrated that systemic administration of TGF-β1 or TGF-β2 when administered prior to or during a relapse, can reduce the incidence and severity of paralytic episodes in antigen-stimulated or adoptive transfer mediated models of EAE. Conversely, administration of neutralizing antibody to TGF-β exacerbates disease incidence and severity. Similarly, treatments which elevate the number of T cells secreting TGF-β1, e.g. oral tolerization with MBP or PLP, IL-4, dietary γ-linoleic acid, also decrease EAE incidence and severity. Other investigators have shown that strain specific differences in levels of inducible TGF-β correlate with susceptibility to, or severity of EAE, i.e. strains or rodents which are highly susceptible to induction of EAE express low levels of TGF-β during disease episodes while strains which are more resistant to EAE express higher levels of TGF-β. The precise pathways by which TGF-β influences disease processes in EAE, or MS are unknown (Pratt and Mcpherson, supra).

Based on the data (described above) regarding the role of TGF-β superfamily ligands in neurodegenerative diseases, compounds that modulate the activity of these cytokines may be useful for treating neurodegenerative diseases.

7. Immunosuppressant

The invention also provides methods of treating diseases that result from immunosuppression.

It has been demonstrated that TGF-β is an immunosuppressive factor which inhibits lymphocyte proliferation. Investigations into the mechanism of TGF-β induced immunosuppression suggest that TGF-β inhibits antigen-induced T cell proliferation by inhibiting the functions of both antigen-presenting cells and T cells (Romeo, 1991, *Dissertation Abstracts International,* 52:1185B).

Compounds which increase or decrease TGF-β activity may be useful for treating diseases characterized by TGF-β induced immunosuppression.

8. Wound healing

Wound healing involves a complex process of cell migration and proliferation, synthesis of extracellular matrix, angiogenesis and remodeling of the collagenous framework that requires many growth factors, such as TGF-beta and platelet-derived growth factor (Amento et al., 1991, *Ciba Foundation Symposium,* 157: 115–123, Hosgood et al., 1993, *Vet. Surg.,* 226: 490–495. Rat and rabbit animal models for wound healing have been demonstrated (Terrell et al., 1993, *International Review Exp. Pathology,* 34 Pt B: 43–67).

One of the most well characterized in vivo actions of TGF-β is its ability to mediate a wound-healing cascade which results in accelerated tissue repair. At the site of a peripheral wound, degranulation of platelets releases a bolous of TGF-β1 which initiates a number of biological responses. Monocytes, lymphocytes, neutrophils and fibroblasts are recruited to the wound site as a result of chemotactic activity of TGF-β. Autoinduction of TGF-βs in a number of cell types maintains high levels of the growth factor in the wound bed where it induces angiogenesis and production of extracellular matrix to aid in tissue repair. If the wound-healing response fails to resolve at the completion of healing or if the tissue is subjected to chronic injury, the deposition of excessive granulation tissue can result in fibrotic disease ( Flanders et al., supra).

Compounds capable of modulating the activity of TGF-β family member ligands may be useful for regulating the process of wound healing.

9. Hereditary Hemorrhage Telangiectasia (HTT)

The invention also provides methods of treating HTT.

HTT, also know as Rendu-Osler-Weber disease is an autosomal dominant inherited disorder of the blood vessels characterized by multisystem vascular dysplasia and recurrent hemorrhage. HTT results in the blood vessels becoming fragile and prone to bleeding. As a result of bleeding under the skin, HTT patients exhibit small red-to violet discolorations on the face, lips, lining of the mouth and nose and tips of fingers and toes. Similar small abnormalities may occur in the gastrointestinal tract. The fragile blood vessels are prone to breakage, thereby causing severe nose bleeds and bleeding from the gastrointestinal tract. HTT can also affect the liver. When the liver is affected, small areas of abnormally wide blood vessels (telangiectasia) develop in the liver. These abnormal blood vessels create short circuits between arteries and veins and can cause severe heart failure which can, in turn, further damage and enlarge the liver. As a result of the shunted blood flow, a continuous 'roaring' noise can be heard through a stethoscope. Scars and non-cancerous tumors of blood vessels can be found in the livers of HTT patients.

Although no specific treatment is available, bleeding can be stopped by applying compresses or astringents, or using a laser beam to destroy the leaking blood vessel. In severe cases of bleeding, the bleeding can be stopped by blocking the leaking artery with a pellet inserted through a catheter or by grafting normal tissue. As a result of recurrent bleeding, iron deficiency anemia can result.

Recent investigation has mapped one of the responsible genes for HTT to chromosome 9q33-q34; subsequently, nine different mutations have been identified in the endoglin gene, which encodes a TGF-β binding protein. TGF-β is a multi-functional cytokine with potent angiogenic action including migration, proliferation, and adhesion of endothelial cells, and increased production of extracellular matrix components by smooth muscle cells and fibroblasts. Thus, it seems plausible that HHT may be caused by abnormalities of TGF-β or its receptor complex. Mutations in the endoglin gene may interrupt the signal transduction of TGF-β necessary for angiogenesis, leading to the occurrence of HHT. Compounds that modulate the activity of TGF-β family member ligands (e.g. proteasome activators or agents that induce oxidation stress) could be useful for treatment of this disease (Berkow et al., supra).

10. Cancer

The invention also provides methods of treating cancer.

Cancer is a disease that is characterized by uncontrolled growth of abnormal or cancerous cells, in most instances as a result of an altered genome in a single abnormal cell. The alteration in the genome is caused by a mutation in one or more genes wherein the probability of the occurrence of a mutation is increased by a variety of factors including i. ionizing radiation, ii. exposure to chemical substances known as carcinogens, iii. some viruses, iv. physical irritation, and v. hereditary predisposition. It is thought that a single mutation is insufficient to convert a normal cell into a cancer cell, and that cancer is caused by several independent genetic alterations (Guyton, supra, Alberts et al., 1994, *Molecular Biology of the Cell,* Garland Publishing, Inc., New York).

Neoplasms including solid tumors such as malignant melanoma, and blood-borne cancers such as leukemia, arise from normal cell populations which have lost the ability to adequately respond to either intracellular or extracellular growth controlling mechanisms. Furthermore, cancer cells are less adherent to each other, as compared to normal cells. As a result, these abnormal cell populations divide at a more rapid rate than their normal cellular counterparts and, in the case of solid tumors, are capable of invading adjacent tissue. Cancerous cells enter the blood stream, migrate to distant sites within the body and eventually colonize secondary organs, a process known as metastasizing. Much of the damage of cancer cells results from the overuse of nutrients by cancer cells (due to the fact that they proliferate indefinitely) as compared to normal cells.

Cancers are classified according to the tissue and cell type from which they are derived and each type of cancer demonstrates characteristics that reflect the cell type of origin. In general, cancers that originate from different cell types are associated with different diseases (Guyton, supra, Alberts et al., supra).

Several therapeutic approaches have been used to slow the progression of dividing tumors. En bloc resection of the primary tumor followed by radiation therapy, chemotherapy or a combination of the two are conventional methods employed to treat the vast majority of tumor types. These modalities, however, can be ineffective and potentially harmful. The site of the tumor, surgical complications such as hemorrhage and the inability to locate tumor masses in a diseased organ can hinder potentially effective operative procedures. In addition, radiotherapy and chemotherapy are associated with ionizing damage of healthy tissue and systemic toxicity respectively.

Alternative approaches to the conventional treatments described above may include the delivery of recombinant molecules which function to either boost the host's immune response to invading metastases or to either directly or indirectly suppress cancerous cell growth. Such molecules may include various cytokines such as interleukin-2 (IL-2), granulocyte-macrophage colony stimulating factor (GM-CSF), interleukin-12 (IL-12) and interferon-gamma (IFN-gamma), anti-angiogenic molecules and tumor associated antigens (Anderson, et al., 1990, *Cancer Res.,* 50: 1853, Stoklosa, et al., 1998, *Ann. Oncol.,* 9:63, Leibson, H. J. et al., 1984, *Nature,* 309:799, Book, et al., 1998, *Semin. Oncol.* 1998, 25:381, Salgaller, et al., 1998, *J. Surg. Oncol.,* 68: 122, Griscelli, et al., 1998, *Proc. Natl. Acad. Sci. USA,* 95: 6367).

Loss of growth-inhibitory response to TGF-β is a common phenomenon in tumor progression. Because TGF-β responsiveness correlates with TGF-β type II receptor levels, attention has been given to mutational changes or deletions of TGF-β type II receptor in cancer cells. In colon and gastric cancers with microsatellite instability, TGF-β type II receptor mutations in the polyadenine tract are common. In head and neck squamous carcinomas, point mutations in the kinase domain have been reported. Also, in T-cell malignancies, retinoblastoma, breast cancer and other types of cancers, genetic changes or loss of TGF-β receptors contribute to aberrant TGF-β responsiveness.

There is also significant evidence that Smads act as tumor suppressors (Massague, 1998, *Ann. Rev. Biochem.,* 67: 753–791; Takagi et al, 1998, *Brit. J. Cancer.* 78: 1152–1155; Powell et al., 1997, *Cancer Res.,* 57: 4221–4224; Le Dai et al., 1998, *Cancer Res.,* 58: 4592–4597; Takei et al., 1998, *Cancer Res.,* 58: 3700–3705; Grau et al., 1997, *Cancer Res.,* 57: 3929–3934; Takenoshita et al., 1998, *Carcinogenesis,* 19: 803–807; Zhu et al., 1998, *Cell,* 94: 703–714; Nakao et al., 1997, *J. Biol. Chem.* 272: 2896–2900; Zavadil et al., 1997, *Leukemia,* 11: 1187–1192; Wu et al., 1997, *Mol. Cell. Biol.,* 17: 2521–2528; Weinstein et al., 1998, *Proc. Natl. Acad. Sci. U.S.A.,* 95: 9378–9383; Zhou et al., 1998, *Proc. Natl. Acad. Sci. U.S.A.,* 95: 2412–2416; Howe et al., 1998, *Science,* 280: 1086–1088; Lemoine, 1997, *Digestion,* 58: 550–556; Sirivatanauksom et al., 1998, *Langenbeck's Arch. Surg.,* 383: 105–115; Hata et al., 1998, *Mol. Med. Today,* 4: 257–262; Villaneuva et al., 1998, *Oncogene,* 17: 1969–1978; Reiss, 1997, *Oncol. Res.,* 9: 447–457), such that loss of Smad activity may contribute to the transformed phenotype.

11. Eye Diseases

The invention also provides methods of treating disorders of the eye.

There is data suggesting that TGF-β may be involved in the pathogenesis of various diseases of the eye including but not limited to proliferative vitreoretinopathy and diabetic retinopathy.

Proliferative vitreoretinopathy (PVR), the most common cause of failure in retinal reattachment surgery, is an ocular disorder characterized by excessive fibrosis on both surfaces of the retina and within the vitreous cavity. The intraocular fibrous tissue is composed of retinal pigment epithelial cells, glial cells, fibroblasts, and macrophages as well as an extensive accumulation of extracellular matrix proteins. The fibrosis results in the development of contractile forces on the retina causing retinal folding and traction retinal detachments (Connor et al., 1989, *J. Clin. Invest.,* 83:1661–1666).

Several studies have suggested that retinal pigment epithelial cells play a central role in the development of PVR. Recently, we have found that cultures of human retinal pigment epithelial cells can synthesize and release significant amounts of TGF-β, thus providing a possible link between TGF-β and the fibrotic process of PVR. To determine if TGF-β might play a role in the fibrosis occurring in PVR, intraocular fluid specimens for patients with varying degrees of intraocular fibrosis have been analyzed for the presence of TGF-β. It has been demonstrated that specimens from eyes with intraocular fibrosis associated with PVR have elevated levels of TGF-β when compared to specimens from eyes with uncomplicated retinal detachment without fibrosis and that these levels correlate with the degree of intraocular fibrosis (Connor et al., supra).

TGF-β is a proposed antiangiogenic factor in the eye. Vitreous fluid from patients with proliferative diabetic retinopathy (PDR) has been analyzed for the presence of TGF-β. TGF-β2 was found to be the predominant isoform of TGF-β in the vitreous. The total amount of TGF-β2 was not altered in PDR patients. Furthermore, the active fraction of TGF-β was decreased by 30% and 70% in PDR and non-diabetic retinal ischemia patients, respectively. In view of the proposed role of TGF-β as an antiangiogenic factor in vitreous, the loss of TGF-β in the vitreous of these patients is likely to disinhibit new vessel growth. These data suggest that TGF-β may represent an important antiangiogenic factor in normal vitreous (Pfeiffer et al., 1997, *Diabetes,* 46: S26–S30).

Compounds such as proteasome inhibitors and antioxidants which mediate the activity of TGF-β family member ligands may be therapeutically useful for treating disorders of the eye that are associated with aberrant levels of TGF-β activity.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated or used in the formulation. Such penetrants are generally known in the art.

Manufacture and Storage of Pharmaceutical Compounds

The pharmaceutical compositions of the present invention may be manufactured in a manner that known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. . . Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a Ph Range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, or in animal models, usually mice, rabbits, dogs, or pigs. The animal model is also used to achieve a desirable concentration range and route of administration. Such information can then be use to determine useful doses and routes for administration in humans.

A therapeutically effective dose refers to that amount of protein or its antibodies, antagonists, or inhibitors which ameliorate the symptoms or conditions. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animals studies is used in formulating a range of dosage for human use. The dosage of such compounds lies preferably within a range of circulating concentrations that include the ED50 with little or no toxicity. The dosage varies within this range depending upon the dosage from employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on a half-life and clearance rate of the particular formulation.

Dosage amounts may vary from 0.1 to 100,000 micrograms per person per day, for example, 1 ug, 10 ug, 100 ug, 500 ug, 1 mg, 10 mg, and even up to a total dose of about 1 g per person per day, depending upon the route of administration. Guidance as to particular dosages and methods of delivery is provided in the literature. See U.S. Pat. Nos. 4,657,760; 5,206,344; or 5,225,212, hereby incorporated by reference. Those skilled in the art will employ different formulations for nucleotides than for proteins or their inhibitors. Similarly, delivery of polynucleotide or polypeptides will be specific to particular cells, conditions, locations, etc..

Identified Smad Protein Interactors

Through the use of methods described herein, proteins which bind to Smad1, Smad2, Smad3 and Smad4 have been identified.

The following is a list of Smad1 interactors identified using the yeast two-hybrid system:

1. HsN3 (β subunit of 20S proteasome), clones S1+5, S1+6, S1+8 and S1+18, GenBank ID No. D2660 (S1+5 starts at nt. 125, S1+6 starts at nt. 17, S1+8 starts at nt. 89 and S1+18 starts at nt. 26 of the GenBank sequence, respectively);
2. AIP4 (ubiquitin ligase);
3. Uba 52 (ubiquitin fusion protein), clone S1+21, GenBank ID No. X56997 (starts at nt. 2380 of the GenBank sequence);
4. Uba 80 (ubiquitin fusion protein), clones S1+36 and S1+38, GenBank ID No. X63237 (both clones start at nt. 6 of the GenBank sequence);
5. antizyme (involved in targeting proteins to the proteasome), clone S1+15, GenBank ID No. U09202 (starts at nt. 395 of GenBank sequence);
6. PAG (an antioxidant protein), clone S1+35, GenBank ID No. X67951 (starts at nt. 183 of the GenBank sequence); homologous to human NKEFA (GenBank ID No. L19184); human HBP23 (GenBank ID No. D30035), mouse OSF-3 (GenBank ID No. D21252), mouse MSP23 (GenBank ID No. D16142), Newt mRNA for ABP-25 (GenBank ID No. D37808), Brugia malayi thiredoxin peroxidase 1 (Bm-tpx-1), (GenBank ID No. U34251); bovine antioxidant protein and substrate for mitochondrial ATP-dependent protease mRNA (GenBank ID No. D82025); human mRNA for thiol-specific antioxidant (GenBank ID No. X82321);
7. GST (involved in intracellular redox regulation), clone S1+13, GenBank ID No. J05459 (starts at nt. 230 of GenBank sequence);
8. Clone Smad1$^+$ (S1$^+$)27 (novel, FIG. 1, SEQ ID No. 1 (protein sequence); FIG. 36, SEQ ID No. 26 (DNA sequence)), clone S1+27, named SIP2, is homologous to the human mRNA for follistain-related protein (FRP), 3' to the coding region of FRP, GenBank ID No. D89937 (starts nt. 2278 of the GenBank sequence). When aligned with the cloned full length gene SIP2, homology starts at amino acid 92 after the putative first methionine (starting sequence of SIP2: MEESLNIV (SEQ ID NO: 28));

9. Clone S1+28 (novel, FIG. 2, SEQ ID No. 2 (protein sequence); FIG. 37, SEQ ID No. 27 (DNA sequence)), human homologue of yeast translocation elongation factor (GenBank ID No. AL023704 (homology starts at nt. 1489 of full length clone 28, and includes 73% positives and 38% identities);

10. Clone S1+19 (SNIP-1, novel, FIG. 3, SEQ ID No.3 (protein sequence), starts at nt 471, amino acid 157 of submitted full length SNIP1 sequence); FIG. 33, SEQ ID No. 23 (DNA sequence); SNIP-1 is a forkhead domain-containing protein, is homologous to the forkhead domain of NIPP-1 (FIG. 4, SEQ ID No. 4), the nuclear inhibitor of PP-1, and is cleaved by the proteasome in a Smad1, DPC4 and antizyme-dependent fashion. SNIP1 is only cleaved by the proteasome upon BMP type I receptor activation; the sequence of the Smad1 binding domain (SBD) of SNIP1 has been identified according to methods described herein and is shown in FIG. 5 (SEQ ID No. 5); a C. elegans sequence with homology to the SBD of SNIP-1 (SEQ ID No. 5) is given by SEQ ID No. 6 (FIG. 6), which represents amino acids 137 to 299 of GenBank ID No. U88308;

11. Clone S1+12 (novel, FIG. 7, SEQ ID No. 7 (protein sequence)) has strong homology to sorting nexins 2, 1A and 1. In addition to the original clone S1+12, encoding a 181 amino acid protein, two longer versions have been cloned. The first, designated clone 12-2 (FIG. 8, SEQ ID No. 8 (protein sequence); FIG. 34, SEQ ID No. 24 (DNA sequence)), has an open reading frame of 415 amino acids, and the second, designated clone 12-5 (FIG. 9, SEQ ID No. 9 (protein sequence); FIG. 35, SEQ ID No. 25 (DNA sequence)), has an open reading frame of 295 amino acids. Clone S1+12 contains amino acids 9 to 190 of the clone 12-2 open reading frame; clone 12-2 and clone 12-5 may be alternatively spliced forms. The open reading frame of clone 12-5 partially overlaps that of clone 12-2; amino acids 139–415 of the clone 12-2 open reading frame are identical to 10-295 of clone 12-5. Thus clone 12-5 lacks the domain that binds to Smad1, but contains the domain that is homologous to sorting nexins (GenBank ID No.s AF065482, 065484, 065483, U53225, AF043453, AF034546, AF062483, AF062482, AF062484), VPS5 (GenBank ID No. Q9233 1) in S. cerevisiae, and the cell division protein FtsY, (GenBank ID No.s AE000714, KIAA0640 and AB014540);

12. enolase (an enzyme involved in glucose metabolism; also known to regulate c-Myc oncogene transcription), clones S1+14 and S1+37, GenBank ID No. X84907 (clone S1+37 starts at nt 783 of the GenBank sequence);

13. Smad1 (homomeric complex has been reported in mammalian cells);

14. Smad2 (Smad2 is a TGF-β and activin responsive Smad; the interaction has not been reported);

15. Smad3 (Smad3 is also a TGF-β and activin responsive Smad; the interaction has not been reported);

16. Smad1 MH1 domain interacts with the Smad1 MH2 domain; the MH1 domain of Smad2 has been shown to be inhibitory to MH2, and binds to MH2 directly; the interaction between the MH1 and MH2 domain of Smad1 has not been reported; since the interaction is inhibitory to the MH2 domain, the interaction can be used as the target to identify compounds that can abolish the interaction, thereby activating Smad1 in the absence of ligands);

17. S1−31 (known gene, called tumor associated gene, unknown function SEQ ID No. 10), human mRNA for translationally controlled tumor protein, GenBank ID No. X16064 (starts at nt. 212 of the GenBank sequence);

18. Clone S3−1 (novel, FIG. 10, SEQ ID No. 10 (DNA), FIG. 11, SEQ ID No. 11 (protein)), see Smad3 interactors, below;

19. Clone S3+12 (novel, FIG. 12, SEQ ID No. 12 (DNA), FIG. 13, SEQ ID No. 13 (protein)), see Smad3 interactors, below;

20. Clone S3+103 (novel, FIG. 14, SEQ ID No. 14 (DNA), FIG. 15, SEQ ID No. 15 (protein)), see Smad3 interactors, below;

21. Clone S3+124, known gene with unknown function, GenBank ID No, P49406, see Smad3 interactors, below;

22. Clone S3+125 (novel, FIG. 16, SEQ ID No. 16 (DNA), FIG. 17. SEQ ID No. 17 (protein)), see Smad3 interactors, below;

23. HnRNP A1, see Smad3 interactors, below:

24. U1 SnRNP C (a ribonuclear protein involved in mRNA splicing), human mRNA for U1 small nuclear RNP-specific C. protein, GenBank ID No. X12517 (starts at nt. 8 of the Genbank sequence);

25. FKBP25 (a prolyl-isomerase), clone S3+127, GenBank ID No. M90820 (starts at nt. 362 of the GenBank sequence);

26. TRIP-4 (an interactor of thyroid hormone receptor), clone S3+75, thyroid receptor interactor TRIP4, GenBank ID No. L40371 (starts at nt. 333 of the GenBank sequence);

27. RBP2 (an interactor of the tumor suppressor RB protein), clone S3+63, RBP2, GenBank ID No. S66431 (starts at nt. 4040 of the GenBank sequence);

28. Tryptophanyl tRNA synthetase, clone S1+20, GenBank ID No. M77804 (starts at nt. 951 of GenBank sequence);

29. M gene for M1-type and M2-type pyruvate kinase, clone S1+23, GenBank ID No. X56494 (starts at nt.9734 of GenBank sequence); human Opa-interacting protein OIP3, GenBank ID No. AF025439 (starts at nt. 497 of GenBank sequence); human TCBgene encoding cytosolic thyroid hormone-binding protein. GenBank ID No. M26252 (starts at nt. 1687 of GenBank sequence);

30. COX4AL, human gegne of unknown function, clone S1+25, GenBank ID No. AF005888 (starts at nt.151 of GenBank sequence);

31. Ran-GTP binding protein 5, clone S1+32, GenBank ID No.Y08890 (starts at nt.788 of the GenBank sequence);

32. Clone S1+30 (novel, FIG. 18, SEQ ID No. 18 (DNA), FIG. 19, SEQ ID No. 19 (protein)) has homology with: SMK1-yeast sporulation-specific mitogen-activated protein kinase (Map kinase SMK1) GenBank ID No. P41808 (homology region between amino acids 104 to 139); MAP kinase, GenBank ID No. L35047; SmK1p, GenBank ID No. Z49219; Smk1p, GenBank ID No. Z71255. This clone is also homologous to C-FES (GenBank ID No. P16879) and the mouse proto-oncogene tyrosine protein kinase FES/FPS, GenBank ID No.s 148347 and X12616 (homology region between amino acids 323–357 of FES-mouse (GenBank ID No. P16879). This clone is also homologous to ribonucleotide reductase large subunit of human herpesvirus 6, GenBank ID No. L25528 (homology region between amino acids 697 and 726);

33. β-tubulin, clone S1+3, GenBank ID No. AF070561 (starts at nt. 770, amino acid 258 of the GenBank sequence); and 34. Acidic ribosomal phosphoprotein PO mRNA, clone S1+11, GenBank ID No. M17885 (starts at nt. 132 of the GenBank sequence).

The following is a list of Smad2 interactors identified using the yeast two hybrid system:
1. S3+124, see Smad3 interactors, below;
2. TRIP4;
3. AIP4;
4. GST;
5. SNIP-1 (SEQ ID No. 3); and
6. Uba52.

The following is a list of Smad3 interactors identified using the yeast two hybrid system:
1. S3+1 (novel, SEQ ID No. 11) has homology to drosophila trithorax gene (GenBank ID No.s Z31725, Z50152, Z50038), and human homologues of trithorax, HTX (GenBank ID No. A44265) as well as ALL-1 protein (GenBank ID No. Z69744). The conserved region comprises a zinc finger region. S3+112 is the same gene, but lacks the first 37 nt of S3+1;
2. S3+125 (novel, FIG. 17, SEQ ID No. 17) is homologous to a *C. elegans* protein containing a DNAJ-like domain (GenBank ID No. U80451);
3. S3−124 is a known gene with unknown function, with GenBank ID No. P49406 (starts at amino acid 12 of the GenBank sequence); S3+124 is also homologous to a putative 60S ribosomal protein, KIAA 00104 (GenBank ID No. D14660, homology starts at nt. 1 of KIAA0104);
4. S3−122, 119, 54 and 77 encode Hn RNP core protein A1, GenBank ID No. X79536 (all starts at nt. 482 of the GenBank sequence); clones S3+122, 34, 65 and 60 start at nt. 348 of the GenBank sequence;
5. S3+12 (novel, FIG. 13, SEQ ID No. 13) bears homology to several other proteins in several different regions. The amino-terminal segment exhibits homology to the homeobox protein HOX-A5 (GenBank ID No. P09021) and the yeast protein KCS1 (GenBank ID No. S54640). It has an internal long proline stretch, followed by a lysine and glutamate rich carboxyl-terminal domain which is homologous to HMG1 (GenBank ID No. X80457) and the developmental protein DG1071 (GenBank ID No. AF081799) of *Dictyostelium discoideum;*
6. S3+14 (novel, FIG. 20, SEQ ID No. 20 (5' DNA), FIG. 21, SEQ ID No. 21 (3' DNA), FIG. 22, SEQ ID No. 22 (protein)) bears homology with numerous other proteins over several different regions of the protein. The amino terminal domain is serine rich, a motif found in proteins such as epidermal granular cell layer-specific S protein (GenBank ID No. L20815), differentiated keratinocyte S protein (GenBank ID No. A48679), corneodesmosin (GenBank ID No. AF030130), a protein similar to mouser A-RAF proto-oncogene serine/threonine kinase (GenBank ID No. Z68296), TR3 beta (GenBank ID No. D85245), titin (GenBank ID No. I38344), and NGFI-B orphan nuclear receptor (GenBank ID No.s P51666 and X97226); the amino terminal domain is also highly homologous to the homeodomain protein six8 (GenBank ID No. AF030283), RB18A protein (GenBank ID No. Y13467), thyriod hormone receptor associated protein complex component TRAP 220 (GenBank ID No. AF055994), thymidine kinase (GenBank ID No. AB009255), TR3 orphan receptor (GenBank ID No. P22736), a probable nuclear hormone receptor, NAK1 (GenBank ID No. A3725 1), and a DNA binding protein with GenBank ID No. D49728.

The central region of the protein bears a histidine rich domain which is found in proteins such as the transcription factor and Ets-1 repressor which inhibits erythroid differentiation, MAFB (GenBank ID No. X96511), as well as in the homeobox domain protein OTX1, which defines layers and regions in developing cerebral cortex and cerebellum. Histidine-rich domains are also found in the transcription factor FKH-4, homeobox protein DLX2, GSH-2, THNF-3 and other fork head family transcription factors.

The carboxyl-terminal segment of clone S3+14 bears a glutamic acid-rich domain, a motif found in proteins such as: UBF1 (GenBank ID No. P25977), a nucleolar transcription factor; ribosomal transcription factor (GenBank ID No.s JC5112 and JC5113).

The combination of structural motifs of clone S3+14 with homology to numerous transcription factors indicates its function lies in transcriptional regulation;
7. S3+103 (novel, FIG. 15, SEQ ID No. 15) has homology with a hypothetical anaphase promoting factor component in *S. pombe* (GenBank ID No.s AL021746, AL031174, and AB012919 (Apc10), yeast hypothetical 32.8 Kd protein in RTRF1-CSF1 intergenic region (GenBank ID No. P53068), HRC 283 gene product (GenBank ID No. Z49149), KIAA0076 (GenBank ID No. D38548), KIAA0708 (GenBank ID No. AB014608), and the nuclear envelope pore protein POM 121 (p145, GenBank ID No. P52591);
8. U1SnRNP;
9. FKBP25;
10. TRIP4;
11. RBP2;
12. AIP4;
13. HEF1, Human enhancer of filamentation, GenBank ID No. L43821 (starts at nt. 1527 of the GenBank sequence); HEF1 is a docking protein which plays a critical role in integrin pathways and is essential for ODC and ras-induced cell transformation;
14. Smad1;
15. Uba52;
16. HsN3;
17. Uba80;
18. SNIP1 (SEQ ID No. 3);
19. antizyme; and
20. S3+42, human strophin-1 interacting protein 4, GenBank ID No. AF038564 (starts at nt. 417 of the GenBank sequence). This gene is also highly homologous to a novel mouse ubiquitin ligase. GenBank ID No. AF037454 (Perry et al., 1998, *Nature Genet,* 18: 143–146).

The following is a list of the identified Smad1 interactors which interact with HsN3:
1. S1+12 (SEQ ID No. 7);
2. enolase;
3. antizyme;
4. HsN3;
5. SNIP-1 (SEQ ID No. 3);
6. Uba52;
7. S1+28 (SEQ ID No. 2);
8. S1+31, see Smad1 interactors, above;
9. HEF1;
10. Smad3;
11. Smad3 MH2 domain;
12. Smad4;
13. Smad4 MH2 domain; and
14. The complex of type I and type II receptors of TGF-β and the BMP type I receptor.

The following is a list of Smad1 interactors which interact with antizyme:
1. S1+12 (SEQ ID NO. 7);
2. enolase;
3. antizyme;
4. HsN3;
5. SNIP-1 (SEQ ID No. 3);

6. Uba52;
7. S1⁺27 (SEQ ID No. 1);
8. S1⁺28 (SEQ ID No. 2);
9. S1⁻31, see Smad1 interactors, above;
10. PAG; and
11. HEF1.

The following is a list of identified Smad1 interactors which interact with S1⁺12 (SEQ ID No. 7):
1. Uba80; and
2. S1⁺12 (SEQ ID No. 7).

It has also been found through the use of methods described herein that known small compounds which inhibit proteasome activities can inhibit the biological activities of TGF-β family members. Additionally, there is evidence that compounds which inhibit cell oxidative stress can inhibit the biological activities of TGF-β family members. Further, there is evidence that the identified protein:protein interactions between Smads and proteasome pathway components (HsN3, antizyme, AIP4, uba 52, uba 80) and redox-regulating proteins (PAG, GST, enolase) play critical roles in the biological activities of the TGF-β family ligands (data not shown). Therefore, these interactions are important molecular targets for screening small compounds or peptides that can modulate the interactions, thereby modulating the activities of TGF-β family ligands. Since GST and enolase are enzymes, their enzymatic activities may also serve as molecular targets for the screen (as may the activity of any other enzyme found to interact with the signal transduction machinery of the TGF-β family ligands).

Proteins that bind to a β subunit of the 20S proteasome (HsN3) have been identified using the assays described herein. HsN3 has been shown to be a functional partner of the Smad proteins. Thus, HsN3 involved interactions are important molecular targets for screening small compounds or peptides that can modulate the interactions, thereby modulating the biological activities of the TGF-β family ligands. Since HsN3 may serve to link signaling pathways of the TGF-β family ligands with proteasome mediated degradation, and since HsN3 is processed and assembled into the proteasome, a process which may be regulated by the TGF-β family ligands, the processing and assembly of HsN3 are also an important target for screening assays that may yield modulators of TGF-β family ligands.

Proteins that bind to antizyme, a substrate docking protein for the degradation of ornithine decarboxylase by the proteasome, have also been identified using the methods described herein. There is evidence that antizyme binds to HsN3 directly via sites identified on both HsN3 and antizyme using methods described herein. Further, a Smad1 binding protein (SNIP1, SEQ ID No. 3), which binds to antizyme and to HsN3, and whose degradation is dependent upon the presence of antizyme, Smad1, and Smad4 has been identified. Further, evidence has been obtained that the proteasome-mediated degradation of Smads is regulated by antizyme, as is the proteasome-mediated degradation of PAG. In addition, antizyme itself is also a substrate of the proteasome in the presence of Smads. Thus, antizyme involved interactions are important molecular targets for screening assays that may yield modulators of TGF-β family ligands.

Through use of the assays described herein, the Smad1 binding domain of SNIP-1 has been identified. This domain on SNIP-1 is homologous to a domain on NIPP1 (SEQ ID No. 4), FIG. 4, which regulates PP1 activity; PP1 is therefore be a potential target for screening assays.

Since ornithine decarboxylase (ODC) is regulated by antizyme, the finding of TGF-β-mediated regulation of antizyme proteolysis leads to a prediction that ODC activity may be regulated by the TGF-β family ligands. Thus ODC is another potential target for screening assays (assays for ODC activity are described by Hua et al., 1995, *J. Biol. Chem.*, 270: 10264–10271). Thus, the following enzymes are considered targets for screening assays that may yield biological modulators of the TGF-β family ligands: GST, enolase, ODC, and PP1.

An interaction between HsN3 and the receptors of TGF-β family ligands has been identified using methods described herein. There is evidence that TGF-β family receptors are downregulated by proteasome-mediated degradation; the interaction between HsN3 and the receptors may serve to bring the receptors to the proteasome. Thus, the interactions between HsN3 and the receptors are important targets for screens that may yield modulators of the TGF-β family receptor turnover, thereby modulating the biological activity of the ligands and duration of the TGF-β family ligand response.

An interaction between SNIP-1 and the TGF-β family receptors has been identified using the methods described herein, as has an interaction between SNIP-1 and another Smad1 binding protein, S1+12 (SEQ ID No. 7). S1+12 is a sorting nexin-like protein which is known to downregulate the EGF-receptor via proteasome-mediated degradation. SNIP-1 is a forkhead domain-containing protein. This domain has been shown previously to have the ability to bind to a membrane serine/threonine kianse and inhibit the kinase activity. Thus, the interaction between SNIP1 and the TGF-β family receptor is a promising target for screen assays that may yield compounds that modulate the biological activities of TGF-β family ligands. The interactions between SNIP-1 and HsN3, SNIP-1 and antizyme, SNIP1 and S1+12, SNP1 and Smad1, and SNIP1 and Smad2 are also important targets for the screening assays.

NF-κB activities have also been identified as playing a role in BMP signaling pathways; NF-κB activation pathways and genes that are regulated by NF-κB are also targets for screening assays. Assays for NF-κB proteolytic processing are described by Coux & Goldberg, 1998, *J. Biol. Chem.*, 1998, 273: 8820–8828. Assays for NF-κB DNA binding activity and transactivation are described by Bellas et al., 1997, *Am. J. Pathol.*, 1997, 151:891–896.

Compounds, identified according to screening methods of the invention, which inhibit the activity of the TGF-β family ligand-activated signal transduction pathways may be useful in treatment of diseases such as those of the kidney associated with inappropriately high TGF-β family ligands or pathway activities. Such inhibitors may affect proteasome activity, redox status of the cell, activity of NF-κB family proteins. Activity of genes regulated by NT-κB family proteins, protein:protein interactions in the transduction pathway, proteolysis of proteins in the pathway, activity of enzymes which interact with proteins in the pathway, or the turnover of TGF-β family receptors.

Compounds, identified according to screening methods of the invention, which enhance or mimic the activity of the TGF-β family ligand-activated signal transduction pathways may be useful in treatment of diseases such as cancer and osteoporosis which are associated with deficiencies in TGF-β family ligands or pathway activities. Such enhancing or mimicking compounds may affect the activity of the proteasome, the redox status of the cell, activity of NF-κB family proteins, activity of genes regulated by NF-κB family proteins, protein:protein interactions in the transduction pathway, proteolysis of proteins in the pathway, activity of enzymes which interact with proteins in the pathway, or the turnover of TGF-β family receptors.

The invention is illustrated by the following nonlimiting examples wherein the following materials and methods are employed. The entire disclosure of each of the literature references cited hereinafter are incorporated by reference herein.

EXAMPLE 1

Smad1 Interacts with Multiple Proteins Functionally Linked to the 20S Proteasome A modified yeast two-hybrid system was used to screen a human fetal brain library (Zervos et al., 1993). A construct comprising full length Smad1 was used as the bait. For the yeast two-hybrid screen, full length Smad1 was subcloned into BamH1/Not1 sites of PEG202 by a PCR method, resulting in an inframe fusion between the LexA DNA binding domain (1–202) and Smad1. The Smad1 (G419S) mutant was a kind gift from J. Wrana (Hoodless et al., 1996). The subcloning of Smad1 (G419S), Smad1NL (1–270), Smad1L (146–270) into pEG202 were all carried out by the PCR approach described above.

Thirteen different cDNAs were identified from a total of forty interaction positive yeast (FIG. 23). The predominant interactor of Smad1 (represented by clone 18 in FIGS. 24A & B), which was isolated 8 times from the screen, is HsN3 (Thomson and Rivett 1996; Kopp et al., 1995; Cruz et al., 1997), a β subunit of the 20S proteasome (for review, see Coux et al., 1996). One of the interactors is Smad1 itself, which is known to form homomeric complexes in mammalian cells (Lagna et al., 1996). We also detected strong interaction between Smad1 and its functional partner DPC4 in yeast, in the absence of the BMP receptors (data not shown). In mammalian cells, such an interaction has been detected, but a stable interaction only occurs after BMP-induced Smad1 activation (Lagna et al., 1996). Thus the strong interaction between Smad1 and DPC4 in yeast may suggest that Smad1 is somehow in a constitutively active conformation in yeast. If so, the isolated Smad1 interactors, including HsN3, could be those proteins that can associate with the activated Smad1.

Besides HsN3, Smad1 interacts with several other proteins that are known to be directly or indirectly related to the functions of the 20S proteasome: two ubiquitin fusion proteins, UbA 52 (Baker et al., 1991) and UbA 80 (Baker et al., 1991), (both UbA 52 and UbA 80 require their amino-terminal ubiquitin portion to bind Smad1 (not shown)); antizyme, the protein that targets ornithine decarboxylase (ODC) for proteasome mediated degradation (for review, see Hayashi et al., 1996), was also isolated as an interactor of Smad1; a ubiquitin ligase was isolated as a common interactor for Smad3 and Smad1 (Liu et al., unpublished); a novel interactor of Smad1 (Wang & Lechleider, unpublished) contains a domain highly homologous to NIPP-1, whose function is associated with proteolysis, possibly by proteasome. NIPP-1 generates heat-stable proteolytic intermediates that bind and inhibit the catalytic subunit of nuclear protein phosphatase 1 (Jagiello et al., 1995, Van Eynde et al., 1995). Although each pair of interactions detected in the yeast two-hybrid system needs to be confirmed in mammalian cells, the observation that Smad1 interacts with a group of proteins all related to the proteolytic activity and functions of the 20S proteasome suggests an interesting possibility that Smad1 may somehow play a part in, or utilize the 20S proteasome-mediated proteolysis after its activation by a BMP receptor.

The isolated Smad1 interactors can be divided into three groups: 1) integral components of the proteolytic machinery (e.g., HsN3 and a ubiquitin ligase); 2) known modifiers of the proteasome substrates (e.g., UbA52, UbA80 and antizyme); and 3) potential substrates of the proteasome. The ability of Smad1 to interact with both the modifiers of proteasome substrates and an integral component of the proteolytic machinery suggests that Smad1 may function in the docking of substrates to the degradation machinery.

EXAMPLE 2

HsN3 Binding to Smad1 Via the Carboxyterminal Effector Domain of Smad1

Figure 24:
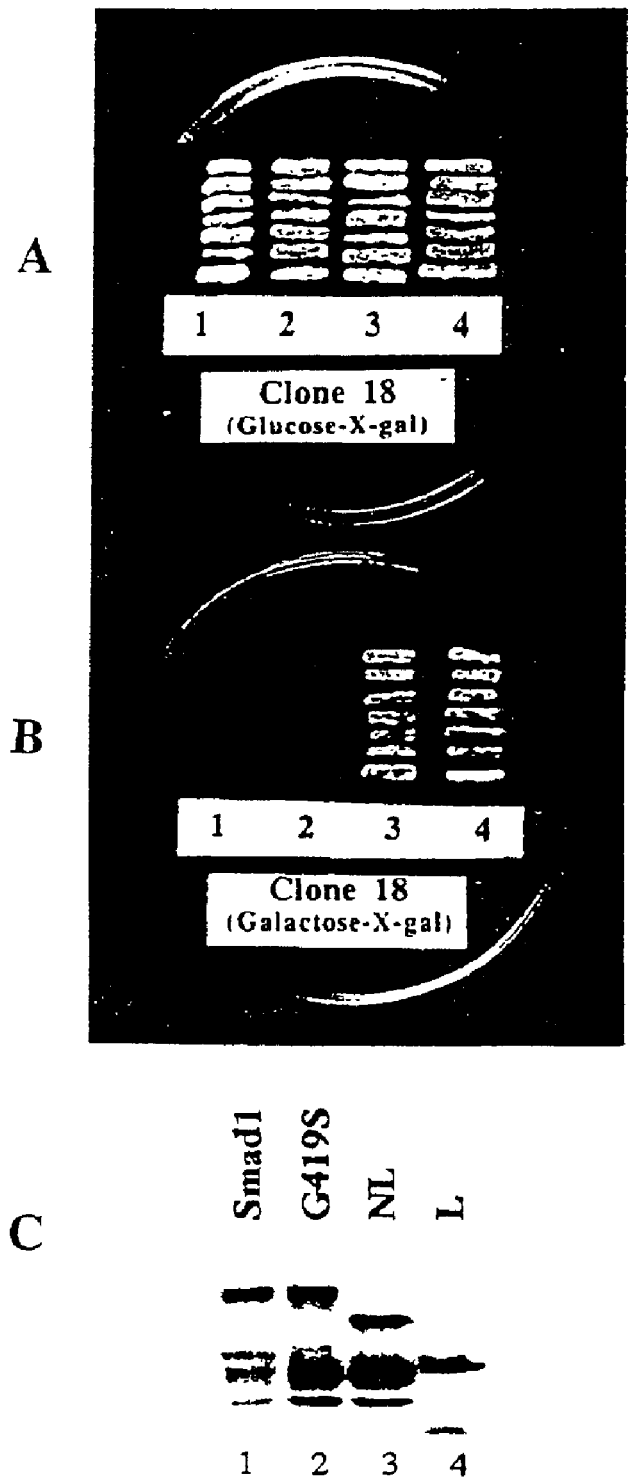
FIG. 24 shows yeast two-hybrid assays to identify the domain of Smad1 which interacts with HsN3. Panel A shows growth of HsN3 on Glucose-X-Gal plates: Panel B shows growth on Galactose-X-Gal Plates; Panel C shows a Western blot analysis of various yeast cell lysates using anti-LexA antibodies.

Like other members of the Smad family, Smad1 can be subdivided into three domains: the conserved aminoterminal domain (N, or MHI domain), the serine and proline rich middle linker region (L domain). and the conserved carboxyterminal domain (C, or MH2 domain). The C domains of Smads are considered to be the functional effector domains (Baker and Harland, 1996), while the N domains have been shown to inhibit C domains, possibly via an intramolecular interaction with the C domains (Hata et al., 1997). It has been demonstrated that the N domain of Smad1 has DNA binding activity (Kim et al., 1997), and the C domain has transcriptional activation activity (Liu et al, 1996). However, since both properties were detected only by analysis of mutants of Smad1 (Kim et al., 1997), or fusion proteins comprising Smad1 and a DNA binding protein (Liu et al, 1996), the physiological relevance of these properties are yet to be established, To determine which of these subdomains of Smad1 mediates HsN3 binding, B42-HsN3 fusion protein and several LexA fusion proteins of Smad1 mutants (described in Example 1) were coexpressed in yeast (FIG. 24 & B). B42-HsN3 was isolated from a human fetal brain library using the yeast two-hybrid screen described in Example 1 according to the following method. Total mRNA from a human fetal brain was purified and inserted into the EcoR1/Xho1 sites of the yeast vector pJG4-5. B42-HsN3 was isolated from a yeast that demonstrated a positive interaction with LexA-Smad1. Sequence analysis demonstrated that the HsN3 fragment was full length, contained six bases of 5' upstream sequence (ACTAAG), and that the first ATG of HsN3 was fused in frame with the upstream B42 sequence of the pJG4-5 vector. The expression of B42-HsN3 is under the control of the GAL1 promoter. Thus only LexA fusion proteins were expressed in the yeast transformants grown on the glucose plate (FIG. 24A), while B42-HsN3 and the tested LexA-Smad1 fusion proteins were both expressed in the same yeast transformants grown on the galactose plate (FIG. 24B). A positive interaction was monitored by the expression of β-galactosidase, which turns the tested yeast cells blue on X-Gal containing plates. HsN3 (represented by clone 18) interacts with the full length Smad1 (FIG. 24B, lane 1), but failed to interact with either the Smad1 deletion mutant (named as "NL") lacking the C-terminal domain (a.a. 271–465) (FIG. 24B, lane 3), or with the central linker region of Smad1 (a.a. 146–270, named as "L") (FIG. 24B, lane 4). Thus, the C domain of Smad1 is required for HsN3 binding. We have also shown that this domain is sufficient to bind the histidine-tagged HsN3 purified from E. coli (data not shown). A point mutation (G419S) within the C domain of Smad1, which abolishes Smad1 phosphorylation by the activated type I receptor (Hoodless et al., 1996), did not alter Smad1 binding to HsN3 (FIG. 24B. lane 2). Thus, distinct regions of the Smad1 C domain may mediate the interaction of Smad1 with the type I receptor and HsN3. The level of expression of the LexA fusion proteins comprising either the full length or deleted versions of Smad1 in the tested yeast cells was monitored by Western blot using an anti-LexA antiserum (FIG. 24C).

EXAMPLE 3

The Carboxyterminal Domain of Smad1 Binds to HsN3 Before the Incorporation of HsN3 into the 20S Proteasome HsN3 is one of the seven β subunits of the 20S proteasome, the catalytic core for 26S proteasome, which mediates both the ubiquitin-dependent and independent proteolysis of most cytoplasmic and nuclear proteins (for review, see Hochstrasser, 1996; Coux et al., 1996; Hilt & Wolf, 1996). Three out of the seven β subunits (XB1, delta and Z in human, replaced by LMP7, LMP2 and MECL1 upon γ-interferon treatment) have been shown to mediate most of the known peptidase activities associated with the 20S proteasome. HsN3 and three other β subunits have been suggested to be inactive β subunits (Seemtiller et al., 1995; Groll et al., 1997). However, direct evidence to completely rule out the possibility that HsN3 has proteolytic activity is not yet available. All three active β subunits are synthesized in an inactive form containing a short propeptide, which is processed to expose a threonine, whose hydroxyl group serves as the active site nucleophile. HsN3 also contains a propeptide which is processed, possibly upon the incorporation of HsN3 into the 20S proteasome (Thomson & Rivett, 1996; Cruz et al., 1997). The propeptides of the β subunits have been shown to play an important role in the assembly of the β subunits (Chen & Hochstrasser, 1996), as well as in the stabilization of the structure of the 20S proteasome (Groll et al., 1997). To determine if Smad1 and HsN3 interact in mammalian cells, we measured the Smad1 HsN3 interaction in COS cells. The endogenous level of HsN3 in COS cells and in several other tested cell lines is below the sensitivity of Western blot analysis using a monoclonal anti-HsN3 antibody (not shown). We therefore made two mammalian HsN3 expression constructs: N3-F, comprising a Flag epitope at the C-terminus of HsN3, and F-ΔN3, comprising a Flag epitope placed immediately in front of the first threonine of the mature HsN3, thereby deleting the 45 amino-acid HsN3 prosequence (Thomsen & Rivett, 1996; Cruz et al., 1997).

The N3-F vector was produced according to the following method. Full length HsN3 was PCR amplified from B42-HsN3 and inserted as an EcoR1 and EcoRV fragment into pFLAG-CMV5C (Kodak) and subcloned into the EcoR1 and Sal1 sites of F-pCMV6. Sequence analysis demonstrated that HsN3 was fused in frame to the upstream Flag epitope. It has been demonstrated that proteasome β subunits fused to a C-terminal epitope tag are successfully processed and assembled into the 20S proteasome when expressed in yeast or mammalian cells (Chen & Hochstrasser, 1996; Ramos et al., 1998; Reits et al., 1997). F-ΔN3 was produced by the following method. An HsN3 sequence lacking the amino terminal 45 amino acid prosequence was PCR amplified (with PCR primers that attached EcoR1 and Xho1 sites to the 5' and 3' ends respectively. The PCR product was subcloned into the EcoR1 and Sal1 sites of F-pCMV6, as described above.

Figure 25:
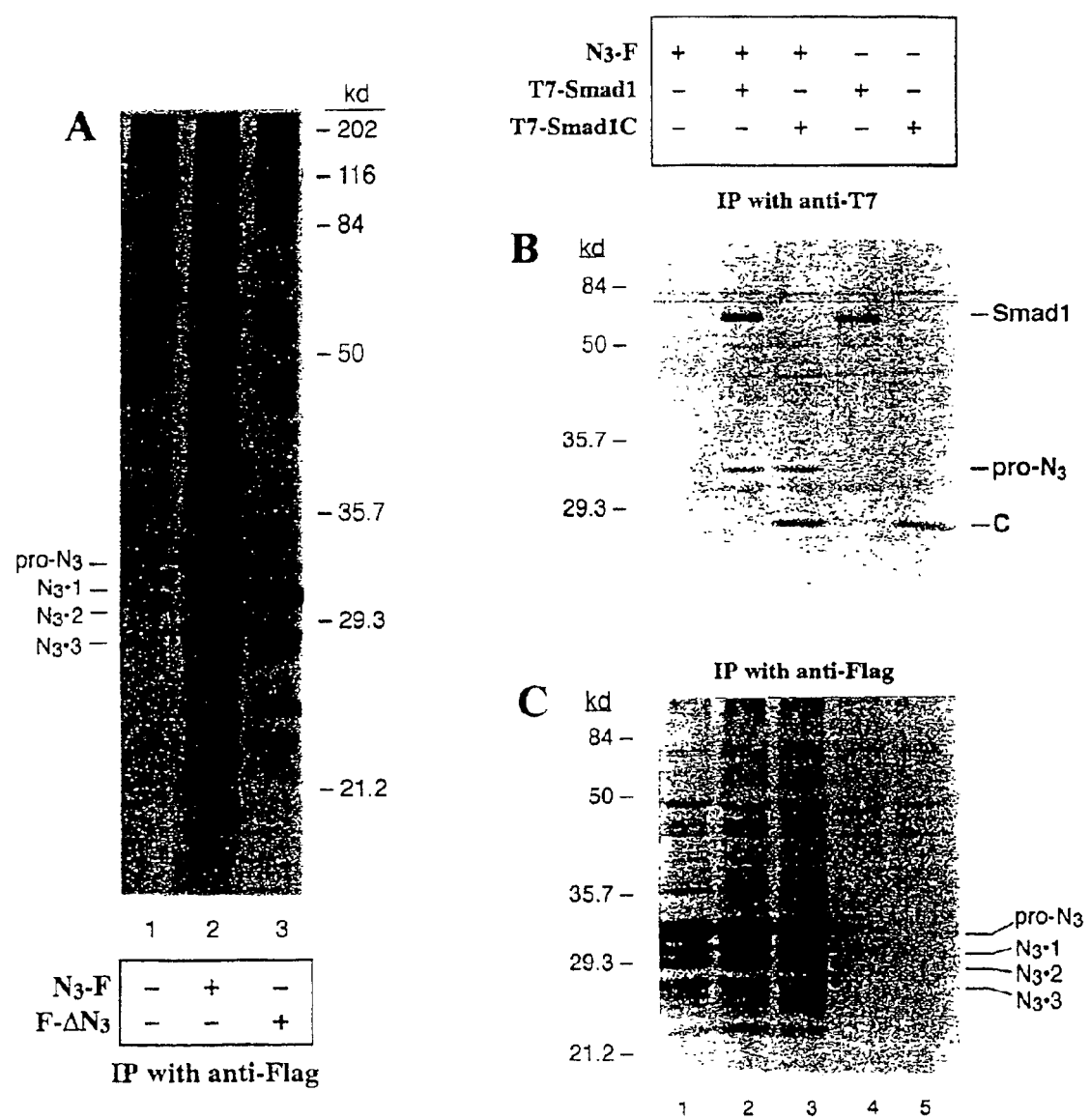
FIG. 25 shows experiments examining the expression, processing and assembly of HsN3-containing complexes. Panel A shows results of an immunoprecipitation experiment. Immunoprecipitation of $N_3$-F (lane2) and HsN3 proteins lacking the prosequence (F-$\Delta N_3$) (lane 3) were carried out to provide a measure of the molecular weight of the processed form of N3-F. Panels B and C show results of immunoprecipitation experiments performed on COS cells transfected with N3-F (lanes 1). T7-Smad1 (lanes 4). Smad1C (lanes 5), or cotransfected with N3-F and T7-Smad1 (lanes 2), or N3-F and T7-Smad1C (lanes 3).
Figure 26:
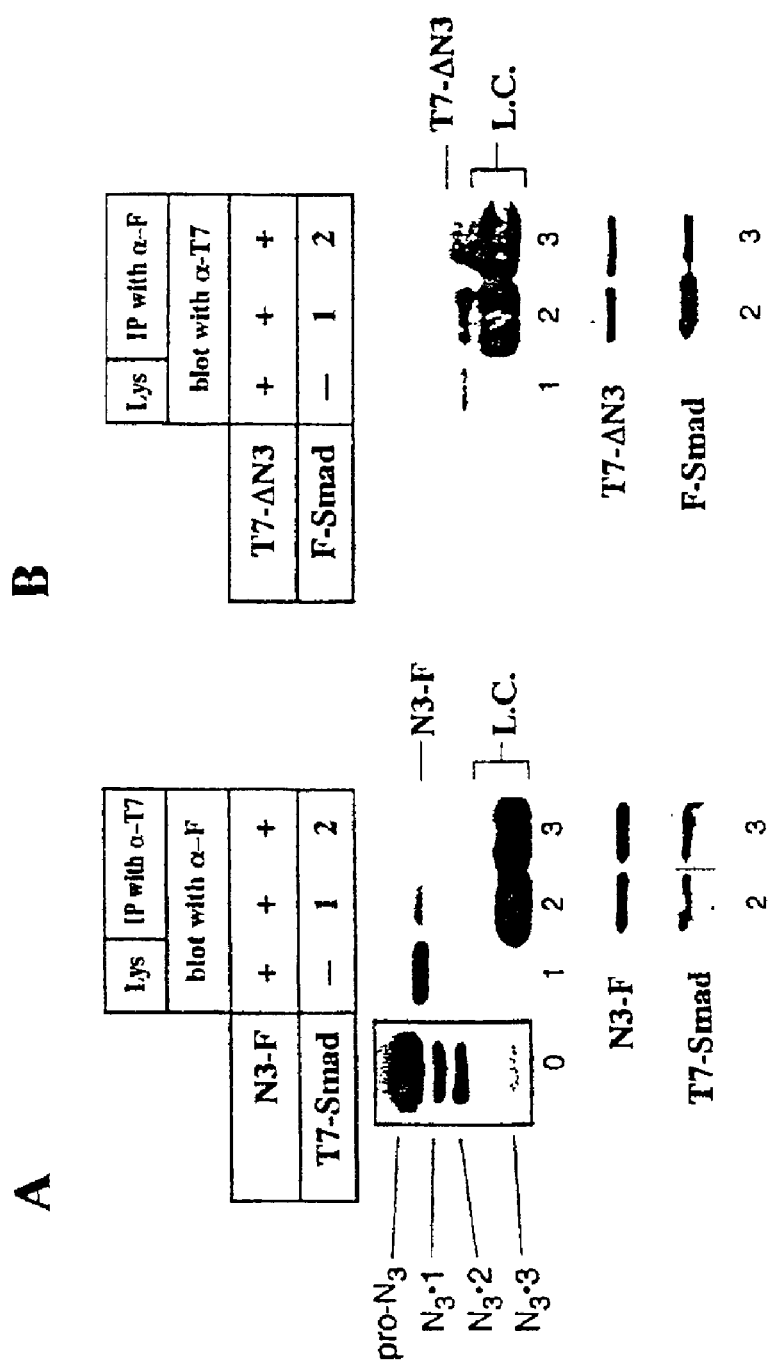
FIG. 26 shows experiments examining the association of Smad1 with HsN3 relative to HsN3 assembly into proteasome complexes. COS cells were cotransfected with N3-F and T7-Smad1, or N3-F and T7-Smad2. and the lysates were first immunoprecipitated with anti-T7 antibody and then analyzed by Western blot with anti-Flag antibody (Panel A). Panel B shows specific coprecipitation of F-Smad1 with the prosequence-less HsN3 (T7-DN3).
Figure 25:
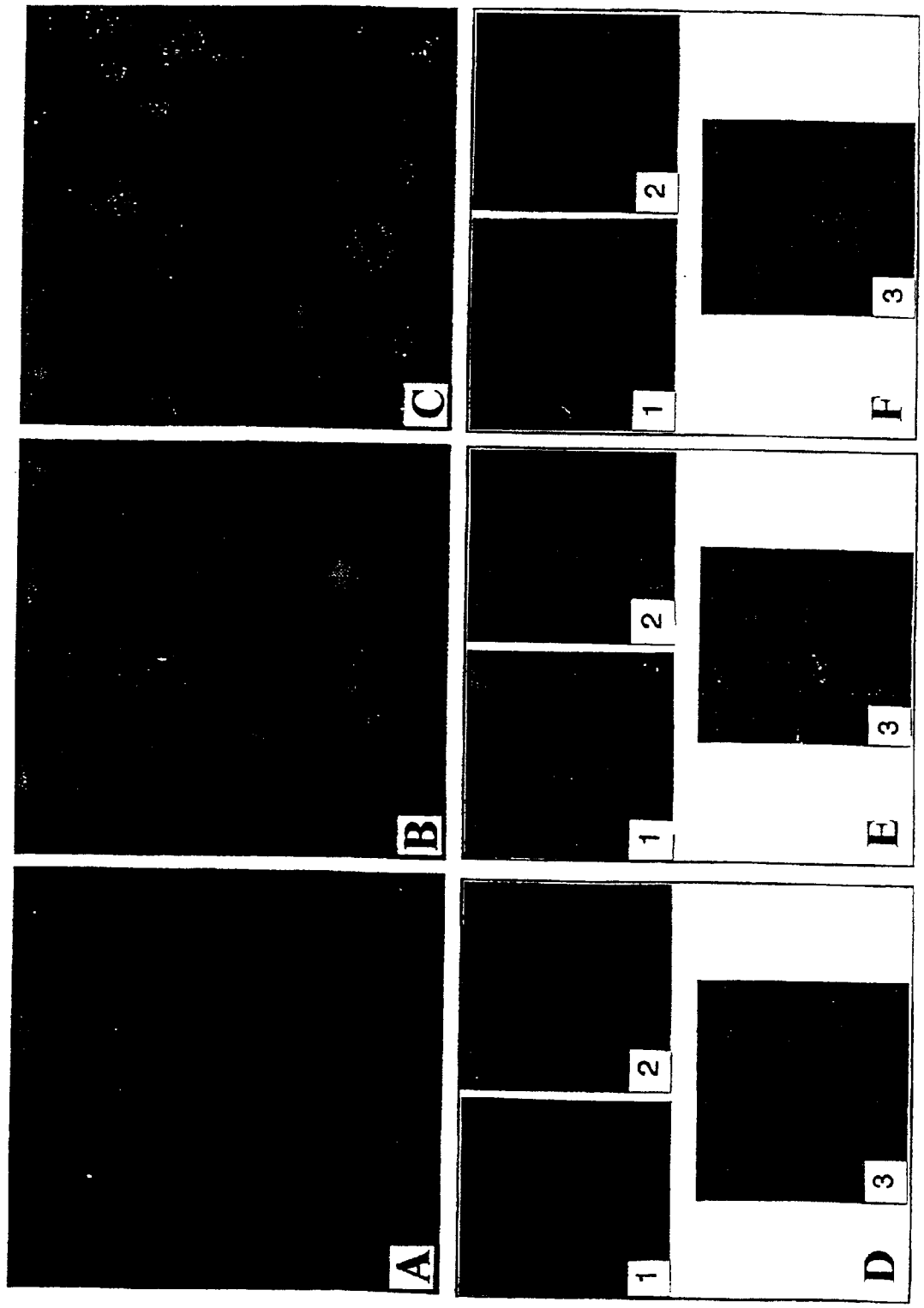

In order to monitor the expression, processing and assembly of N3-F in COS cells, cells transfected with N3-F were labeled with $^{35}$S-methionine for four hours. The cell lysates were precipitated with anti-Flag antibody to detect the expression of Flag-tagged HsN3 proteins. Immunoprecipitation of F-ΔN3 was also carried out to provide a measure of the molecular weight of the processed form of N3-F. As shown in FIG. 25A, the transiently expressed N3-F appears to be incorporated into multimeric complexes (lane 2). In contrast, HsN3 proteins lacking the prosequence were not incorporated into multimeric complexes (lane 3). This is consistent with the previous observation that prosequences of beta subunits are required for their successful incorporation into the 20S proteasome (Chen & Hochstrasser, 1996). Four of the predominant bands in lane 2 of FIG. 25A are derived from the expression of N3-F, since they are detected by Western blot analysis with an anti-Flag antibody (FIG. 26A, lane 0). In addition to the unprocessed HsN3 protein (labeled as pro-N3), three other more rapidly migrating forms of HsN3 are always detected (labeled as N3.1, N3. 2 and N3.3). Since N3.1 comigrates with the prosequence-less F-ΔN3 in lane 3, we suspect that N3.1 represents the processed form of HsN3 that lacks the first 45 amino acids. N3.2 and N3.3 could be novel processed forms of N3-F, or degradation products resulting from HsN3 overexpression. Other $^{35}$S-labeled proteins that specifically coprecipitate with HsN3 may represent a mixture of the endogenous components of mature 20S proteasome, proteasome assembly intermediates and the 19S regulatory complex.

To test HsN3 interaction with Smad1, or with the carboxyterrninal domain of Smad1 (designated as Smad1 C), COS cells were transfected with N3-F (FIG. 25B & C, lanes 1), T7-Smad1 (lanes 4), Smad1C (lanes 5), or cotransfected with N3-F and T7-Smad1 (lanes 2), or N3-F and T7-Smad1C (lanes 3).

T7-Smad1 was constructed according to the following method. Two complementary oligonucleotides containing a T7 epitope and multiple restriction sites in the following order: EcoR1, HindIII, BamH1, Sma1, Sal1 were annealed and inserted between the EcoR1 and Sal1 sites of pCMV6' to create T7-pCMV6. Smad1 was PCR amplified and inserted into the BamH1 and Not1 sites of the yeast vector PEG202. The insert was excised by digesting with BamH1 and Xho1 and then subcloned into the BamH1 and Sal1 sites of T7-pCMV6 to produce T7-Smad1 or F-pCMV6 to produce F-Smad1.

T7 -Smad1C was constructed by the following method. The MH2 domain of Smad1 (271–465 of Smad1) was PCR amplified with PCR primers that produced a product with EcoR1 and Xho1 sites at the 5' and 3' ends, respectively. This product was subcloned into the EcoR1 and Xho1 sites of F-pCMV6 to create F-Smad1 C or T7-pCMV6 to create T7-Smad1C.

Cells were labeled with $^{35}$S-methionine for four hours before they were lysed and immunoprecipitated with either anti-T7 antibody to detect Smad1 and Smad1 C (FIG. 25B), or anti-Flag antibody to detect N3-F (FIG. 25C). The immunoprecipitates were analyzed on the same SDS-polyacrylamide gel, but are presented in two separate panels for illustration convenience (FIG. 25B & C). Among the four detected forms of Flag-tagged HsN3, only pro-N3 was detected in the immunoprecipitates of both T7-Smad1 (FIG. 25B, lane 2) and T7-Smad1C (FIG. 25B, lane 3). Coimmunoprecipitation of Smad1 and HsN3 has also been detected with untagged HsN3 protein (not shown). The observed interaction did not result from the epitope-induced misfolding of Smad1, since the Flag epitope is placed at the N-terminus of Smad1, and has been shown not to affect its function at that position (Hoodless et al., 1996; Lagna et al., 1996).

To further demonstrate the specificity of the interaction between HsN3 and Smad1, we compared the ability of HsN3 to interact with Smad1 and Smad2 in COS cells, since the latter did not exhibit HsN3 binding in yeast (see FIG. 23). COS cells were cotransfected with N3-F and T7-Smad1, or N3-F and T7-Smad2, and the lysates were first immunoprecipitated with anti-T7 antibody and then analyzed by Western blot with anti-Flag antibody (FIG. 26A).

T7-Smad2 was constructed according to the following method. The full length Smad2 protein was PCR amplified using PCR primers that produced a product with EcoR1 and Xho1 sites on the 5' and 3' ends, respectively. This PCR product was subcloned into the EcoR1 and Xho1 sites of F-pCMV6.

Only pro-N3, and not N3.1, was detected in the immunoprecipitates of Smad1 (FIG. 26A, top panel, lane 2). The interaction between Smad1 and HsN3 is specific, since pro-N3 was not detected in the Smad2 immunoprecipitates (FIG. 26A, top panel, lane 3), although both Smads and N3-F were expressed at an equivalent level in the tested cell lysates (FIG. 26A, bottom panel, compare lanes 2 & 3).

The observation that only pro-N3 but not the mature form of HsN3 coprecipitated specifically with Smad1 suggests that the prosequence of HsN3 may mediate Smad1 binding. Alternatively, since HsN3 is processed into its mature form upon its assembly into the 20S proteasome (Cruz et al., 1997), the absence of mature HsN3 or any other 20S proteasome subunits in the immunoprecipitates of Smad1 could be an indication that Smad1 only interacts with HsN3 prior to incorporation of HsN3 into the 20S proteasome. To distinguish between these two possibilities, we tested whether the prosequence of HsN3 is required for Smad1 binding. As shown in FIG. 26B, specific coprecipitation of F-Smad1 with the prosequence-less HsN3 (T7-DN3) was again detected (FIG. 26B, lane 2), suggesting that the prosequence of HsN3 is dispensable for Smad1 binding. Thus, Smad1 may interact with HsN3 only before HsN3 is fully assembled into the 20S proteasome complex.

EXAMPLE 4

Smad1 Interaction with HsN3 is Enhanced Upon the Activation of the BMP-type I Receptor ALK3

To determine how Smad1 activation by the BMP type I receptor regulates Smad1 interaction with pro-N3, coprecipitation of HsN3 and Smad1 was tested in COS cells in the presence or absence of a constitutively active BMP type I receptor mutant (ALK3 Q233D, provided by Joan Massague). This protein harbors a point mutation within the juxtamembrane region, allowing it to signal in the absence of the type II receptor or BMP ligands (Wieser et al., 1995; Hoodless et al., 1996; Krettschmar et al., 1997a). Although an equivalent amount of N3-F plasmid was used in each transfection, the expression of HsN3 is higher in cells cotransfected with N3-F, Smad1 and ALK3Q233D (FIG. 27B, lane 3), compared with the level in cells cotransfected with either N3-F and Smad1 alone (FIG. 27B, lane 2), or N3-F and ALK3Q233D alone (FIG. 27B, lane 5). Such an increase has been confirmed by Western blot analysis using anti-Flag antibody (not shown). In addition to the increased level of HsN3 protein, HsN3 coprecipitated with an increased amount of endogenous proteins, which are likely components of the 26S proteasome (FIG. 27B, lane 3). The level of T7-Smad1 is less than that of HsN3 in the cotransfected cells (FIG. 27A, lanes 2 & 3), and is not increased upon coexpression of N3-F, Smad1 and ALK3Q233D (FIG. 27A, lane 3 compared with lane 2). Immunoprecipitation of T7-Smad1 with 3 ug of anti-T7 antibody precipitated all of the T7-Smad1 in the lysates (not shown). In the T7-Smad1 immunoprecipitates, more pro-N3 is detected in cells cotransfected with both Smad1 and ALK3Q233D (FIG. 27A, lane 3), compared with cells cotransfected with Smad1 alone (FIG. 27A, lane 2). The increased coprecipitation of pro-N3 with Smad1 in lane 3 can only be accounted for by an increased interaction between these two proteins, since an equal amount of T7-Smad1 was precipitated in both lanes, while HsN3 is expressed in excess of Smad1 even in lane 2. The increased level of HsN3 in lane 3 of FIG. 27B could be a result of stable complex formation between HsN3 and Smad1 due to the presence of the activated type I receptor.

Receptor activation of Smads is known to abolish an inhibitory intramolecular interaction between the N and C domains of the Smad protein (Hata et al., 1997). The receptor activation induced increase in HsN3 binding to Smad1 is therefore consistent with the observation that HsN3 binds to the C-terminal domain of Smad1. These data suggest that the binding may normally be inhibited by the intramolecular interaction within Smad1. So far, DPC4 is the only other molecule known to exhibit increased binding to Smad1 upon activation of the type I receptor (Lagna et al., 1996).

EXAMPLE 5

HsN3 is Translocated into the Nucleus and Colocalizes with the Nuclear Smad1 in Response to the Activation of BMP type I Receptors Since the activation of BMP type I receptors, either by BMP ligands in the presence of the type II receptor, or by the presence of a point mutation (Q233D), can induce the translocation of Smad1 from the cytoplasm to the nucleus (Hoodless et al., 1996, Wang et al., unpublished data), we examined whether the intracellular localization of the Smad1 interactor HsN3 is also regulated by the constitutively activated BMP type I receptor ALK3Q233D. The localization of endogenous HsN3 in COS cells in the presence or absence of activated Smad1 was studied by immunocytochemistry and confocal microscopy (FIG. 28). In untransfected COS cells, weak signals from endogenous HsN3 were detected in both the cytoplasm and the nucleus, with a monoclonal anti-HsN3 antibody and a FITC-conjugated anti-mouse secondary antibody (FIG. 28A). Overexpression of Smad1 did not cause a detectable change in the localization of HsN3 (FIG. 28B). However, overexpression of both Smad1 and the constitutively active mutant BMP type I receptor ALK3Q233D, which induces Smad1 nuclear translocation in the cotransfected cells (not shown), increased the nuclear signal of HsN3 (FIG. 28C). The total amount of HsN3 signal also increased (as shown in FIG. 28C). This observation is consistent with the previous observation that the protein level of N3-F increases in the presence of Smad1 and ALK3Q233D (FIG. 27B, lane 3).

Figure 29:
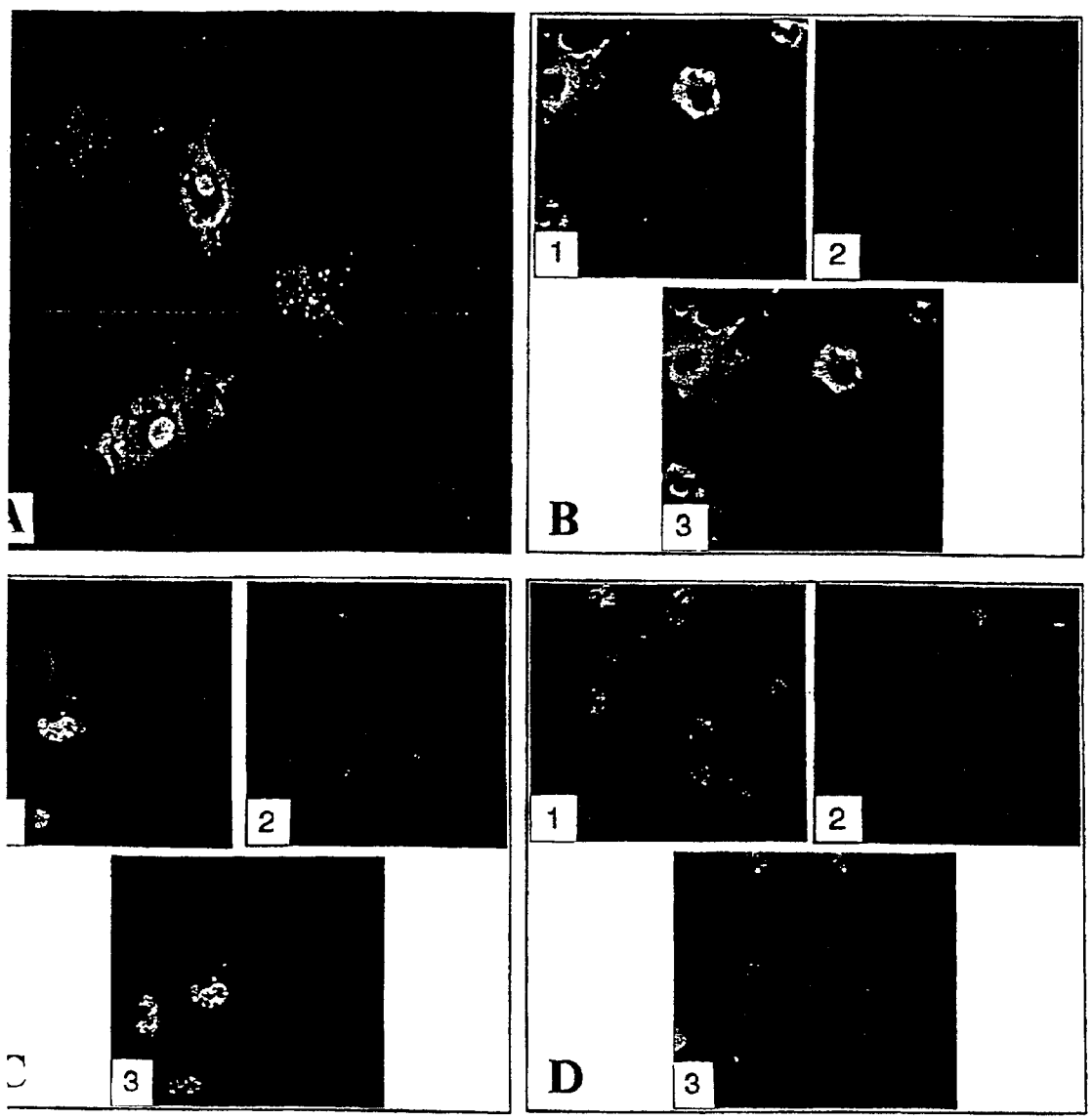
FIG. 29 shows experiments examining the localization of HsN3 and Smad1. Panels A–D show representative confocal micrographs of COS cells overexpressing Smad1, HsN3 and ALK3Q233D in COS cells. Sub-Panels B1, C1 and D1 show HsN3 localization. Sub-panels B2, C2 and D2 show Smad1 localization, and Sub-Panels B3, C3 and D3 show co-localization of HsN3 and Smad1.

To directly study how BMPs regulate the localization of HsN3, COS cells were transfected with the wild type BMP type I receptor ALK3 the BMP type II receptor and Smad1. Cells were treated with BMP7 (20 ng/ml) for either 30 mins (FIG. 28E), or 60 mins (FIG. 27F), and compared with untreated cells (FIG. 28D). In cells not treated with BMP7, the endogenous HsN3 produced a weak signal in both the cytoplasm and the nucleus that was detected with a FITC conjugated secondary antibody (FIG. 28D1), while the expressed Smad1 also produced a signal located throughout the transfected cells that was detected by Rodamine conjugated secondary antibody (FIG. 28D2). 30 mins after BMP7 treatment, only a nuclear HsN3 signal of increased intensity was detected (FIG. 28E1). This pattern wherein a weak signal located in both the cytoplasm and nucleus was replaced by a more intense nuclear signal was similar to the pattern presented in FIG. 28C. The nuclear translocation of Smad1 also began at this time point, as indicated by a decrease in the Smad1 signal in the peripheral areas of the transfected cells (FIG. 28E2). Strong Smad1 signals were also detected around the nucleus in some cells in FIG. 6E2. This localization could reflect an intermediate step that occurs prior to the nuclear translocation of these Smad1 proteins. At 60 mins after BMP7 treatment, both endogenous HsN3 and most of the overexpressed Smad1 were both accumulated in the nucleus (FIG. 28F1, F2). The colocalization of endogenous HsN3 and overexpressed Smad1 was demonstrated by overlaying the signals from these two proteins, as shown in D3, E3 and F3. Clear colocalization of nuclear HsN3 and Smad1 is detected 30 mins after BMP7 treatment (E3). Nuclear translocation and colocalization of both Smad1 and HsN3 was also detected by overexpressing Smad1, HsN3 and ALK3Q233D in COS cells (see FIG. 29). The nuclear accumulation of HsN3 is dependent upon the activation of Smad1, since replacing ALK3Q233D with the constitutively active type I receptors of activin and TGF-β abolishes such changes in the localization of HsN3 (not shown).

The rapid, BMP-induced nuclear translocation of HsN3, and the colocalization of HsN3 with Smad1 confirmed the biochemical observation that Smad1 binds to HsN3, and further suggests that Smad1 and HsN3 first form a complex in the cytoplasm, and then are translocated together into the nucleus upon receptor activation. Different proteasome subunits have been reported to be located at different intracellular sites, and subjected to differential regulation by different stimuli, or during different developmental stages (Scherrer et al., 1994; Briane et al., 1992; Dawson et al., 1995; Jones et al., 1995; Bureau et al., 1997). The differential localization and regulation of proteasome components suggest the presence of heterogeneous subpopulations of proteasomes presumably with specialized functions (for reviews, see Coux et al., 1996). The observed physical interaction between HsN3 and Smad1, and the nuclear accumulation of both Smad1 and HsN3 in response to the activation of the type I receptor of BMP provide the first example of regulation of the localization of a proteasome subunit via a signal transducer of an extracellular growth factor.

EXAMPLE 6

Proteasome Mediated Proteolysis of a Nuclear Interactor of Smad1 (SNIP-1) is Stimulated by BMP Type I Receptor Activation and Requires Smad1, DPC4 and Antizyme Interactions between proteasome subunits and non-proteasome components have been reported previously in several systems. HsN3 and a proteasome alpha subunit HC9 were shown to interact with Tax, a viral protein of the T-cell leukemia virus HTLV-1 (Rousset et al., 1996). The observation that Tax simultaneously interacts with proteasome subunits and p105, a protein which can be processed into the p50 NF-κB subunit via cotranslational processing in the proteasome (Lin et al., 1998), suggested that Tax may play a role in anchoring p105 to the proteasome (Rousset et al., 1996). Multiple subunits of the 19S regulatory complex of the 26S proteasome have also been suggested to interact with non-proteasome components and to target substrates to the proteolytic machinery (Tanaka & Tsurumi, 1997; Seeger et al., 1997).

Figure 31:
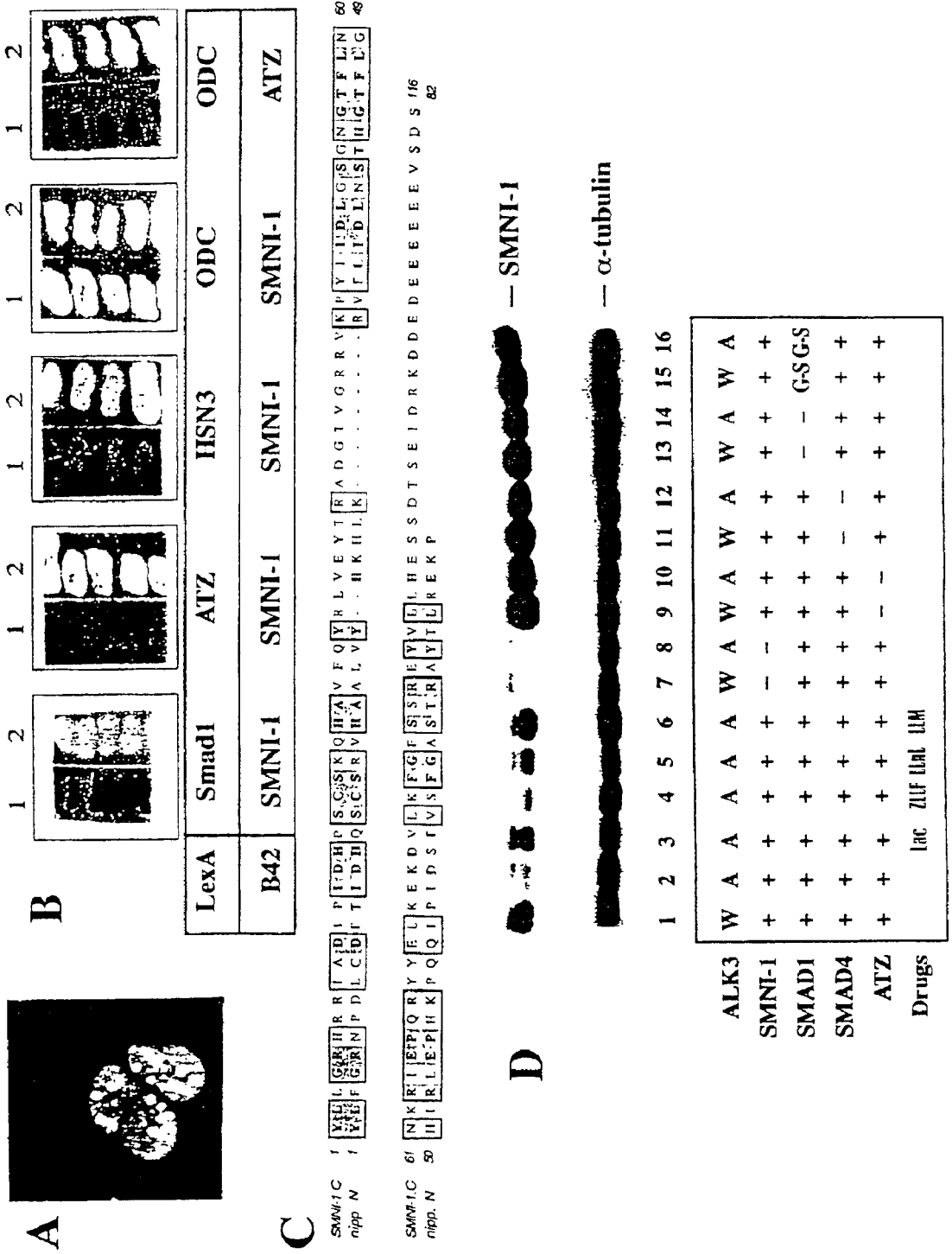
FIG. 31 shows experiments examining the proteasome-mediated degradation of SNIP1 (SEQ ID No. 3), (referred to in this figure as SMNI1). Panel A shows the nuclear localization of SNIP1 as determined by immmunofluorescence Panel B shows the interaction between SMNI-1 and Smad1, SMNI-1 and ATZ, SMNI-1 and HsN3, SMNI-1 and ODC, and ATZ and ODC. Panel C shows an alignment between SMNI-1 and the N-terminus of nipp N. Panel D shows results of a proteasome-mediated degradation of SMNI-1. The protein level of SNIP-1 in 100 ug of total protein lysate was determined by Western blot using anti-T7 monoclonal antibody, and equal loading was confirmed by Western blot using anti-a tubulin.

The binding and nuclear translocation of the activated Smad1 and a proteasome component suggest that Smad1 and HsN3 may be involved in the degradation of nuclear proteins by proteasome. The ability of Smad1 to also interact with two modifiers of proteasome substrates (ubiquitin and antizyme) suggests that Smad1 may bring antizyme bound proteins or ubiquitinated proteins to the proteasome. Interestingly, among the isolated thirteen interactors of Smad1, all but two also interact with antizyme in the yeast two-hybrid assays (see FIG. 30). We thus suspected that Smad1 interactors are potential proteasome substrates whose degradation may be dependent upon antizyme binding. This proved to be the case for two tested Smad1 interactors. The data on antizyme dependent degradation of one Smad1 interactor is shown in FIG. 31.

The novel Smad1 interactor is a nuclear proteip (termed as Smad1 Nuclear Interactor Protein 1, SNIP-1, SEQ ID No. 3), with a carboxyterminal domain that is highly homologous to the aminoterminus of the nuclear inhibitor of protein phosphatase 1 (NIPP-1) (Wang & Lechleider, unpublished) (FIG. 31A & C). NIPP-1 (VanEynde et al., 1995) is known to be rapidly processed into smaller heat-stable intermediates, a process that may be mediated by proteasome (see Discussion in Jagiello et al., 1995). SNIP-1 is a strong interactor of Smad1, that also binds to both antizyme and HsN3 in the yeast two-hybrid assays (FIG. 311B). In order to determine whether SNIP-1 is a substrate of proteasome, SNIP-1 (tagged with a T7-epitope at its aminoterminus) was coexpressed with Smad1, DPC4, antizyme and either the inactive wild type BMP type I receptor ALK3 (FIG. 31D, top panel, lane 1), or with the constitutively active mutant ALK3 (ALK3Q233D) (FIG. 31D, top panel, lane 2).

T7-SNIP-1 was constructed according to the following method. The full length SNIP-1 clone was isolated from a SuperScript human heart cDNA library constructed in the pCMV-SPORT vector. The insert (ligated into Mlu1 and Not1 sites) was excised by digestion with Sma1 and Xho1. The insert was then ligated into the Sma1 and Sal1 sites of T7--pCMV6 to create T7-SNIP-1.

Forty-eight hours after transfection, COS cells were lysed in an equal volume of lysis buffer (300 ul/plate), and the total protein concentration of each sample was measured. No major difference in protein concentration was detected among the lysates. The protein level of SNIP-1 in 100 ug of total protein lysate was determined by Western blot using anti-T7 monoclonal antibody. The level of SNIP-1 is greatly reduced in ALK3Q233D transfected cells, compared with ALK3 transfected cells. Such a decrease is dependent upon the coexpression of Smad1, DPC4 and antizyme, since replacing each of these three proteins with an unrelated protein (β galactosidase) abolishes such a decrease in ALK3Q233D transfected cells (FIG. 31D, top panel, lanes 9-14). The involvement of Smad1 activation in the decreased level of SNIP-1 is suggested by the observation that replacing the wild type Smad1 with an activation defective mutant Smad1 also abolishes the ALK3Q233D-induced reduction in the level of SNIP-1 (FIG. 31C, top panel, lanes 15 & 16). The degradation of SNIP-1 has also been observed in COS cells transfected with Smad1, DPC4, antizyme and both the BMP type II and type I (ALK3) receptors and treated with BMP7 (not shown). The total amount of proteins in the tested lanes was normalized before loading, and equal loading was confirmed by Western blot using anti-a tubulin (FIG. 31D, bottom panel).

To determine whether the decrease in the level of SNIP-1 protein level is caused by proteasome mediated degradation, we used inhibitors of the proteasome. Proteasome inhibitors that selectively block different proteolytic activities of the proteasome are powerful tools for studying the role of proteasomes in many aspects of cell growth, differentiation and apoptosis (Hilt et al., 1993; Palomebella et al., 1994; Figueiredo-Pereira et al., 1994; Thraenckner et al., 1994; Read et al., 1995; Grimm et al., 1996, for reviews, see Coux et al., 1996). Peptidyl aldhydes that mimic the proteasome substrates function as reversible inhibitors of the proteolytic activities of the proteasome β subunits (Vinitsky et al., 1992; Grimm et al., 1996). Lactacystin, a metabolite of Streptomyces, was found to form irreversible covalent bonds with a threonine in the catalytic sites of active β subunits, thereby specifically inhibiting several proteolytic activities of the 20S proteasome (Fenteany et al., 1995; Craiu et al., 1997). Lactacystin is the most specific proteasome inhibitor, and does not inhibit the activity of other proteases such as calpain, cathepsin B, chymotrypsin, trypsin and papain (Fenteany et al., 1995). We therefore tested lactacystin, as well as two peptidyl aldehydes (LLnL and LLM) in ALK3Q233D transfected cells for their ability to increase or decrease SNIP-1 protein levels. The ALK3Q233D induced decrease of SNIP-1 protein level was reversed by all three inhibitors (when the inhibitors were added 10 hours before cell lysis (FIG. 31 C, top panel, lanes 3-6). No apparent toxicity was observed in drug treated cells during the 10 hr treatment, although prolonged treatment (over 24 hrs) did cause a reduction in cell number. It was determined that an equal amount of total protein was loaded into each lane, as described above.

The dynamic interaction between Smad1 and the preassembled proteasome beta subunit HsN3 and the proteolysis of a nuclear interactor of Smad1 suggest that BMP-induced type I receptor activation may activate the ability of Smad1 to serve as a docking protein thereby bringing nuclear proteins to the proteasome for either complete degradation, or for partial processing. Ubiquitin independent degradation of proteins involving proteasome have been reported for several proteins, such as c-fos, c-Jun and ornithine decarboxylase (ODC) (Jariel-Encontre et al., 1995 & 1997; Hayashi et al., 1996). Little is known about the mechanism by which these proteins are targeted to the proteasome. Antizyme dependent degradation has only been documented for ODC (for review, see Hayashi et al., 1996). However, we observed that antizyme interacts with many other proteins besides ODC in mammalian cells (unpublished). Furthermore, multiple Smad1 interactors are found to interact with antizyme in the yeast two-hybrid system, with an affinity similar to the affinity with which antizyme binds to ODC (see FIG. 30). SNIP-1 is one of the Smad1 interactors that also binds to antizyme and HsN3 in the two-hybrid system (FIG. 31B). The antizyme-dependent proteolysis of SNIP-1 and another antizyme-binding Smad1 interactor (not shown) suggests that antizyme, like ubiquitin, may be a general modifier of proteins targeted to the proteasome for ubiquitin-independent proteolysis. The observation that both Smad1 activation and the presence of DPC4 are required for SNIP-1 proteolysis provides a mechanistic explanation for the partnership of Smad1 and DPC4, and suggests that Smad1 and DPC4 may play distinct roles in targeting proteins for antizyme-dependent proteolysis.

EXAMPLE 7

Proteasome Inhibitors Functionally Block the OP-1 Induced Dendritic Growth of Rat Sympathetic Neurons If Smad1 and DPC4 signal through proteasome mediated proteolysis, proteasome inhibitors should block the signaling of BMPs. We thus directly tested the effects of the proteasome inhibitors on the signaling pathways of BMPs that signal via Smad1 activation. OP-1 (BMP7) and other BMPs, such as BMP2 and 4, have been shown to induce dendritic growth in rat sympathetic neurons (Lein et al., 1995). Such an activity is associated with the activation of Smad1, as indicated by the rapid nuclear translocation of Smad1 from the cytoplasm to the nucleus upon OP-1 treatment of sympathetic neurons (FIG. 32, top panel A&B). Pretreatment of sympathetic neurons for 4 hours with the irreversible inhibitor lactacystin resulted in a concentration-dependent decrease in their ability to form dendrites in the presence of either OP-1 (FIG. 32, middle panel, A-C, and bottom panel A), or BMP-6 (not shown). This inhibition was specific because lactacystin did not affect either axonal growth or cell survival (FIG. 32, middle panel C and bottom panel A). The EC50 for the inhibitory activity of lactacystin was ~100 nM and maximal effects were obtained with 4–6 hour pretreatments (not shown). Inhibition of OP-1 induced dendritic growth was also observed with the reversible peptidyl aldehyde inhibitors LLnL and LLM. In particular, LLnL inhibited OP-1 activity at lower concentrations than LLM (FIG. 32, bottom panel A). This is consistent with the fact that LLnL is a more potent inhibitor of proteasome activity than LLM (Vinitsky et al, 1992; Grimm et al., 1996).

To determine the time course of sensitivity to lactacystin with respect to the signaling pathway of OP-1, lactacystin was added to the media at various time points after the addition of OP-1 (FIG. 32, bottom panel B). OP-1 induced dendritic growth was fully inhibited if lactacystin was added within 3 hrs of OP-1 exposure. However, resistance to the inhibitory effects developed after 3 hrs and are apparent after 8 hrs. Since nuclear translocation of Smad1 occurs during the first 2 hours of OP-1 exposure in these sympathetic neurons (FIG. 32, top panel), these data suggest that critical proteasome functions occur subsequent to that event.

The importance of proteasome activity in another Smad1-involved BMP response in kidney has also been detected using proteasome inhibitors (data not shown). We recently also tested the effects of proteasome inhibitors in the TGF-β signaling pathways and observed similar time and dose dependent inhibition of two TGF-β responses that involve Smad3. A TGF-β response that does not involve Smad3 was not effected by proteasome inhibitors (data not shown). Interaction of HsN3, antizyme and Smad3 has also been detected in mammalian cells (data not shown). Thus, proteasome function is intimately linked to the functions of several different Smads via the ability of Smads to interact with HsN3 and antizyme.

EXAMPLE 8

HEF1 Is Targeted to the Proteasome Through Interaction with Smad3, in Response to TGF-β Signaling HEF1 belongs to a family of multi-domain adapter proteins including p130Cas and Efs (or Sin), all of which have been implicated in coordinating multiple intracellular signaling events that regulate cell shape, cell adhesion and migration. Each member of this family has an aminoterminal SH3 domain that binds focal adhesion kinase (FAK) and/or the related PyK2, followed by multiple YXXP motifs and a highly conserved novel domain at the carboxylterminus. Predominantly found in lymphoid and epithelial cells, HEF1 is known to be an important cytoplasmic adapter protein that becomes phosphorylated upon the activation of multiple receptors, such as the integrins, the antigen receptors of T and B lymphocyte as well as the G-protein-coupled calcitonin receptor (Astier et al., 1997, J. Biol. Chem. 272: 19719; Hunter et al., 1997, J. Immunol. 159: 4806; Kanda et al., 1997, Eur. J. Immunol. 27: 2113; Manie et al., 1997, J. Biol. Chem. 272: 4230; Ohashi et al., 1998, J. Biol. Chem. 273: 6446; Sattler et al., 1997, J. Biol. Chem. 272: 14320; Tachibana et al., 1997, J. Biol. Chem. 272: 29083; Zhang et al., 1999, J. Biol. Cjem. 274: 25093; Kamiguchi et al., 1999, J. Immunol. 163; Law et al., 1998, Mol. Cell. Biol. 18: 3540). HEF1 is localized at the focal adhesion sites and has been implicated in regulating lymphocyte attachment and migration. Various post-translational modifications, such as phosphorylation, caspase-mediated cleavage and cell cycle-regulated processing of HEF1 have been reported and may serve to regulate different functions of HEF1.

Two different forms of HEF1, p115HEF1 and p105HEF1, have been previously reported to be derived from differential phosphorylation (Law et al., 1996, Mol. Cell. Boil. 16: 3327; Minegishi et al., 1996, J. Exp. Med. 184: 1365; Lae et al., 1998, supra). Both forms of HEF1 were detected at a similar level in 293 cells after HEF1 transfection for 24 hrs (data not shown). However, p115HEF1 was the predominant form that associates with Smad3, and to a much lesser extent, with Smad1 and Smad2. Neither p115HEF1 nor p105HEF1 was detected in the immunoprecipitates of Smad4. Therefore, p115HEF1 interacts strongly with Smad3, weakly with Smad1 and Smad2, but does not appear to interact with Smad4 in a mammalian overexpression system. Interestingly, the steady-state level of p115HEF1 was dramatically reduced in cells co-expressing Smad3 whereas the steady-state level of p105HEF1 was only slightly decreased (FIG. 1B, bottom panel, lane 4). The fact that the protein levels of p115HEF1 and p105HEF1 were differentially regulated by Smad3 suggests that the reduction of p115HEF1 is not caused by non-specific cell toxicity nor the result of a general inhibition of transcription.

It was tested whether the observed reduction of HEF1 level by Smad3 is regulated by TGF-β and activin type I receptor activation and whether the reduction is mediated by proteasomal degradation. The Smad3-mediated reduction of HEF1 protein level was further enhanced in the presence of the overexpressed wildtype TGF-β type I receptor and wildtype activin type I receptor, as well as the constitutively active mutant TGF-β type I receptor (R4T204D) and the activated mutant activin type I receptor (R2T206D)). The effect of the overexpressed wildtype TGF-β and activin type I receptors on HEF1 could be the result of leaky signaling due to overexpression, as evidenced by the inability of the kinase-deficient mutant type I receptors of TGF-β (R4KR) and activin (R2RK) in inducing HEF1 degradation. A peptidyl aldehyde proteasome inhibitor LLnL (N-acetyl-L-Leucinyl-L-Leucinal-L-norleucinal) was able to block Smad3-induced reduction of HEF1 protein level in the presence or absence of the TGF-β and activin type I receptors, suggesting the role of proteasomal degradation in the observed reduction of HEF1. Since LLnL is not a specific proteasome inhibitor, a highly specific proteasome inhibitor lactacystin was tested in the above assays. Like LLnL, lactacystin blocked the Smad3 induced degradation of HEF1 in the presence or absence of the TGF-β type I receptor. Thus, increasing Smad3 protein level in 293 cells is sufficient to induce proteasomal degradation of HEF1 and the activation of TGF-β or activin type I receptor further enhances the Smad3-induced HEF 1 degradation.

Like other Smad family proteins, Smad3 can be divided into three subdomains: an amino-terminal MH1 domain, a central linker region and a carboxyl-terminal MH2 domain The N-terminal MH1 domain of Smad3 (Smad3N) has the ability to bind to specific DNA sequences (Massague, 1998, supra; Derynck et al., 1998, Cell 95: 737; Wrana, 2000, Cell 100: 189), whereas the C-terminal MH2 domain interacts with the TGF-β type I receptor as well as multiple transcriptional regulators (Massague, 1998, supra; Derynck, 1998, supra; Wrana, 2000, supra). To further delineate the subdomain(s) of Smad3 that directly contribute(s) to its ability to induce HEF1 degradation, HEF1 was co-expressed with either Smad3N (aa 1-144) or Smad3C (aa 231–424). Smad3N mimicked the full length Smad3, albeit weaker, in its ability to reduce the level of HEF1, especially the p115HEF1 form. The Smad3N-mediated reduction of p115HEF1 was also blocked by LLNL. In contrast, p115HEF1 level was unchanged in the presence of Smad3C. Therefore, the ability of Smad3 to induce the proteasomal degradation of HEF1 appears to reside primarily within its MH1 domain. In cells that were not treated with LLnL, p115HEF1 and smaller amount of p105HEF1 were detected in the immunoprecipitates of Smad3N, Smad3C and full length Smad3, with the strongest HEF1 signal detected in the immunoprecipitates of Smad3C. Given that the total amount of HEF1 was greatly reduced in cells expressing Smad3N and full length Smad3 but not in cells expressing Smad3C, the highest amount of HEF1 detected in the immunoprecipitates of Smad3C was likely due to the highest level of total HEF1 in these cells. In fact, when LLnL stabilizes HEF1, the highest amount of HEF1 was detected in the immunoprecipitates of full length Smad3. Thus both Smad3N and Smad3C are able to bind full length HEF1, while only Smad3N is sufficient to mimic the full length Smad3 to induce HEF1 degradation.

To further understand how the two separate domains of Smad3 can both bind to HEF1, the abilities of full length Smad3, Smad3N and Smad3C to interact with the different deletion mutants of HEF1 were tested. First, their interaction (s) with the N-terminal domain of HEF1 from amino acids 1 to 505, which contains the SH3 domain, all of the SH2 binding sites and a serine rich region were tested. Like full length HEF1, HEF1(1–505) was also expressed in two different forms, designated as tHEF1(1–505) and bHEF1 (1–505) respectively. In the immunoprecipitates of Smad3 and Smad3N, strong signals of tHEF1(1–505) but not bHEF1(1–505) was detected. Much weaker signal of tHEF1 (1–505) was detected in the immunoprecipitates of Smad3C. Thus, the N-terminal domain of HEF1 preferentially associates with Smad3 and Smad3N compared with Smad3C. The abilities of Smad3, Smad3N and Smad3C to bind to the C-terminal subdomains of HEF1 were then tested. A set of four deletion constructs, named M2 (aa 651–834), M2/N (aa 651–759), M2/M (aa 695–759) and M2/C (aa 695–832) were used. All four tested HEF1 deletions strongly interacted with Smad3C, but not with Smad3N or full length Smad3. In summary, these domain mapping studies have revealed a unique feature in the mutual interaction between Smad3 and HEF1. The two proteins appear to interlock with each other through their modular domains, with Smad3N contacting the HEF1 N-domain and Smad3C binding to the HEF1 C-domain.

The above domain mapping data indicates that the N-terminal 505 amino-acid domain of HEF1 is sufficient for binding to full length Smad3 and Smad3N. Since Smad3 and Smad3N can induce HEF1 degradation, it was tested whether the ability of Smad3 and Smad3N to induce HEF1 degradation is dependent upon their physical interaction with HEF1 through the N-terminal 505 amino-acid domain of HEF1. Thus, HEF1(1–505) was used as a dominant negative mutant whose overexpression was applied to inhibit the interaction between Smad3 and the N-terminal domain of HEF1. Overexpression of HEF1 (1-505) efficiently blocked Smad3-induced proteasomal degradation of HEF1 in a dose-dependent fashion. Interestingly, higher molecular weight ladders of HEF1 signal were detected when HEF1 was fully stabilized by high levels of HEF1 (1–505). The stabilization of HEF1 by overexpressing HEF1 (1-505) is constantly accompanied by the detection of higher molecular ladders of HEF1, which are likely the accumulated ubiquitinated forms of HEF1. Consistent with this hypothesis, overexpression of HEF1 (1–505) blocked the degradation of p115HEF1 induced by Smad3, Smad3N or by co-expression of Smad3 and the activated TGF-β and activin type I receptors. Thus, the physical interaction between the N-terminal HEF1 and Smad3 is critical in Smad3-induced HEF1 degradation.

The ability of TGF-β to regulate the protein level of endogenous HEF1 in TGF-β responsive cells was tested. The human T lymphoblastoid H9 cells were either not exposed to TGF-β or pre-treated with TGF-β for different time periods. Cells were then harvested at the same time and HEF1 protein level was determined by Western blot using anti-HEF1 antibody. The steady-state levels of both p115 and p105 HEF1 started to decrease after 30 min exposure to TGF-β, which was manifested at 1 hr. After 3 hrs of TGF-β treatment, p115HEF1 was almost undetectable while p105HEF1 was greatly reduced. To further demonstrate that the TGF-β induced decrease of HEF1 steady-state level is a result of enhanced protein degradation, H9 cells were pulse-labeled with 3S-Met/Cys for 30 min and then chased for different time periods in the absence or presence of TGF-β. The predominant form of HEF1 labeled within the 30 min pulse period is p105HEF1. The pulse-labeled p105HEF1 was reduced to basal level within 60 min in TGF-β-stimulated cells but took more than 120 min in the absence of TGF-β. Thus, TGF-β can enhance HEF1 degradation in native H9 cells.

In A549 lung carcinoma cells, which predominantly express p115HEF1, a decrease of endogenous p115HEF1 was detected after 15 min exposure to TGF-β. Furthermore, LLnL was able to block the TGF-β induced decrease of endogenous HEF1, indicating the involvement of the proteasome in this event. The change of p105HEF1 in response to TGF-β was also observed, but not as apparent as p115HEF1 due to the very low level of p105HEF1 in this cell line. It was noted that the steady-state level of both p115HEF1 and p105HEF1 increased after 3 hrs of TGF-β stimulation. The increase can be inhibited by actinomycin D, suggesting that the increase in HEF1 protein level is due to new synthesis of HEF1 mRNA. To directly test this, we performed a time-course Northern blot on HEF1 mRNA isolated from A549 cells treated with TGF-β for different time periods. TGF-β dramatically increased the level of HEF1 mRNA as early as 1 hr after treatment in A549 cells. Similarly, induction of HEF1 mRNA by TGF-β was observed in HaCaT cells. Thus, TGF-β down-regulates HEF1 protein level via proteasomal degradation and also induces HEF1 mRNA level via transcriptional activation, which may serve as a negative feedback mechanism to restore HEF1 protein level.

It is believed that HsN3 and AIP4 contribute to the ability of Smad3 to regulate HEF1 degradation, and it is also believed that antizyme binds to HEF1.

The mapping of a Smad3-binding-domain of HEF1, HEF1 (1-505), and the identification of its ability to selectively block TGF-β-induced HEF1 degradation provides a method for testing of the specific roles of HEF1 degradation in various aspects of TGF-β and activin signaling.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. An antibody which bonds to an isolated, native SNIP1 polypeptide having the amino acid sequence of SEQ ID NOS: 3 or 5.

* * * * *

SEQUENCE LISTING

<160> NUMBER OF SEQ ID NOS: 28

<210> SEQ ID NO 1
<211> LENGTH: 277
<212> TYPE: PRT
<213> ORGANISM: Unknown
<220> FEATURE:
<223> OTHER INFORMATION: Isolated using yeast two hybrid system, Clone
      S1 + 27

<400> SEQUENCE: 1

Lys Ser Ser Pro Leu Leu Ile Arg Met Glu Glu Ser Leu Asn Ile Val
1               5                   10                  15

Lys Tyr Thr Ala Phe Leu Tyr Asn Asp Gln Leu Ile Trp Ser Gly Leu
            20                  25                  30

Glu Gln Asp Asp Met Arg Ile Leu Tyr Lys Tyr Leu Thr Thr Ser Leu
        35                  40                  45

Phe Pro Arg His Ile Glu Pro Glu Leu Ala Gly Arg Asp Ser Pro Ile
    50                  55                  60

```
Arg Ala Glu Met Pro Gly Asn Leu Gln His Tyr Gly Arg Phe Leu Thr
 65                  70                  75                  80

Gly Pro Leu Asn Leu Asn Asp Pro Asp Ala Lys Cys Arg Phe Pro Lys
                 85                  90                  95

Ile Phe Val Asn Thr Asp Asp Thr Tyr Glu Glu Leu His Leu Ile Val
            100                 105                 110

Tyr Lys Ala Met Ser Ala Ala Val Cys Phe Met Ile Asp Ala Ser Val
                115                 120                 125

His Pro Thr Leu Asp Phe Cys Arg Arg Leu Asp Ser Ile Val Gly Pro
        130                 135                 140

Gln Leu Thr Val Leu Ala Ser Asp Ile Cys Glu Gln Phe Asn Ile Asn
145                 150                 155                 160

Lys Arg Met Ser Gly Ser Glu Lys Glu Pro Gln Phe Lys Phe Ile Tyr
                165                 170                 175

Phe Asn His Met Asn Leu Ala Glu Lys Ser Thr Val His Met Arg Lys
                180                 185                 190

Thr Pro Ser Val Ser Leu Thr Ser Val His Pro Asp Leu Met Lys Ile
            195                 200                 205

Leu Gly Asp Ile Asn Ser Asp Phe Thr Arg Val Asp Glu Asp Glu Glu
        210                 215                 220

Ile Ile Val Lys Ala Met Ser Asp Tyr Trp Val Gly Lys Lys Ser
225                 230                 235                 240

Asp Arg Arg Glu Leu Tyr Val Ile Leu Asn Gln Lys Asn Ala Asn Leu
                245                 250                 255

Ile Glu Val Asn Glu Val Lys Lys Leu Cys Ala Thr Gln Phe Asn Asn
                260                 265                 270

Ile Phe Phe Leu Asp
            275

<210> SEQ ID NO 2
<211> LENGTH: 543
<212> TYPE: PRT
<213> ORGANISM: Unknown
<220> FEATURE:
<223> OTHER INFORMATION: Clone S1 + 28  protein

<400> SEQUENCE: 2

Phe Ala Val Asp Ala Lys Ala Leu Pro Gln Asn Lys Pro Arg Pro Leu
 1               5                  10                  15

Thr Gln Glu Glu Ile Ala Gln Arg Arg Glu Arg Ala Arg Gln Arg His
                 20                  25                  30

Ala Glu Lys Leu Ala Ala Ala Gln Gly Gln Ala Pro Leu Glu Pro Thr
                 35                  40                  45

Gln Asp Gly Ser Ala Ile Glu Thr Cys Pro Lys Gly Asp Glu Pro Arg
         50                  55                  60

Gly Asp Glu Gln Gln Val Glu Ser Met Thr Pro Lys Pro Val Leu Gln
 65                  70                  75                  80

Glu Glu Asn Asn Gln Glu Ser Phe Ile Ala Phe Ala Arg Val Phe Ser
                 85                  90                  95

Gly Val Ala Arg Arg Gly Lys Lys Ile Phe Val Leu Gly Pro Lys Tyr
                100                 105                 110

Ser Pro Leu Glu Phe Leu Arg Arg Val Pro Leu Cys Phe Ser Ala Pro
            115                 120                 125

Pro Asp Gly Leu Pro Gln Val Pro His Met Ala Tyr Cys Ala Leu Glu
        130                 135                 140
```

```
Asn Leu Tyr Leu Leu Met Gly Arg Glu Leu Glu Tyr Leu Glu Glu Val
145                 150                 155                 160

Pro Pro Gly Asn Val Leu Gly Ile Gly Gly Leu Gln Asp Phe Val Leu
            165                 170                 175

Lys Ser Ala Thr Leu Cys Ser Leu Pro Ser Cys Pro Pro Phe Ile Pro
        180                 185                 190

Leu Asn Phe Glu Ala Thr Pro Ile Val Arg Val Ala Val Glu Pro Lys
    195                 200                 205

His Pro Ser Glu Met Pro Gln Leu Val Lys Gly Met Lys Leu Leu Asn
210                 215                 220

Gln Ala Asp Pro Cys Val Gln Ile Leu Ile Gln Glu Thr Gly Glu His
225                 230                 235                 240

Val Leu Val Thr Ala Gly Glu Val His Leu Gln Arg Cys Leu Asp Asp
                245                 250                 255

Leu Lys Glu Arg Phe Ala Lys Ile His Ile Ser Val Ser Glu Pro Ile
            260                 265                 270

Ile Pro Phe Arg Glu Thr Ile Thr Lys Pro Pro Lys Val Asp Met Val
        275                 280                 285

Asn Glu Glu Ile Gly Lys Gln Gln Lys Val Ala Val Ile His Gln Met
290                 295                 300

Lys Glu Asp Gln Ser Lys Ile Pro Glu Gly Ile Gln Val Asp Ser Asp
305                 310                 315                 320

Gly Leu Ile Thr Ile Thr Thr Pro Asn Lys Leu Ala Thr Leu Ser Val
                325                 330                 335

Arg Ala Met Pro Leu Pro Glu Glu Val Thr Gln Ile Leu Glu Glu Asn
            340                 345                 350

Ser Asp Leu Ile Arg Ser Met Glu Gln Leu Thr Ser Ser Leu Asn Glu
        355                 360                 365

Gly Glu Asn Thr His Met Ile His Gln Lys Thr Gln Glu Lys Ile Trp
370                 375                 380

Glu Phe Lys Gly Lys Leu Glu Gln His Leu Thr Gly Arg Arg Trp Arg
385                 390                 395                 400

Asn Ile Val Asp Gln Ile Trp Ser Phe Gly Pro Arg Lys Cys Gly Pro
                405                 410                 415

Asn Ile Leu Val Asn Lys Ser Glu Asp Phe Gln Asn Ser Val Trp Thr
            420                 425                 430

Gly Pro Ala Asp Lys Ala Ser Lys Glu Ala Ser Arg Tyr Arg Asp Leu
        435                 440                 445

Gly Asn Ser Ile Val Ser Gly Phe Gln Leu Ala Thr Leu Ser Gly Pro
450                 455                 460

Met Cys Glu Glu Pro Leu Met Gly Val Cys Phe Val Leu Glu Lys Trp
465                 470                 475                 480

Asp Leu Ser Lys Phe Glu Glu Gln Gly Ala Ser Asp Leu Ala Lys Glu
                485                 490                 495

Asp Arg Arg Lys Met Lys Pro Val Leu Val Glu Met Lys Thr Lys Ser
            500                 505                 510

Tyr Lys Met Ala Ala Leu Arg Pro Leu Arg Arg Gly His His Arg Lys
        515                 520                 525

Glu Asn Leu His Ser Leu Thr Ala Met Asp Leu Ser Gln Asp Ser
530                 535                 540
```

<210> SEQ ID NO 3
<211> LENGTH: 396
<212> TYPE: PRT

<213> ORGANISM: Unknown
<220> FEATURE:
<223> OTHER INFORMATION: Clone S1 + 19

<400> SEQUENCE: 3

```
Met Lys Ala Val Lys Ser Glu Arg Glu Arg Gly Ser Arg Arg His
1               5                  10                  15

Arg Asp Gly Asp Val Val Leu Pro Ala Gly Val Val Lys Gln Glu
            20                  25                  30

Arg Leu Ser Pro Glu Val Ala Pro Pro Ala His Arg Arg Pro Asp His
            35                  40                  45

Ser Gly Gly Ser Pro Ser Pro Pro Thr Ser Glu Pro Ala Arg Ser Gly
    50                  55                  60

His Arg Gly Asn Arg Ala Arg Gly Val Ser Arg Ser Pro Pro Lys Lys
65                  70                  75                  80

Lys Asn Lys Ala Ser Gly Arg Arg Ser Lys Ser Pro Arg Ser Lys Arg
                85                  90                  95

Asn Arg Ser Pro His His Ser Thr Val Lys Val Lys Gln Glu Arg Glu
                100                 105                 110

Asp His Pro Arg Gly Arg Glu Asp Arg Gln His Arg Glu Pro Ser
            115                 120                 125

Glu Gln Glu His Arg Arg Ala Arg Asn Ser Asp Arg Asp Arg His Arg
130                 135                 140

Gly His Ser His Gln Arg Arg Thr Ser Asn Glu Arg Pro Gly Ser Gly
145                 150                 155                 160

Gln Gly Gln Gly Arg Asp Arg Asp Thr Gln Asn Leu Gln Ala Gln Glu
                165                 170                 175

Glu Glu Arg Glu Phe Tyr Asn Ala Arg Arg Glu His Arg Gln Arg
            180                 185                 190

Asn Asp Val Gly Gly Gly Ser Glu Ser Gln Glu Leu Val Pro Arg
            195                 200                 205

Pro Gly Gly Asn Asn Lys Glu Lys Glu Val Pro Ala Lys Glu Lys Pro
210                 215                 220

Ser Phe Glu Leu Ser Gly Ala Leu Leu Glu Asp Thr Asn Thr Phe Arg
225                 230                 235                 240

Gly Val Val Ile Lys Tyr Ser Glu Pro Pro Glu Ala Arg Ile Pro Lys
                245                 250                 255

Lys Arg Trp Arg Leu Tyr Pro Phe Lys Asn Asp Glu Val Leu Pro Val
            260                 265                 270

Met Tyr Ile His Arg Gln Ser Ala Tyr Leu Leu Gly Arg His Arg Arg
    275                 280                 285

Ile Ala Asp Ile Pro Ile Asp His Pro Ser Cys Ser Lys Gln His Ala
    290                 295                 300

Val Phe Gln Tyr Arg Leu Val Glu Tyr Thr Arg Ala Asp Gly Thr Val
305                 310                 315                 320

Gly Arg Arg Val Lys Pro Tyr Ile Ile Asp Leu Gly Ser Gly Asn Gly
                325                 330                 335

Thr Phe Leu Asn Asn Lys Arg Ile Glu Pro Gln Arg Tyr Tyr Glu Leu
            340                 345                 350

Lys Glu Lys Asp Val Leu Lys Phe Gly Phe Ser Ser Arg Glu Tyr Val
            355                 360                 365

Leu Leu His Glu Ser Ser Asp Thr Ser Glu Ile Asp Arg Lys Asp Asp
    370                 375                 380

Glu Asp Glu Glu Glu Glu Glu Val Ser Asp Ser
```

```
385             390             395
```

<210> SEQ ID NO 4
<211> LENGTH: 82
<212> TYPE: PRT
<213> ORGANISM: Unknown
<220> FEATURE:
<223> OTHER INFORMATION: Protein Sequence of NIPP-1 domain homologous to
      SNIP 1

<400> SEQUENCE: 4

```
Tyr Leu Phe Gly Arg Asn Pro Asp Leu Cys Asp Phe Thr Ile Asp His
1               5                   10                  15

Gln Ser Cys Ser Arg Val His Ala Ala Leu Val Tyr His Lys His Leu
            20                  25                  30

Lys Arg Val Phe Leu Ile Asp Leu Asn Ser Thr His Gly Thr Phe Leu
        35                  40                  45

Gly His Ile Arg Leu Glu Pro His Lys Pro Gln Gln Ile Pro Ile Asp
    50                  55                  60

Ser Thr Val Ser Phe Gly Ala Ser Thr Arg Ala Tyr Thr Leu Arg Glu
65                  70                  75                  80

Lys Pro
```

<210> SEQ ID NO 5
<211> LENGTH: 255
<212> TYPE: PRT
<213> ORGANISM: Unknown
<220> FEATURE:
<223> OTHER INFORMATION: Clone S1 + 19 Smad binding domain sequence

<400> SEQUENCE: 5

```
Arg His Arg Gly His Ser His Gln Arg Arg Thr Ser Asn Glu Arg Pro
1               5                   10                  15

Gly Ser Gly Gln Gly Gln Gly Arg Asp Arg Asp Thr Gln Asn Leu Gln
            20                  25                  30

Ala Gln Glu Glu Glu Arg Glu Phe Tyr Asn Ala Arg Arg Arg Glu His
        35                  40                  45

Arg Gln Arg Asn Asp Val Gly Gly Gly Ser Glu Ser Gln Glu Leu
    50                  55                  60

Val Pro Arg Pro Gly Gly Asn Asn Lys Glu Lys Glu Val Pro Ala Lys
65                  70                  75                  80

Glu Lys Pro Ser Phe Glu Leu Ser Gly Ala Leu Leu Glu Asp Thr Asn
            85                  90                  95

Thr Phe Arg Gly Val Val Ile Lys Tyr Ser Glu Pro Pro Glu Ala Arg
        100                 105                 110

Ile Pro Lys Lys Arg Trp Arg Leu Tyr Pro Phe Lys Asn Asp Glu Val
    115                 120                 125

Leu Pro Val Met Tyr Ile His Arg Gln Ser Ala Tyr Leu Leu Gly Arg
130                 135                 140

His Arg Arg Ile Ala Asp Ile Pro Ile Asp His Pro Ser Cys Ser Lys
145                 150                 155                 160

Gln His Ala Val Phe Gln Tyr Arg Leu Val Glu Tyr Thr Arg Ala Asp
            165                 170                 175

Gly Thr Val Gly Arg Arg Val Lys Pro Tyr Ile Ile Asp Leu Gly Ser
        180                 185                 190

Gly Asn Gly Thr Phe Leu Asn Asn Lys Arg Ile Glu Pro Gln Arg Tyr
    195                 200                 205
```

```
Tyr Glu Leu Lys Glu Lys Asp Val Leu Lys Phe Gly Phe Ser Ser Arg
    210                 215                 220

Glu Tyr Val Leu Leu His Glu Ser Ser Asp Thr Ser Glu Ile Asp Arg
225                 230                 235                 240

Lys Asp Asp Glu Asp Glu Glu Glu Glu Glu Val Ser Asp Ser
                245                 250                 255

<210> SEQ ID NO 6
<211> LENGTH: 163
<212> TYPE: PRT
<213> ORGANISM: Unknown
<220> FEATURE:
<223> OTHER INFORMATION: clone S1 +19 protein

<400> SEQUENCE: 6

Gly Ala Leu Thr Glu Asp Thr Asn Thr Phe Arg Gly Val Val Ile Lys
1               5                   10                  15

Tyr Asn Glu Pro Pro Glu Ala Lys Lys Pro Asn Ala Arg Trp Arg Leu
            20                  25                  30

Tyr Pro Phe Lys Gly Glu Glu Ser Leu Gln Val Leu Tyr Ile His Arg
        35                  40                  45

Gln Ser Ala Tyr Leu Ile Gly Arg Asp His Lys Ile Ala Asp Ile Pro
    50                  55                  60

Val Asp His Pro Ser Cys Ser Lys Gln His Ala Val Leu Gln Phe Arg
65                  70                  75                  80

Ser Met Pro Phe Thr Arg Asp Asp Gly Thr Lys Ala Arg Arg Ile Met
                85                  90                  95

Pro Tyr Ile Ile Asp Leu Gly Ser Gly Asn Gly Thr Phe Leu Asn Glu
            100                 105                 110

Lys Lys Ile Glu Pro Gln Arg Tyr Ile Glu Leu Gln Glu Lys Asp Met
        115                 120                 125

Leu Lys Phe Gly Phe Ser Thr Arg Glu Tyr Val Val Met Lys Glu Arg
    130                 135                 140

Glu Ile Thr Glu Glu Glu Leu Ala Glu Gly Glu Asp Val Lys Lys Glu
145                 150                 155                 160

Glu Ser Asp

<210> SEQ ID NO 7
<211> LENGTH: 198
<212> TYPE: PRT
<213> ORGANISM: Unknown
<220> FEATURE:
<223> OTHER INFORMATION: Clone S1 + 12 Protein

<400> SEQUENCE: 7

Glu Phe Gly Thr Arg Arg Met Met Glu Gly Leu Asp Asp Gly Pro Asp
1               5                   10                  15

Phe Leu Ser Glu Glu Asp Arg Gly Leu Lys Ala Ile Asn Val Asp Leu
            20                  25                  30

Gln Ser Asp Ala Ala Leu Gln Val Asp Ile Ser Asp Ala Leu Ser Glu
        35                  40                  45

Arg Asp Lys Val Lys Phe Thr Val His Thr Lys Ser Ser Leu Pro Asn
    50                  55                  60

Phe Lys Gln Asn Glu Phe Ser Val Val Arg Gln His Glu Glu Phe Ile
65                  70                  75                  80

Trp Leu His Asp Ser Phe Val Glu Asn Glu Asp Tyr Ala Gly Tyr Ile
                85                  90                  95
```

```
Ile Pro Pro Ala Pro Pro Arg Pro Asp Phe Asp Ala Ser Arg Glu Lys
            100                 105                 110

Leu Gln Lys Leu Gly Glu Gly Glu Gly Ser Met Thr Lys Glu Glu Phe
        115                 120                 125

Thr Lys Met Lys Gln Glu Leu Glu Ala Glu Tyr Leu Ala Ile Phe Lys
    130                 135                 140

Lys Thr Val Ala Met His Glu Val Phe Leu Cys Arg Val Ala Ala His
145                 150                 155                 160

Pro Ile Leu Arg Arg Asp Leu Asn Phe His Val Phe Leu Glu Tyr Asn
                165                 170                 175

Gln Asp Leu Ser Val Arg Gly Lys Lys Lys Lys Asn Ser Arg Ser
            180                 185                 190

Phe Gly Leu Leu Arg Gln
        195

<210> SEQ ID NO 8
<211> LENGTH: 414
<212> TYPE: PRT
<213> ORGANISM: Unknown
<220> FEATURE:
<223> OTHER INFORMATION: Clone S1+12 -2 protein Sequence

<400> SEQUENCE: 8

His Ala Ser Gly Leu Gly Ala Ala Met Met Glu Gly Leu Asp Asp Gly
1               5                   10                  15

Pro Asp Phe Leu Ser Glu Glu Asp Arg Gly Leu Lys Ala Ile Asn Val
            20                  25                  30

Asp Leu Gln Ser Asp Ala Ala Leu Gln Val Asp Ile Ser Asp Ala Leu
        35                  40                  45

Ser Glu Arg Asp Lys Val Lys Phe Thr Val His Thr Lys Ser Ser Leu
    50                  55                  60

Pro Asn Phe Lys Gln Asn Glu Phe Ser Val Val Arg Gln His Glu Glu
65                  70                  75                  80

Phe Ile Trp Leu His Asp Ser Phe Val Glu Asn Glu Asp Tyr Ala Gly
                85                  90                  95

Tyr Ile Ile Pro Pro Ala Pro Pro Arg Pro Asp Phe Asp Ala Ser Arg
            100                 105                 110

Glu Lys Leu Gln Lys Leu Gly Glu Gly Glu Gly Ser Met Thr Lys Glu
        115                 120                 125

Glu Phe Thr Lys Met Lys Gln Glu Leu Glu Ala Glu Tyr Leu Ala Ile
    130                 135                 140

Phe Lys Lys Thr Val Ala Met His Glu Val Phe Leu Cys Arg Val Ala
145                 150                 155                 160

Ala His Pro Ile Leu Arg Arg Asp Leu Asn Phe His Val Phe Leu Glu
                165                 170                 175

Tyr Asn Gln Asp Leu Ser Val Arg Gly Lys Asn Lys Lys Glu Lys Leu
            180                 185                 190

Glu Asp Phe Phe Lys Asn Met Val Lys Ser Ala Asp Gly Val Ile Val
        195                 200                 205

Ser Gly Val Lys Asp Val Asp Asp Phe Phe Glu His Glu Arg Thr Phe
    210                 215                 220

Leu Leu Glu Tyr His Asn Arg Val Lys Asp Ala Ser Ala Lys Ser Asp
225                 230                 235                 240

Arg Met Thr Arg Ser His Lys Ser Ala Ala Asp Asp Tyr Asn Arg Ile
                245                 250                 255
```

```
Gly Ser Ser Leu Tyr Ala Leu Gly Thr Gln Asp Ser Thr Asp Ile Cys
                260                 265                 270

Lys Phe Phe Leu Lys Val Ser Glu Leu Phe Asp Lys Thr Arg Lys Ile
            275                 280                 285

Glu Ala Arg Val Ser Ala Asp Glu Asp Leu Lys Leu Ser Asp Leu Leu
        290                 295                 300

Lys Tyr Tyr Leu Arg Glu Ser Gln Ala Ala Lys Asp Leu Leu Tyr Arg
305                 310                 315                 320

Arg Ser Arg Ser Leu Val Asp Tyr Glu Asn Ala Asn Lys Ala Leu Asp
                325                 330                 335

Lys Ala Arg Ala Lys Asn Lys Asp Val Leu Gln Ala Glu Thr Ser Gln
            340                 345                 350

Gln Leu Cys Cys Gln Lys Phe Glu Lys Ile Ser Glu Ser Ala Lys Gln
        355                 360                 365

Glu Leu Ile Asp Phe Lys Thr Arg Arg Val Ala Ala Phe Arg Lys Asn
    370                 375                 380

Leu Val Glu Leu Ala Glu Leu Glu Leu Lys His Ala Lys Gly Asn Leu
385                 390                 395                 400

Gln Leu Leu Gln Asn Cys Leu Ala Val Leu Asn Gly Asp Thr
                405                 410

<210> SEQ ID NO 9
<211> LENGTH: 294
<212> TYPE: PRT
<213> ORGANISM: Unknown
<220> FEATURE:
<223> OTHER INFORMATION: Clone S1+12 -5 protein

<400> SEQUENCE: 9

Met Thr Thr Leu Thr Glu Ile Lys Leu Leu Pro Ser Leu Val Leu Leu
1               5                   10                  15

Val Cys Cys Glu Tyr Leu Ala Ile Phe Lys Lys Thr Val Ala Met His
            20                  25                  30

Glu Val Phe Leu Cys Arg Val Ala Ala His Pro Ile Leu Arg Arg Asp
        35                  40                  45

Leu Asn Phe His Val Phe Leu Glu Tyr Asn Gln Asp Leu Ser Val Arg
    50                  55                  60

Gly Lys Asn Lys Lys Glu Lys Leu Glu Asp Phe Phe Lys Asn Met Val
65                  70                  75                  80

Lys Ser Ala Asp Gly Val Ile Val Ser Gly Val Lys Asp Val Asp Asp
                85                  90                  95

Phe Phe Glu His Glu Arg Thr Phe Leu Leu Glu Tyr His Asn Arg Val
            100                 105                 110

Lys Asp Ala Ser Ala Lys Ser Asp Arg Met Thr Arg Ser His Lys Ser
        115                 120                 125

Ala Ala Asp Asp Tyr Asn Arg Ile Gly Ser Ser Leu Tyr Ala Leu Gly
    130                 135                 140

Thr Gln Asp Ser Thr Asp Ile Cys Lys Phe Phe Leu Lys Val Ser Glu
145                 150                 155                 160

Leu Phe Asp Lys Thr Arg Lys Ile Glu Ala Arg Val Ser Ala Asp Glu
                165                 170                 175

Asp Leu Lys Leu Ser Asp Leu Leu Lys Tyr Tyr Leu Arg Glu Ser Gln
            180                 185                 190

Ala Ala Lys Asp Leu Leu Tyr Arg Arg Ser Arg Ser Leu Val Asp Tyr
        195                 200                 205
```

```
Glu Asn Ala Asn Lys Ala Leu Asp Lys Ala Arg Ala Lys Asn Lys Asp
    210                 215                 220

Val Leu Gln Ala Glu Thr Ser Gln Gln Leu Cys Cys Gln Lys Phe Glu
225                 230                 235                 240

Lys Ile Ser Glu Ser Ala Lys Gln Glu Leu Ile Asp Phe Lys Thr Arg
                245                 250                 255

Arg Val Ala Ala Phe Arg Lys Asn Leu Val Glu Leu Ala Glu Leu Glu
                260                 265                 270

Leu Lys His Ala Lys Gly Asn Leu Gln Leu Leu Gln Asn Cys Leu Ala
            275                 280                 285

Val Leu Asn Gly Asp Thr
            290
```

```
<210> SEQ ID NO 10
<211> LENGTH: 989
<212> TYPE: DNA
<213> ORGANISM: Unknown
<220> FEATURE:
<223> OTHER INFORMATION: Clone S3-1 DNA Sequence. Called tumor
      associated gene in homo sapiens, unknown function
<221> NAME/KEY: misc_feature
<222> LOCATION: (1)..(989)
<223> OTHER INFORMATION: n can be any nucleotide

<400> SEQUENCE: 10
atgtcaagtg gaatttggca gagaggcaaa gaagaagaag gagtttatgg tttttctaata      60 gaagatatca ggaaggaagt gaatagagct tctaaactga aatgctgtgt ttgcaagaaa     120
aatggtgctt caattggatg tgttgcaccc cgatgtaaac gaagttatca tttcccatgt     180
ggacttcaga gagaatgtat tttccagttt actggcaatt ttgcgtcatt ttgttgggac     240
catcgacctg ttcaaataat tacatctaat aattatagag agtccttacc atgcaccatt     300
tgcttggaat ttattgagcc tattccaagt tataacatat tacgaagtcc ttgttgtaag     360
aacgcttggt ttcatagaga ctgtttacag gttcaagcaa taaatgcggg agtgttttttc    420 tttaggtgta caatatgcaa taatagtgac atctttcaga aagagatgtt gagaatggga     480
attcatattc ctgaaaaaga tgcttcctgg gaattagagg aaaacgctta tcaagagctt     540
ctgcagcact atgagcgttg tgatgttcga agatgtcgtt gcaaagaagg gcgagactat     600
aatgcacctg atagcaaatg ggaaataaag cgctgtcagt gttgtggttc cagtggcaca     660
catttagcct gctcctcatt acggtcatgg gagcaaaatt gggagtgttt ggaatgtagg     720
ggtattatct acaattcagg agagttccaa acagccaaaa acatgtatt acccaattct      780 aataatgtgg ggattacaga ttgtttgttg gaagagtcat cacctaaatt acccagacag     840
tcacctggat cccagagtaa agatctactg aggcaaggca gcaaatttag aagaaatgta     900
tcaacactat taatagagtt aggattccaa attaaaaaaa aaaaaaaaaa actcgagaag     960
nttggantnt tcgccagagg tttggtcaa                                       989
```

```
<210> SEQ ID NO 11
<211> LENGTH: 329
<212> TYPE: PRT
<213> ORGANISM: Unknown
<220> FEATURE:
<223> OTHER INFORMATION: Clone S3-1 protein Sequence
<221> NAME/KEY: MISC_FEATURE
<222> LOCATION: (1)..(329)
<223> OTHER INFORMATION: X can be any amino acid

<400> SEQUENCE: 11
```

```
Met Ser Ser Gly Ile Trp Gln Arg Gly Lys Glu Glu Gly Val Tyr
1               5                   10                  15

Gly Phe Leu Ile Glu Asp Ile Arg Lys Glu Val Asn Arg Ala Ser Lys
            20                  25                  30

Leu Lys Cys Cys Val Cys Lys Lys Asn Gly Ala Ser Ile Gly Cys Val
        35                  40                  45

Ala Pro Arg Cys Lys Arg Ser Tyr His Phe Pro Cys Gly Leu Gln Arg
50                  55                  60

Glu Cys Ile Phe Gln Phe Thr Gly Asn Phe Ala Ser Phe Cys Trp Asp
65              70                  75                  80

His Arg Pro Val Gln Ile Ile Thr Ser Asn Asn Tyr Arg Glu Ser Leu
                85                  90                  95

Pro Cys Thr Ile Cys Leu Glu Phe Ile Glu Pro Ile Pro Ser Tyr Asn
            100                 105                 110

Ile Leu Arg Ser Pro Cys Cys Lys Asn Ala Trp Phe His Arg Asp Cys
        115                 120                 125

Leu Gln Val Gln Ala Ile Asn Ala Gly Val Phe Phe Phe Arg Cys Thr
    130                 135                 140

Ile Cys Asn Asn Ser Asp Ile Phe Gln Lys Met Leu Arg Met Gly
145                 150                 155                 160

Ile His Ile Pro Glu Lys Asp Ala Ser Trp Glu Leu Glu Glu Asn Ala
                165                 170                 175

Tyr Gln Glu Leu Leu Gln His Tyr Glu Arg Cys Asp Val Arg Arg Cys
            180                 185                 190

Arg Cys Lys Glu Gly Arg Asp Tyr Asn Ala Pro Asp Ser Lys Trp Glu
        195                 200                 205

Ile Lys Arg Cys Gln Cys Gly Ser Ser Gly Thr His Leu Ala Cys
    210                 215                 220

Ser Ser Leu Arg Ser Trp Glu Gln Asn Trp Glu Cys Leu Glu Cys Arg
225                 230                 235                 240

Gly Ile Ile Tyr Asn Ser Gly Glu Phe Gln Thr Ala Lys Lys His Val
                245                 250                 255

Leu Pro Asn Ser Asn Asn Val Gly Ile Thr Asp Cys Leu Leu Glu Glu
            260                 265                 270

Ser Ser Pro Lys Leu Pro Arg Gln Ser Pro Gly Ser Gln Ser Lys Asp
        275                 280                 285

Leu Leu Arg Gln Gly Ser Lys Phe Arg Arg Asn Val Ser Thr Leu Leu
    290                 295                 300

Ile Glu Leu Gly Phe Gln Ile Lys Lys Lys Lys Lys Leu Glu Lys
305                 310                 315                 320

Xaa Gly Xaa Phe Ala Arg Gly Leu Val
                325
```

<210> SEQ ID NO 12
<211> LENGTH: 1673
<212> TYPE: DNA
<213> ORGANISM: Unknown
<220> FEATURE:
<223> OTHER INFORMATION: Clone S3-12 DNA sequence

<400> SEQUENCE: 12
aggaaagcta cagaaattag cactgcagtg gttcagaggt cagctaccat tggcagttct       60
ccagttctct atagccagtc agctatagct acaggtcacc aggcagcagg gattggaaac     120
caggcaacag gaattggaca tcagacaata ccagttagcc ttccagcagc aggaatgggt     180

-continued

```
catcaggcca gaggaatgag cctgcagtca aattaccttg gactagcggc agcacctgca      240
attatgagtt atgcagaatg ttctgtccca attggagtga ctgctccctc attgcagcca      300
gttcaggccc gaggtgctgt gcctaccgct accattatag aaccaccacc accacctcct      360
cctcctcctc ctccaccacc accagctccc aaaatgccac cacctgaaaa dacaaaaaaa      420
ggaaggaaag acaaggcaaa gaagagtaag accaaaatgc catctttggt aaaaaagtgg      480
cagagtatcc agcgtgagtt agatgaagag dacaattcta gttccagtga agaggatcgg      540
gaatcaactg cacagaagcg aattgagag tggaaacagc agcagctggt tagtggcatg       600
gcagagagaa atgctaattt tgaagccctt cctgaggatt ggagagcaag ctgaagaga        660 aggaaaatgg ctccaaacac atagtttta gttttttaaa actttttgt attattgttt        720 gttttgtgtt cagttcaaag tcttaaccag ttttattgtc aaataaacta taatgttat        780 gggggagatc ttataaattt cctgggcaag agtgtatgca tacaaagttt tcacttttgt      840
gaaatgtaat ttttctgttt ttgcaaaggg atgaggtgat tggaattgct ttgaccatgc      900
tgcctttatt ctcaaactgg caaacttagc atgttaggtg tattaacctc atcagtcttg      960
aagaacatgt ggctcatgag tataacactt ctgtagagga ctccctgaca aaagtgaaga     1020
attaacttct cctccagaac aagtgcaatt cagaaggcag ctctgcattc taccttgctt     1080
gactggaatt gtctgaagct ttttctggcc tcttttctct agtcggccac ccctgaagtg     1140
ctgaggtcta agtggtttac ctcgtgctga tagatggcca cactctttag agtagttctc     1200
ataagttcta gaactggtag ctcggtcgtt tcgcacacta ggtggcatac aggcagcagc     1260
aggtgttcat atccttgatt ttgagaattt cccctcaagt atgtggcagt aaatacaaca     1320
agacactcta tgtattaatg tctccattgt cttaaccctg ttccaaaaca aaattcacct     1380
cctttcttta tgtgaatgta ttctccataa aattccagta tttaaaaagc agtttactgt     1440
tctgtacttt ctgttgtatc acaatcaggt aaaagtcact ttaaactgag gaaacggcaa     1500
attgtgtttt aaagctcttt gtatttctcc agtttctgac cttgtaaatt tgtatatatg     1560
cactaataaa gcttttttta taatcctgaa aaaaaaaaa aaaaaaaaaa aaaactcgag     1620
aagctttgga cttcttcgcc agaggtttgg tcaagtctcc aatcaaggtt gtc           1673
```

<210> SEQ ID NO 13
<211> LENGTH: 233
<212> TYPE: PRT
<213> ORGANISM: Unknown
<220> FEATURE:
<223> OTHER INFORMATION: Clone S3 +12 protein

<400> SEQUENCE: 13

```
Glu Phe Gly Thr Arg Arg Lys Ala Thr Glu Ile Ser Thr Ala Val
1               5                   10                  15

Val Gln Arg Ser Ala Thr Ile Gly Ser Ser Pro Val Leu Tyr Ser Gln
            20                  25                  30

Ser Ala Ile Ala Thr Gly His Gln Ala Gly Ile Gly Asn Gln Ala
        35                  40                  45

Thr Gly Ile Gly His Gln Thr Ile Pro Val Ser Leu Pro Ala Ala Gly
    50                  55                  60

Met Gly His Gln Ala Arg Gly Met Ser Leu Gln Ser Asn Tyr Leu Gly
65                  70                  75                  80

Leu Ala Ala Ala Pro Ala Ile Met Ser Tyr Ala Glu Cys Ser Val Pro
                85                  90                  95

Ile Gly Val Thr Ala Pro Ser Leu Gln Pro Val Gln Ala Arg Gly Ala
```

-continued

```
                100             105             110
Val Pro Thr Ala Thr Ile Ile Glu Pro Pro Pro Pro Pro Pro
        115                 120             125

Pro Pro Pro Pro Pro Ala Pro Lys Met Pro Pro Glu Lys Thr
130                 135                 140

Lys Lys Gly Arg Lys Asp Lys Ala Lys Lys Ser Lys Thr Lys Met Pro
145                 150                 155                 160

Ser Leu Val Lys Lys Trp Gln Ser Ile Gln Arg Glu Leu Asp Glu Glu
                165                 170                 175

Asp Asn Ser Ser Ser Glu Glu Asp Arg Glu Ser Thr Ala Gln Lys
            180                 185                 190

Arg Ile Glu Glu Trp Lys Gln Gln Gln Leu Val Ser Gly Met Ala Glu
                195                 200                 205

Arg Asn Ala Asn Phe Glu Ala Leu Pro Glu Asp Trp Arg Ala Arg Leu
    210                 215                 220

Lys Arg Arg Lys Met Ala Pro Asn Thr
225                 230
```

<210> SEQ ID NO 14
<211> LENGTH: 926
<212> TYPE: DNA
<213> ORGANISM: Unknown
<220> FEATURE:
<223> OTHER INFORMATION: Clone S3 + 103 DNA sequence

<400> SEQUENCE: 14

```
gaattcggca cgaggcggac gtcattgagc tgcgacccct gttcaacgcc gttgggcaag      60
ccagctgctg gaggtgccga gaatctgagt ttcggcaagc agccaggtct ggaaactaat     120
attttaaaaa tgactacacc aaacaagaca cctcctggtg ctgaccccaa gcagttggaa     180
aggactggaa cagtacggga aattgggtca caagctgttt ggtcactctc atcttgcaaa     240
ccaggatttg gagtggatca gttacgagat gacaatctag aaacttattg caatcagat      300
ggttcccagc ctcatttagt gaacatccaa ttcagaagaa aaacaacagt gaagacatta     360
tgtatttatg cagactacaa atctgatgaa agctatactc caagcaagat ctcagtcaga     420
gtaggaaata attttcacaa ccttcaagaa attcggcaac ttgagttggt ggaaccaagt     480
ggctggattc atgttcccct aactgacaat cataagaagc caactcgtac attcatgata     540
cagattgctg ttctagccaa tcaccagaat ggaagagaca cccatatgag acaaattaaa     600
atatacacac cagtagaaga gagctccatt ggtaaatttc ctagatgtac aactatagat     660
ttcatgatgt atcgttcaat aaggtgactt taaaatgaga cgaaaatcat taaacgtatc     720
tttgttctta tcctgtattt aaataatata tcatgtacct ttattgaaca aggcatccgt     780
tatatctaat tttgtatatg tttaaaaata ttttattgta actttgacaa ataaatttgg     840
ggtcatatta tctttatttt ctttaacatg taataaagct cacatatttt acattaaaaa     900
aaaaaaaaaa aaaaaactc gagaag                                           926
```

<210> SEQ ID NO 15
<211> LENGTH: 301
<212> TYPE: PRT
<213> ORGANISM: Unknown
<220> FEATURE:
<223> OTHER INFORMATION: Clone S3 + 103 prtoein Sequence

<400> SEQUENCE: 15

Glu Phe Gly Thr Arg Arg Thr Ser Leu Ser Cys Asp Pro Cys Ser Thr

```
                1               5                  10                 15
        Pro Leu Gly Lys Pro Ala Ala Gly Gly Ala Glu Asn Leu Ser Phe Gly
                        20                  25                  30
        Lys Gln Pro Gly Leu Glu Thr Asn Ile Leu Lys Met Thr Thr Pro Asn
                        35                  40                  45
        Lys Thr Pro Pro Gly Ala Asp Pro Lys Gln Leu Glu Arg Thr Gly Thr
         50                  55                  60
        Val Arg Glu Ile Gly Ser Gln Ala Val Trp Ser Leu Ser Ser Cys Lys
         65                  70                  75                  80
        Pro Gly Phe Gly Val Asp Gln Leu Arg Asp Asp Asn Leu Glu Thr Tyr
                        85                  90                  95
        Trp Gln Ser Asp Gly Ser Gln Pro His Leu Val Asn Ile Gln Phe Arg
                        100                 105                 110
        Arg Lys Thr Thr Val Lys Thr Leu Cys Ile Tyr Ala Asp Tyr Lys Ser
                        115                 120                 125
        Asp Glu Ser Tyr Thr Pro Ser Lys Ile Ser Val Arg Val Gly Asn Asn
                        130                 135                 140
        Phe His Asn Leu Gln Glu Ile Arg Gln Leu Glu Leu Val Glu Pro Ser
        145                 150                 155                 160
        Gly Trp Ile His Val Pro Leu Thr Asp Asn His Lys Lys Pro Thr Arg
                        165                 170                 175
        Thr Phe Met Ile Gln Ile Ala Val Leu Ala Asn His Gln Asn Gly Arg
                        180                 185                 190
        Asp Thr His Met Arg Gln Ile Lys Ile Tyr Thr Pro Val Glu Glu Ser
                        195                 200                 205
        Ser Ile Gly Lys Phe Pro Arg Cys Thr Thr Ile Asp Phe Met Met Tyr
                210                 215                 220
        Arg Ser Ile Arg Leu Asn Glu Thr Lys Ile Ile Lys Arg Ile Phe Val
        225                 230                 235                 240
        Leu Ile Leu Tyr Leu Asn Asn Ile Ser Cys Thr Phe Ile Glu Gln Gly
                        245                 250                 255
        Ile Arg Tyr Ile Phe Cys Ile Cys Leu Lys Ile Phe Tyr Cys Asn Phe
                        260                 265                 270
        Asp Lys Ile Trp Gly His Ile Ile Phe Ile Phe Phe Asn Met Ser Ser
                        275                 280                 285
        His Ile Leu His Lys Lys Lys Lys Lys Asn Ser Arg
                        290                 295                 300

<210> SEQ ID NO 16
<211> LENGTH: 844
<212> TYPE: DNA
<213> ORGANISM: Unknown
<220> FEATURE:
<223> OTHER INFORMATION: Clone S3 + 125 DNA Sequence
<221> NAME/KEY: misc_feature
<222> LOCATION: (1)..(844)
<223> OTHER INFORMATION: n Can be any nucleotide

<400> SEQUENCE: 16
caggaatctg tccgaagata attgaggcag aagagtccag aatgggcctc atcatcgtca        60
atgcctggta cgggaacttt gtcaatgaca gagcaggaa gagcgagaag gtgaaggtga       120
ttgacgtgac tgtgccctgc agtgcctggg taaggactcg aagctcatcc tcacgaggcc      180
tccaagctgg gctgcctggc ttttatgacc cgtgtgtggg ggaagagaag aacctgaaag      240
tgctctatca gttccggggc gtcctgcatc aggtgatggt gctggacagt gaggccctcc      300
```

-continued

```
ggataccaaa gcagtcccac aggatcgata cagatggata aactgccaag aaccagattt      360
ttaaaaggcc gcaaaaaatc ttttcctggg agtctacaaa tttggaaatg aaaaaaccca      420
gacatcagat gtttttattt tatattatta ttatagaagg tggtaccatt atcaattatg      480
tgaagggaca tgcagacacc ccagcactgg tatctgagta acggctaaga acctccttcc      540
tctggttttg aaaagcagtt cgggttgtcc aattctgtaa cattcatctc cattttttaa      600
aaaggtttct ctgacggccc cacggcccga gccgcggtga gcgtcgtgtt gcatgagcct      660
gggccccggg cttcccgtgc gcctctgccg caggtgcttc tgggcaccca tcctctgcgt      720
ttcatttgca gtcgactgta cagaaggcac tcaccacaat aaacctttcc tgaaagcaaa      780
aaaaaaaaaa aaaaaactcg agaaggtttg gacttgttcg ccagaggttt ggtcaagtnt      840
ccaa                                                                   844
```

<210> SEQ ID NO 17
<211> LENGTH: 118
<212> TYPE: PRT
<213> ORGANISM: Unknown
<220> FEATURE:
<223> OTHER INFORMATION: Clone S3 + 125 Protein Sequence
<400> SEQUENCE: 17

```
Ile Arg His Glu Ala Ala Gly Ile Cys Pro Lys Ile Ile Glu Ala Glu
  1               5                  10                  15

Glu Ser Arg Met Gly Leu Ile Ile Val Asn Ala Trp Tyr Gly Asn Phe
             20                  25                  30

Val Asn Asp Lys Ser Arg Lys Ser Glu Lys Val Lys Val Ile Asp Val
         35                  40                  45

Thr Val Pro Cys Ser Ala Trp Val Arg Thr Arg Ser Ser Ser Ser Arg
     50                  55                  60

Gly Leu Gln Ala Gly Leu Pro Gly Phe Tyr Asp Pro Cys Val Gly Glu
 65                  70                  75                  80

Glu Lys Asn Leu Lys Val Leu Tyr Gln Phe Arg Gly Val Leu His Gln
                 85                  90                  95

Val Met Val Leu Asp Ser Glu Ala Leu Arg Ile Pro Lys Gln Ser His
            100                 105                 110

Arg Ile Asp Thr Asp Gly
        115
```

<210> SEQ ID NO 18
<211> LENGTH: 216
<212> TYPE: DNA
<213> ORGANISM: Unknown
<220> FEATURE:
<223> OTHER INFORMATION: Clone S1 + 30 DNA Sequence
<400> SEQUENCE: 18

```
gaattcggca cgaggcggac aaagggaatc aaagttgtgg gaaatggaa  ggaagtgaag       60 attgacccaa atatgtttgc agatggacag atggatgact tggtgtgctt tgaggaattg      120
acagattacc agttggtctc ccctgccaag aattccctcc agctctcttc tcaaaggaag      180
cacccaagag aaaggcacaa gctgtttcag aagaag                                216
```

<210> SEQ ID NO 19
<211> LENGTH: 72
<212> TYPE: PRT
<213> ORGANISM: Unknown
<220> FEATURE:
<223> OTHER INFORMATION: Clone S1 + 30 Protein Sequence

```
<400> SEQUENCE: 19

Glu Phe Gly Thr Arg Arg Thr Lys Gly Ile Lys Val Val Gly Lys Trp
1               5                   10                  15

Lys Glu Val Lys Ile Asp Pro Asn Met Phe Ala Asp Gly Gln Met Asp
            20                  25                  30

Asp Leu Val Cys Phe Glu Leu Thr Asp Tyr Gln Leu Val Ser Pro
        35                  40                  45

Ala Lys Asn Ser Leu Gln Leu Ser Ser Gln Arg Lys His Pro Arg Glu
    50                  55                  60

Arg His Lys Leu Phe Gln Lys Lys
65                  70

<210> SEQ ID NO 20
<211> LENGTH: 261
<212> TYPE: DNA
<213> ORGANISM: Unknown
<220> FEATURE:
<223> OTHER INFORMATION: Clone S3+14 5' DNA sequence

<400> SEQUENCE: 20
cgatttctag cgtatatgga ggatcgcaga aaacagaagt ggcaaagatg taaaaaaaat    60
aataaggcag aattgaactg tttgggaatg gaaccagtac agacagctaa ctctagaaat   120
gggaaaaagg gtcatcacac tgaaacggtg ttcaaccggg ttttgccagg gcctattgca   180
ccagagagca gcaagaagcg gcccgtagat gcgaccagac ctttctaaga tgatggccct   240
catgcaggtg aagcatcgg t                                              261

<210> SEQ ID NO 21
<211> LENGTH: 547
<212> TYPE: DNA
<213> ORGANISM: Unknown
<220> FEATURE:
<223> OTHER INFORMATION: Clone S3+14 3' DNA sequence

<400> SEQUENCE: 21
agaggccctc atgcagggtg gaagcactgg gtctctatct ctgcataaca cgttccaaca    60
cagcagtagt ggcctacagt ctgtgtcatc tttgggtcac agcagtgcca cttctgcatc   120 tttgccttt atgccatttg tgatgggtgg tgcaccatca tcccctcatg tagactccag   180
caccatgctt catcaccacc accaccaccc caccccccac catcaccacc atcaccatcc   240
aggcttgaga gccctggct accccctcttc accagtgact accgcctctg gtactacctt   300
gcggttgcca ccactgcaac ctgaggagga tgacgatgag gatgaagaag atgatgatga   360
cttatctcag ggctatgata gctcagaaag ggacttctca ctcattgatg atcctatgat   420
gccagctaac tcagactcca gtgaagatgc tgatgactga agcccagca tgggccccat    480 tgcttgggcg gctgctgtat tttcatttac tctggcccctt ggactatgga aacgtgggag   540
gggcagg                                                             547

<210> SEQ ID NO 22
<211> LENGTH: 152
<212> TYPE: PRT
<213> ORGANISM: Unknown
<220> FEATURE:
<223> OTHER INFORMATION: Clone S3+14 protein sequence

<400> SEQUENCE: 22

Glu Ala Leu Met Gln Gly Gly Ser Thr Gly Ser Leu Ser Leu His Asn
```

```
                1               5                  10                 15
        Thr Phe Gln His Ser Ser Ser Gly Leu Gln Ser Val Ser Ser Leu Gly
                        20                  25                  30

His Ser Ser Ala Thr Ser Ala Ser Leu Pro Phe Met Pro Phe Val Met
                        35                  40                  45

Gly Gly Ala Pro Ser Ser Pro His Val Asp Ser Ser Thr Met Leu His
                        50                  55                  60

His His His His His Pro His Pro His His His His His His His Pro
        65                  70                  75                  80

Gly Leu Arg Ala Pro Gly Tyr Pro Ser Ser Pro Val Thr Thr Ala Ser
                        85                  90                  95

Gly Thr Thr Leu Arg Leu Pro Pro Leu Gln Pro Glu Glu Asp Asp Asp
                        100                 105                 110

Glu Asp Glu Glu Asp Asp Asp Leu Ser Gln Gly Tyr Asp Ser Ser
                        115                 120                 125

Glu Arg Asp Phe Ser Leu Ile Asp Asp Pro Met Met Pro Ala Asn Ser
                        130                 135                 140

Asp Ser Ser Glu Asp Ala Asp Asp
        145                 150

<210> SEQ ID NO 23
<211> LENGTH: 2496
<212> TYPE: DNA
<213> ORGANISM: Unknown
<220> FEATURE:
<223> OTHER INFORMATION: Clone s1+19 cDNA sequence

<400> SEQUENCE: 23
gaggagctca actgatctgt tttctttcgc ccagccaaaa tcacagaatg aaggcggtga      60
agagcgaacg ggagcgaggg agccggcgaa gacaccggga cggggacgtg gtgctgccgg     120
cgggggtggt ggtgaagcag gagcgtctca gcccagaagt cgcacctccc gcccaccgcc     180
gtccggacca ctccggtggt agcccgtctc cgccgaccag cgagccggcc cgctcgggcc     240
accgcgggaa ccgagcccga ggagttagcc ggtccccacc caaaaagaaa acaaggcct      300 cagggagaag aagcaagtct cctcgcagta agagaaaccg aagtcctcac cactcaacag     360
tcaaagtgaa gcaggagcgt gaggatcatc cccggagagg acgggaggat cggcagcaca     420
gggaaccatc agaacaggaa cacaggagag ctaggaacag tgacgggac agacaccggg     480 gccattccca ccaaaggaga acgtctaacg agaggcctgg gagtgggcag ggtcagggac     540
gggatcgaga cactcagaac ctgcaggctc aggaagaaga gcgggagttt tataatgcca     600
ggcgacggga gcatcgccag aggaatgacg ttggtggtgg cggcagtgag tctcaggagt     660
tggttcctcg gcctggtggc aacaacaaag aaaagaggt gcccgctaaa gaaaaaccaa     720
gctttgaact ttctgggca cttcttgagg acaccaacac tttccggggt gtagtcatta     780
aatatagtga gcccccagaa gcacgtatcc ccaaaaaacg gtggcgtctc tacccattta     840
aaaatgatga ggtgcttcca gtcatgtaca tactcgacag agtgcgtac ctactgggtc     900 gacaccgccg cattgcagac attccaattg atcacccgtc ttgttcaaag cagcatgcgg     960
tctttcaata tcggcttgtg gaatatacccgtgctgatgg cacagttggc cgaagagtga    1020
agccctacat cattgacctt ggctcaggca atgaaccctt cttaaacaac aaacgtattg    1080
agccacagag atactatgaa ctaaaagaaa aggatgtact caaatttgga ttcagtagca    1140
gagaatacgt cttgctccat gagtcgtcgg acacttctga aatagacagg aaagatgacg    1200
```

```
aggatgagga ggaggaggaa gaagtgtctg acagctagca aactaagaac ccaaactatt    1260
gatacacggt ttccttcttg gaagtctttg attgactcag agagcactat ggtggtgggt    1320
ccagcactat ggtgctctct gtaatgcctc ttactgcctt aagtctttcc tctgttgctg    1380
accagattgt gttaccattt gaatacactg actaatgttt gttaaacttt ttctgtggca    1440
ccttggccac atgcctgcag gcatttgttt tcagaacagt ctcaccaatt acaacacacc    1500
gtgttttagt agaagtgttg tggttttagt tggtgctttc agaactgctg cctaggaaac    1560
tataaaccct tggttaaggg gaaatcatgg cttgttctct ttgtacagtt actttattta    1620
tataggtgtt aagctttgtg gaccaggtgt ttttcttttg gggcgaaccc ctgagcagag    1680
aatcttacta ggctttggtt atcaccaaaa caacctccag tatataccaa agctttgact    1740
tgtttgagct cttgagctta gaagttgatt ttgcacttat tttttggggg ggtgggaatg    1800
tactgcagtc agtaaacatt attgactgtt taacttaaac agatgcttta tggcacctgc    1860
tcaagcccgt gactgtacag aaggatcctg gttgctacca gtgggtgctg attcagcatc    1920
acaagtgact gaaattggct gtggatctgt tctttgtgaa agaattcctg atttctccat    1980
ggagcatgta cacaacaatt ttgatcatat taactgtact tcagttttgc attttttattc    2040 aaatgttatc tcttttttc tttgagaaat aaactgtcac tgatgtgaca gcgttctttc    2100
tttattctaa taacatgtat agatctaaag caggttgtgt tgtttacatg tttctacaca    2160
tttcatcctt taaaaagttg ttgagagagg ttgtatttac cttcccaagg ttggaaagca    2220
ggggaatttc ccagtgtcct agttttccac cagaggaata tgtgtaagta gcaaagtatt    2280
tgctgcttac atatagtgtg tatgtatgta tatatgtaaa ttgtgtgtta aagagctgat    2340
actgattttc atatgacaat gttaggcaaa ggcctccctg catttgaaga gcaggttttc    2400
atttatatgt attttgggga taaaaaaata aaatttgtaa atatagcccc caaaaaaaaa    2460
aaaaaaaaaa aaaaaaaaaa aaaaaaaaaa aaaaaa                              2496

<210> SEQ ID NO 24
<211> LENGTH: 1965
<212> TYPE: DNA
<213> ORGANISM: Unknown
<220> FEATURE:
<223> OTHER INFORMATION: Clone S1+12-2 cDNA sequence

<400> SEQUENCE: 24
cccacgcgtc cggcctcgga gcagccatga tggaaggcct ggacgacggc ccggacttcc     60
tctcagaaga ggaccgcgga cttaaagcaa taaatgtaga tcttcaaagt gatgctgctc    120
tgcaggtgga catttctgat gctcttagtg agcgggataa agtaaaattc actgttcaca    180
caaagagttc attgccaaat tttaaacaaa acgagttttc agttgttcgg caacatgagg    240
aatttatctg gcttcatgat tcctttgttg aaaatgaaga ctatgcaggt tatatcattc    300
caccagcacc accaagacct gattttgatg cttcaaggga aaaactacag aagcttggtg    360
aaggagaagg gtcaatgacg aaggaagaat tcacaaagat gaaacaggaa ctggaagctg    420
aatatttggc aatattcaag aagacagttg cgatgcatga agtgttcctg tgtcgtgtgg    480
cagcacatcc tattttgaga agagatttaa atttccatgt cttcttggaa tataatcaag    540
atttgagtgt gcgaggaaaa aataaaaaag agaaacttga agacttcttt aaaaacatgg    600
ttaaatcagc agatggagta atcgtttcag gagtaaagga tgtagatgat ttcctttgagc    660 acgaacgaac atttcttttg gagtatcata accgagttaa ggatgcatct gctaaatctg    720
atagaatgac aagatcccac aaaagtgctg cagatgatta caatagaatt ggttcttcat    780
```

```
tatatgcttt aggaactcag gattctacag atatatgcaa gttttttctc aaagtttcag      840
aactgttcga taaaacaaga aaaatagaag cacgagtgtc tgctgatgaa gacctcaaac      900
tttctgatct tttaaaatat tacttaagag aatctcaagc tgctaaggat ctcctgtatc      960
gaaggtctag gtcactagtg gattatgaaa atgctaataa agcactggat aaagcaagag     1020
caaaaaataa agatgttcta caggccgaaa cttcccaaca attatgttgt cagaaatttg     1080
aaaaaatatc tgagtctgca aaacaagaac ttatagattt taagacaaga agagttgctg     1140
cattcagaaa aaatttagtg gaactggcag agttagaact gaagcatgca aagggtaatc     1200
tacagttgct gcagaactgc ctggcagtgt taaatggaga cacataagcc acactccgcc     1260
ttcctgttaa aaagggctgc cttccttcaa atttttatttt tgttttctta atgatgttaa     1320
gcatttatgc tcactggaaa caaacaaaaa gcagctgaaa aagtgcatca actcctcttt     1380
ttctgagaaa catggagcag cgcacgccca ggcgatgcca gtctgtgtgc cgtgatgccg     1440
cactgtgttc cccatgacag tggtccatca tcgtgcactc gtcatactca gaagtccaaa     1500
gttcattctt ctttaaagta gcctctataa ctctgtttat tttataaata gtattcctta     1560
tggctgccac tcttatttac ctttaaataa tttctgaaat ttaaccttt cagaatgcat      1620 tgttgaaaca agataaagat tgcctttttt gaattttta aattttgttt ttaaaagcat      1680
ataccacctt agttcattca tgtatcctgg taaagcatct taatcagact tattttaat      1740 tactgaatat ttcttagacg ttttgggaca gatttatgt aatctttata agtatgattt      1800
ctgaagaaaa gcaaatgcat tagtatgttt gccttaaact tgtagactaa accaagtatt     1860
gtaaaataaa cagcgataac agtgatagtt tttaactcta tggtcattgt atcactctgg     1920
aaaatgtgga gtagctgtaa taaatctact cctgtattat gcttt                    1965
```

<210> SEQ ID NO 25
<211> LENGTH: 2269
<212> TYPE: DNA
<213> ORGANISM: Unknown
<220> FEATURE:
<223> OTHER INFORMATION: Clone S1+12-5 cDNA sequence

<400> SEQUENCE: 25

```
gcggcgccga gtcccgggag cgcggtgggg gcagcgggcg cggggcgggc gcggggaccg       60
cgccagcctg tcactaatgt ctccctttgt gtctccccca tctcatcctt ttccccggcg      120
cgccgtgccc gccgacccca caggaaggcc tggacgacgg cccggacttc ctctcagaag      180
aggaccgcgg acttaaagca ataaatgtag atcttcaaag tgatgctgct ctgcaggtgg      240
acatttctga tgctcttagt gagcgggata aagtaaaatt cactgttcac acaaagagtt      300
cattgccaaa ttttaaacaa aacgagtttt cagttgttcg gcaacatgag gaatttatct      360
ggcttcatga ttcctttgtt gaaaatgaag actatgcagg ttatatcatt ccaccagcac      420
caccaagacc tgattttgat gcttcaaggg aaaaactaca gaagcttggt gaaggagaag      480
ggtcaatgac gaaggaagaa ttcacaaaga tgaaacagga actggaagcg ggttggataa      540
cagagaacct tgggtttatt ctactgctac ctccatcctc tgcatccttc ttttttgtct      600
tcactgaatg actaccctca cagagatcaa acttctccca tcattggtcc tgctggtttg      660
ctgtgaatat ttggcaatat tcaagaagac agttgcgatg catgaagtgt tcctgtgtcg      720
tgtggcagca catcctattt tgagaagaga tttaaatttc catgtcttct tggaatataa      780
tcaagatttg agtgtgcgag gaaaaaataa aaaagagaaa cttgaagact tctttaaaaa      840
```

-continued

| | |
|---|---|
| catggttaaa tcagcagatg gagtaatcgt ttcaggagta aaggatgtag atgatttctt | 900 |
| tgagcacgaa cgaacatttc ttttggagta tcataaccga gttaaggatg catctgctaa | 960 |
| atctgataga atgacaagat cccacaaaag tgctgcagat gattacaata gaattggttc | 1020 |
| ttcattatat gctttaggaa ctcaggattc tacagatata tgcaagtttt ttctcaaagt | 1080 |
| ttcagaactg ttcgataaaa caagaaaaat agaagcacga gtgtctgctg atgaagacct | 1140 |
| caaactttct gatcttttaa atattactt aagagaatct caagctgcta aggatctcct | 1200 |
| gtatcgaagg tctaggtcac tagtggatta tgaaaatgct aataaagcac tggataaagc | 1260 |
| aagagcaaaa aataaagatg ttctacaggc cgaaacttcc caacaattat gttgtcagaa | 1320 |
| atttgaaaaa atatctgagt ctgcaaaaca agaacttata gattttaaga caagaagagt | 1380 |
| tgctgcattc agaaaaaatt tagtggaact ggcagagtta aactgaagc atgcaaaggg | 1440 |
| taatctacag ttgctgcaga actgcctggc agtgttaaat ggagacacat aagccacact | 1500 |
| ccgccttcct gttaaaaagg gctgccttcc ttcaaatttt attttttgttt tcttaatgat | 1560 |
| gttaagcatt tatgctcact ggaaacaaac aaaaagcagc tgaaaaagtg catcaactcc | 1620 |
| tcttttctg agaaacatgg agcagcgcac gcccaggcga tgccagtctg tgtgccgtga | 1680 |
| tgccgcactg tgttccccat gacagtggtc catcatcgtg cactcgtcat actcagaagt | 1740 |
| ccaaagttca ttcttcttta agtagcctc tataactctg tttatttat aaatagtatt | 1800 |
| ccttatggct gccactctta tttacctta ataatttct gaatttaac cttttcagaa | 1860 |
| tgcattgttg aaacaagata aagattgcct ttttttgaatt ttttaaattt tgttttttaaa | 1920 |
| agcatatacc accttagttc attcatgtat cctggtaaag catcttaatc agacttattt | 1980 |
| ttaattactg aatatttctt agacgttttg ggacagattt tatgtaatct ttataagtat | 2040 |
| gatttctgaa gaaaagcaaa tgcattagta tgtttgcctt aaacttgtag actaaaccaa | 2100 |
| gtattgtaaa ataacagcg ataacagtga tagttttttaa ctctatggtc attgtatcac | 2160 |
| tctggaaaat gtggagtagc tgtaataaat ctaatcctgt attatgcttt aaaaaaaaaa | 2220 |
| aaaaaaaaaa aaaaaaaaaa aaaaaaaaa aaaaaaaaa aaaaaaaa | 2269 |

<210> SEQ ID NO 26
<211> LENGTH: 1834
<212> TYPE: DNA
<213> ORGANISM: Unknown
<220> FEATURE:
<223> OTHER INFORMATION: clone S1+27 cDNA sequence

<400> SEQUENCE: 26

| | |
|---|---|
| gtcgacccac gcgtccggcg ggccgtggga gggtcccgag gtgggggtcg gggcgggatg | 60 |
| gctgcagcgg cggccggggc cgggagcggg ccctgggcgg cccaggagaa gcagttcccg | 120 |
| ccggcgctgc tgagtttctt catctacaac ccgcgcttcg ggccgcgcga aggacaggag | 180 |
| gaaaataaga ttttattta tcatccaaat gaggtagaaa agaatgagaa gattagaaat | 240 |
| gtcggattgt gtgaagctat tgtacagttt acaaggacat ttagcccatc aaaacctgca | 300 |
| aaatctttac atacacagaa gaacagacag ttcttcaatg aaccagaaga aaatttctgg | 360 |
| atggtcatgg ttgttcggaa tcctataatt gaaaaacaga gtaaagatgg aaaaccagtt | 420 |
| attgaatatc aagaggagga gttgttggac aaggtttata gctcggtgct gcggcagtgc | 480 |
| tacagcatgt acaagctttt taatggtaca tttctgaaag ccatggaaga cggaggcgtc | 540 |
| aagcttctga agaaaaaatt agagaaattc ttccatcggt atttgcaaac gctacatttg | 600 |
| cagtcatgtg acctacttga cattttttggt ggaatcagct tcttcccgtt ggataaaatg | 660 |

-continued

```
acttatttga aaatccagtc ctttattaat aagaatggag gaaagcctga atatagtcaa      720
atacactgct tttctctata acgatcagct catctggagt ggattagaac aagatgacat      780
gagaatttta tacaaatacc ttaccacctc ccttttccca aggcacatcg aacctgagtt      840
agcaggaagg gattctccaa taagagcaga aatgccagga aatcttcaac actatggaag      900
atttcttacc ggaccttga acctcaatga tccagatgca aaatgcagat tccccaaaat      960
ttttgtaaat acagatgaca cttatgaaga gctccattta atcgtttata aggccatgag     1020
tgcggctgtg tgctttatga tcgacgcctc tgtccaccca acgttggatt tttgccgaag     1080
actggacagc atcgttgggc cccagctcac agtgctggcc tctgacatct gtgaacagtt     1140
taacatcaac aagaggatgt ccgggtctga aaagaaccc cagtttaagt ttatctactt      1200
caaccacatg aatctcgccg agaagagcac agttcacatg aggaaaacgc ccagcgtgtc     1260
gctcacttcc gtgcacccgg atttaatgaa gattctcggt gacatcaaca gtgactttac     1320
cagagtggat gaagatgagg agatcattgt gaaggccatg agtgattact gggttgttgg     1380
aaagaagtct gatcggcggg agctctatgt tattttgaat caaaaaaatg caaacctgat     1440
tgaagtaaat gaggtcaaga aactttgtgc aacgcagttc aacaacatct tcttcttgga     1500
ttgacggatg acggctcact gagagcatat ctaaaaaaca ctctgcaaac atttggtcac     1560
atgcaagtta gtggtcatat gacggactgc attcaggaca agggtaaagc aatacttgct     1620
ttgaagaatc acatttcgac tcggtctgct gatctgaggt ttttagattt taaatattta     1680
tgtggaatta attaaaggta gttggctata tcgctatcat ttcattcttt tgacattatg     1740
tgaatatttt actggaaaat aagactaata aattgttaaa agttttaaa aaaaaaaaa      1800 aaaaaaaaaa aaaaaaaaaa aaaaagggc ggcc                                  1834
```

<210> SEQ ID NO 27
<211> LENGTH: 2276
<212> TYPE: DNA
<213> ORGANISM: Unknown
<220> FEATURE:
<223> OTHER INFORMATION: clone S1+28 cDNA sequence

<400> SEQUENCE: 27

```
gtttgcagtt gatgctaagg ccttgcctca gaataagcca aggcctctca ctcaagaaga       60
aattgctcag agacgtgagc gtgcaagaca aaggcatgca gagaagcttg cagcagcaca      120
gggacaggca cccttggagc ccacccaaga tgggagtgcc attgaaacat gtccaaaagg      180
agacgagcca agaggtgacg agcaacaggt ggaaagtatg accctaaac ctgtgctcca      240 ggaagaaaac aaccaagagt cttttattgc atttgctcgg gtgttcagtg gtgtggctcg      300
aagaggaaag aaaattttg tcttggggcc caaatacagt cctcttgagt ttttacgaag      360
ggtaccatta tgcttctcag ctccaccaga tggcctcccc caagtcccc acatggcata      420 ctgtgctctg gaaacctgt atcttctgat gggaagggaa ctggaatatc tagaggaggt      480
acctccagga aatgtgctag gaataggagg ccttcaagat tttgtgctga aatctgcaac      540
actgtgtagc ctgccatcct gcccaccatt tataccactc aacttcgaag ccactcctat      600
tgtgagagtt gctgttgaac caaaacatcc aagtgaaatg cctcagctcg taaaggaat      660 gaaactgtta aaccaggctg atccctgtgt ccagatttta attcaggaaa cgggagagca      720
cgttttagtc acagcaggag aagtccacct tcagcgatgc ctggatgact aaaagaaag      780 gtttgcaaag attcatatca gtgtatctga acctattatt ccattcagag aaacaatcac      840
```

```
                                                         -continued
aaaaccccca aaagttgaca tggtcaatga agaaataggc aaacagcaaa aagttgcagt      900
catacaccaa atgaaagaag atcaaagcaa aatccctgaa ggaatccaag ttgactctga      960
cgggctaatc accataacaa ctcccaataa acttgccacg ctcagtgttc gagccatgcc     1020
ccttccagaa gaagtcaccc agattctgga agaaaatagt gatttgattc gttctatgga     1080
gcagttgaca tcctctttga atgagggtga aaatactcac atgattcatc agaagaccca     1140
agagaaaatt tgggaattca aggaaaact ggagcaacac ctaacaggga gaagatggag      1200
gaacattgtt gaccaaatct ggtcatttgg cccaagaaaa tgtgggccca acatactagt     1260
caataaaagt gaagattttc agaactcagt atggacaggt ccagctgaca aagcttcaaa     1320
agaagccagt agataccgag atttgggcaa tagcattgtg agtggcttcc aactagcaac     1380
cctctctggc cccatgtgtg aggagcctct catgggtgtc tgttttgttc tggaaaaatg     1440
ggacctaagt aaatttgagg aacaaggagc aagtgatctg gcaaagagg acaggaggaa      1500 aatgaaacct gttctggtgg aaatgaaaac caagagctac aagatggctg ctctgaggcc     1560
tttgagaaga ggacatcaca gaaggagaa tctccactca ctgactgcta tggacctttc      1620
tcaggacagc taattgccac catgaaagaa gcatgtcgct atgcactgca agtgaaacct     1680
cagcgcctga tggcagctat gtacacatgt gacatcatgg ccactggtga tgttctcggt     1740
cgagtctatg ctgtcttgtc aaagagagaa ggtcgggtac ttcaagaaga aatgaaagaa     1800
gggacagaca tgttcatcat caaggctgtg ctgcctgttg ctgaaagctt tggttttgct     1860
gatgaaatca ggaagaggac aagtggcctg gccagcccac aactagtatt cagccattgg     1920
gagatcattc ccagtgaccc ttctgggtgc caactactga ggaggaatac ttgcactttg     1980
gggagaaggc tgactctgag aaccaagccc ggaagtacat gaacgcagta cgaaagcgga     2040
agggctttta tgtggaagaa aagattgtgg agcatgcaga aaagcagagg acactcagca     2100
aaaataagta gctacctact actggtggat tcttttcctt atagtgaatt taaaagtatc     2160
atcaagggtt taatattggg aaaatttctt tttgccacat tatctctgtt tattcactt      2220 caataaagtt gatccatata aatattttaa agaggatgtt aaaaaaaaaa aaaaaa         2276
```

<210> SEQ ID NO 28
<211> LENGTH: 8
<212> TYPE: PRT
<213> ORGANISM: Unknown
<220> FEATURE:
<223> OTHER INFORMATION: Starting sequence of SIP2

<400> SEQUENCE: 28

```
Met Glu Glu Ser Leu Asn Ile Val
1               5
```